United States Patent
Gray et al.

(10) Patent No.: US 10,316,002 B2
(45) Date of Patent: Jun. 11, 2019

(54) KINASE INHIBITORS FOR THE TREATMENT OF DISEASE

(71) Applicant: Dana-Farber Cancer Institute, Inc., Boston, MA (US)

(72) Inventors: Nathanael Gray, Boston, MA (US); Hwan Geun Choi, Daegu (KR); Li Tan, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/696,309

(22) Filed: Sep. 6, 2017

(65) Prior Publication Data

US 2017/0369449 A1 Dec. 28, 2017

Related U.S. Application Data

(63) Continuation of application No. 14/903,650, filed as application No. PCT/US2014/046022 on Jul. 9, 2014, now Pat. No. 9,783,504.

(60) Provisional application No. 61/901,808, filed on Nov. 8, 2013, provisional application No. 61/844,304, filed on Jul. 9, 2013.

(51) Int. Cl.
| | | |
|---|---|---|
| C07D 239/48 | (2006.01) | |
| C07D 471/04 | (2006.01) | |
| C07D 409/14 | (2006.01) | |
| C07D 409/12 | (2006.01) | |
| C07D 405/14 | (2006.01) | |
| C07D 405/12 | (2006.01) | |
| C07D 401/12 | (2006.01) | |
| C07D 403/12 | (2006.01) | |
| C07D 487/04 | (2006.01) | |
| A61K 31/505 | (2006.01) | |
| A61K 45/06 | (2006.01) | |
| A61K 31/5377 | (2006.01) | |
| A61K 31/519 | (2006.01) | |
| A61K 31/517 | (2006.01) | |
| A61K 31/506 | (2006.01) | |

(52) U.S. Cl.
CPC .......... *C07D 239/48* (2013.01); *A61K 31/505* (2013.01); *A61K 31/506* (2013.01); *A61K 31/517* (2013.01); *A61K 31/519* (2013.01); *A61K 31/5377* (2013.01); *A61K 45/06* (2013.01); *C07D 401/12* (2013.01); *C07D 403/12* (2013.01); *C07D 405/12* (2013.01); *C07D 405/14* (2013.01); *C07D 409/12* (2013.01); *C07D 409/14* (2013.01); *C07D 471/04* (2013.01); *C07D 487/04* (2013.01); *Y02A 50/411* (2018.01)

(58) Field of Classification Search
CPC .. A61K 31/506; A61K 31/505; A61K 31/517; A61K 31/519; A61K 31/5377; A61K 45/06; A61K 2300/00; C07D 403/12; C07D 405/12; C07D 405/14; C07D 239/48; C07D 409/12; C07D 409/14; C07D 471/04; C07D 487/04; C07D 401/12; Y02A 50/411

See application file for complete search history.

(56) References Cited

U.S. PATENT DOCUMENTS

| | | | | |
|---|---|---|---|---|
| 7,504,396 | B2* | 3/2009 | Nunes ................. | C07D 213/82 514/235.8 |
| 2003/0158188 | A1* | 8/2003 | Lee et al. ............ | A61K 31/506 |

FOREIGN PATENT DOCUMENTS

| | | |
|---|---|---|
| CN | 102816162 | 12/2012 |
| EP | 1 801 112 | 6/2007 |
| WO | WO 1999/061444 A2 | 12/1999 |
| WO | WO 2001/066099 | 9/2001 |
| WO | WO 2004/041822 | 5/2004 |
| WO | WO 2005/011597 | 2/2005 |
| WO | WO 2006/000420 | 1/2006 |
| WO | WO 2007/035873 | 3/2007 |
| WO | WO 2007/071752 | 6/2007 |
| WO | WO 2007/136465 | 11/2007 |
| WO | WO 2010/129053 | 11/2010 |
| WO | WO 2011/071821 A1 | 6/2011 |
| WO | WO 2011/075620 A1 | 6/2011 |
| WO | WO 2011/099764 | 8/2011 |
| WO | WO 2012/167415 | 12/2012 |
| WO | WO 2013/087725 A1 | 6/2013 |
| WO | WO 2013/136070 A1 | 9/2013 |
| WO | WO 2014/007951 A2 | 1/2014 |
| WO | WO 2014/011900 A2 | 1/2014 |

OTHER PUBLICATIONS

Li Tan et al., Development of covalent inhibitors that can overcome resistance to the first-generation FGFR kinase inhibitors, Proceedings of the National Academy of Sciences of the United States of America (2014), 111 (45), E4869-E4877.*

Brugel T. A. et al., "Development of N-2,4-pyrimidine-N-phenyl-N'-phenyl ureas as inhibitors of tumor necrosis factor alpha (TNF-a) synthesis. Part 1", *Bioorganic & Medicinal Chemistry Letters* 2006, vol. 16, No. 13, pp. 3510-3513.

Drizin I. et al., "Structure-activity studies of a novel series of 5,6-fused heteroaromatic ureas as TRPV1 antagonists", *Bioorganic & Medicinal Chemistry* 2006, vol. 14, No. 14, pp. 4740-4749.

(Continued)

*Primary Examiner* — Alexander R Pagano
*Assistant Examiner* — Ebenezer O Sackey
(74) *Attorney, Agent, or Firm* — Cooley LLP; Heidi A. Erlacher; Chen Chen

(57) ABSTRACT

The invention relates to compounds and their use in the treatment of disease. Novel irreversible inhibitors of wild-type and mutant forms of EGFR, FGFR, ALK, ROS, JAK, BTK, BLK, ITK, TEC, and/or TXK and their use for the treatment of cell proliferation disorders are described.

18 Claims, 33 Drawing Sheets

(56) References Cited

OTHER PUBLICATIONS

Fukuoka M., et al. "Biomarker analyses and final overall survival results from a phase III, randomized, open-label, first-line study of gefitinib versus carboplatin/paclitaxel in clinically selected patients with advanced non-small-cell lung cancer in Asia (IPASS)", *Journal of Clinical Oncology*, 2011, vol. 29, No. 21, p. 2866-74.

Gomtsyan A. et al., "Novel Transient Receptor Potential Vanilloid 1 Receptor Antagonists for the Treatment of Pain: Structure-Activity Relationships for Ureas with Quinoline, Isoquinoline, Quinazoline, Phthalazine, Quinoxaline, and Cinnoline Moieties", *Journal of Medicinal Chemistry* 2005, vol. 48, No. 3, pp. 744-752.

Jetter M. C. et al., "N-Isoquinolin-5-yl-N'-aralkyl-urea and -amide antagonists of human vanilloid receptor 1", *Bioorganic & Medicinal Chemistry Letters* 2004, vol. 14, No. 12, pp. 3053-3056.

Maier et al., "Development of N-2,4-pyrimidine-N-phenyl-N'-alkyl ureas as orally active inhibitors of tumor necrosis factor alpha (TNF-a) synthesis. Part 2", *Bioorganic & Medicinal Chemistry Letters* 2006, vol. 16, No. 13, pp. 3514-3518.

Maier J A. et al., "Development of N-4,6-pyrimidine-N-alkyl-N'-phenyl ureas as orally active inhibitors of lymphocyte specific tyrosine kinase" *Bioorganic & Medicinal Chemistry Letters* 2006 vol. 16, No. 14, , pp. 3646-3650.

Morikawa N., et al. "Prospective analysis of the epidermal growth factor receptor gene mutations in non-small cell lung cancer in Japan", *Journal of Clinical Oncology*, 2006, vol. 24, No. 18S, Abstract 7077.

Inoue A., et al. "Prospective Phase II Study of Gefitinib for Chemotherapy—Naïve Patients With Advanced Non-Small-Cell Lung Cancer With Epidermal Growth Factor Receptor Gene Mutations", *Journal of Clinical Oncology*, 2006, vol. 24, No. 21, p. 3340-6.

Okamoto I., et al. "EGFR mutation-based phase II multicenter trial of gefitinib in advanced non-small cell lung cancer (NSCLC) patients (pts): Results of West Japan Thoracic Oncology Group trial (WJTOG0403)", *Journal of Clinical Oncology*, 2006, vol. 24, No. 18S, Abstract 7073.

Paz-Ares L., et al. "A prospective phase II trial of erlotinib in advanced non-small cell lung cancer (NSCLC) patients (p) with mutations in the tyrosine kinase (TK) domain of the epidermal growth factor receptor (EGFR)", *Journal of Clinical Oncology* 2006, vol. 24, No. 18S, Abstract 7020.

Sequist L. V., et al. *Journal of Clinical Oncology*, 2007 ASCO Annual Meeting Proceedings 2007, vol. 25, No. 18S, Abstract 7504.

Shaohua Chang et al., "Design, Synthesis, and Biological Evaluation of Novel Conformationally Constrained Inhibitors Targeting Epidermal Growth Factor Receptor Threonine$^{790}$ → Methionine$^{790}$ Mutant", *Journal of Medicinal Chemistry* 2012, vol. 55, No. 6, pp. 2711-2723.

Shilin et al., Design, Synthesis, and Biological Evaluation of 2-oxo-3,4-dihydropyrimido[4,5d]pyrimidinyl Derivitives as New Irreversible Epidermal Growth Factor Receptor Inhibitors with Improved Pharmacokinetic Properties, *Journal of Medicinal Chemistry*, 2013, vol. 56, No. 21, p. 8803-8813.

Sutani A., et al. "Phase II study of gefitinib for non-small cell lung cancer (NSCLC) patients with epidermal growth factor receptor (EGFR) gene mutations detected by PNA-LNA PCR clamp", *Journal of Clinical Oncology*, 2006, vol. 24, No. 18S, Abstract 7076.

Zhou W., et al. "A Structure-Guided Approach to Creating Covalent FGFR Inhibitors", *Chemistry & Biology*, 2010, 17, p. 285-295.

CAS RN 1222867-14-2, STN Entry Date May 13, 2010.

\* cited by examiner

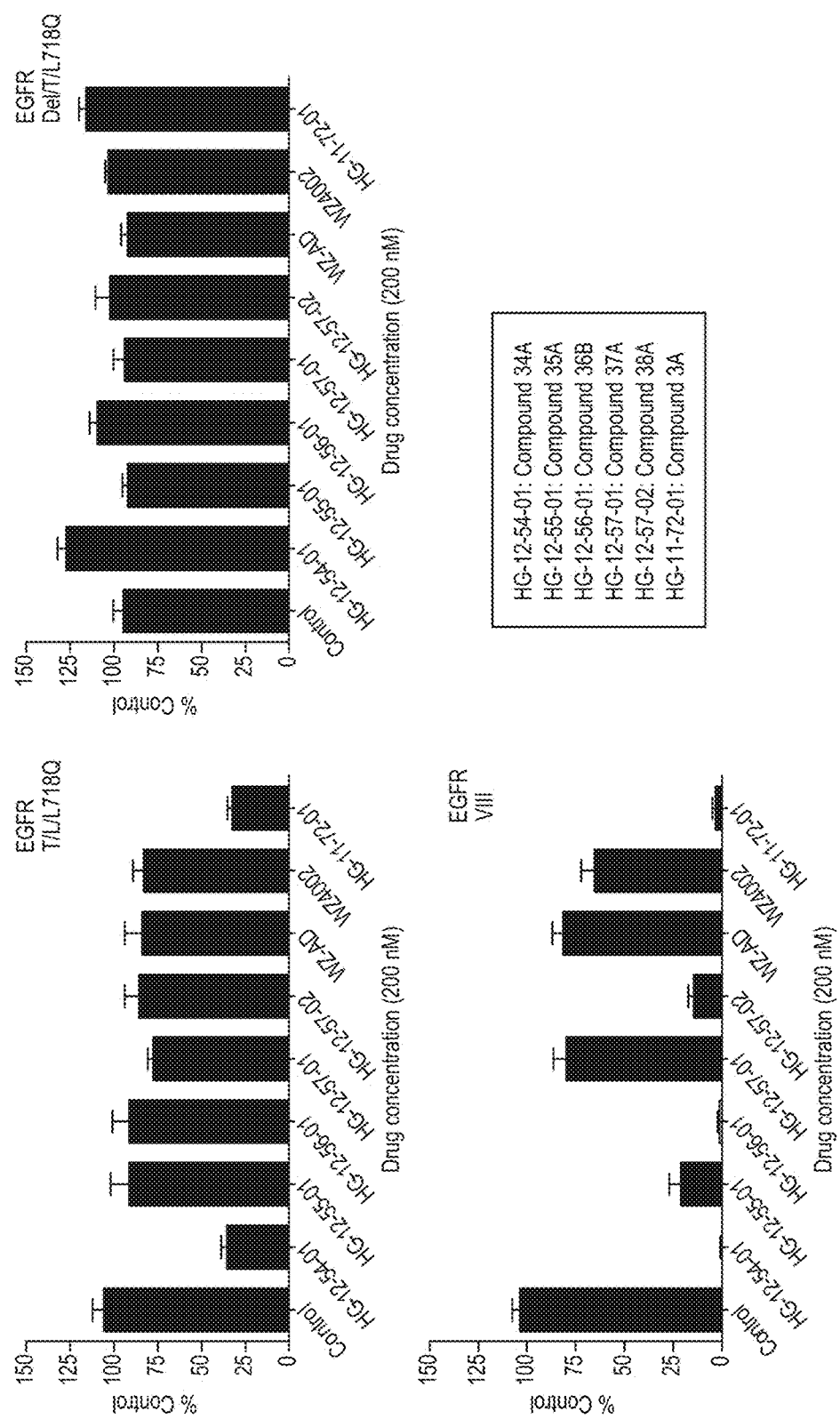

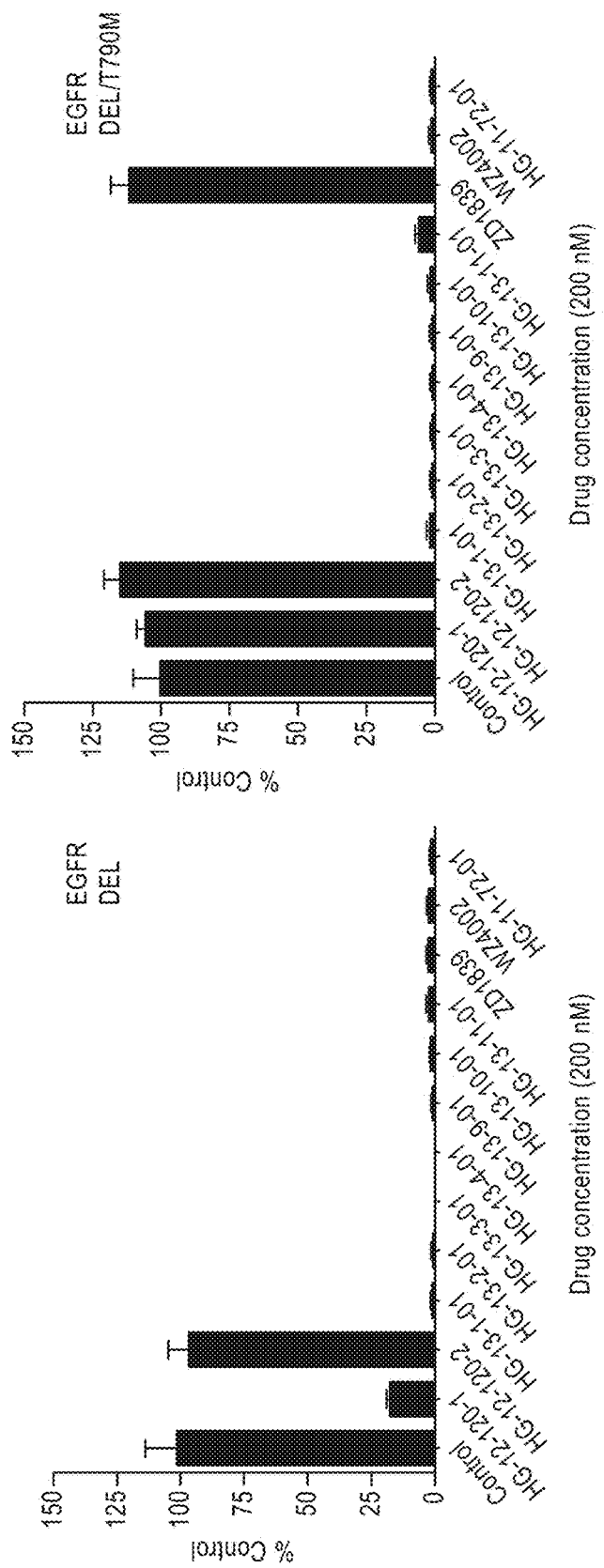

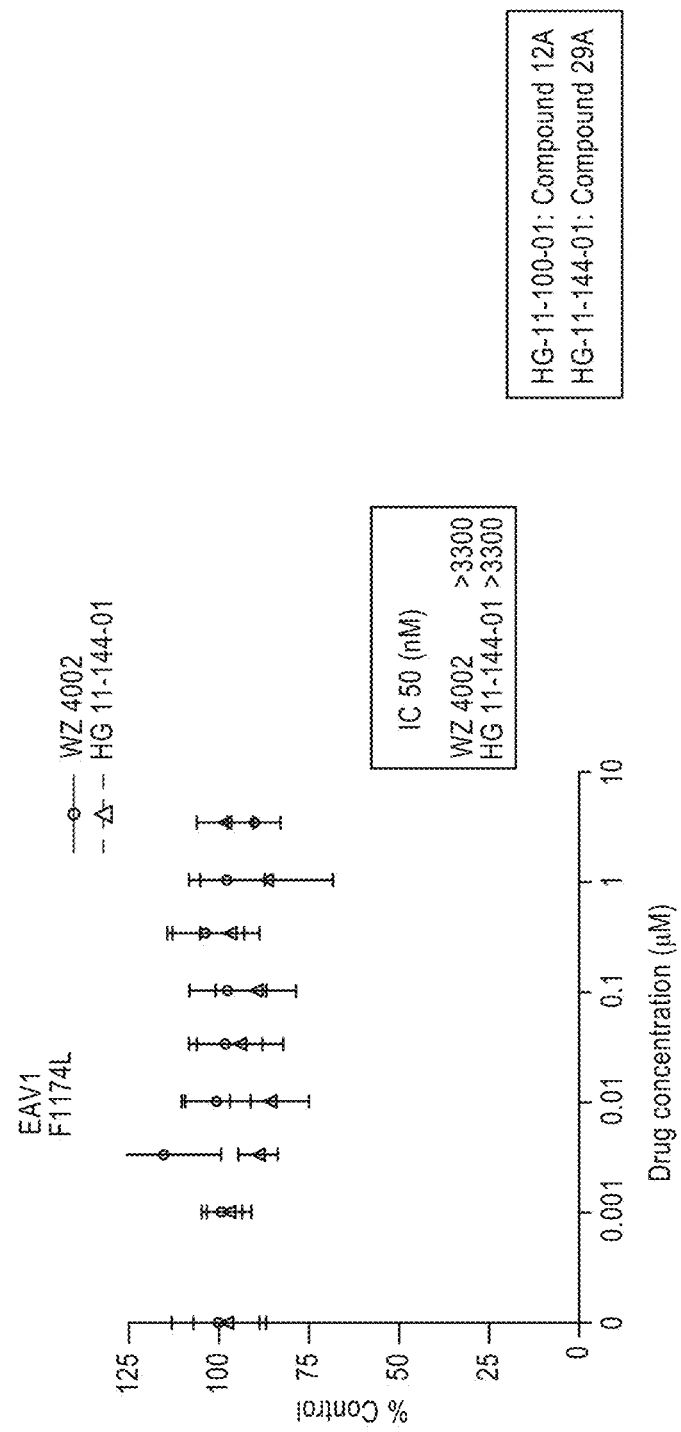

KINASE INHIBITORS FOR THE TREATMENT OF DISEASE

CROSS-REFERENCE TO RELATED APPLICATIONS

This application is a continuation of U.S. application Ser. No. 14/903,650, filed Jan. 8, 2016 (now allowed), which is a U.S. National Phase application, filed under 35 U.S.C. § 371, of International Application No. PCT/US2014/046022, filed Jul. 9, 2014, which claims priority to, and the benefit of, U.S. Provisional Application Nos. 61/844,304, filed Jul. 9, 2013, and 61/901,808, filed Nov. 8, 2013, the contents of each of which are incorporated herein by reference in their entireties.

BACKGROUND

Lung cancer is the most common cause of cancer related deaths in both men and women in the United States (Jemal, A., Cancer Statistics, 2007, CA Cancer J. Clin. 2007; 57: 43-66). The majority of patients (80%) will have non-small cell lung cancer (NSCLC) and will present with advanced stage lung cancer which is incurable with currently available therapies. For patients with advanced NSCLC, chemotherapy is the mainstay of treatment and is associated with a median survival of 8-10 months. These figures have changed very little in the last 25 years.

An important research goal has been to understand critical molecular alterations in NSCLC which may lead to the identification of effective therapies for NSCLC patients. A compelling example of this approach was the discovery of somatic mutations in the epidermal growth factor receptor (EGFR) and their association with dramatic clinical benefits in patients with EGFR mutant NSCLC treated with EGFR tyrosine kinase inhibitors (TKIs). EGFR TKIs have been shown to be effective therapeutic agents for patients with non-small cell lung cancer (NSCLC) with tumors that harbor somatic activating mutations in EGFR. In prospective clinical trials, 60-80% of NSCLC patients with EGFR mutations, exhibited tumor regression when treated with gefitinib or erlotinib lasting on average 9-13 months (Inoue, A., et al. J Clin Oncol 2006; 24: 3340-6; Paz-Ares, et al. Journal of Clinical Oncology 2006; 24: Abstract 7020; Okamoto, I., et al. Journal of Clinical Oncology 2006; 24: Abstract 7073; Sutani, A., et al. Journal of Clinical Oncology 2006; 24: Abstract 7076; Morikawa, N., Journal of Clinical Oncology 2006; 24: Abstract 7077; Sequist, L. V., et al. Journal of Clinical Oncology, 2007 ASCO Annual Meeting Proceedings 2007; 25: a7504).

In a phase III clinical trial chemotherapy naïve NSCLC patients with EGFR mutations had a significantly longer progression free survival when treated with an EGFR™ than with conventional chemotherapy. EGFR mutations are only found in 10-15% of all NSCLC patients. Responders typically relapse 6-19 months after taking EGFR TKIs as a consequence of becoming resistant to the inhibitors. There is currently no FDA approved therapy for NSCLC patients that develop resistance to EGFR TKIs. The most common mechanism of resistance is mutation of the EGFR ATP-binding site in a manner that renders the site less sensitive to drug inhibition. For example the most common resistance mutation occurs at the gatekeeper T790M position. This mechanism of resistance is found in 50% of EGFR mutant NSCLC patients that develop resistance to EGFR kinase inhibitors gefitinib or erlotinib. Another mechanism of resistance involves upregulation of alternative signal transduction pathways.

More recently the EML4-ALK fusion protein has been found to be an oncogenic driver in non-small cell lung cancer and the first targeted therapy, crizotinib has been approved for the treatment of this patient subset by the FDA. Cancer genomics efforts have recently also resulted in the identification of oncogenic driver mutations in two other receptor tyrosine kinases: ROS1 and FGFR.

There is a need for the development of small molecule inhibitors that potently and selectively inhibit the activity of wild-type and mutant forms of EGFR, FGFR, ALK, ROS1, JAK, BTK, BLK, ITK, TEC, and TXK for the treatment of cancer, including NSCLC.

SUMMARY OF THE INVENTION

The present invention relates to compounds that inhibit EGFR, FGFR, ALK, ROS1 JAK, BTK, BLK, ITK, TEC, and/or TXK kinase, and methods of preparing the compounds. Specifically, the present invention provides a compound of Formula I:

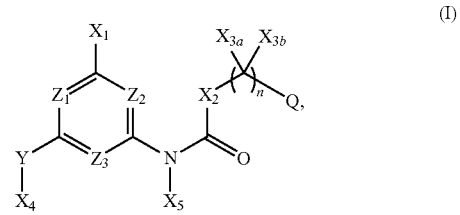

or a pharmaceutically acceptable salt thereof, wherein $X_1$, $X_2$, $X_{3a}$, $X_{3b}$, $X_4$, $X_5$, Y, $Z_1$, $Z_2$, $Z_3$, Q, and n are each selected from the various groups of chemical moieties defined or illustrated herein.

The present invention also relates to a pharmaceutical composition comprising a compound of the invention, or a pharmaceutically acceptable salt thereof, and a pharmaceutically acceptable carrier or excipient.

The present invention also relates to methods of treating or preventing a disease or disorder mediated by a kinase, such as EGFR, by administering to a subject in need thereof, a therapeutically effective amount of a compound of the present invention, or a pharmaceutically acceptable salt thereof, in combination with a pharmaceutically acceptable carrier or excipient, such that the disease or disorder is treated or prevented.

The present invention also relates to the manufacture of a medicament for treating or preventing a disease or disorder mediated by a kinase, such as EGFR, wherein the medicament comprises a compound of the invention, or a pharmaceutically acceptable salt thereof.

The present invention also relates to a composition for use in a method of treating or preventing a disease or disorder mediated by a kinase, such as EGFR, wherein the composition comprises a compound of the invention, or a pharmaceutically acceptable salt thereof.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar to or equivalent to those described herein can be used in the practice and testing of the invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Definitions

Figure 1A:
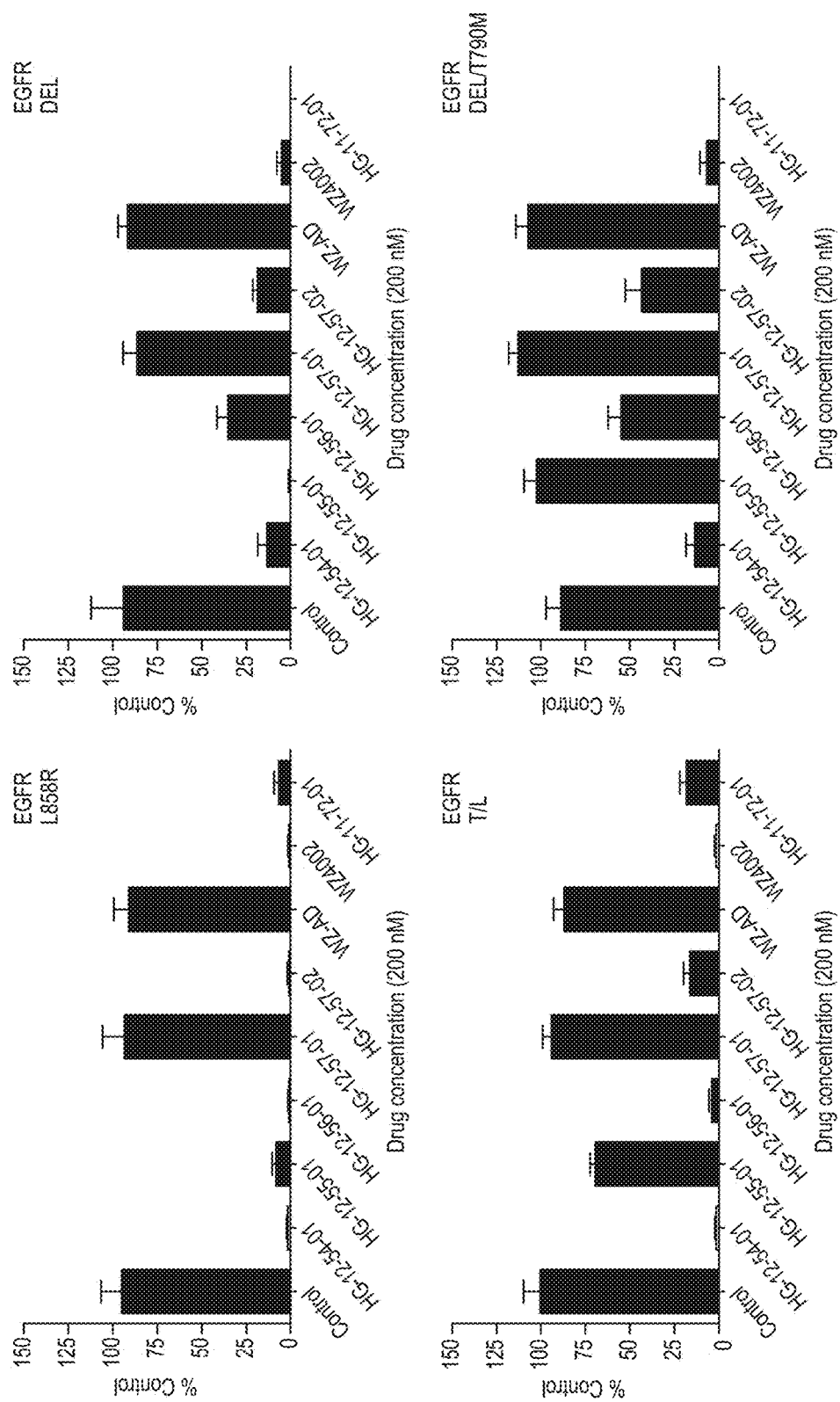
FIG. 1A is a series of bar graphs showing percentage of EGFR activity in samples treated with various compounds of the invention as compared to samples treated with control, WZ-AD, or WZ4002.
Figure 1B:
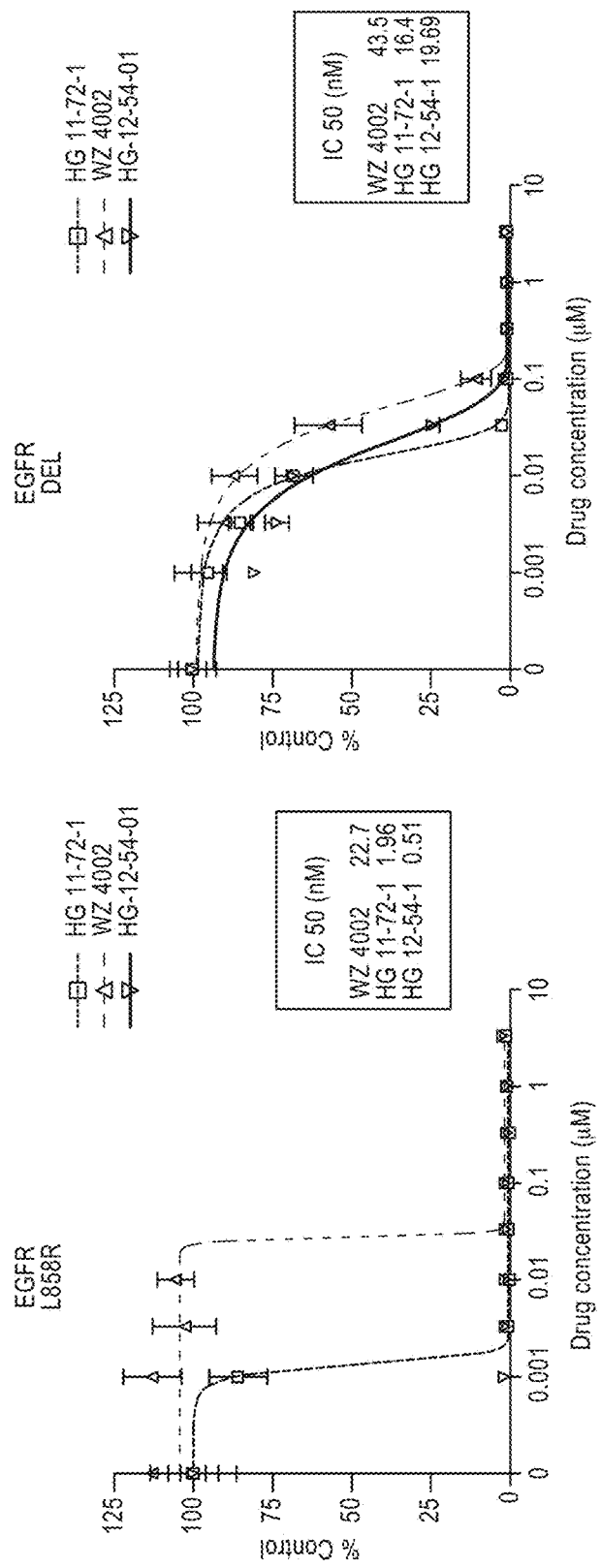
FIG. 1B is a series of plots displaying decrease in EGFR activity upon treatment with increasing concentrations of various compounds of the invention as compared to WZ4002.
Figure 1B:
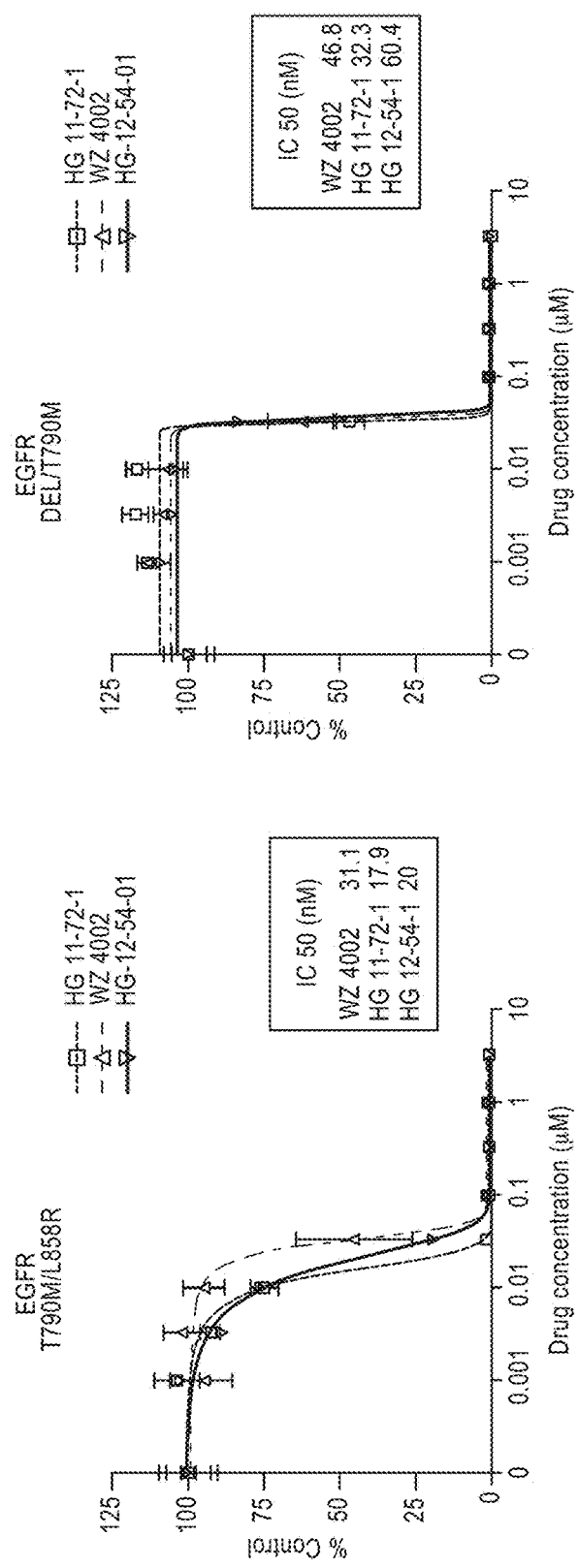
Figure 1B:
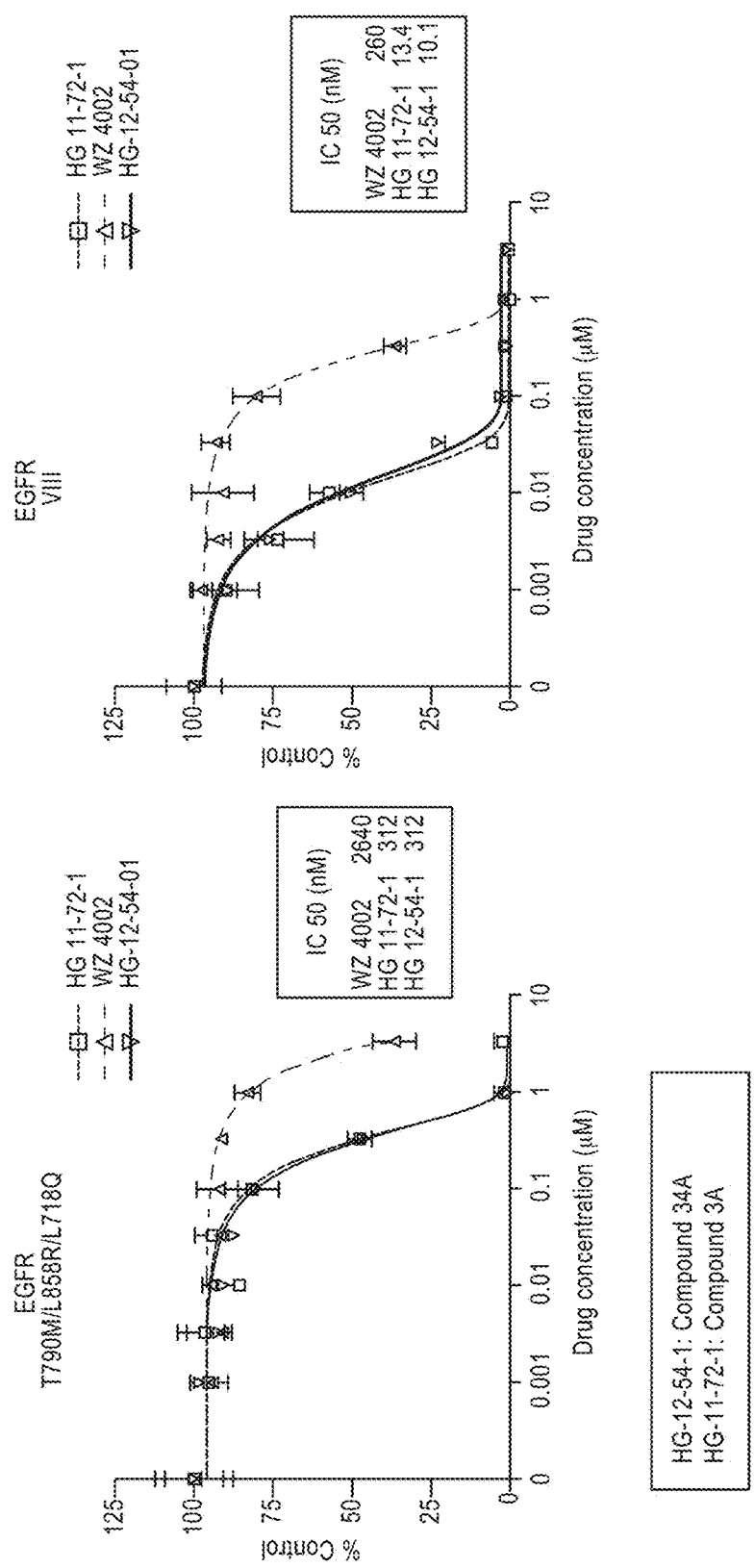
Figure 2A:
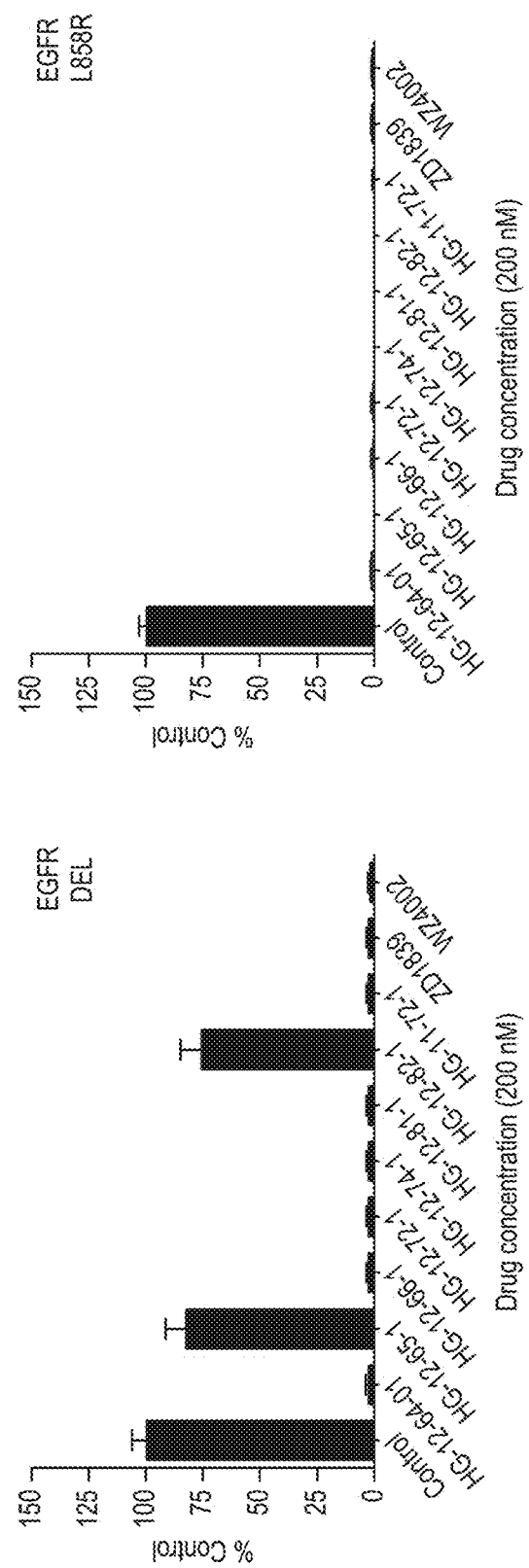
FIG. 2A is a series of bar graphs showing percentage of EGFR activity in samples treated with various compounds of the invention as compared to samples treated with control, ZD1839, or WZ4002.
Figure 2A:
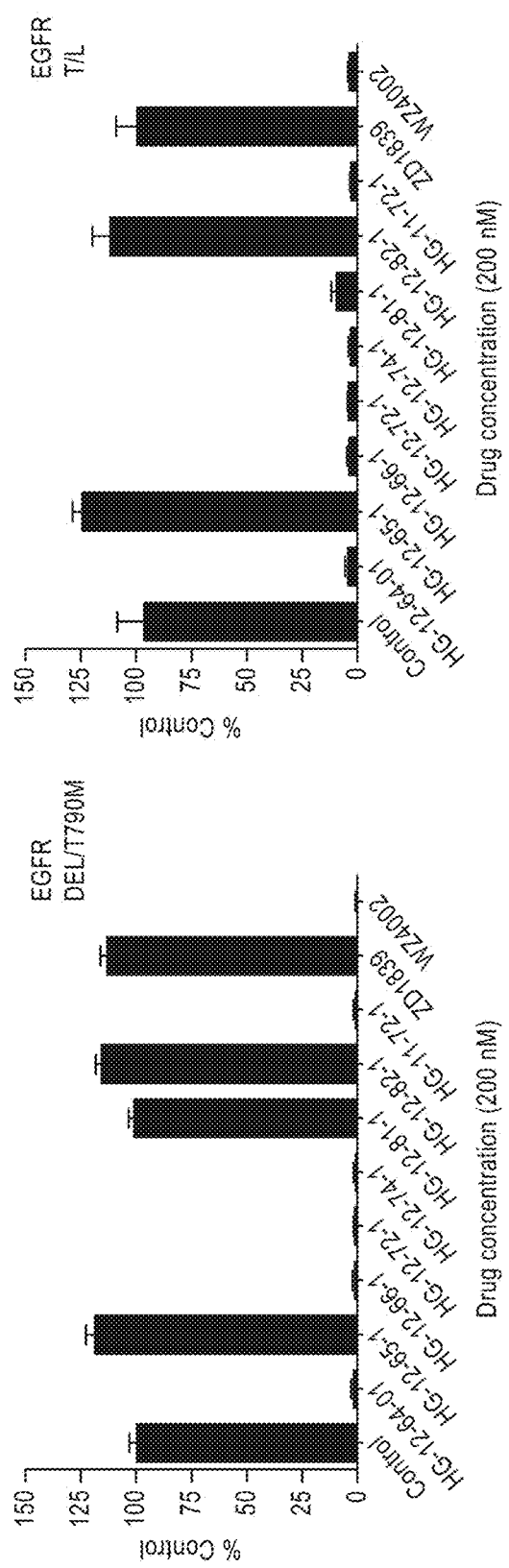
Figure 2A:
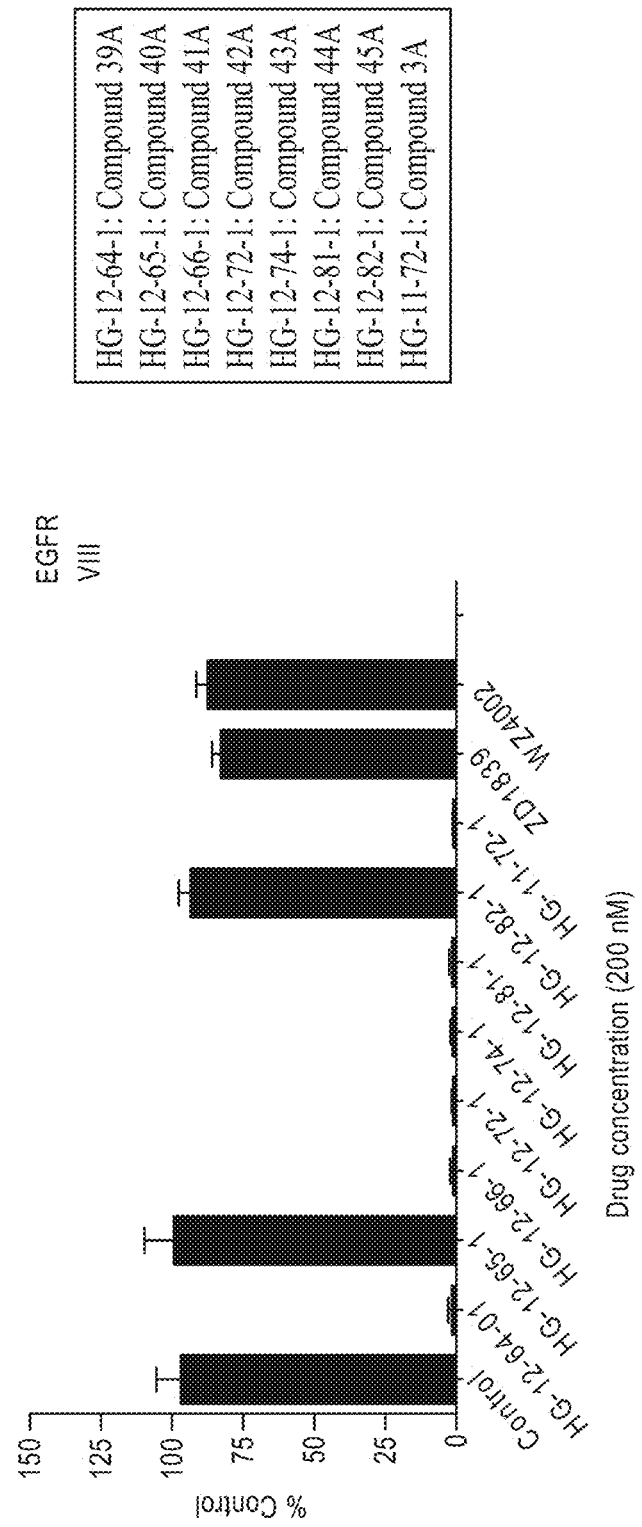
Figure 2B:
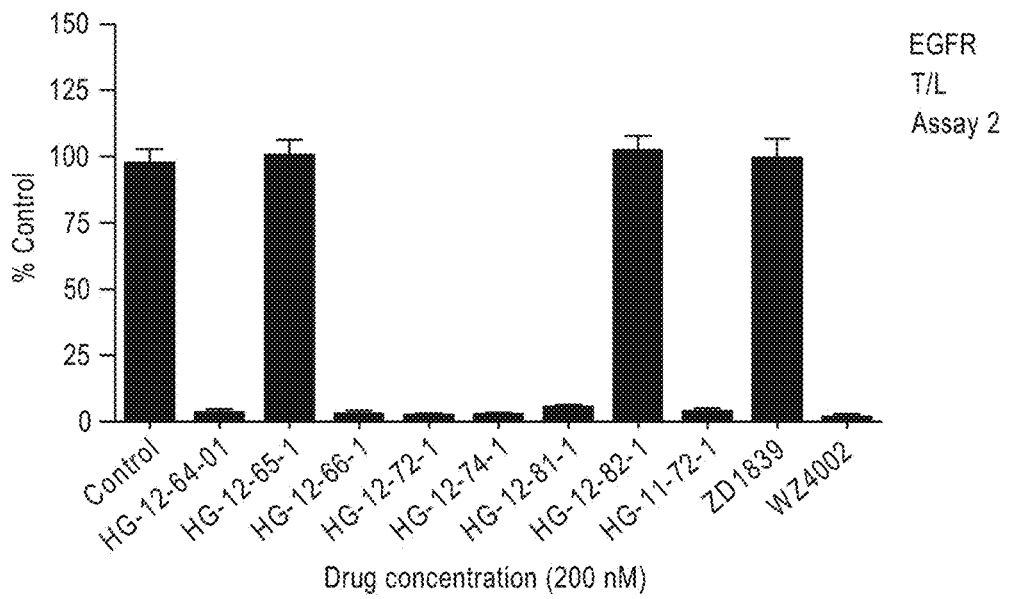
FIG. 2B is a series of bar graphs showing percentage of EGFR activity in samples treated with various compounds of the invention as compared to samples treated with control, ZD1839, or WZ4002.
Figure 2B:
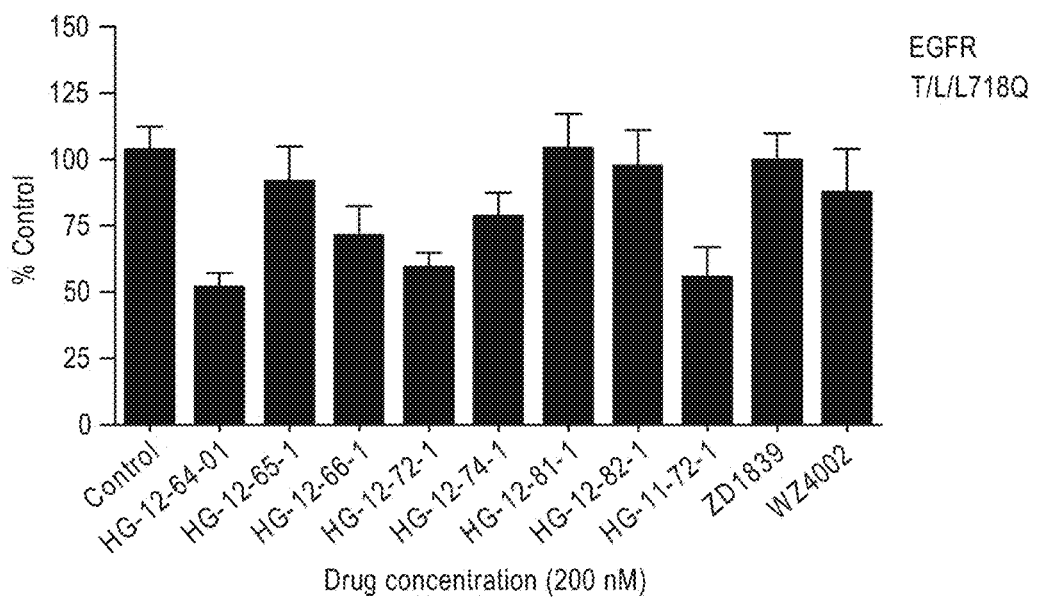
Figure 2B:
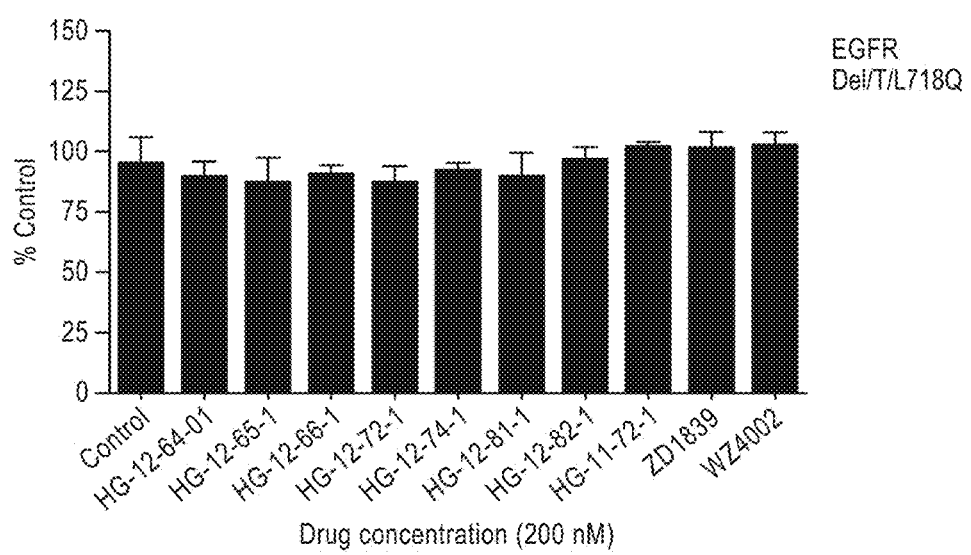
Figure 3A:
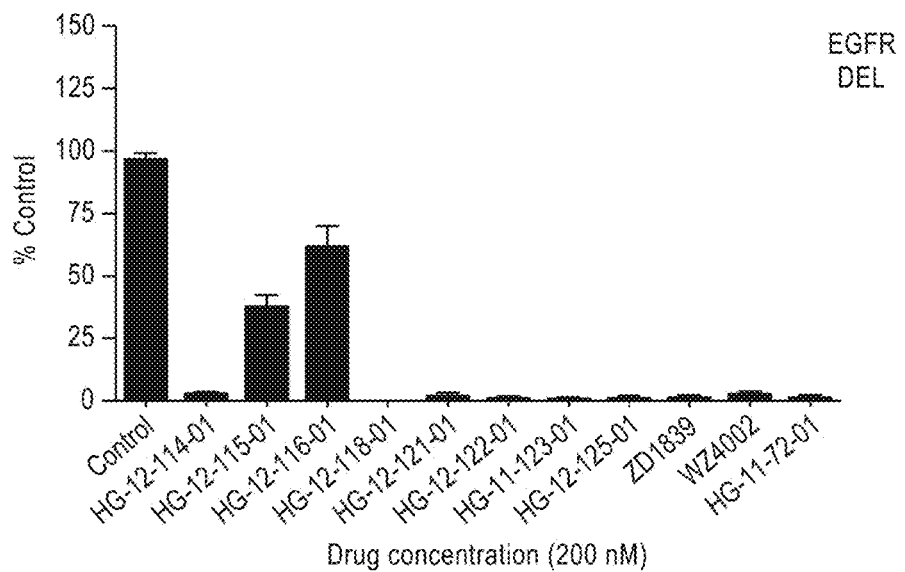
FIG. 3A is a series of bar graphs showing percentage of EGFR activity in samples treated with various compounds of the invention as compared to samples treated with control, ZD1839, or WZ4002.
Figure 3A:
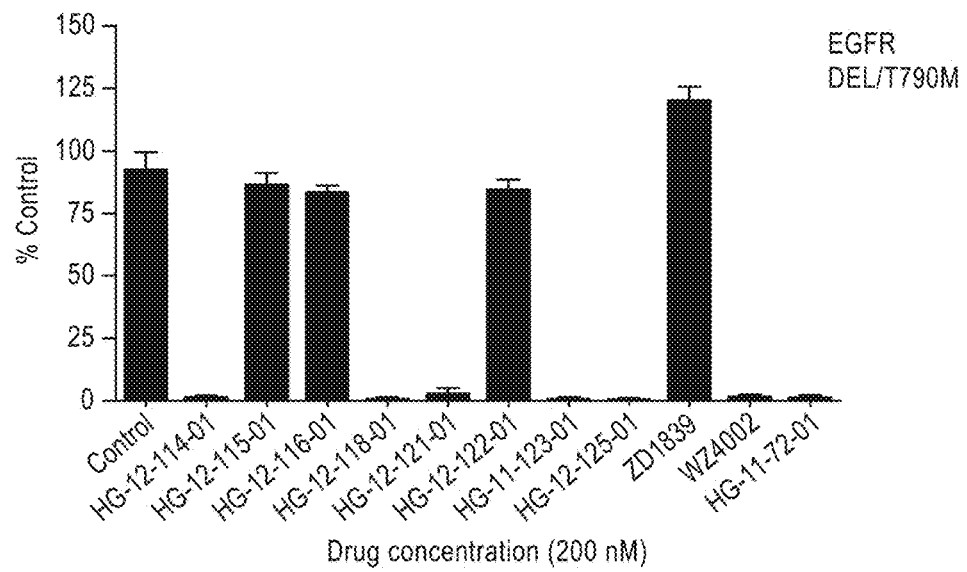
Figure 3A:
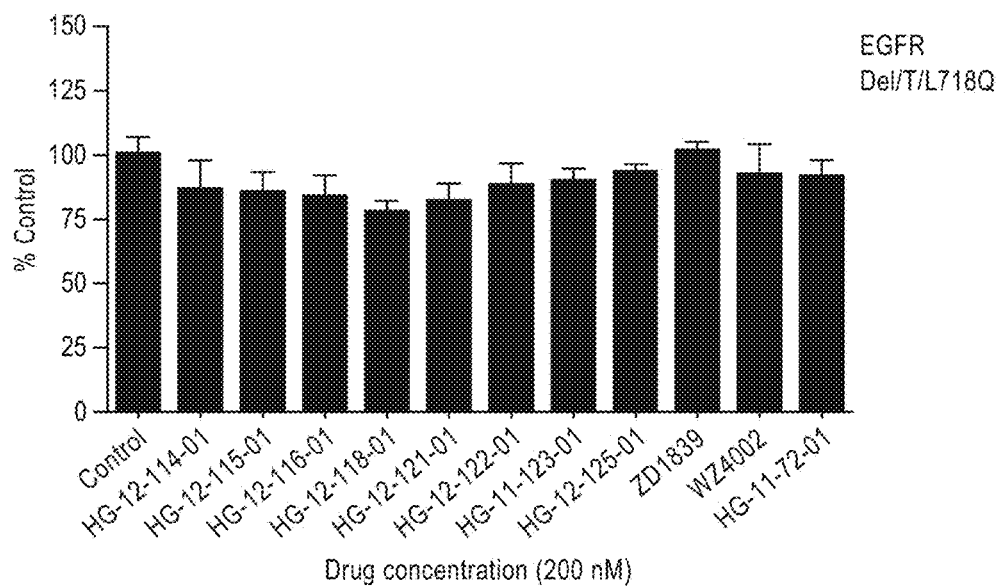
Figure 3B:
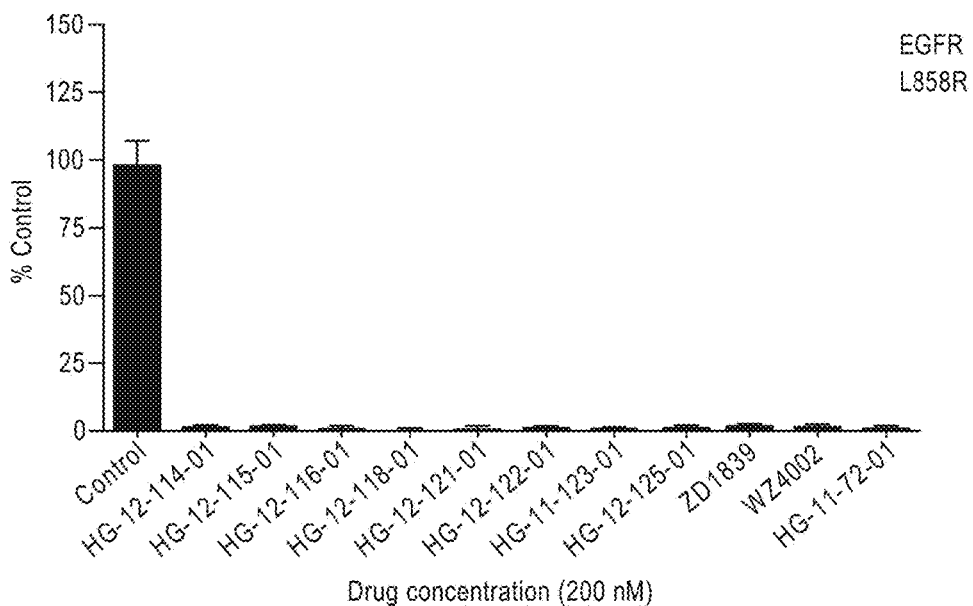
FIG. 3B is a series of bar graphs showing percentage of EGFR activity in samples treated with various compounds of the invention as compared to samples treated with control, ZD1839, or WZ4002.
Figure 3B:
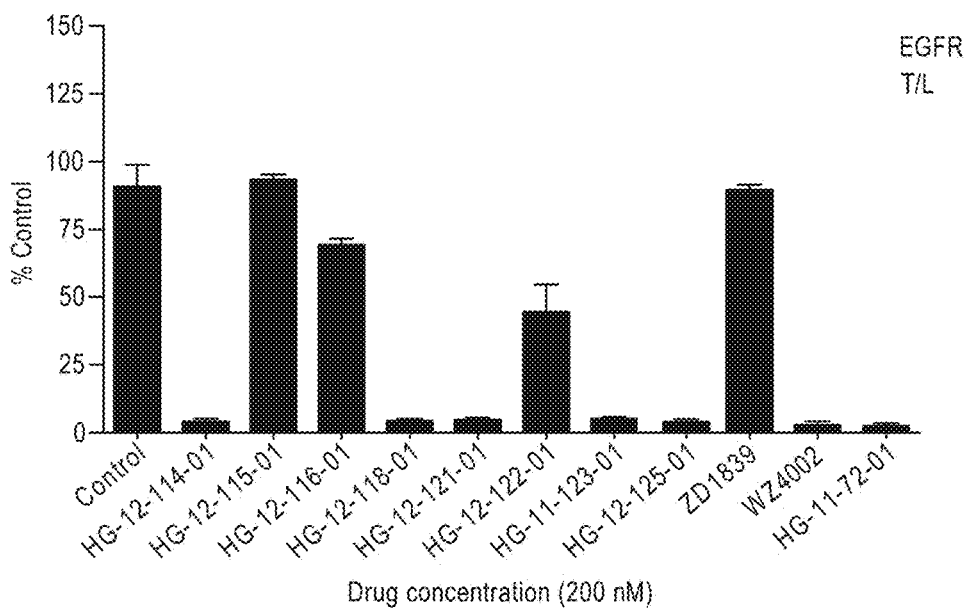
Figure 3B:
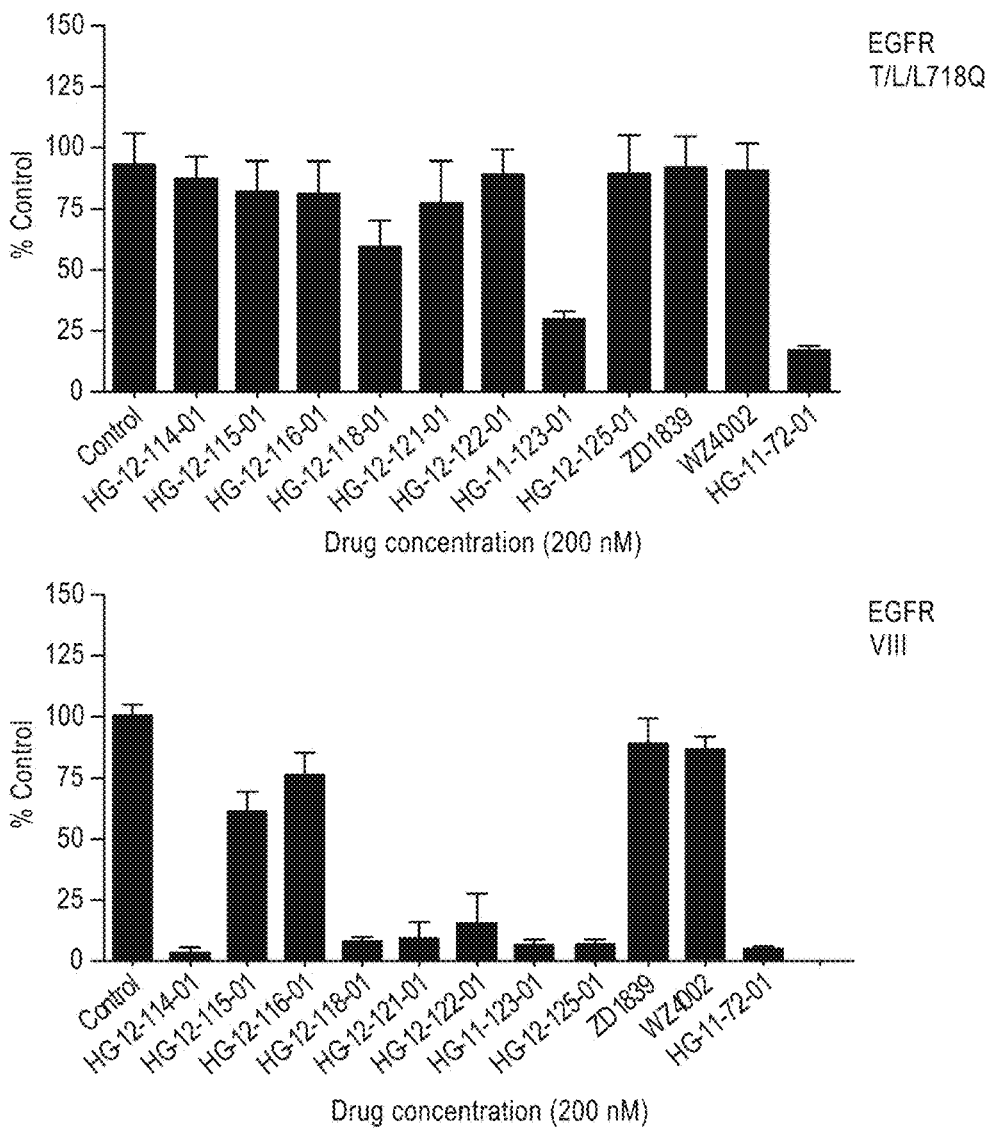
Figure 4A:
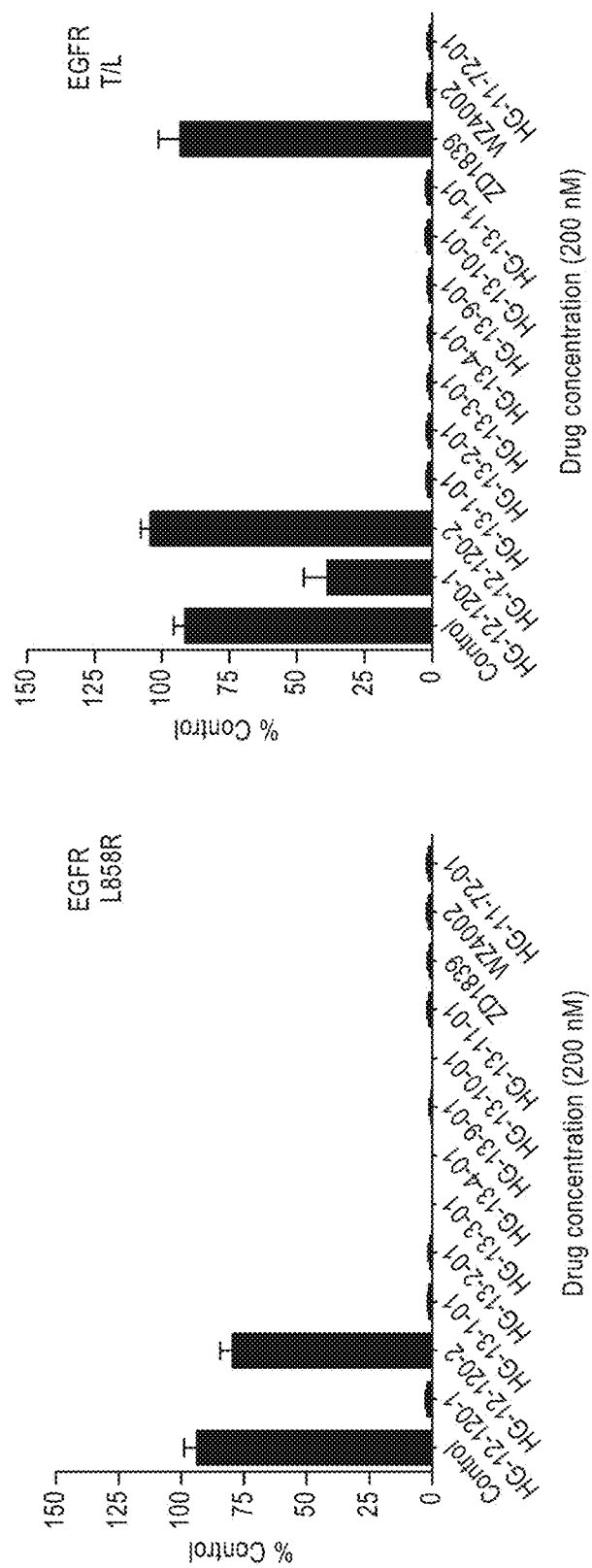
FIG. 4A is a series of bar graphs showing percentage of EGFR activity in samples treated with various compounds of the invention as compared to samples treated with control, ZD1839, or WZ4002.
Figure 4A:
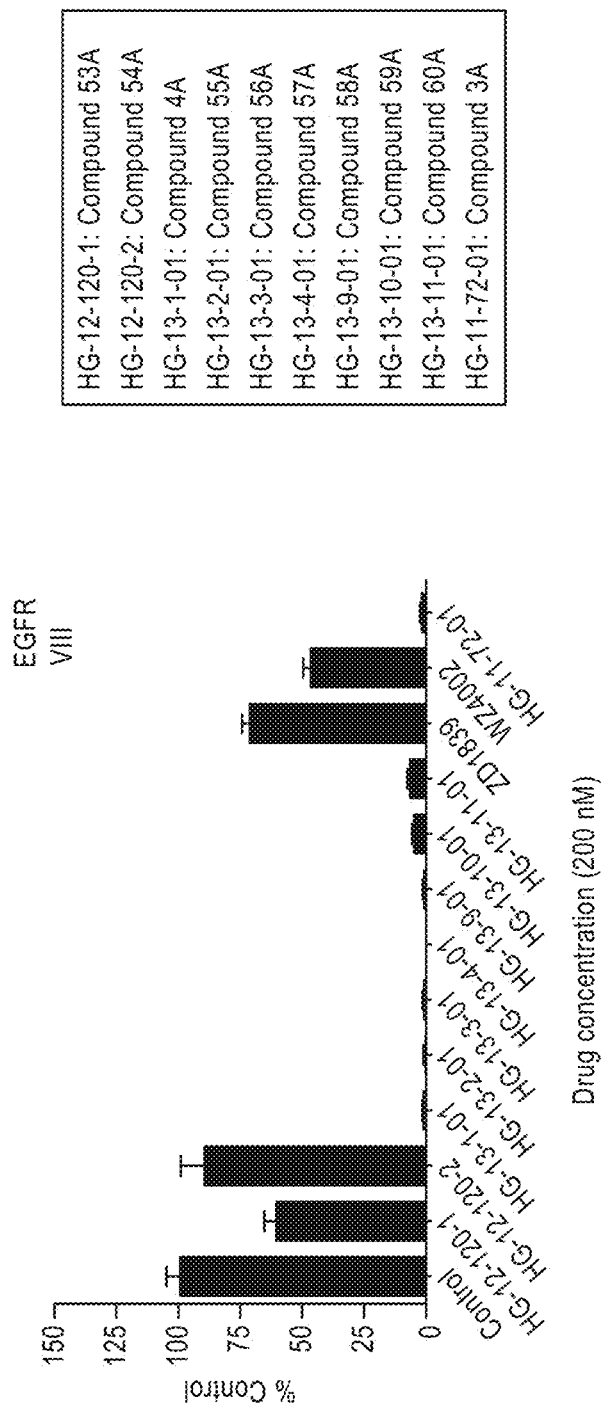
Figure 4B:
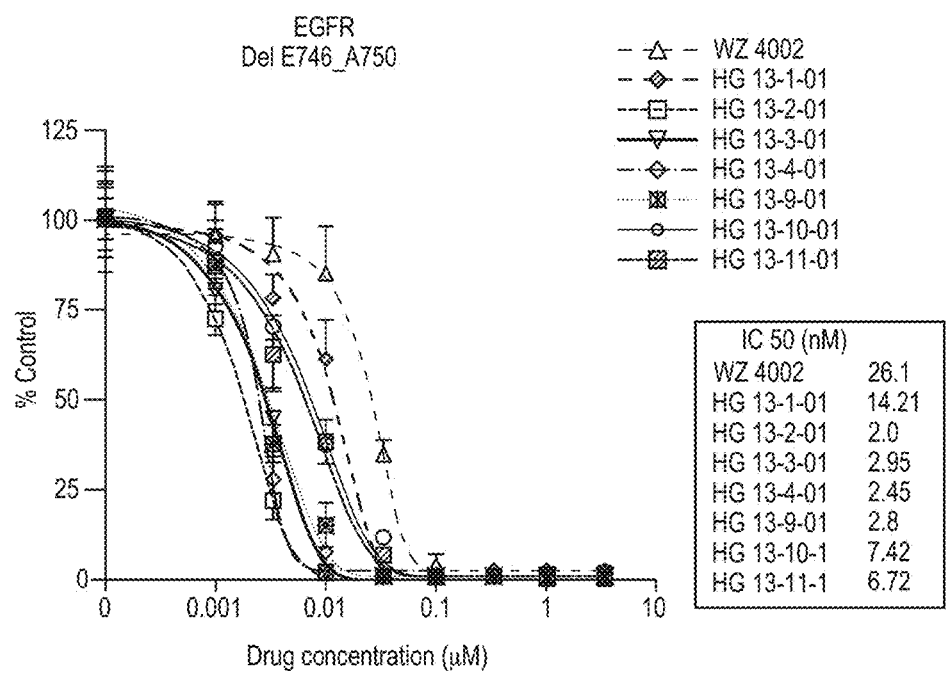
FIG. 4B is a series of plots displaying decrease in EGFR activity upon treatment with increasing concentrations of various compounds of the invention as compared to WZ4002.
Figure 4B:
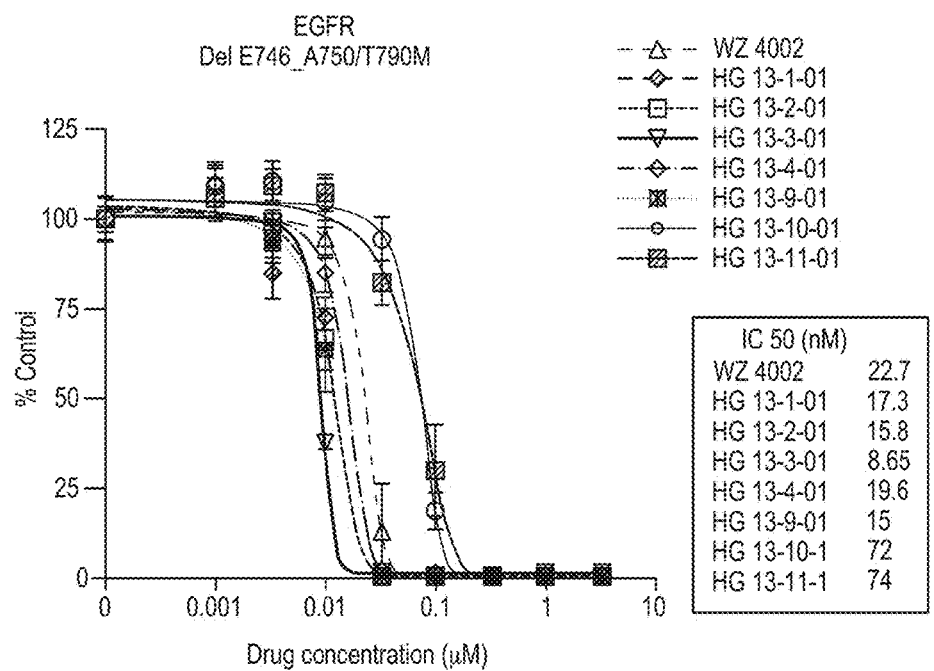
Figure 4B:
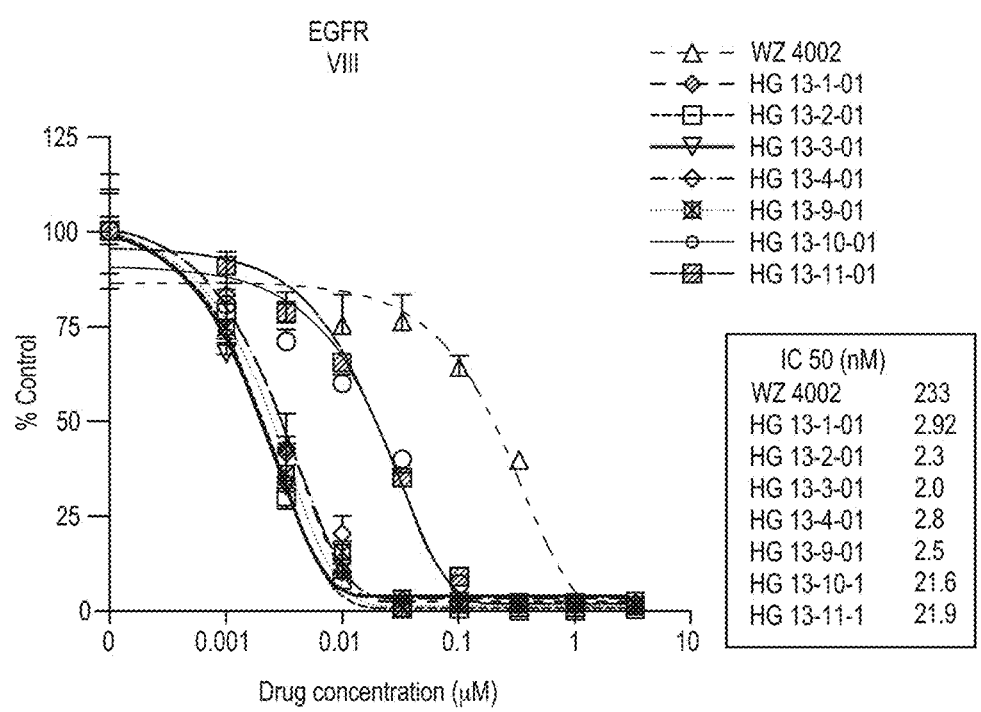
Figure 4C:
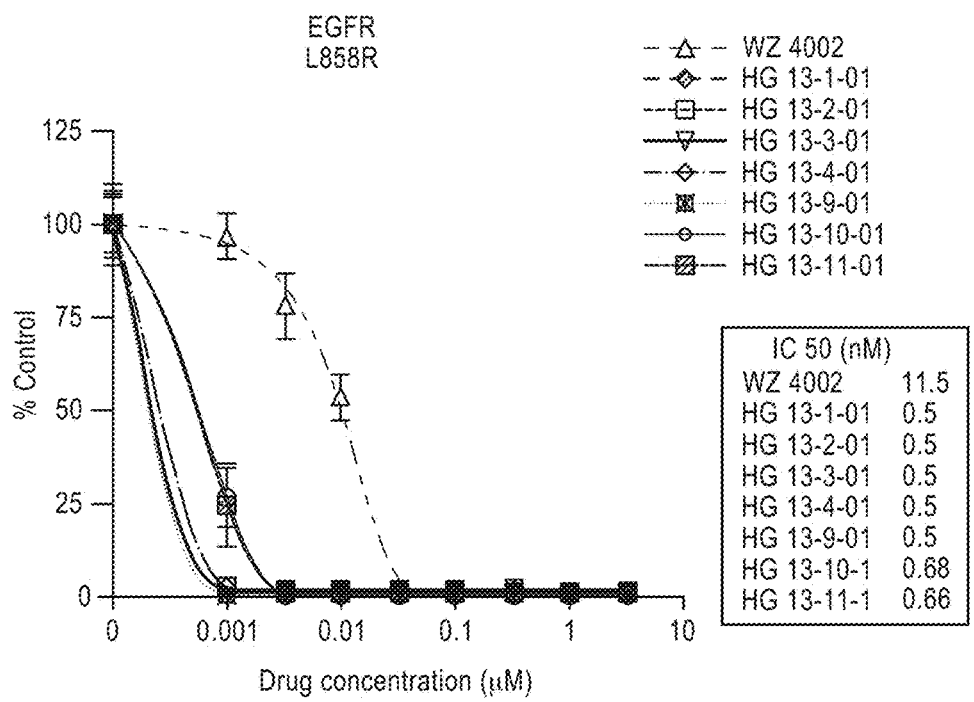
FIG. 4C is a series of plots displaying decrease in EGFR activity upon treatment with increasing concentrations of various compounds of the invention as compared to WZ4002.
Figure 4C:
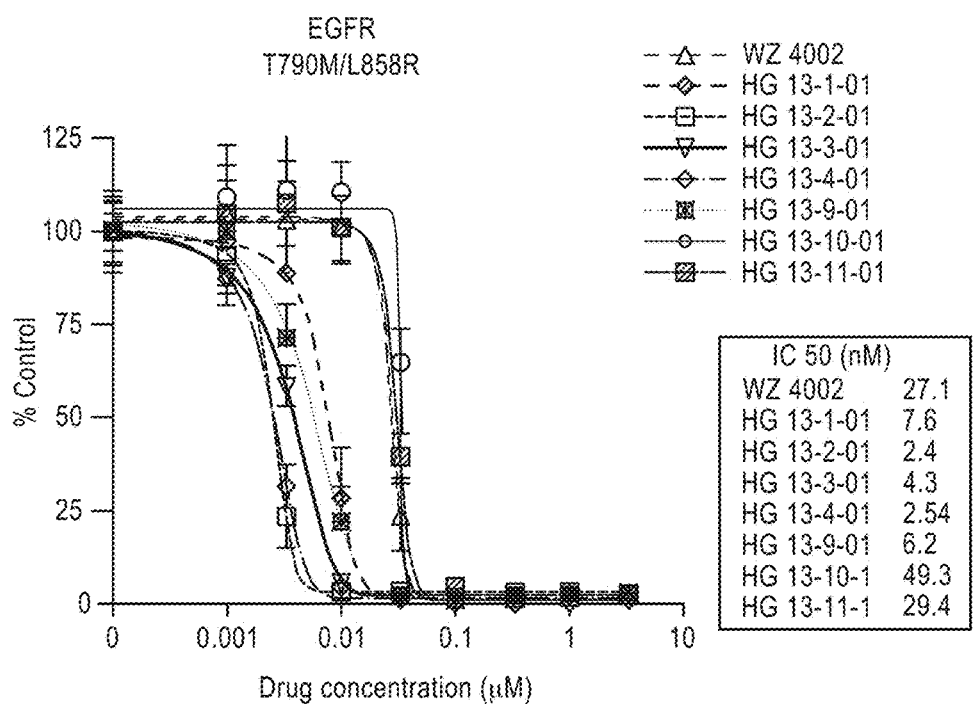
Figure 4C:
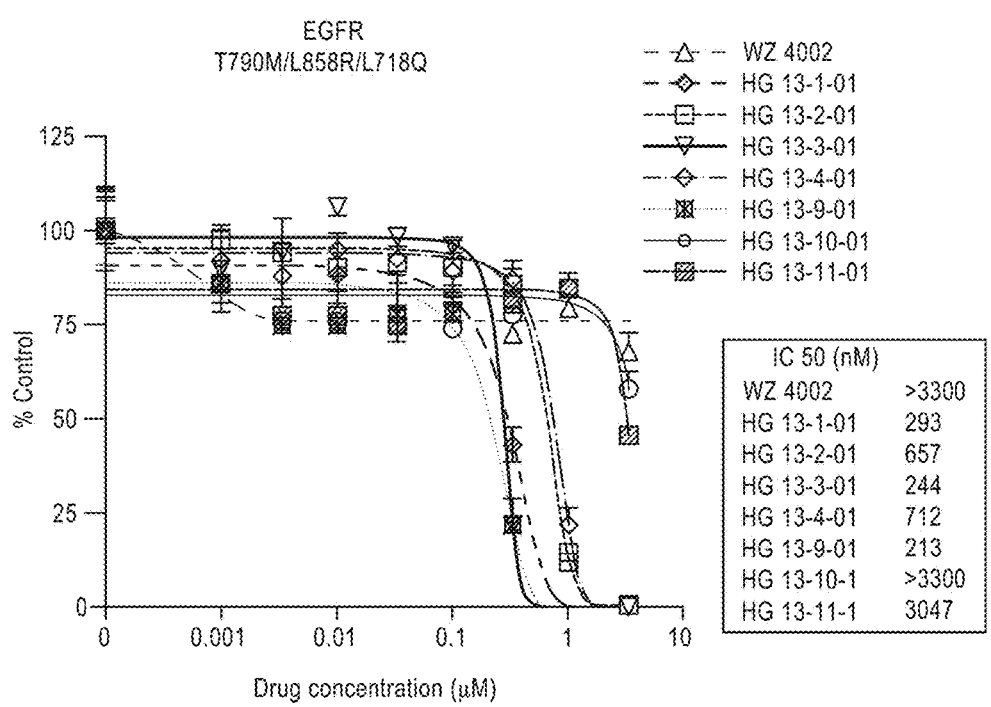
Figure 5A:
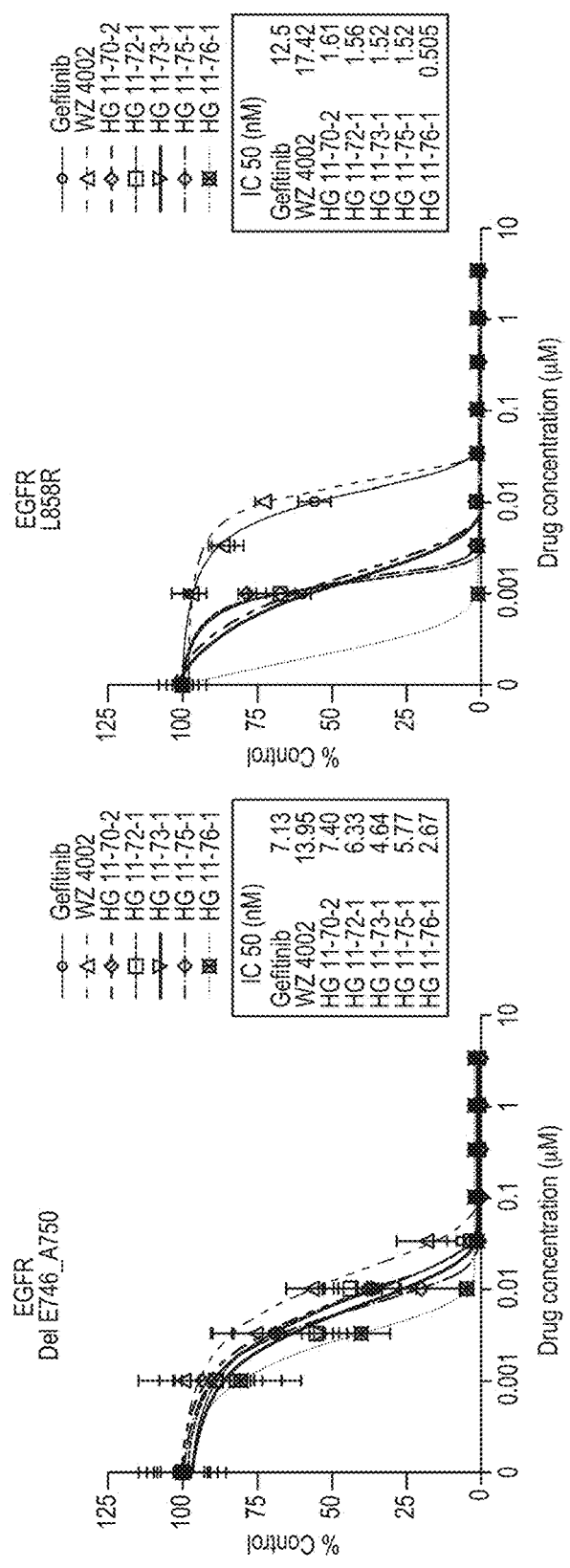
FIG. 5A is a series of plots displaying decrease in EGFR activity upon treatment with increasing concentrations of various compounds of the invention as compared to WZ4002 or Gefitinib.
Figure 5A:
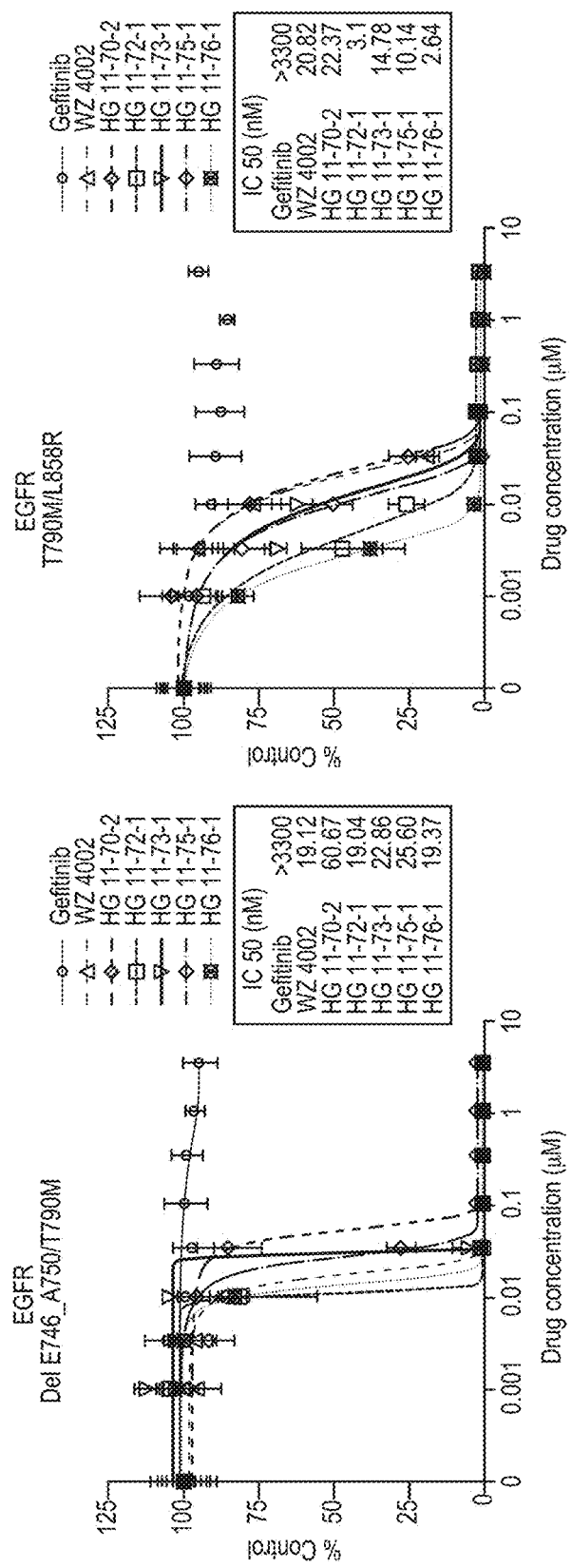
Figure 5A:
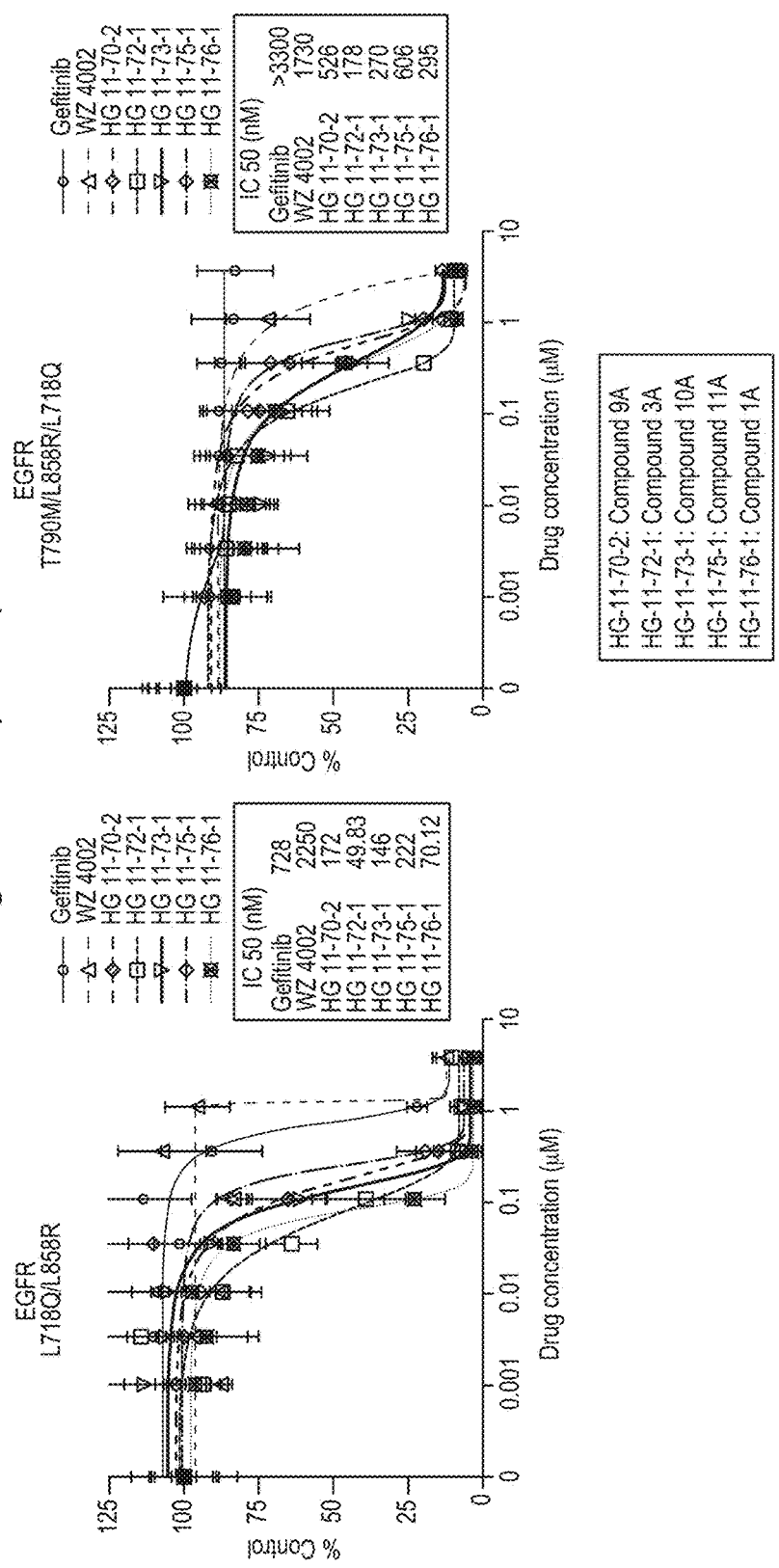
Figure 5B:
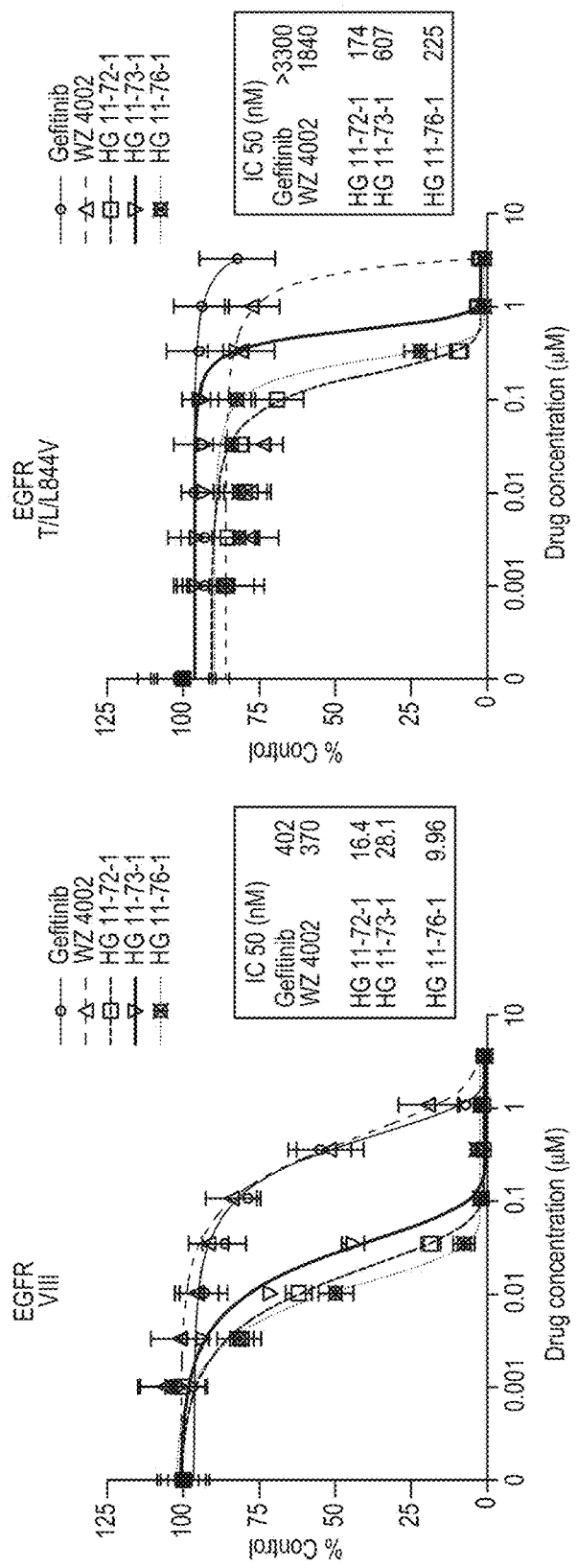
FIG. 5B is a series of plots displaying decrease in EGFR activity upon treatment with increasing concentrations of various compounds of the invention as compared to WZ4002 or Gefitinib.
Figure 5B:
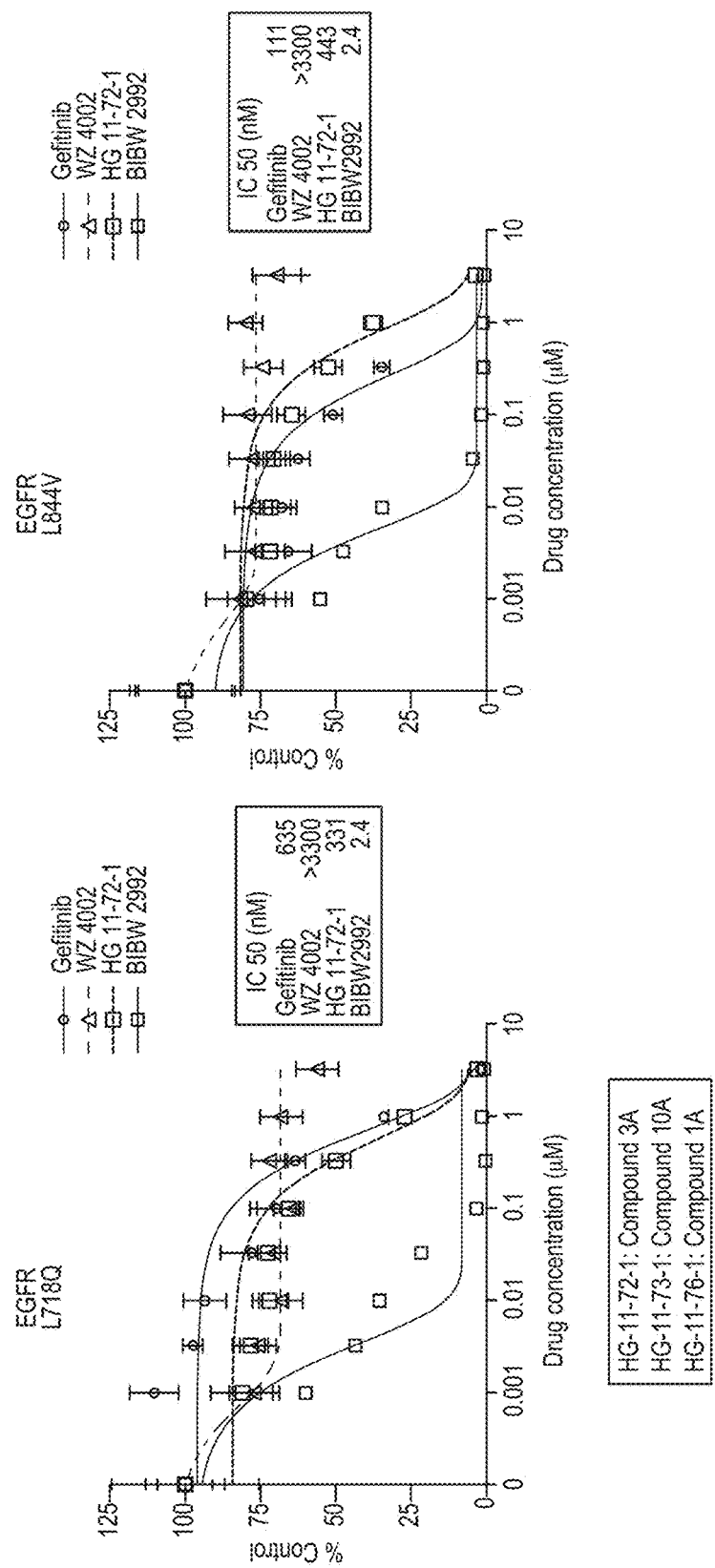
Figure 5C:
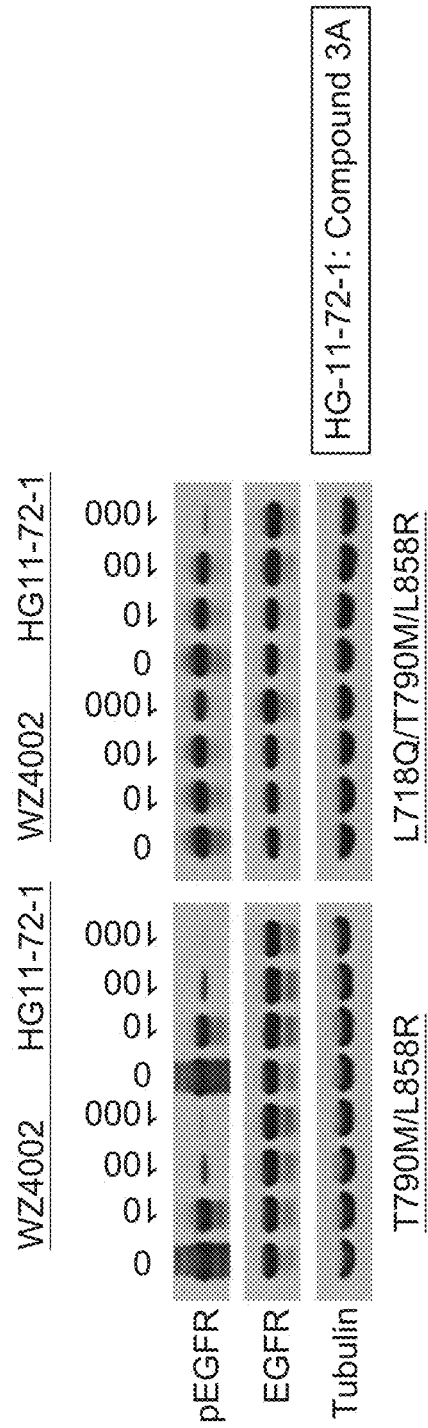
FIG. 5C is a Western blot showing EGFR phosphorylation in samples treated with a compound of the invention or WZ4002.
Figure 6:
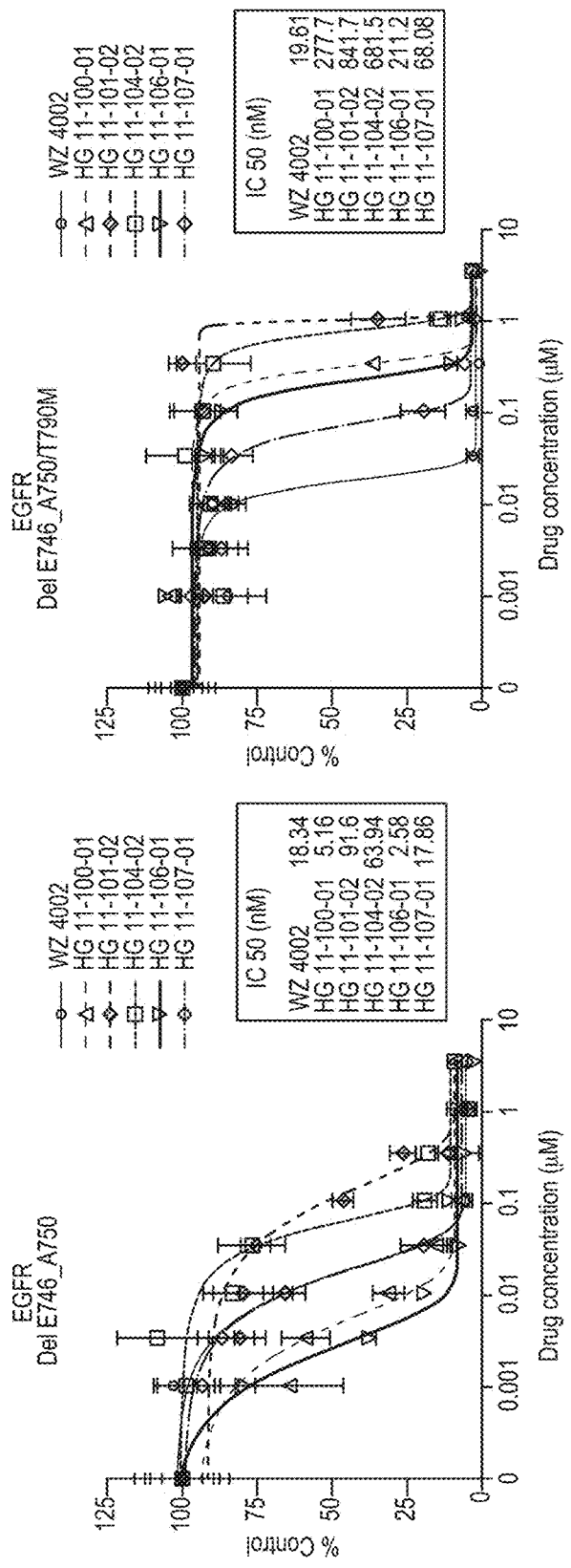
FIG. 6 is a series of plots displaying decrease in EGFR activity upon treatment with increasing concentrations of various compounds of the invention as compared to WZ4002.
Figure 6:
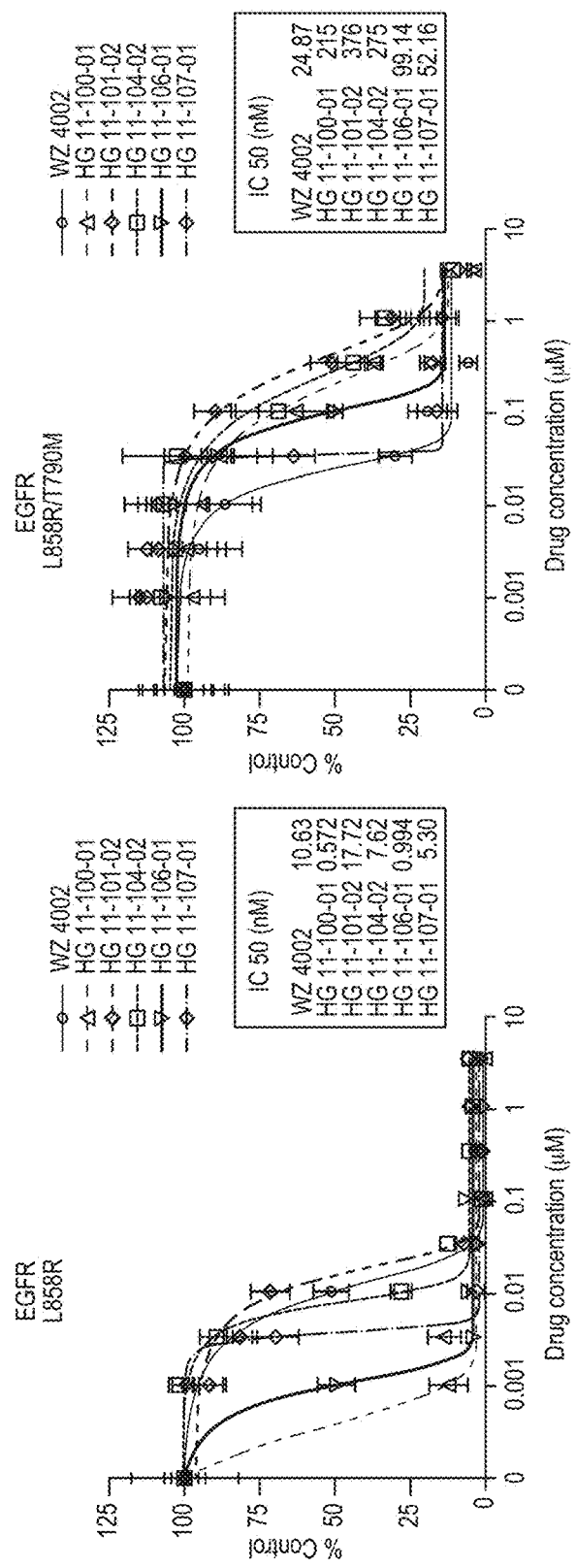
Figure 6:
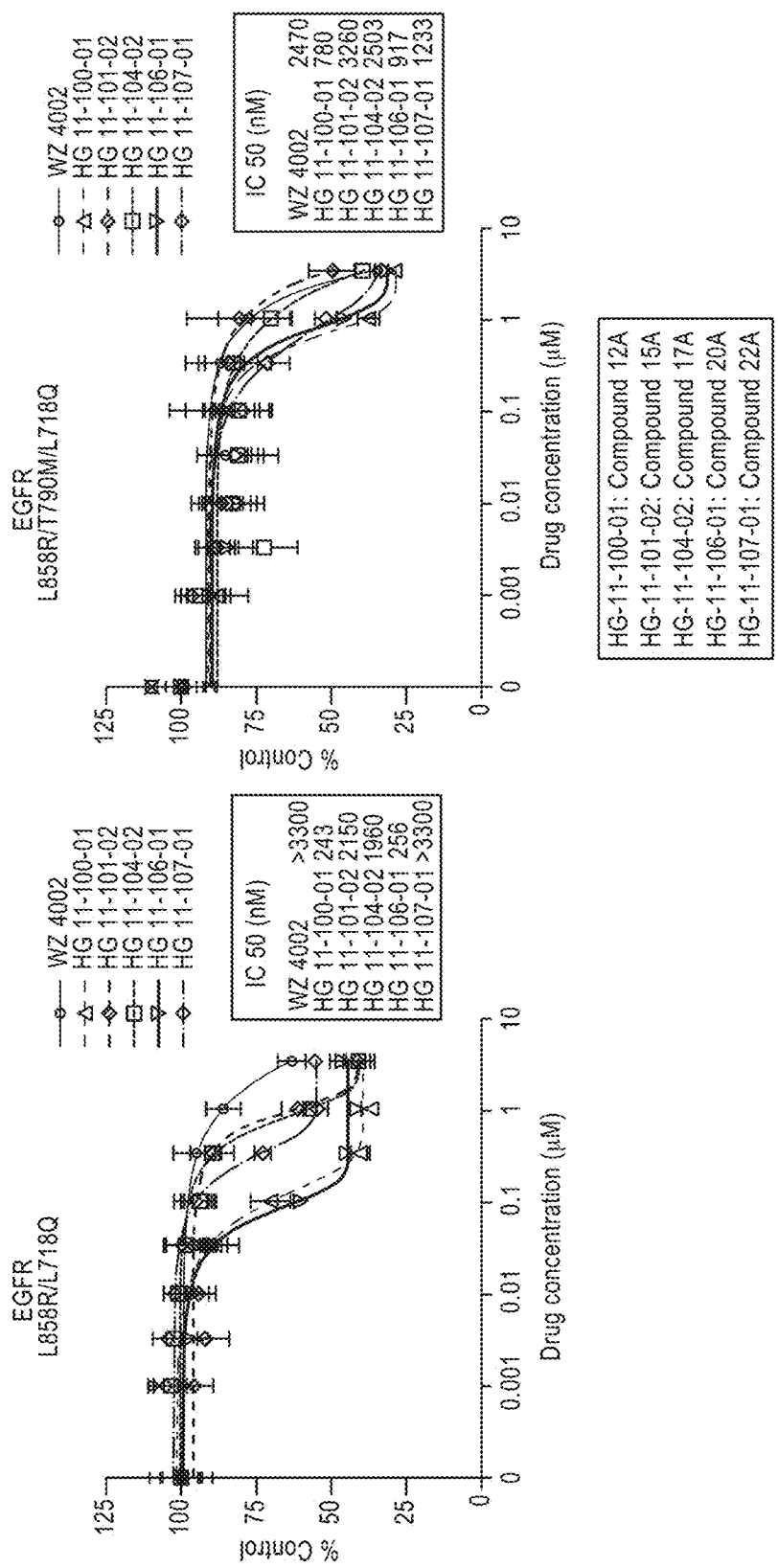
Figure 7:
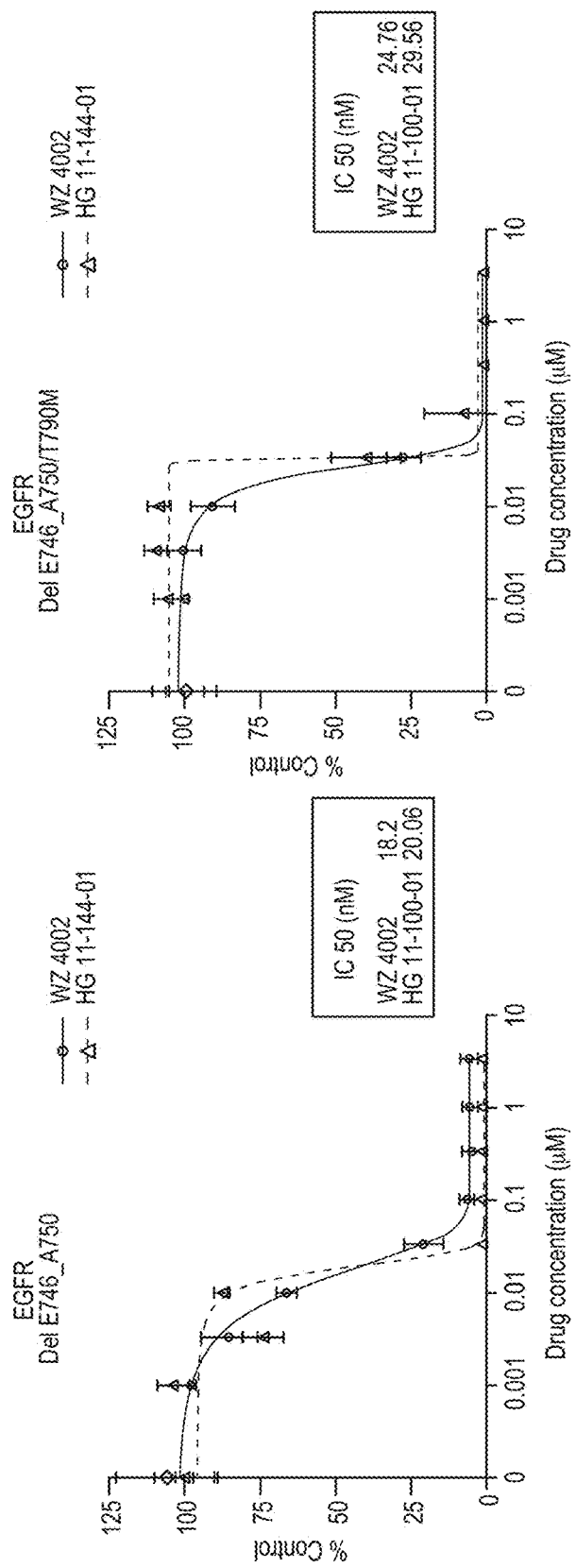
FIG. 7 is a series of plots displaying decrease in EGFR activity upon treatment with increasing concentrations of various compounds of the invention as compared to WZ4002.
Figure 7:
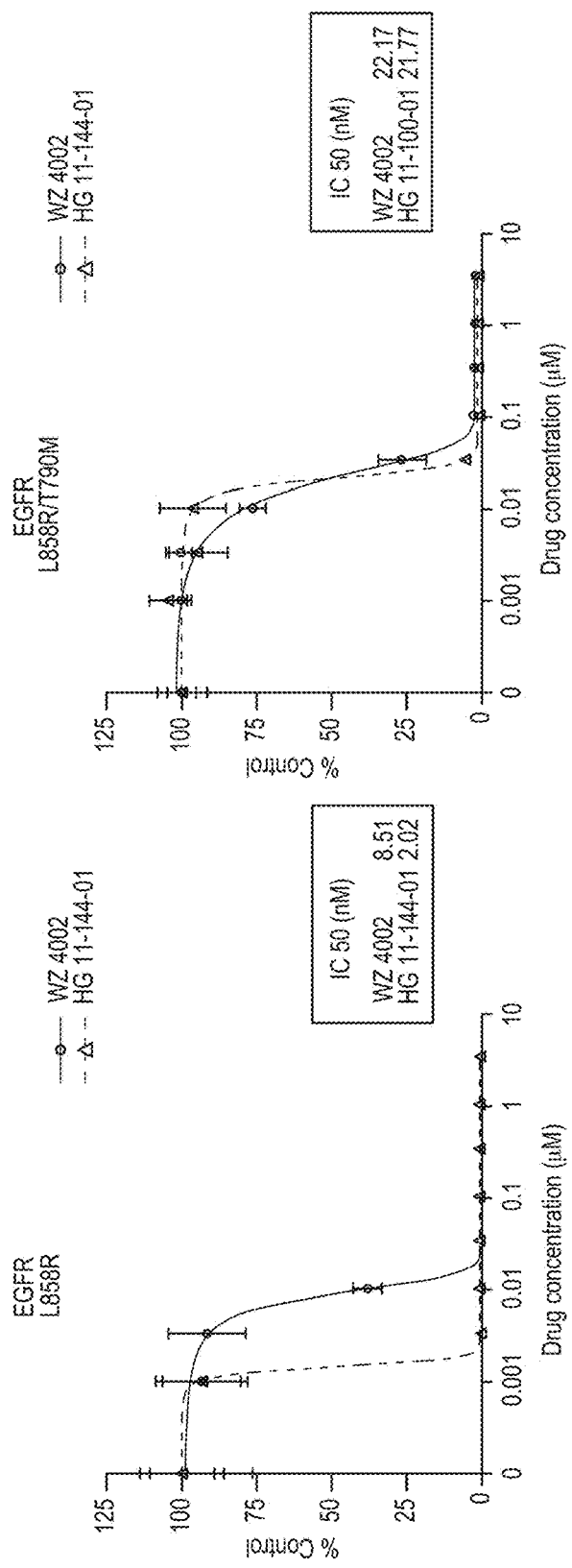

For purposes of the present invention, the following definitions will be used (unless expressly stated otherwise): The term "a compound of the invention" or "compounds of the invention" refers to a compound(s) disclosed herein e.g., a compound(s) of the invention includes a compound(s) of any of the formulae described herein including formulae I, IIa, IIb, III, IV, Va, Vb, VIa, VIb, VIIa, VIIb, VIIIa, VIIIb, IXa, IXb, Xa, Xb, XIa, and XIb, and/or a compound(s) explicitly disclosed herein. Whenever the term is used in the context of the present invention it is to be understood that the reference is being made to the free base and the corresponding pharmaceutically acceptable salts thereof, provided that such is possible and/or appropriate under the circumstances. It is understood that formulae IIa, IIb, III, IV, Va, Vb, VIa, VIb, VIIa, VIIb, VIIIa, VIIb, IXa, IXb, Xa, Xb, XIa, and XIb described herein are subsets of formula I.

The term "alkyl," as used herein, refers to saturated, straight- or branched-chain hydrocarbon radicals containing, in certain embodiments, between one and six, or one and eight carbon atoms, respectively. Examples of $C_1$-$C_6$ alkyl radicals include, but are not limited to, methyl, ethyl, propyl, isopropyl, butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals. The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Examples of $C_2$-$C_8$ alkenyl groups include, but are not limited to, for example, ethenyl, propenyl, butenyl, 1-methyl-2-buten-1-yl, heptenyl, octenyl and the like.

The term "alkoxy" refers to an —O-alkyl radical.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, idenyl and the like. The term aryl includes indoline.

The term "cycloalkyl," as used herein, denotes a monovalent group derived from a monocyclic or polycyclic saturated or partially unsaturated carbocyclic ring compound. Examples of $C_3$-$C_8$-cycloalkyl (3- to 8-membered cycloalkyl) include, but not limited to, cyclopropyl, cyclobutyl, cyclopentyl, cyclohexyl, cyclopentyl and cyclooctyl; and examples of $C_3$-$Ci_2$-cycloalkyl include, but not limited to, cyclopropyl, cyclobutyl, cyclopentyl, cyclohexyl, bicyclo [2.2.1] heptyl, and bicyclo [2.2.2] octyl. Also contemplated is a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O and N; zero, one or two ring atoms are additional heteroatoms independently selected from S, O and N; and the remaining ring atoms are carbon. The term "5- or 6-membered heteroaryl" is taken to mean a ring having five or six ring atoms of which one ring atom is selected from S, O, and N. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "3- to 8-membered heterocyclic" as used herein, refers to a non-aromatic 3-, 4-, 5-, 6-7-, or 8-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

In accordance with the invention, any of the aryls, substituted aryls, heteroaryls and substituted heteroaryls described herein, can be any aromatic group. Aromatic groups can be substituted or unsubstituted.

The terms "hal," "halo," and "halogen," as used herein, refer to an atom selected from fluorine, chlorine, bromine and iodine.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent.

Unless otherwise indicated, an optionally substituted group may have a substituent at each substitutable position of the group, and when more than one position in any given structure may be substituted with more than one substituents selected from a specified group, the substituent may be either the same or different at every position.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "EGFR kinase" herein refers to epidermal growth factor receptor kinase.

The term "FGFR kinase" herein refers to fibroblast growth factor receptor tyrosine kinase.

The term "HER" or "Her" herein refers to human epidermal growth factor receptor kinase.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient. As used herein, the term "treat," "treating," or "treatment" herein, is meant decreasing the symptoms, markers, and/or any negative effects of a disease in any appreciable degree in a patient who currently has the disease. Treatment refers to a method of alleviating or abating a disease and/or its attendant symptoms.

As used herein, the term "prevent," "prevention," or "preventing" refers to any method to partially or completely prevent or delay the onset of one or more symptoms or features of a disease. Prevention may be administered to a subject who does not exhibit signs of a disease.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, /7-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention.

"Prodrug", as used herein means a compound which is convertible in vivo by metabolic means (e.g., by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 1 13-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002). This invention also encompasses pharmaceutical compositions containing, and methods of treating disorders through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this invention are only those that result in the formation of stable compounds.

The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Some of the compounds of the present invention may exist in unsolvated as well as solvated forms such as, for example, hydrates.

"Solvate" means a solvent addition form that contains either a stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. In the hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates are sesquihydrates, monohydrates, dihydrates or trihydrates. Equally suitable are the hydrates of salts of the compounds of the invention.

The invention also includes metabolites of the compounds described herein.

When any variable (e.g., $R_{28}$) occurs more than one time in any constituent or formula for a compound, its definition at each occurrence is independent of its definition at every other occurrence. Thus, for example, if a group is shown to be substituted with one or more $R_{28}$ moieties, then $R_{28}$ at each occurrence is selected independently from the definition of $R_{28}$. Also, combinations of substituents and/or variables are permissible, but only if such combinations result in stable compounds within a designated atom's normal valency.

"WZ4002" means the third generation EGFR inhibitor:

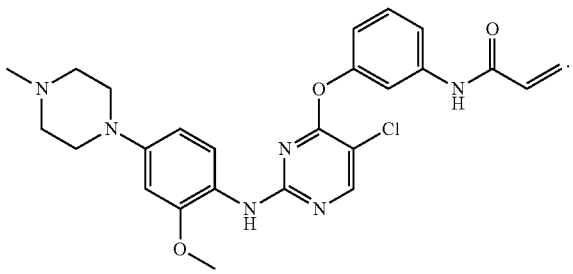 [SMILES: C=CC(=O)Nc1cccc(Oc2nc(Nc3ccc(N4CCN(C)CC4)cc3OC)ncc2Cl)c1]

The problem to be solved by the present invention is the identification of novel compounds for the treatment and/or prevention of disease. The compounds of the invention disclosed herein are small molecule irreversible inhibitors of a number of kinase targets that are validated for the treatment of cancer. In particular, the compounds of the invention are a class of compounds that are capable of covalently modifying ALK, ROS1, EGFR, FGFR, JAK, BTK, BLK, ITK, TEC, and TXK kinases. Specifically the compounds are active at low nanomolar concentrations against the most common "gatekeeper" mutant forms of these enzymes. The compounds of the invention are more potent inhibitors than current clinical candidates against EGFR and FGFR and are the first reported covalent inhibitors of ALK and ROS1. The compounds are capable of targeting a spectrum of mutations that are currently not addressed by available inhibitors. The compounds of the invention provide the advantage of potently and selectively inhibiting the activity of both wild-type and mutant forms of EGFR, FGFR, ALK, ROS1, JAK, BTK, BLK, ITK, TEC, and TXK.

Compounds of the Invention

The present invention relates to novel compounds and their uses. The present invention relates to the synthesis of the compounds of the invention.

The invention provides a compound of formula I:

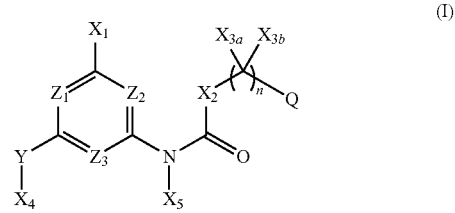

or a pharmaceutically acceptable salt thereof, wherein
$Z_1$ is N or $CR_1$;
$Z_2$ is N or $CR_2$;
$Z_3$ is N or $CR_3$, provided that when Y is $NR_4$, then two of $Z_1$, $Z_2$ or $Z_3$ are N;
$R_1$ is H, $C_1$-$C_8$ alkyl, halogen, or halo($C_1$-$C_8$ alkyl);
$R_2$ is H, $C_1$-$C_8$ alkyl, halogen, or halo($C_1$-$C_8$ alkyl);
$X_2$ is O or $NR_{10}$;
$R_{10}$ is hydrogen or $C_1$-$C_8$ alkyl;
or when $Z_2$ is $CR_2$ and $X_2$ is $NR_{10}$, $R_2$ and $R_{10}$ can be taken together to form a 6-membered heterocyclic ring, wherein said heterocyclic ring is optionally substituted with one or more $R_{28}$;
$R_3$ is H, $C_1$-$C_8$ alkyl, halogen, or halo($C_1$-$C_8$ alkyl);
Y is $NR_4$;
or taken together Y—$X_4$ and $R_3$ form unsubstituted or substituted $C_6$ aryl or unsubstituted or substituted 5- or 6-membered heteroaryl, wherein said substituted aryl or heteroaryl is substituted with one or more $R_5$;
$R_4$ is H or $C_1$-$C_8$ alkyl;
each $R_5$ is independently halogen, $OR_6$, $NR_7R_8$, $NR_7C(O)R_8$, $SR_9$, $C_1$-$C_8$ alkyl, $C_2$-$C_8$ alkynyl optionally substituted with 5- or 6-membered heterocyclic, or halo($C_1$-$C_8$ alkyl);
each $R_6$ is independently hydrogen or $C_1$-$C_8$ alkyl;
each $R_7$ and $R_8$ is independently hydrogen, $C_1$-$C_8$ alkyl, or unsubstituted or substituted 5- or 6-membered heterocyclic, wherein said substituted heterocyclic is substituted with one or more $R_{16}$;
each $R_9$ is independently hydrogen or $C_1$-$C_8$ alkyl;
$X_1$ is H, $C_1$-$C_8$ alkyl, or halogen;
each $X_{3a}$ and $X_{3b}$ are independently hydrogen, $C_1$-$C_8$ alkyl, or absent (when n is 0);
Q is $C_1$-$C_8$ alkyl, unsubstituted or substituted $C_6$-$C_{10}$ aryl, unsubstituted or substituted 5- or 6-membered heteroaryl, unsubstituted or substituted 3- to 8-membered cycloalkyl, or unsubstituted or substituted 3- to 8-membered heterocyclic, wherein said substituted aryl, heteroaryl, cycloalkyl, or heterocyclic is substituted with one or more $R_{11}$;
each $R_{11}$ is independently halogen, $OR_{12}$, $NR_{13}R_{14}$, $SR_{15}$, $C_1$-$C_8$ alkyl, or halo($C_1$-$C_8$ alkyl);
each $R_{12}$ is independently hydrogen or $C_1$-$C_8$ alkyl;
each $R_{13}$ and $R_{14}$ is independently hydrogen or $C_1$-$C_8$ alkyl;

each $R_{15}$ is independently hydrogen or $C_1$-$C_8$ alkyl;

n is 0, 1, 2, 3, or 4;

$X_4$ is unsubstituted or substituted $C_6$-$C_{10}$ aryl, unsubstituted or substituted 5- or 6-membered heteroaryl, unsubstituted or substituted $C_1$-$C_8$ alkyl, or unsubstituted or substituted $(CH_2)_{1-3}$—$C_6$-$C_{10}$ aryl, wherein said substituted aryl, heteroaryl, or alkyl is substituted with one or more $R_{16}$;

each $R_{16}$ is independently halogen, $OR_{17}$, $NR_{18}R_{19}$, $SR_{20}$, unsubstituted or substituted $C_1$-$C_8$ alkyl, halo($C_1$-$C_8$ alkyl), $C(O)(C_1$-$C_8$ alkyl), $C(O)$(halo($C_1$-$C_8$ alkyl)), $C(O)(C_2$-$C_8$ alkenyl), unsubstituted or substituted heterocyclic, or $C(O)$-unsubstituted or substituted heterocyclic, wherein said substituted alkyl or heterocyclic is substituted with one or more $R_{21}$;

each $R_{17}$ is independently hydrogen or $C_1$-$C_8$ alkyl;

each $R_{18}$ and $R_{19}$ is independently hydrogen, $C_1$-$C_8$ alkyl, $C(O)(C_1$-$C_8$ alkyl), $C(O)(C_2$-$C_8$ alkenyl), or $C(O)$-unsubstituted or substituted heterocyclic, wherein said alkyl or alkenyl is optionally substituted with one or more OH, CN, halogen, $C_3$-$C_8$ cycloalkyl, $O(C_1$-$C_8$ alkyl), $NH_2$, $NH(C_1$-$C_8$ alkyl), or $N(C_1$-$C_8$ alkyl)$_2$, and wherein said substituted heterocyclic is substituted with one or more $R_{21}$;

each $R_{20}$ is independently hydrogen or $C_1$-$C_8$ alkyl;

each $R_{21}$ is $C_1$-$C_8$ alkyl, $C(O)(C_1$-$C_8$ alkyl), $C(O)(C_2$-$C_8$ alkenyl), or heterocyclic;

$X_5$ is unsubstituted or substituted $C_6$-$C_{10}$ aryl, unsubstituted or substituted 5- to 8-membered heteroaryl, or unsubstituted or substituted $C_1$-$C_8$ alkyl, wherein said substituted aryl, heteroaryl, or alkyl is substituted with one or more $R_{22}$;

each $R_{22}$ is independently halogen, $OR_{23}$, $NR_{24}R_{25}$, $SR_{26}$, $C_1$-$C_8$ alkyl, halo($C_1$-$C_8$ alkyl), $C(O)(C_1$-$C_8$ alkyl), $C(O)(C_2$-$C_8$ alkenyl), unsubstituted or substituted heterocyclic, unsubstituted or substituted $C_6$-$C_{10}$ aryl, or $C(O)$-unsubstituted or substituted heterocyclic, wherein said substituted heterocyclic or aryl is substituted with one or more $R_{27}$;

or two or more $R_{22}$, together with the atoms to which they attach, form an unsubstituted or substituted 3- to 8-membered cycloalkyl, or unsubstituted or substituted 5- to 6-membered heterocyclic, wherein said cycloalkyl or heterocyclic is substituted with one or more $R_{27}$;

each $R_{23}$ is independently hydrogen or $C_1$-$C_8$ alkyl;

each $R_{24}$ and $R_{25}$ is independently hydrogen, $C_1$-$C_8$ alkyl, $C(O)(C_1$-$C_8$ alkyl), or $C(O)(C_2$-$C_8$ alkenyl), wherein said alkyl or alkenyl is optionally substituted with one or more OH, CN, halogen, $C_3$-$C_8$ cycloalkyl, $O(C_1$-$C_8$ alkyl), $NH_2$, $NH(C_1$-$C_8$ alkyl), or $N(C_1$-$C_8$ alkyl)$_2$;

each $R_{26}$ is independently hydrogen or $C_1$-$C_8$ alkyl;

each $R_{27}$ is halogen, $C_1$-$C_8$ alkyl, $C(O)(C_1$-$C_8$ alkyl), $C(O)(C_2$-$C_8$ alkenyl), $NR_{29}C(O)(C_1$-$C_8$ alkyl), or $NR_{29}C(O)(C_2$-$C_8$ alkenyl);

each $R_{28}$ is halogen, $C_1$-$C_8$ alkyl, or halo($C_1$-$C_8$ alkyl);

or taken together two $R_{28}$ and the carbon to which they are attached form C=O; and each $R_{29}$ is hydrogen or $C_1$-$C_8$ alkyl.

The phrase "when $Z_2$ is $CR_2$ and $X_2$ is $NR_{10}$, $R_2$ and $R_{10}$ can be taken together to form a 6-membered heterocyclic ring, wherein said heterocyclic ring is optionally substituted with one or more $R_{28}$" is further illustrated with the structures shown below. When $R_2$ and $R_{10}$ are taken together to form a 6-membered heterocyclic ring, a compound of formula IVA is formed:

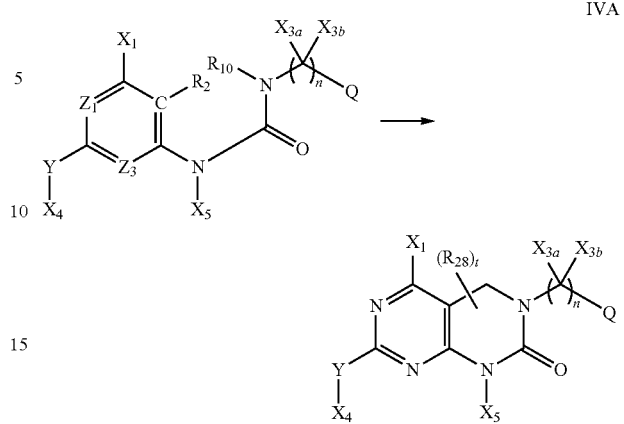

In one aspect, the invention includes a compound selected from formulae IIa, IIb, III, and IV:

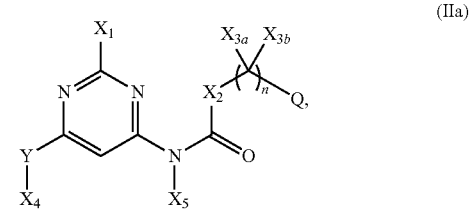

(IIa)

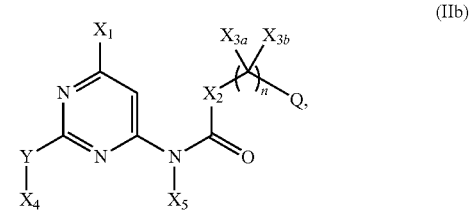

(IIb)

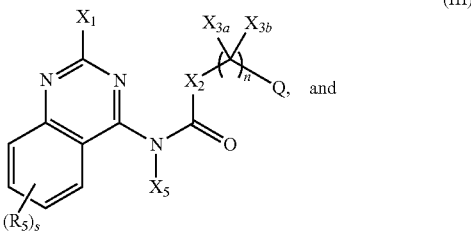

(III)

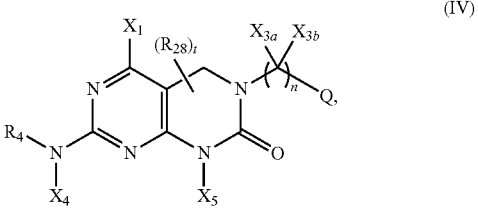

(IV)

or a pharmaceutically acceptable salt thereof, wherein s is 1, 2, 3, or 4 and t is 0, 1, or 2 and $R_4$, $R_5$, $R_{28}$, $X_1$, Y, $X_2$, $X_{3a}$, $X_{3b}$, Q, n, $X_4$, and $X_5$ are as defined for formula I.

In one subclass, the invention includes a compound of formula Va or Vb:

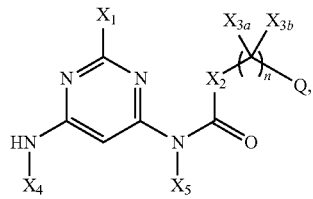
(Va)

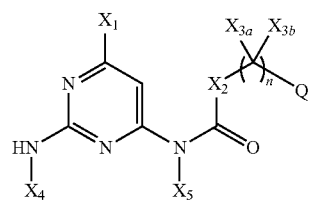
(Vb)

or a pharmaceutically acceptable salt thereof, wherein $X_1$, $X_2$, $X_{3a}$, $X_{3b}$, Q, n, $X_4$, and $X_5$ are as defined for formula I.

In a further example, the invention includes a compound of formula VIa or VIb:

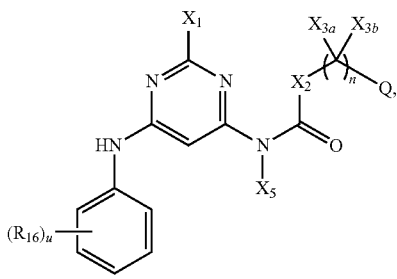
(VIa)

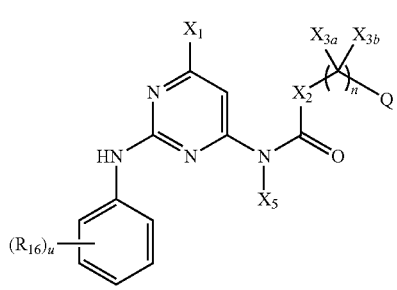
(VIb)

or a pharmaceutically acceptable salt thereof, wherein u is 0, 1, 2, 3, 4, or 5 and $R_{16}$, $X_1$, $X_2$, $X_{3a}$, $X_{3b}$, Q, n, and $X_5$ are as defined for formula I.

In another example, the invention includes a compound of formula VIIa or VIIb:

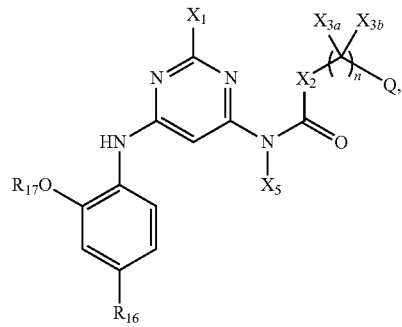
(VIIa)

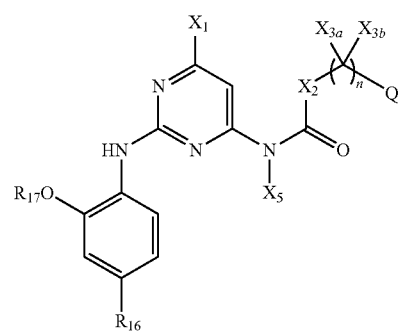
(VIIb)

or a pharmaceutically acceptable salt thereof, wherein $R_{16}$, $R_{17}$, $X_1$, $X_2$, $X_{3a}$, $X_{3b}$, Q, n, and $X_5$ are as defined for formula I.

In yet another example, the invention includes a compound of formula VIIIa or VIIIb:

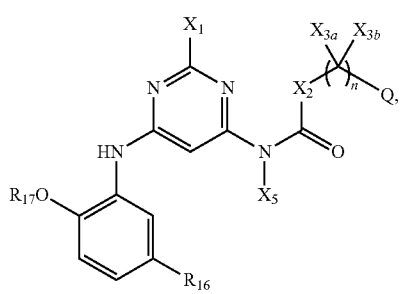
(VIIIa)

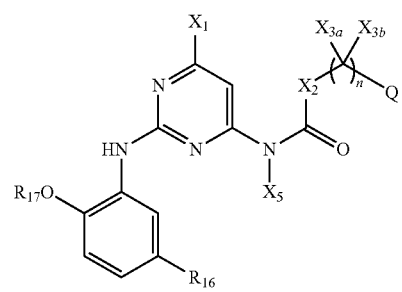
(VIIb)

or a pharmaceutically acceptable salt thereof, wherein $R_{16}$, $R_{17}$, $X_1$, $X_2$, $X_{3a}$, $X_{3b}$, Q, n, $X_5$, and $R_{17}$ are as defined for formula I.

In another example, the invention includes a compound of formula IXa or IXb:

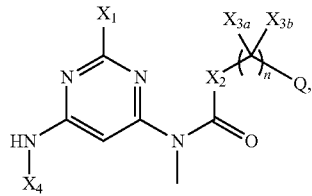
(IXa)

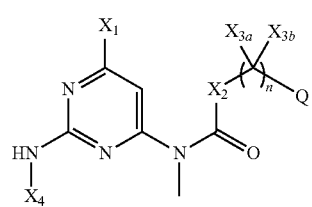
(IXb)

or a pharmaceutically acceptable salt thereof, wherein $X_1$, $X_2$, $X_{3a}$, $X_{3b}$, Q, n, and $X_4$ are as defined for formula I.

In another example, the invention includes a compound of formula Xa or Xb:

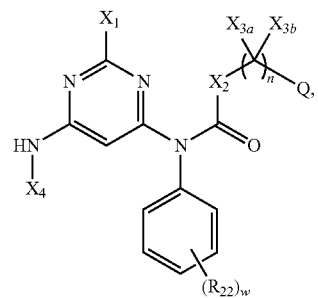
(Xa)

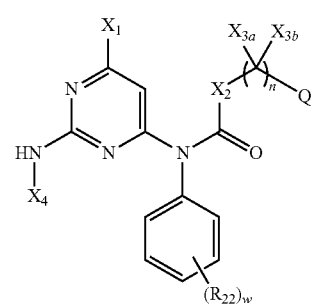
(Xb)

or a pharmaceutically acceptable salt thereof, wherein w is 0, 1, or 2 and $R_{22}$, $X_1$, $X_2$, $X_{3a}$, $X_{3b}$, Q, n, and $X_4$ are as defined for formula I.

In yet another example, the invention includes a compound of formula XIa or XIb:

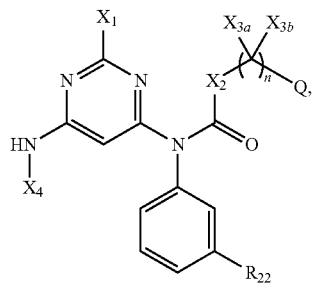
(XIa)

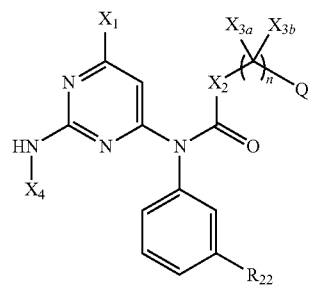
(XIb)

or a pharmaceutically acceptable salt thereof, wherein $X_1$, $X_2$, $X_{3a}$, $X_{3b}$, Q, n, $X_4$, and $R_{22}$ are as defined for formula I.

Illustratively, the invention includes a compound of formula I, IIa, IIb, III, IV, Va, Vb, VIa, VIb, VIIa, VIIb, VIIIa, VIIIb, IXa, IXb, Xa, Xb, XIa, or XIb wherein $X_1$ is hydrogen or halogen. In one aspect, $X_1$ is hydrogen. In one aspect, $X_1$ is halogen. In a further aspect, $X_1$ is chlorine.

The invention includes a compound of formula I, IIa, IIb, III, IV, Va, Vb, VIa, VIb, VIIa, VIIb, VIIIa, VIIIb, IXa, IXb, Xa, Xb, XIa, or XIb wherein n is 0, 1, or 2. In one aspect, n is 0 or 1. In one aspect, n is 0. In one aspect, n is 1.

The invention includes a compound of formula I, IIa, IIb, III, IV, Va, Vb, VIa, VIb, VIIa, VIIb, VIIIa, VIIIb, IXa, IXb, Xa, Xb, XIa, or XIb wherein $X_{3a}$ and $X_{3b}$ are each hydrogen or one of $X_{3a}$ or $X_{3b}$ is methyl and the remaining $X_{3a}$ or $X_{3b}$ is hydrogen. In one aspect, $X_{3a}$ and $X_{3b}$ are each hydrogen. In one aspect, one of $X_{3a}$ or $X_{3b}$ is methyl and the remaining $X_{3a}$ or $X_{3b}$ is hydrogen. In one aspect, the configuration of the carbon atom to which $X_{3a}$ and $X_{3b}$ are attached is the S-configuration.

The invention includes a compound of formula I, IIa, IIb, III, IV, Va, Vb VIa, VIb, VIIa, VIIb, VIIIa, VIIIb, IXa, IXb, Xa, Xb, XIa, or XIb wherein Q is unsubstituted or substituted phenyl or unsubstituted or substituted 5- or 6-membered heteroaryl. In one aspect, Q is unsubstituted phenyl or 5- or 6-membered unsubstituted heteroaryl. In one aspect, Q is unsubstituted phenyl. In one aspect, the heteroaryl is pyridyl or thienyl.

The invention includes a compound of formula I, IIa, IIb, III, IV, Va, Vb VIa, VIb, VIIa, VIIb, VIIIa, VIIIb, IXa, IXb, Xa, Xb, XIa, or XIb wherein Q is $C_1$-$C_8$ alkyl. In one aspect, Q is methyl.

The invention includes a compound of formula I, IIa, IIb, III, IV, Va, Vb VIa, VIb, VIIa, VIIb, VIIIa, VIIIb, IXa, IXb, Xa, Xb, XIa, or XIb wherein Q is unsubstituted or substituted 3- to 8-membered cycloalkyl. In one aspect, Q is cyclopropyl.

The invention includes a compound of formula I, IIa, IIb, III, IV, Va, Vb VIa, VIb, VIIa, VIIb, VIIIa, VIIIb, IXa, IXb, Xa, Xb, XIa, or XIb wherein Q is unsubstituted or substituted 6-membered heterocyclic. In one aspect, Q is tetrahydropyran.

The invention includes a compound of formula I, IIa, IIb, III, IV, Va, Vb VIa, VIb, VIIa, VIIb, VIIIa, VIIIb, IXa, IXb, Xa, Xb, XIa, or XIb wherein Q is substituted with one, two, three or four $R_{11}$. Further illustrating this aspect, each $R_{11}$ is independently methyl, ethyl, propyl, isopropyl, chloro, fluoro, methoxy, ethoxy, propoxy, or isopropoxy. Further exemplifying this aspect, each $R_{11}$ is independently methyl, chloro, or methoxy.

The invention includes a compound of formula I, IIa, IIb, IV, Va, Vb, IXa, IXb, Xa, Xb, XIa, or XIb wherein $X_4$ is substituted phenyl or methyl. In one aspect, $X_4$ is phenyl substituted with one or two $R_{16}$. In one aspect, $X_4$ is phenyl substituted with at least one $R_{16}$ is $OCH_3$. In one aspect, $X_4$ is methyl.

The invention includes a compound of formula I, IIa, IIb, IV, Va, Vb, IXa, IXb, Xa, Xb, XIa, or XIb wherein $X_4$ is unsubstituted or substituted 5- or 6-membered heteroaryl. In one aspect, $X_4$ is heteroaryl substituted with one or two $R_{16}$. In one aspect, $X_4$ is diazolyl substituted with one or two $R_{16}$.

The invention includes a compound of formula I, IIa, IIb, III, IV, Va, Vb, VIa, VIb, VIIa, VIIb, VIIIa, or VIIIb, wherein $X_5$ is substituted phenyl or methyl. In one aspect, $X_5$ is methyl. In one aspect, $X_5$ is phenyl substituted with one or two $R_{22}$. Further defining this aspect, $R_{22}$ is $NR_{24}R_{25}$. Further exemplifying this aspect, one of $R_{24}$ or $R_{25}$ is $C(O)(C_2$-$C_8)$alkenyl and the remaining $R_{24}$ or $R_{25}$ is hydrogen.

The invention includes a compound of formula VIa or VIb, wherein u is one or two.

In one aspect, at least one $R_{16}$ is $OCH_3$.

The invention includes a compound of formula I, IIa, IIb, IV, Va, Vb, VIa, VIb, VIIa, VIIb, VIIIa, VIIIb, IXa, IXb, Xa, Xb, XIa, or XIb, wherein $R_{17}$ is methyl.

The invention includes a compound of formula I, IIa, IIb, IV, Va, Vb, VIa, VIb, VIIa, VIIb, VIIIa, VIIIb, IXa, IXb, Xa, Xb, XIa, or XIb, wherein $R_{16}$ is substituted heterocyclic or $NR_{18}R_{19}$. In one aspect, $R_{16}$ is methylpiperazine. In one aspect, $R_{16}$ is $NHC(O)(C_2$-$C_4$ alkenyl) optionally substituted with $NH_2$, $NH(C_1$-$C_3$ alkyl), or $N(C_1$-$C_3$ alkyl)$_2$.

The invention includes a compound of formula I, IIa, IIb, IV, Va, Vb, VIa, VIb, VIIa, VIIb, VIIIa, VIIIb, Xa, Xb, XIa, or XIb, wherein $R_{22}$ is $NR_{24}R_{25}$. In one aspect, one of $R_{24}$ or $R_{25}$ is $C(O)(C_2$-$C_8$ alkenyl) and the remaining $R_{24}$ or $R_{25}$ is hydrogen.

While all of the compounds of the invention are useful, certain classes are preferred. It will be understood that the above classes may be combined to form additional preferred classes, as for example the combination of preferred selections for two or more substituents. The invention includes a compound selected from Table 1.

| Compound # | Structure |
|---|---|
| 1A | 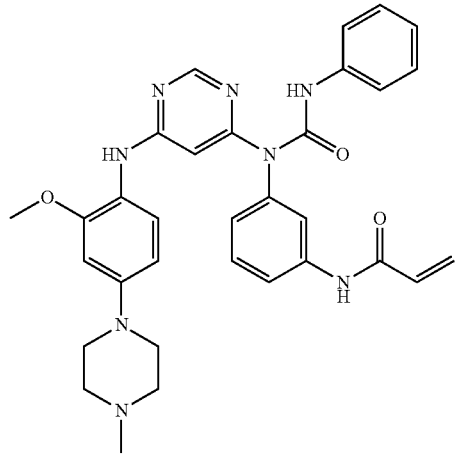 [SMILES: C=CC(=O)Nc1cccc(N(C(=O)Nc2ccccc2)c2cc(Nc3ccc(N4CCN(C)CC4)cc3OC)ncn2)c1] |
| 2A | 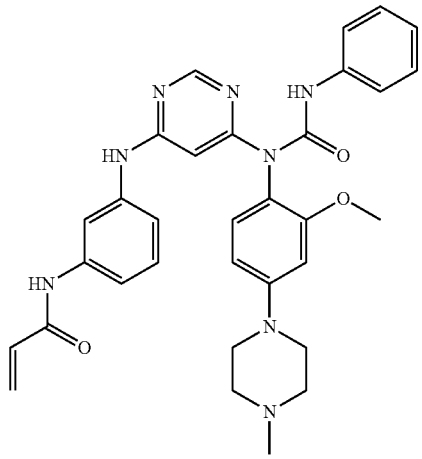 [SMILES: C=CC(=O)Nc1cccc(Nc2cc(N(C(=O)Nc3ccccc3)c3ccc(N4CCN(C)CC4)cc3OC)ncn2)c1] |

-continued
| Compound # | Structure |
|---|---|
| 3A | 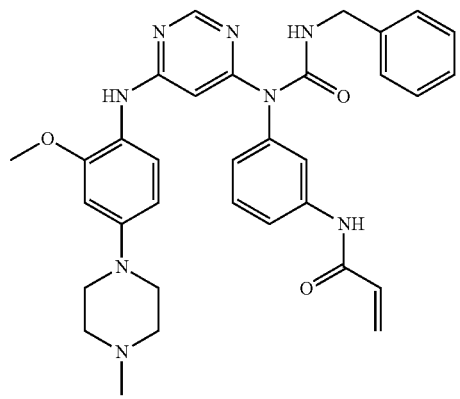 |
| 4A | 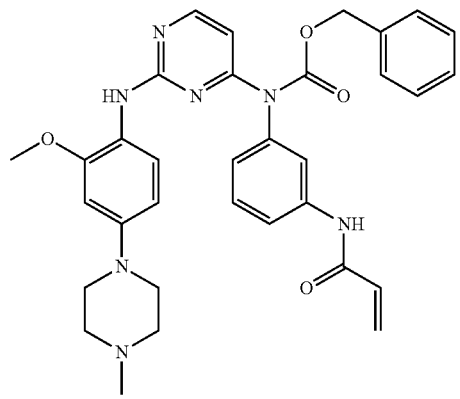 [SMILES: C=CC(=O)Nc1cccc(N(C(=O)OCc2ccccc2)c2ccnc(Nc3ccc(N4CCN(C)CC4)cc3OC)n2)c1] |
| 5A | 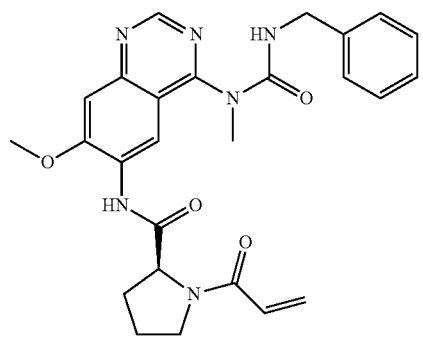 [SMILES: C=CC(=O)N1CCC[C@H]1C(=O)Nc1cc2c(N(C)C(=O)NCc3ccccc3)ncnc2cc1OC] |
| 6A | 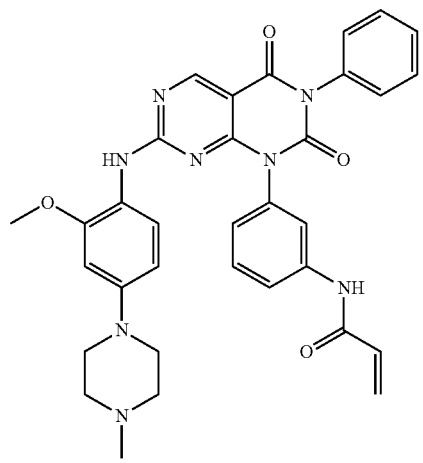 [SMILES: C=CC(=O)Nc1cccc(-n2c(=O)n(-c3ccccc3)c(=O)c3cnc(Nc4ccc(N5CCN(C)CC5)cc4OC)nc32)c1] |

-continued
| Compound # | Structure |
|---|---|
| 7A | 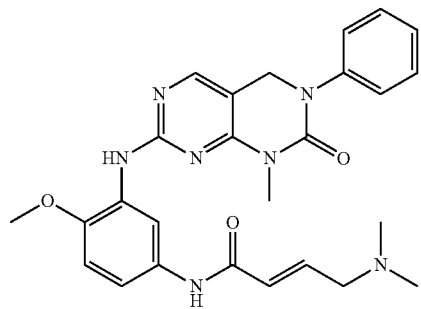 |
| 8A | 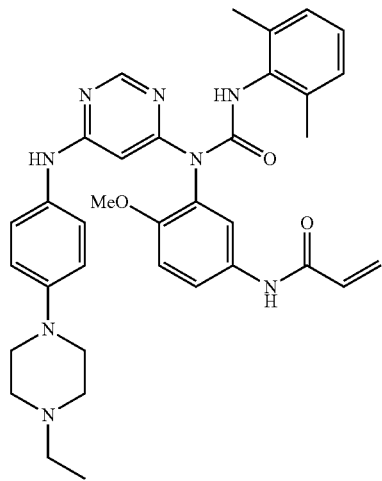 [SMILES: C=CC(=O)Nc1ccc(OC)c(N(C(=O)Nc2c(C)cccc2C)c2cc(Nc3ccc(N4CCN(CC)CC4)cc3)ncn2)c1] |
| 9A | 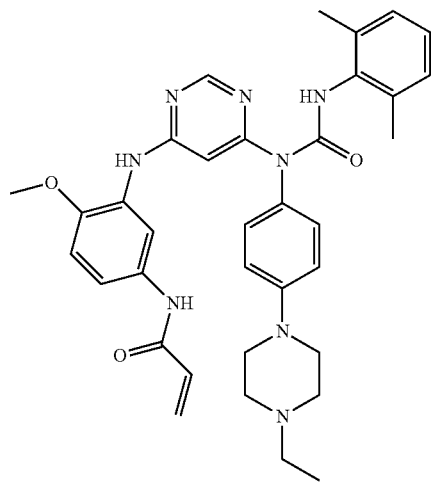 [SMILES: C=CC(=O)Nc1ccc(OC)c(Nc2cc(N(C(=O)Nc3c(C)cccc3C)c3ccc(N4CCN(CC)CC4)cc3)ncn2)c1] |

-continued
| Compound # | Structure |
|---|---|
| 10A | 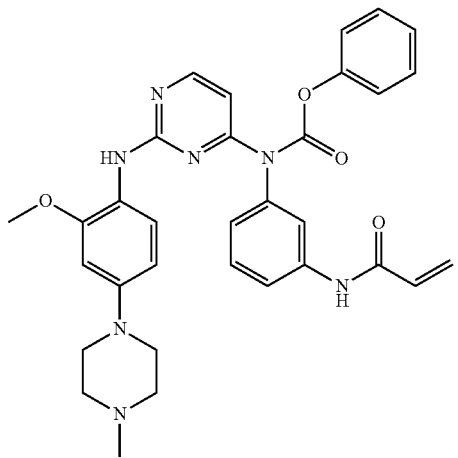 |
| 11A | 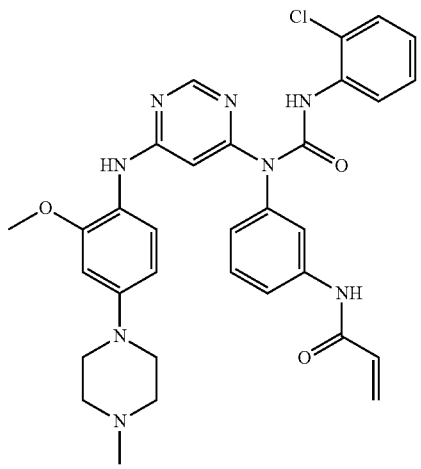 [SMILES: C=CC(=O)Nc1cccc(N(C(=O)Nc2ccccc2Cl)c2cc(Nc3ccc(N4CCN(C)CC4)cc3OC)ncn2)c1] |
| 12A | 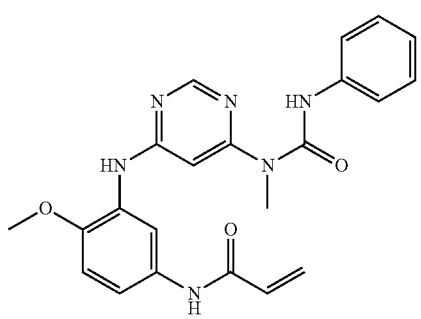 [SMILES: C=CC(=O)Nc1ccc(OC)c(Nc2cc(N(C)C(=O)Nc3ccccc3)ncn2)c1] |
| 13A | 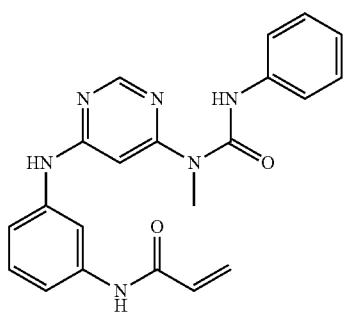 [SMILES: C=CC(=O)Nc1cccc(Nc2cc(N(C)C(=O)Nc3ccccc3)ncn2)c1] |

| Compound # | Structure |
|---|---|
| 14A | 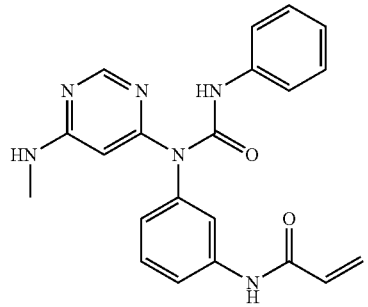 [SMILES: C=CC(=O)Nc1cccc(N(C(=O)Nc2ccccc2)c2cc(NC)ncn2)c1] |
| 15A | 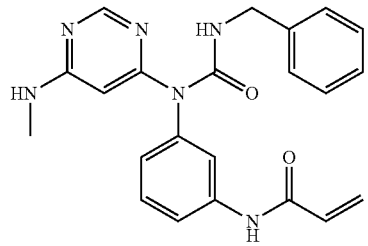 [SMILES: C=CC(=O)Nc1cccc(N(C(=O)NCc2ccccc2)c2cc(NC)ncn2)c1] |
| 16A | 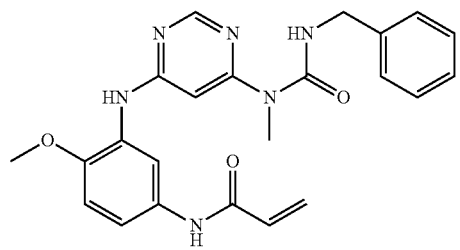 [SMILES: C=CC(=O)Nc1ccc(OC)c(Nc2cc(N(C)C(=O)NCc3ccccc3)ncn2)c1] |
| 17A | 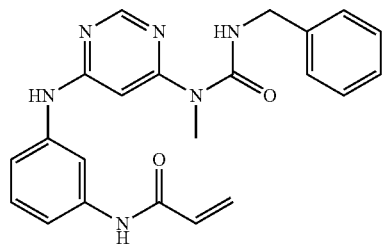 [SMILES: C=CC(=O)Nc1cccc(Nc2cc(N(C)C(=O)NCc3ccccc3)ncn2)c1] |
| 18A | 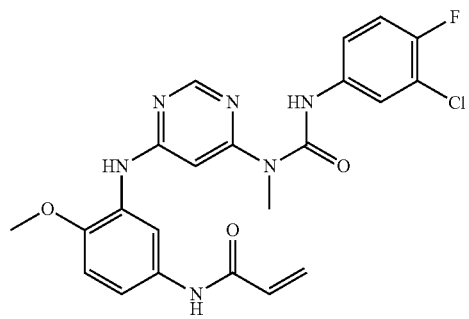 [SMILES: C=CC(=O)Nc1ccc(OC)c(Nc2cc(N(C)C(=O)Nc3ccc(F)c(Cl)c3)ncn2)c1] |

-continued
| Compound # | Structure |
|---|---|
| 19A | 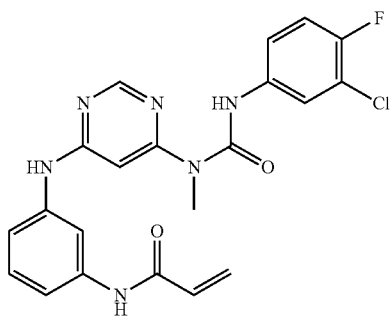 [SMILES: C=CC(=O)Nc1cccc(Nc2cc(N(C)C(=O)Nc3ccc(F)c(Cl)c3)ncn2)c1] |
| 20A | 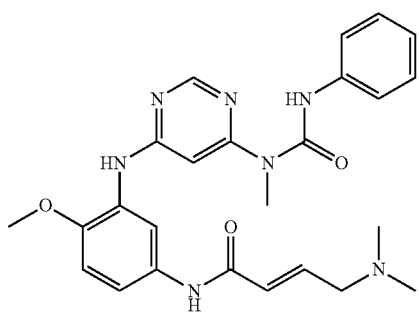 |
| 21A | 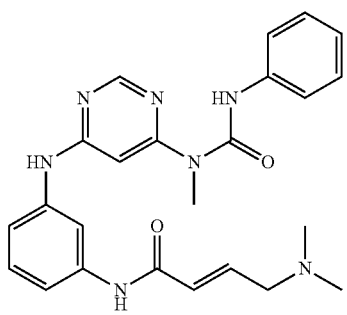 [SMILES: CN(C)C/C=C/C(=O)Nc1cccc(Nc2cc(N(C)C(=O)Nc3ccccc3)ncn2)c1] |
| 22A | 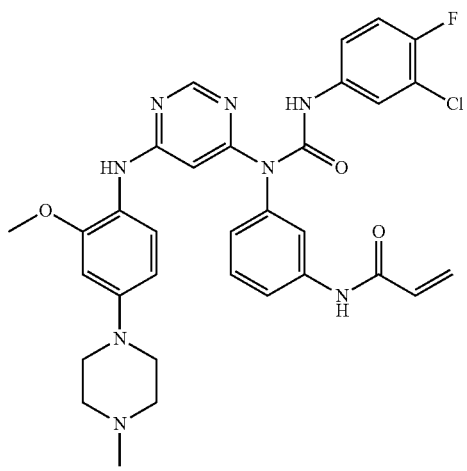 [SMILES: C=CC(=O)Nc1cccc(N(C(=O)Nc2ccc(F)c(Cl)c2)c2cc(Nc3ccc(N4CCN(C)CC4)cc3OC)ncn2)c1] |

-continued
| Compound # | Structure |
|---|---|
| 23A | 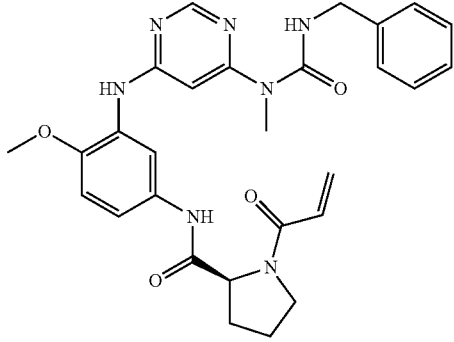 |
| 24A | 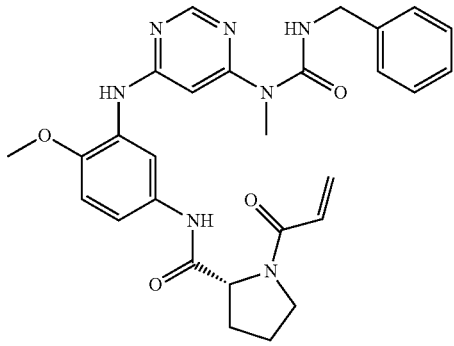 [SMILES: C=CC(=O)N1CCC[C@@H]1C(=O)Nc1ccc(OC)c(Nc2cc(N(C)C(=O)NCc3ccccc3)ncn2)c1] |
| 25A | 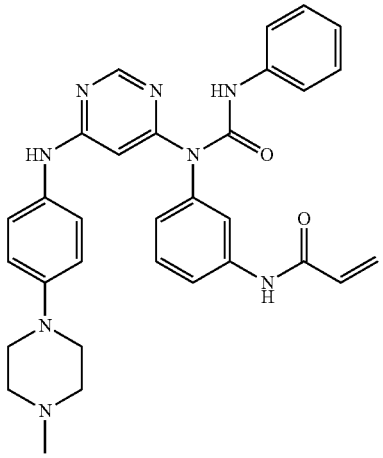 [SMILES: C=CC(=O)Nc1cccc(N(C(=O)Nc2ccccc2)c2cc(Nc3ccc(N4CCN(C)CC4)cc3)ncn2)c1] |
| 26A | 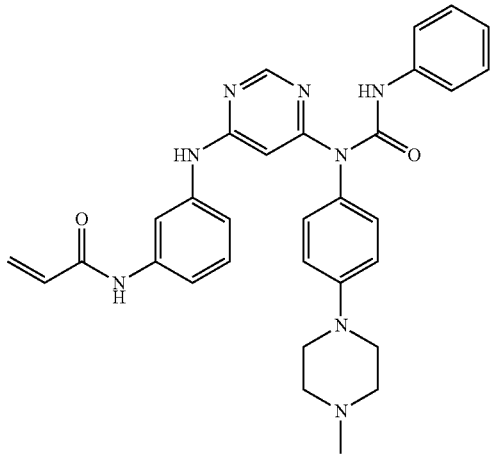 [SMILES: C=CC(=O)Nc1cccc(Nc2cc(N(C(=O)Nc3ccccc3)c3ccc(N4CCN(C)CC4)cc3)ncn2)c1] |

-continued
| Compound # | Structure |
|---|---|
| 27A | 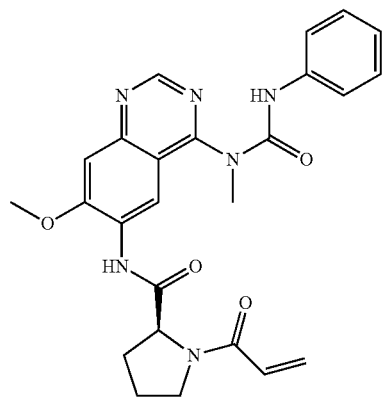 [SMILES: C=CC(=O)N1CCC[C@H]1C(=O)Nc1cc2c(N(C)C(=O)Nc3ccccc3)ncnc2cc1OC] |
| 28A | 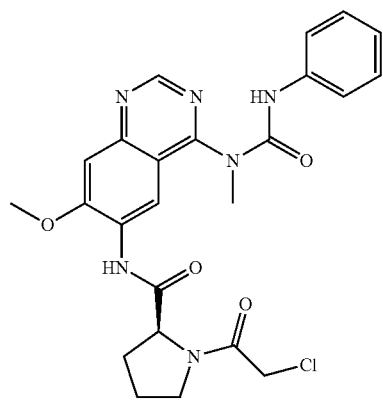 [SMILES: COc1cc2ncnc(N(C)C(=O)Nc3ccccc3)c2cc1NC(=O)[C@@H]1CCCN1C(=O)CCl] |
| 29A | 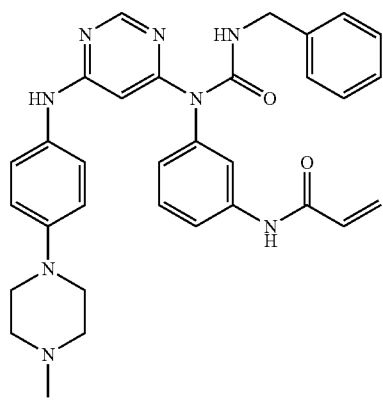 [SMILES: C=CC(=O)Nc1cccc(N(C(=O)NCc2ccccc2)c2cc(Nc3ccc(N4CCN(C)CC4)cc3)ncn2)c1] |
| 30A | 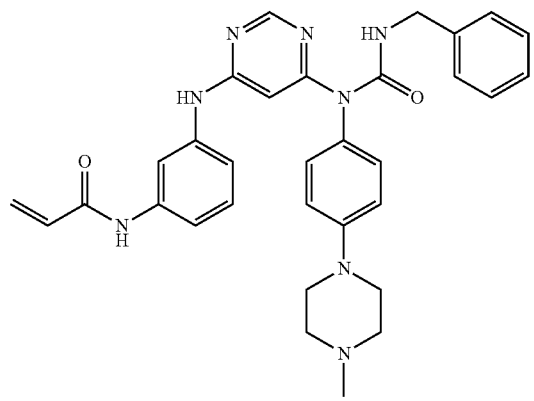 [SMILES: C=CC(=O)Nc1cccc(Nc2cc(N(C(=O)NCc3ccccc3)c3ccc(N4CCN(C)CC4)cc3)ncn2)c1] |

| Compound # | Structure |
|---|---|
| 31A | 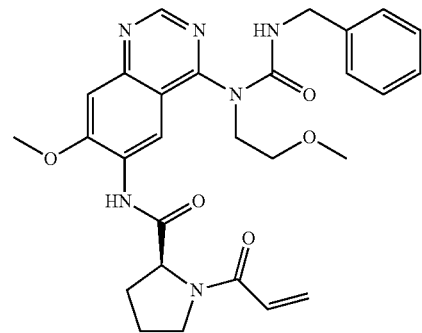 [SMILES: C=CC(=O)N1CCC[C@H]1C(=O)Nc1cc2c(N(CCOC)C(=O)NCc3ccccc3)ncnc2cc1OC] |
| 32A | 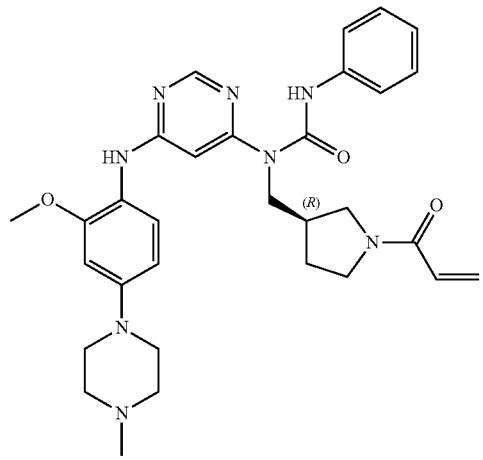 |
| 33A | 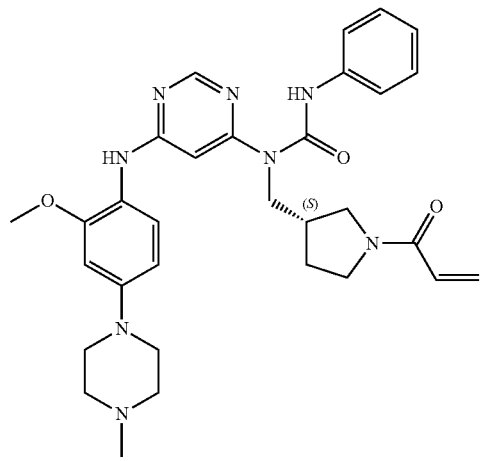 |

| Compound # | Structure |
|---|---|
| 34A | 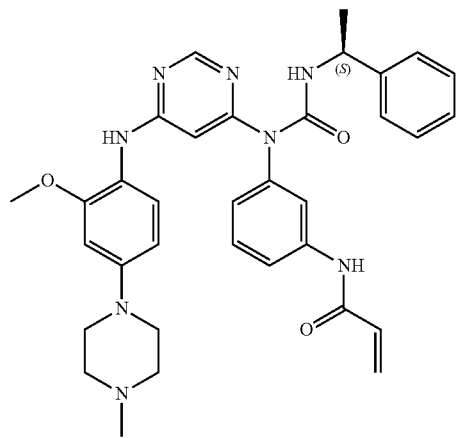 |
| 35A | 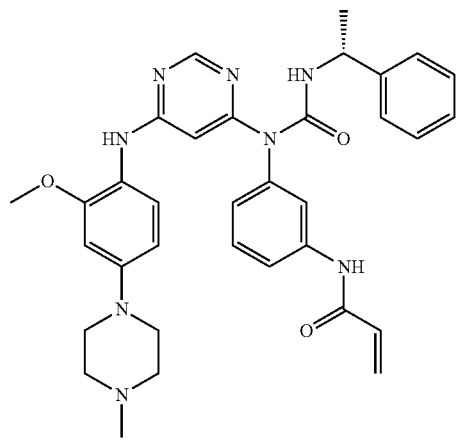 [SMILES: C=CC(=O)Nc1cccc(N(C(=O)N[C@H](C)c2ccccc2)c2cc(Nc3ccc(N4CCN(C)CC4)cc3OC)ncn2)c1] |
| 36A | 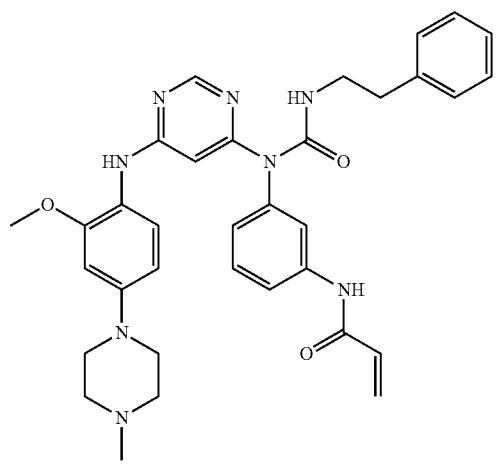 [SMILES: C=CC(=O)Nc1cccc(N(C(=O)NCCc2ccccc2)c2cc(Nc3ccc(N4CCN(C)CC4)cc3OC)ncn2)c1] |

-continued
| Compound # | Structure |
|---|---|
| 36B | 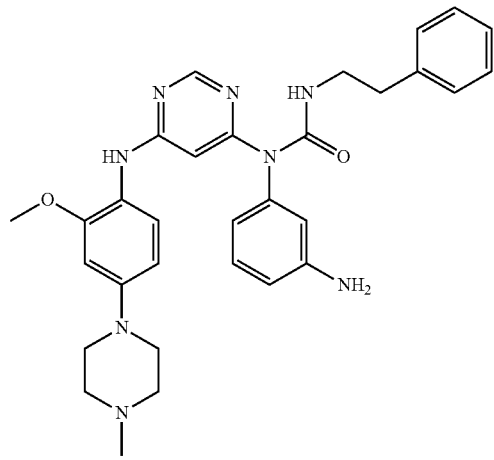 [SMILES: COc1cc(N2CCN(C)CC2)ccc1Nc1cc(N(C(=O)NCCc2ccccc2)c2cccc(N)c2)ncn1] |
| 37A | 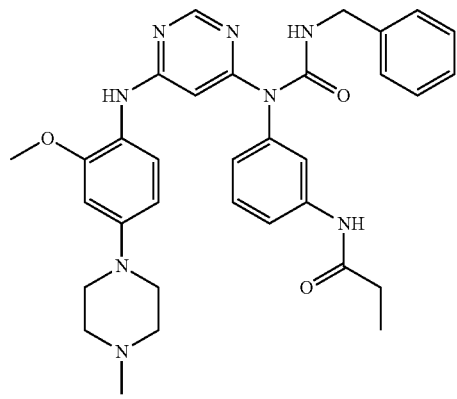 |
| 38A | 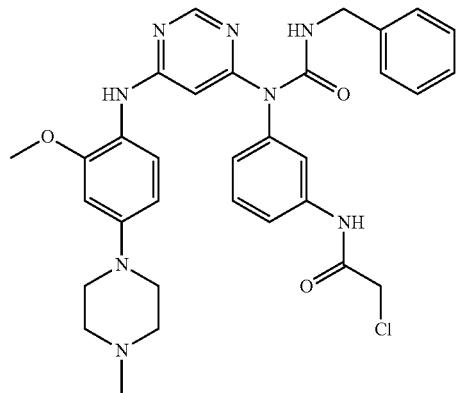 [SMILES: COc1cc(N2CCN(C)CC2)ccc1Nc1cc(N(C(=O)NCc2ccccc2)c2cccc(NC(=O)CCl)c2)ncn1] |

| Compound # | Structure |
|---|---|
| 39A | 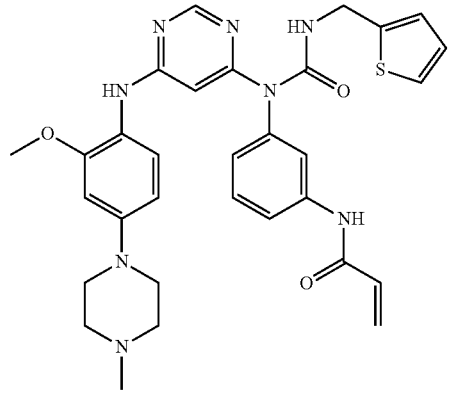 [SMILES: C=CC(=O)Nc1cccc(N(C(=O)NCc2cccs2)c2cc(Nc3ccc(N4CCN(C)CC4)cc3OC)ncn2)c1] |
| 40A | 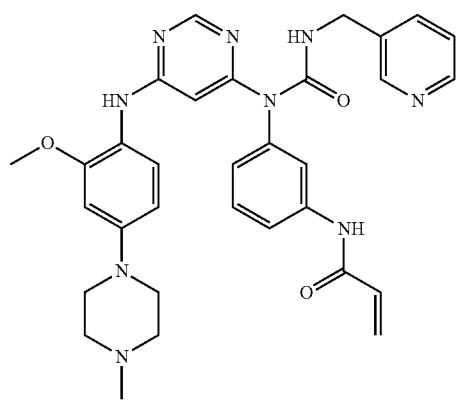 [SMILES: C=CC(=O)Nc1cccc(N(C(=O)NCc2cccnc2)c2cc(Nc3ccc(N4CCN(C)CC4)cc3OC)ncn2)c1] |
| 41A | 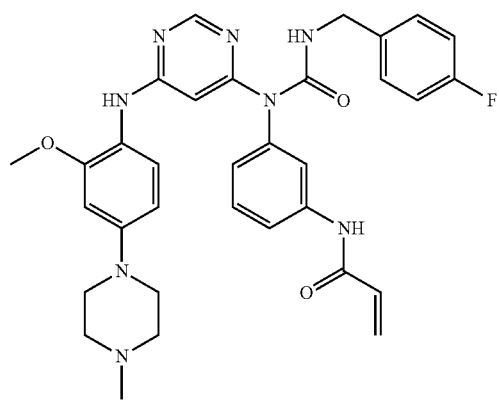 [SMILES: C=CC(=O)Nc1cccc(N(C(=O)NCc2ccc(F)cc2)c2cc(Nc3ccc(N4CCN(C)CC4)cc3OC)ncn2)c1] |
| 42A | 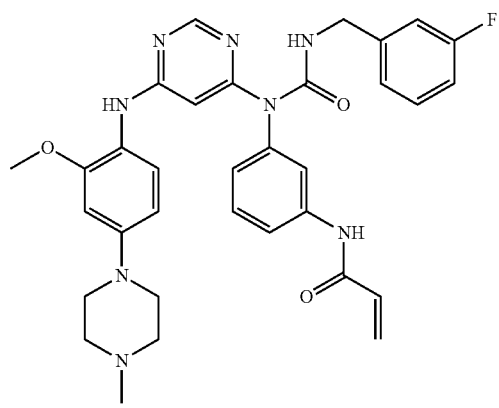 [SMILES: C=CC(=O)Nc1cccc(N(C(=O)NCc2cccc(F)c2)c2cc(Nc3ccc(N4CCN(C)CC4)cc3OC)ncn2)c1] |

| Compound # | Structure |
|---|---|
| 43A | 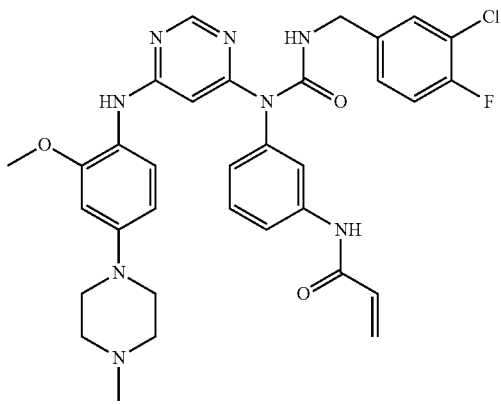 [SMILES: C=CC(=O)Nc1cccc(N(C(=O)NCc2ccc(F)c(Cl)c2)c2cc(Nc3ccc(N4CCN(C)CC4)cc3OC)ncn2)c1] |
| 44A | 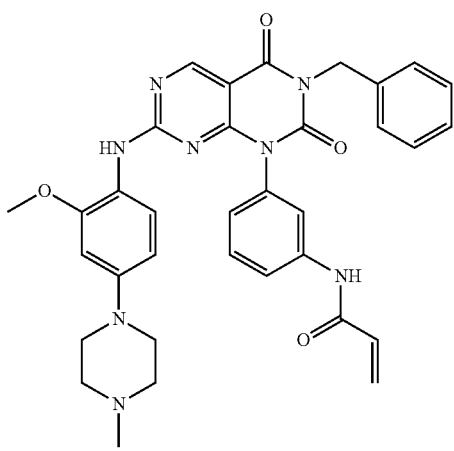 |
| 45A | 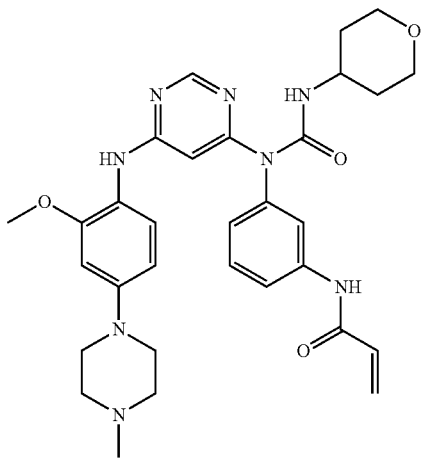 [SMILES: C=CC(=O)Nc1cccc(N(C(=O)NC2CCOCC2)c2cc(Nc3ccc(N4CCN(C)CC4)cc3OC)ncn2)c1] |

| Compound # | Structure |
|---|---|
| 46A | 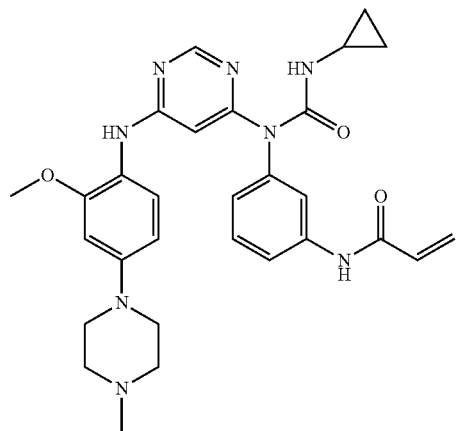 [SMILES: C=CC(=O)Nc1cccc(N(C(=O)NC2CC2)c2cc(Nc3ccc(N4CCN(C)CC4)cc3OC)ncn2)c1] |
| 47A | 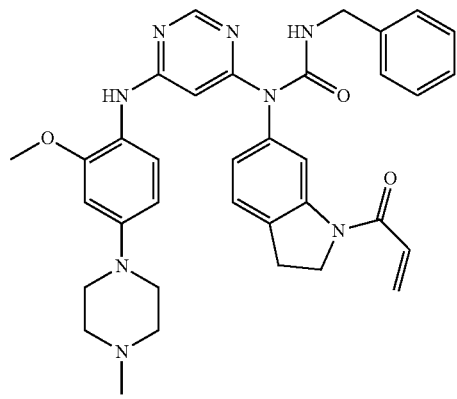 [SMILES: C=CC(=O)N1CCc2ccc(N(C(=O)NCc3ccccc3)c3cc(Nc4ccc(N5CCN(C)CC5)cc4OC)ncn3)cc21] |
| 48A | 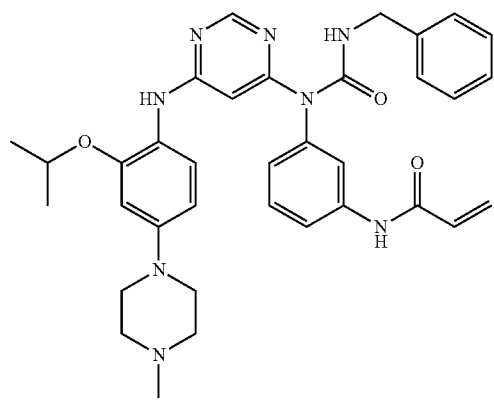 [SMILES: C=CC(=O)Nc1cccc(N(C(=O)NCc2ccccc2)c2cc(Nc3ccc(N4CCN(C)CC4)cc3OC(C)C)ncn2)c1] |

| Compound # | Structure |
|---|---|
| 49A | 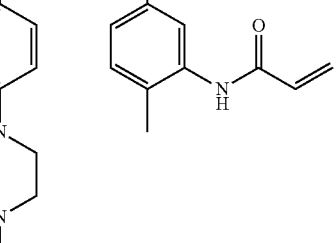 |
| 50A | 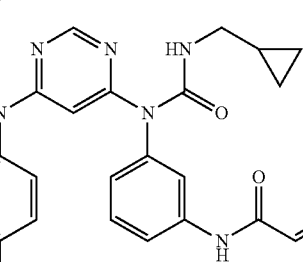 |
| 51A | 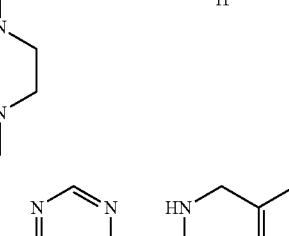 |
| 52A | 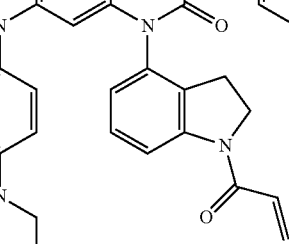 |

-continued
| Compound # | Structure |
|---|---|
| 53A | 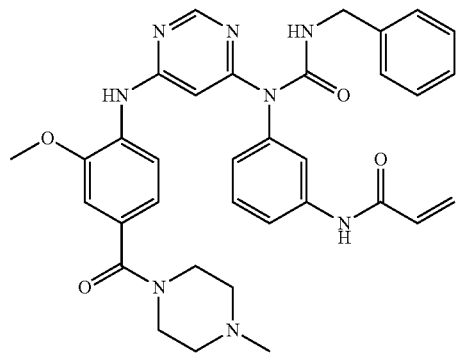 [SMILES: C=CC(=O)Nc1cccc(N(C(=O)NCc2ccccc2)c2cc(Nc3ccc(C(=O)N4CCN(C)CC4)cc3OC)ncn2)c1] |
| 54A | 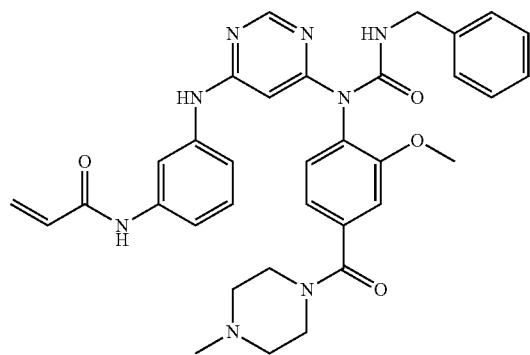 [SMILES: C=CC(=O)Nc1cccc(Nc2cc(N(C(=O)NCc3ccccc3)c3ccc(C(=O)N4CCN(C)CC4)cc3OC)ncn2)c1] |
| 55A | 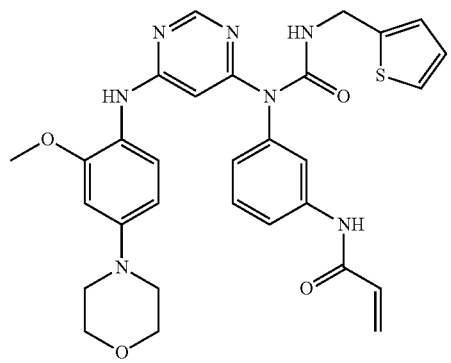 [SMILES: C=CC(=O)Nc1cccc(N(C(=O)NCc2cccs2)c2cc(Nc3ccc(N4CCOCC4)cc3OC)ncn2)c1] |
| 56A | 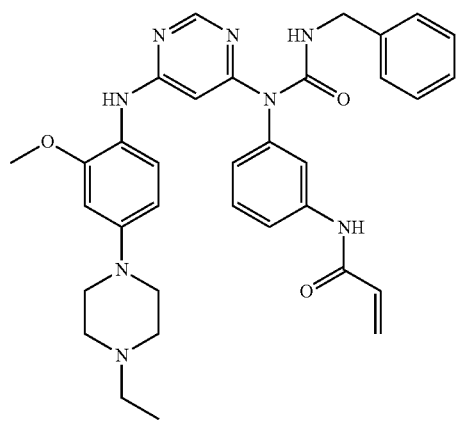 [SMILES: C=CC(=O)Nc1cccc(N(C(=O)NCc2ccccc2)c2cc(Nc3ccc(N4CCN(CC)CC4)cc3OC)ncn2)c1] |

| Compound # | Structure |
|---|---|
| 57A | 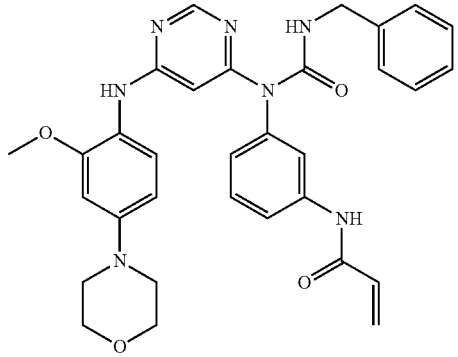 |
| 58A | 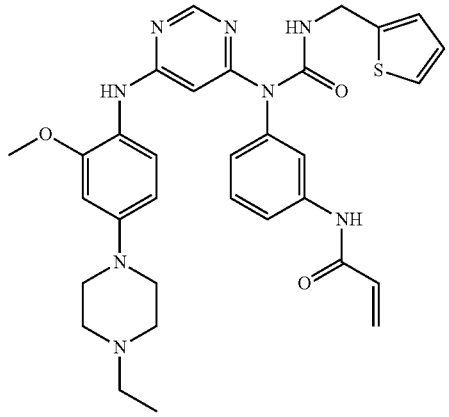 [SMILES: C=CC(=O)Nc1cccc(N(C(=O)NCc2cccs2)c2cc(Nc3ccc(N4CCN(CC)CC4)cc3OC)ncn2)c1] |
| 59A | 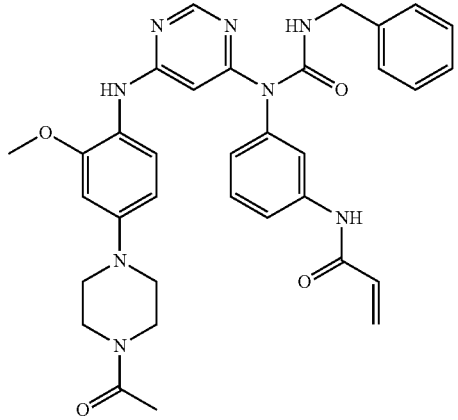 [SMILES: C=CC(=O)Nc1cccc(N(C(=O)NCc2ccccc2)c2cc(Nc3ccc(N4CCN(C(C)=O)CC4)cc3OC)ncn2)c1] |

| Compound # | Structure |
|---|---|
| 60A | 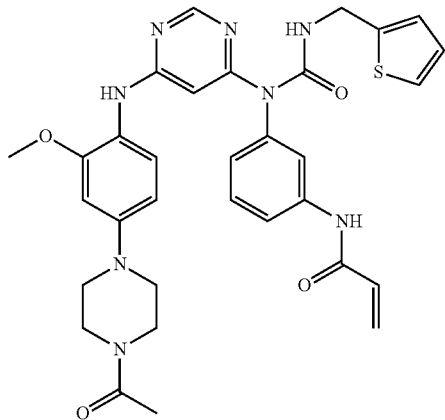 [SMILES: C=CC(=O)Nc1cccc(N(C(=O)NCc2cccs2)c2cc(Nc3ccc(N4CCN(C(C)=O)CC4)cc3OC)ncn2)c1] |
| 61A | 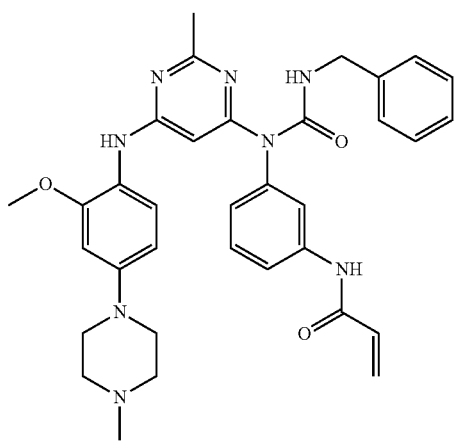 [SMILES: C=CC(=O)Nc1cccc(N(C(=O)NCc2ccccc2)c2cc(Nc3ccc(N4CCN(C)CC4)cc3OC)nc(C)n2)c1] |
| 61B | 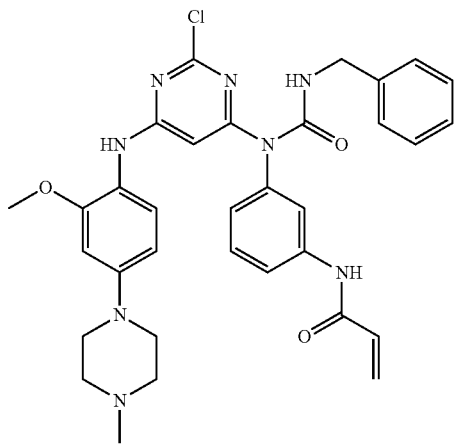 [SMILES: C=CC(=O)Nc1cccc(N(C(=O)NCc2ccccc2)c2cc(Nc3ccc(N4CCN(C)CC4)cc3OC)nc(Cl)n2)c1] |

| Compound # | Structure |
|---|---|
| 62A | 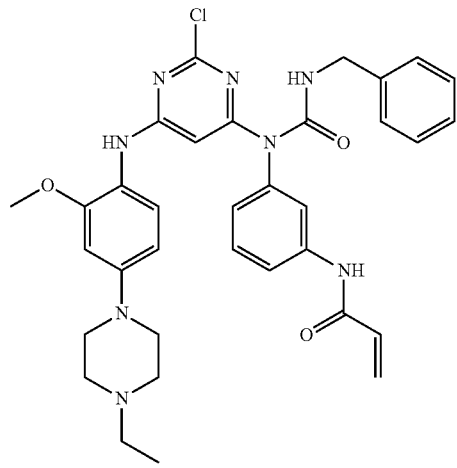 [SMILES: C=CC(=O)Nc1cccc(N(C(=O)NCc2ccccc2)c2cc(Nc3ccc(N4CCN(CC)CC4)cc3OC)nc(Cl)n2)c1] |
| 63A | 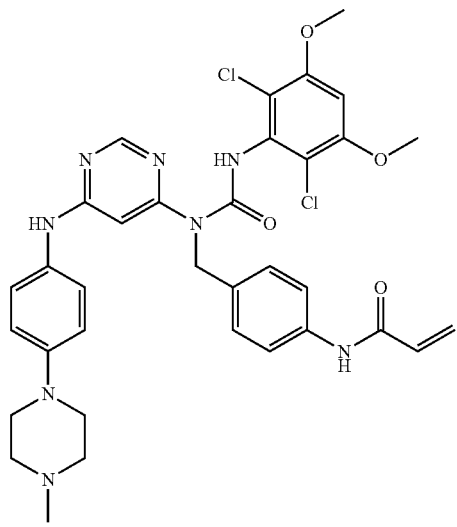 [SMILES: C=CC(=O)Nc1ccc(CN(C(=O)Nc2c(Cl)c(OC)cc(OC)c2Cl)c2cc(Nc3ccc(N4CCN(C)CC4)cc3)ncn2)cc1] |
| 64A | 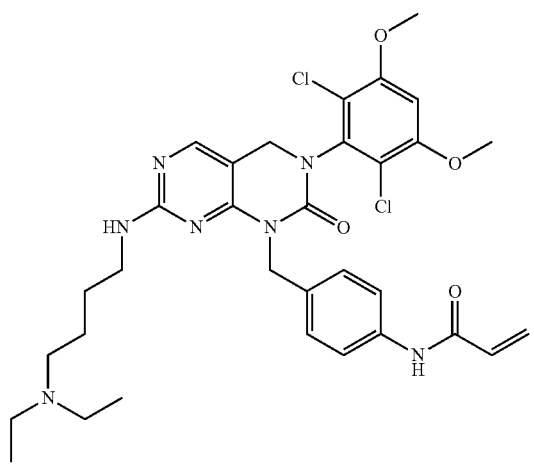 [SMILES: C=CC(=O)Nc1ccc(CN2C(=O)N(c3c(Cl)c(OC)cc(OC)c3Cl)Cc3cnc(NCCCCN(CC)CC)nc32)cc1] |

| Compound # | Structure |
|---|---|
| 65A | 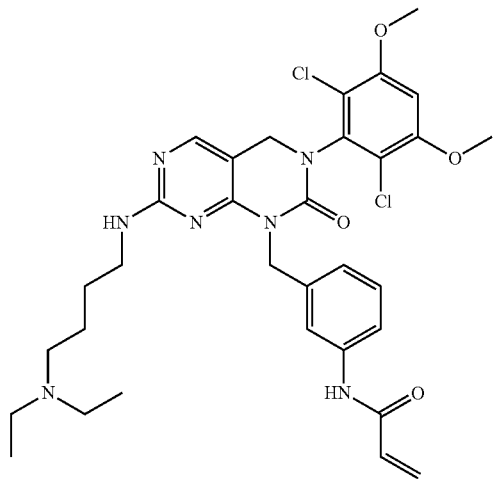 [SMILES: C=CC(=O)Nc1cccc(CN2C(=O)N(c3c(Cl)c(OC)cc(OC)c3Cl)Cc3cnc(NCCCCN(CC)CC)nc32)c1] |
| 66A | 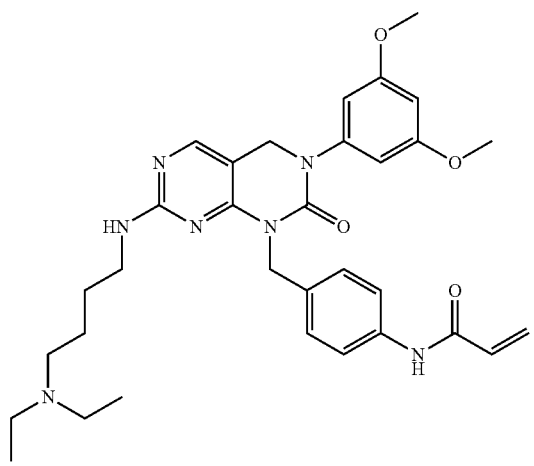 [SMILES: C=CC(=O)Nc1ccc(CN2C(=O)N(c3cc(OC)cc(OC)c3)Cc3cnc(NCCCCN(CC)CC)nc32)cc1] |
| 67A | 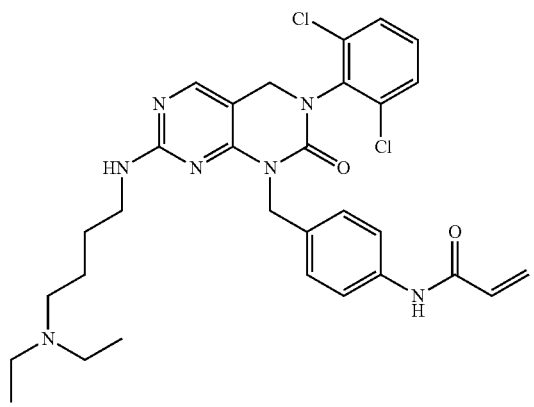 [SMILES: C=CC(=O)Nc1ccc(CN2C(=O)N(c3c(Cl)cccc3Cl)Cc3cnc(NCCCCN(CC)CC)nc32)cc1] |

-continued
| Compound # | Structure |
|---|---|
| 68A | 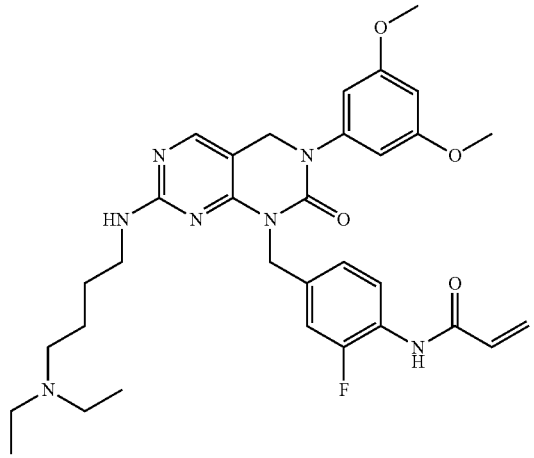 [SMILES: C=CC(=O)Nc1ccc(CN2C(=O)N(c3cc(OC)cc(OC)c3)Cc3cnc(NCCCCN(CC)CC)nc32)cc1F] |
| 69A | 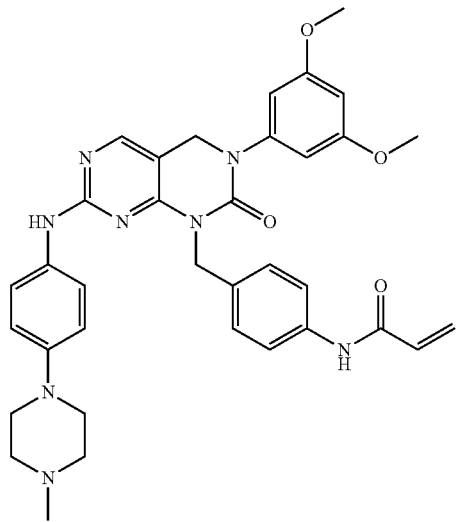 [SMILES: C=CC(=O)Nc1ccc(CN2C(=O)N(c3cc(OC)cc(OC)c3)Cc3cnc(Nc4ccc(N5CCN(C)CC5)cc4)nc32)cc1] |
| 70A | 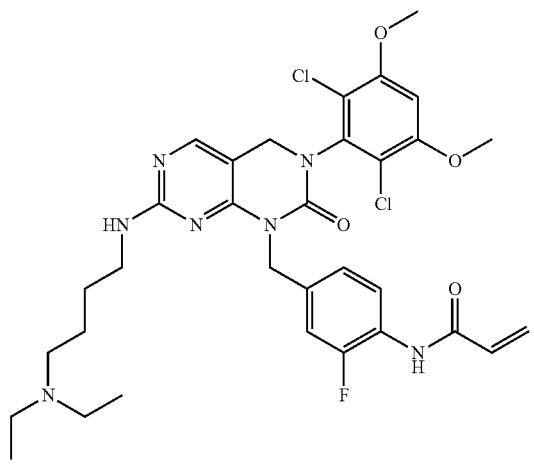 [SMILES: C=CC(=O)Nc1ccc(CN2C(=O)N(c3c(Cl)c(OC)cc(OC)c3Cl)Cc3cnc(NCCCCN(CC)CC)nc32)cc1F] |

-continued
| Compound # | Structure |
|---|---|
| 71A | 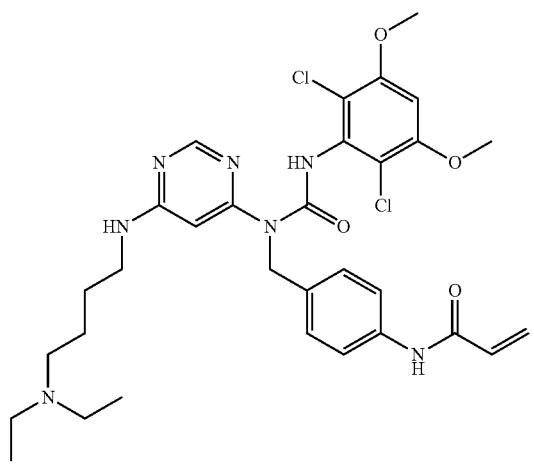 [SMILES: C=CC(=O)Nc1ccc(CN(C(=O)Nc2c(Cl)c(OC)cc(OC)c2Cl)c2cc(NCCCCN(CC)CC)ncn2)cc1] |
| 72A | 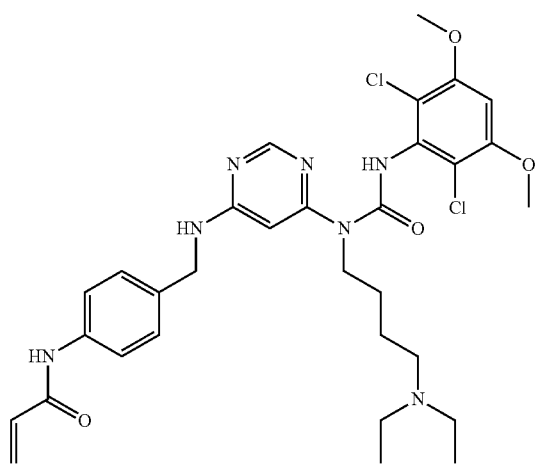 [SMILES: C=CC(=O)Nc1ccc(CNc2cc(N(CCCCN(CC)CC)C(=O)Nc3c(Cl)c(OC)cc(OC)c3Cl)ncn2)cc1] |
| 73A | 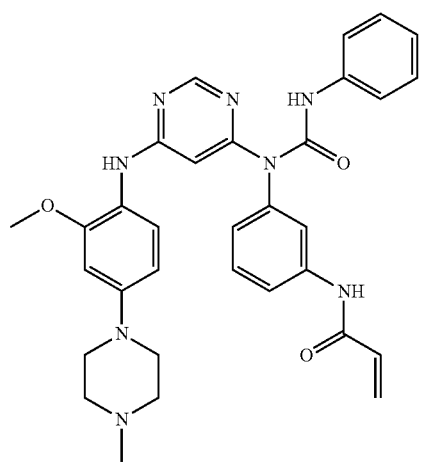 [SMILES: C=CC(=O)Nc1cccc(N(C(=O)Nc2ccccc2)c2cc(Nc3ccc(N4CCN(C)CC4)cc3OC)ncn2)c1] |

| Compound # | Structure |
|---|---|
| 74A | 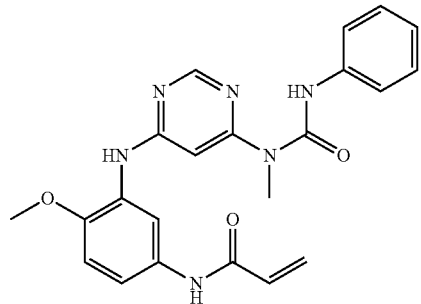 [SMILES: C=CC(=O)Nc1ccc(OC)c(Nc2cc(N(C)C(=O)Nc3ccccc3)ncn2)c1] |
| 75A | 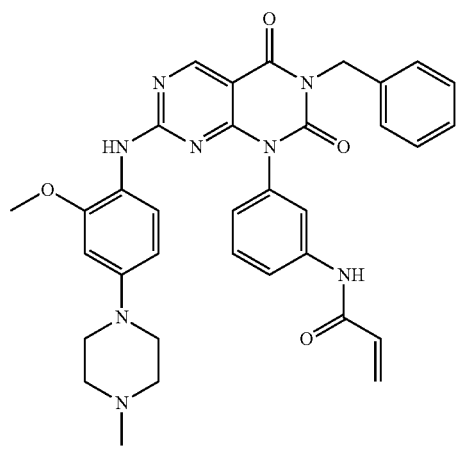 |
| 76A | 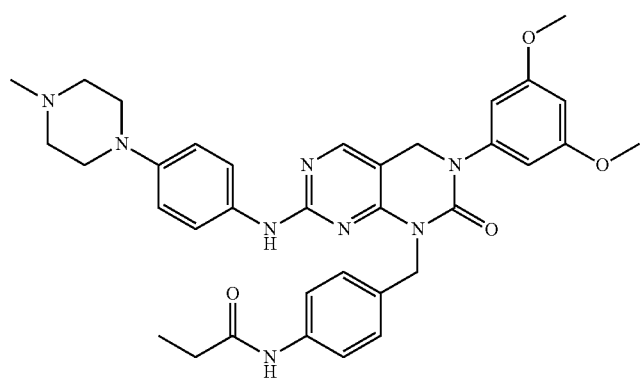 |
| 77A | 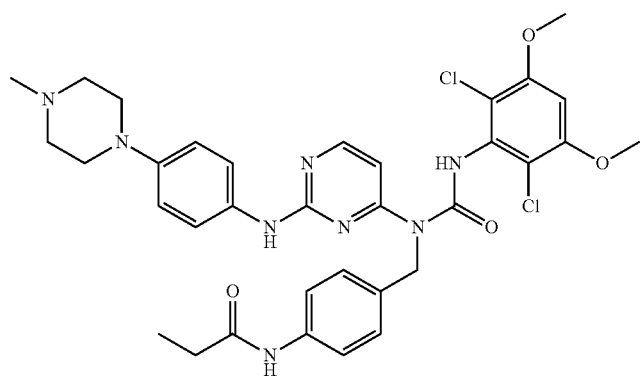 |

| Compound # | Structure |
|---|---|
| 78A | 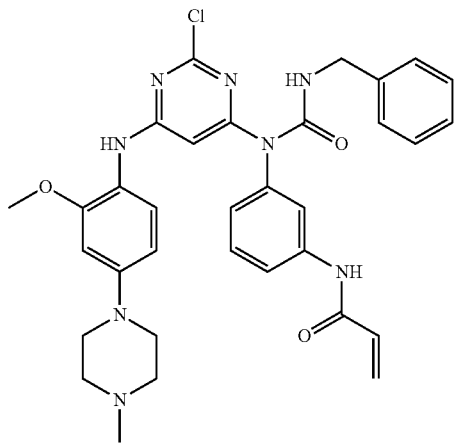 [SMILES: C=CC(=O)Nc1cccc(N(C(=O)NCc2ccccc2)c2cc(Nc3ccc(N4CCN(C)CC4)cc3OC)nc(Cl)n2)c1] |
| 79A | 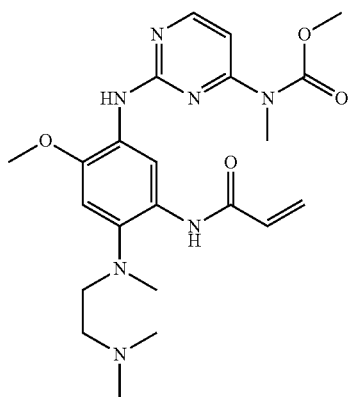 |
| 80A | 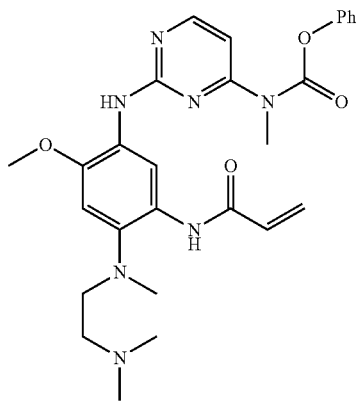 [SMILES: C=CC(=O)Nc1cc(Nc2nccc(N(C)C(=O)Oc3ccccc3)n2)c(OC)cc1N(C)CCN(C)C] |

-continued
| Compound # | Structure |
|---|---|
| 81A | 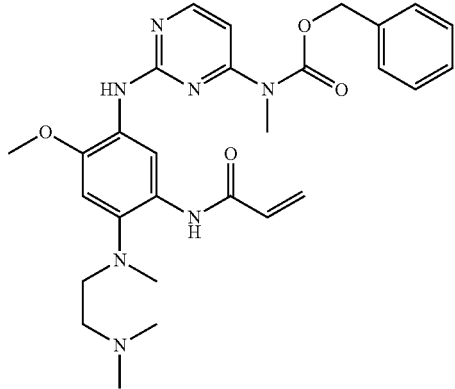 |
| 82A | 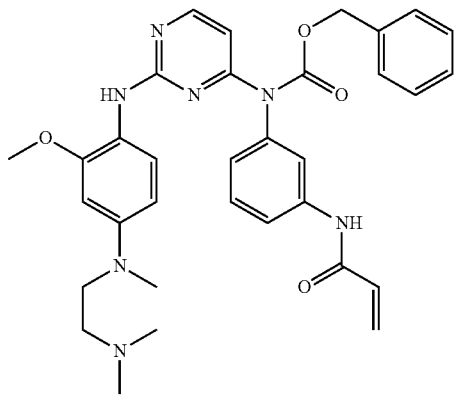 |
| 83A | 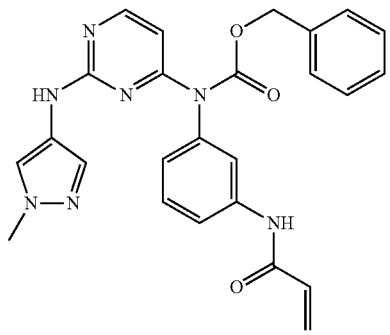 [SMILES: C=CC(=O)Nc1cccc(N(C(=O)OCc2ccccc2)c2ccnc(Nc3cnn(C)c3)n2)c1] |
| 84A | 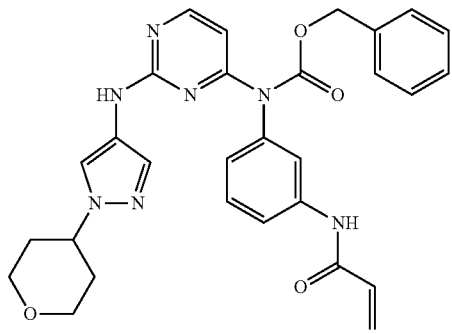 [SMILES: C=CC(=O)Nc1cccc(N(C(=O)OCc2ccccc2)c2ccnc(Nc3cnn(C4CCOCC4)c3)n2)c1] |

-continued
| Compound # | Structure |
|---|---|
| 85A | 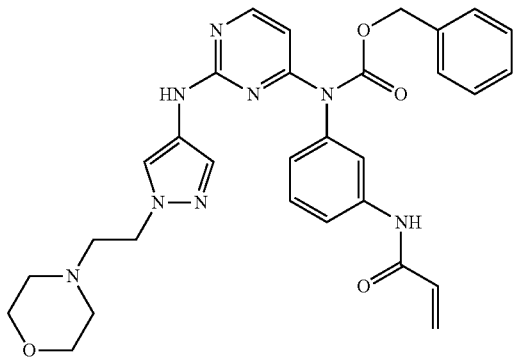 [SMILES: C=CC(=O)Nc1cccc(N(C(=O)OCc2ccccc2)c2ccnc(Nc3cnn(CCN4CCOCC4)c3)n2)c1] |
| 86A | 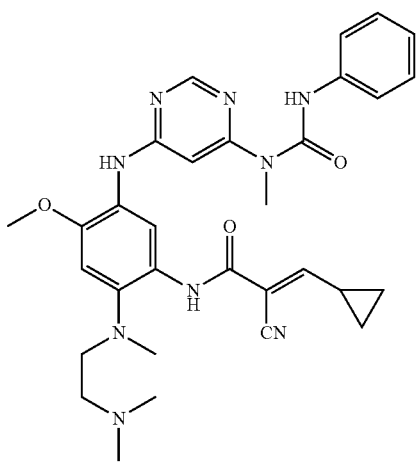 [SMILES: COc1cc(N(C)CCN(C)C)c(NC(=O)/C(C#N)=C/C2CC2)cc1Nc1cc(N(C)C(=O)Nc2ccccc2)ncn1] |
| 87A | 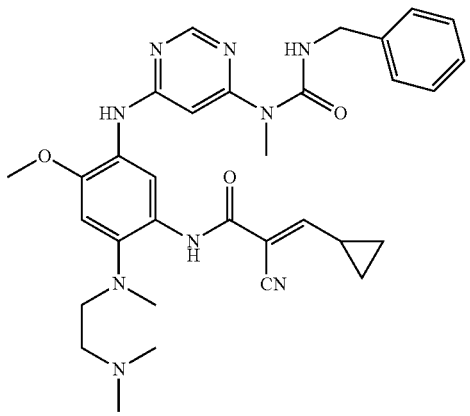 [SMILES: COc1cc(N(C)CCN(C)C)c(NC(=O)/C(C#N)=C/C2CC2)cc1Nc1cc(N(C)C(=O)NCc2ccccc2)ncn1] |

-continued
| Compound # | Structure |
|---|---|
| 88A | 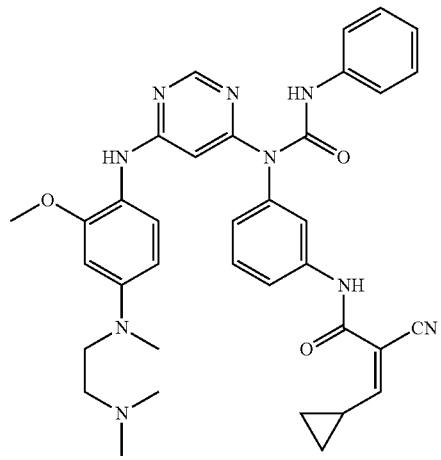 [SMILES: COc1cc(N(C)CCN(C)C)ccc1Nc1cc(N(C(=O)Nc2ccccc2)c2cccc(NC(=O)/C(C#N)=C\C3CC3)c2)ncn1] |
| 89A | 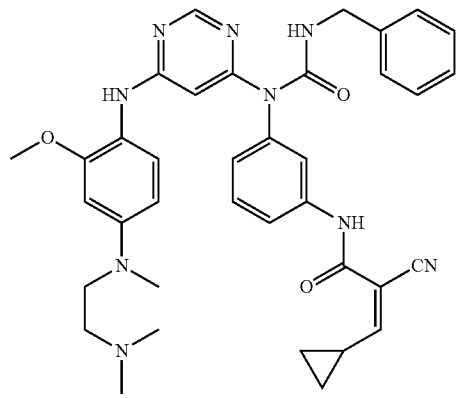 [SMILES: COc1cc(N(C)CCN(C)C)ccc1Nc1cc(N(C(=O)NCc2ccccc2)c2cccc(NC(=O)/C(C#N)=C\C3CC3)c2)ncn1] |
| 90A | 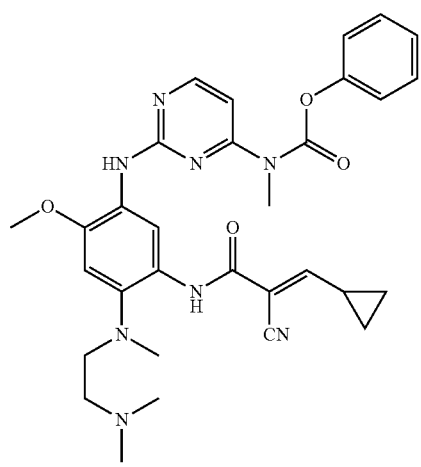 [SMILES: COc1cc(N(C)CCN(C)C)c(NC(=O)/C(C#N)=C/C2CC2)cc1Nc1nccc(N(C)C(=O)Oc2ccccc2)n1] |

| Compound # | Structure |
|---|---|
| 91A | 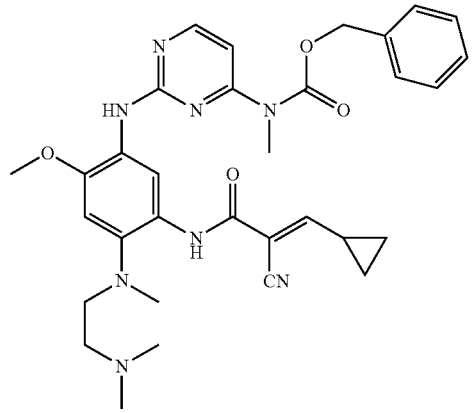 [SMILES: COc1cc(N(C)CCN(C)C)c(NC(=O)/C(C#N)=C/C2CC2)cc1Nc1nccc(N(C)C(=O)OCc2ccccc2)n1] |
| 92A | 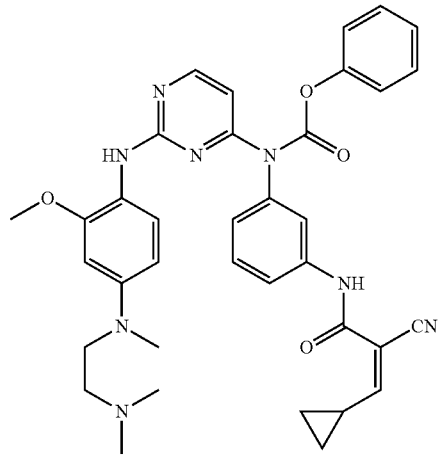 [SMILES: COc1cc(N(C)CCN(C)C)ccc1Nc1nccc(N(C(=O)Oc2ccccc2)c2cccc(NC(=O)/C(C#N)=C\C3CC3)c2)n1] |
| 93A | 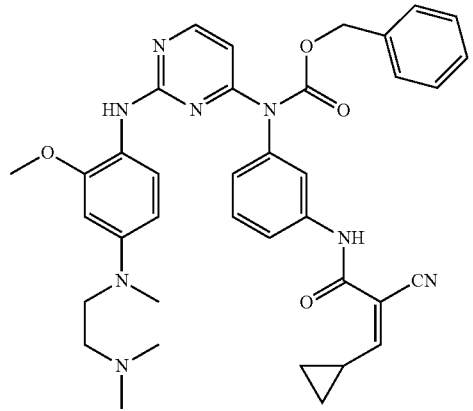 [SMILES: COc1cc(N(C)CCN(C)C)ccc1Nc1nccc(N(C(=O)OCc2ccccc2)c2cccc(NC(=O)/C(C#N)=C\C3CC3)c2)n1] |

| Compound # | Structure |
|---|---|
| 94A | 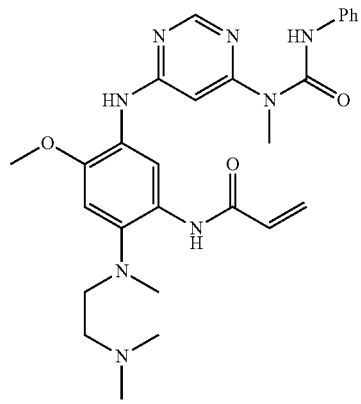 [SMILES: C=CC(=O)Nc1cc(Nc2cc(N(C)C(=O)Nc3ccccc3)ncn2)c(OC)cc1N(C)CCN(C)C] |
| 95A | 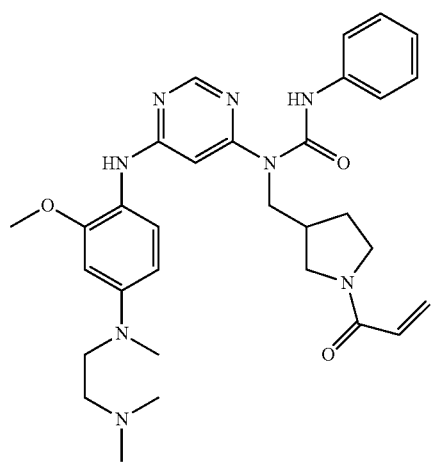 [SMILES: C=CC(=O)N1CCC(CN(C(=O)Nc2ccccc2)c2cc(Nc3ccc(N(C)CCN(C)C)cc3OC)ncn2)C1] |
| 96A | 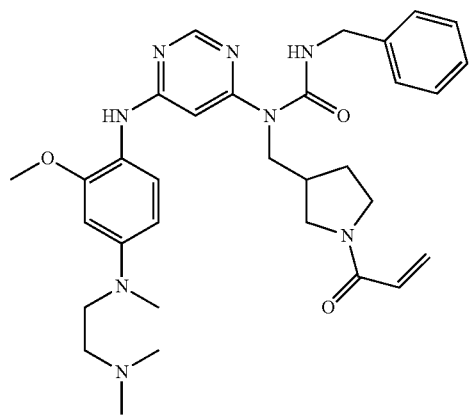 [SMILES: C=CC(=O)N1CCC(CN(C(=O)NCc2ccccc2)c2cc(Nc3ccc(N(C)CCN(C)C)cc3OC)ncn2)C1] |

| Compound # | Structure |
|---|---|
| 97A | 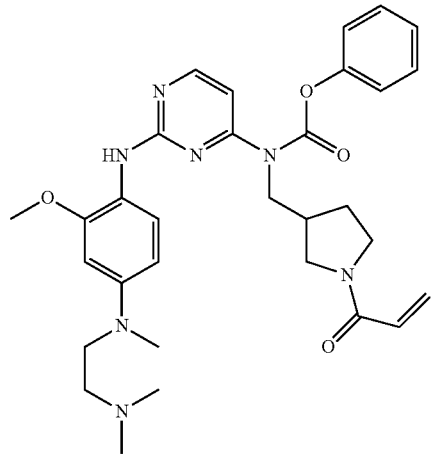 [SMILES: C=CC(=O)N1CCC(CN(C(=O)Oc2ccccc2)c2ccnc(Nc3ccc(N(C)CCN(C)C)cc3OC)n2)C1] |
| 98A | 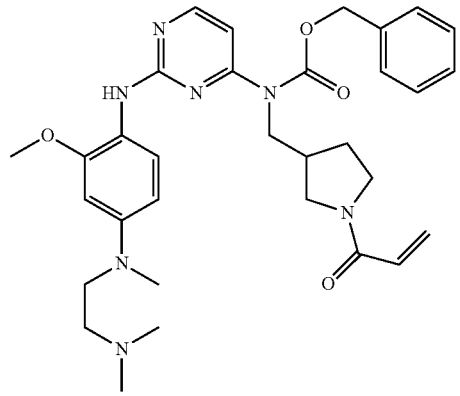 [SMILES: C=CC(=O)N1CCC(CN(C(=O)OCc2ccccc2)c2ccnc(Nc3ccc(N(C)CCN(C)C)cc3OC)n2)C1] |
| 99A | 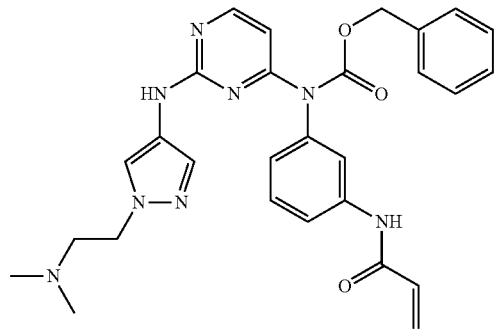 [SMILES: C=CC(=O)Nc1cccc(N(C(=O)OCc2ccccc2)c2ccnc(Nc3cnn(CCN(C)C)c3)n2)c1] |

| Compound # | Structure |
|---|---|
| 100A | 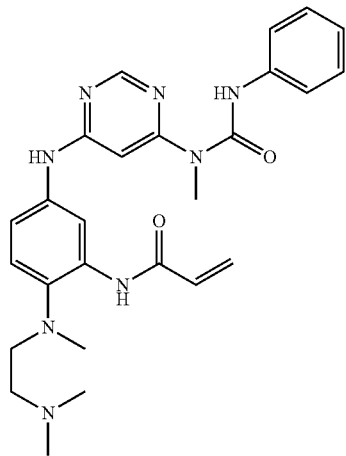 [SMILES: C=CC(=O)Nc1cc(Nc2cc(N(C)C(=O)Nc3ccccc3)ncn2)ccc1N(C)CCN(C)C] |
| 101A | 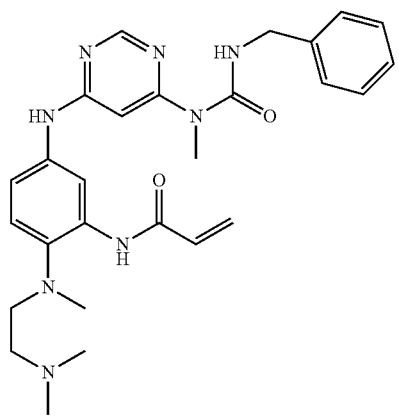 [SMILES: C=CC(=O)Nc1cc(Nc2cc(N(C)C(=O)NCc3ccccc3)ncn2)ccc1N(C)CCN(C)C] |
| 102A | 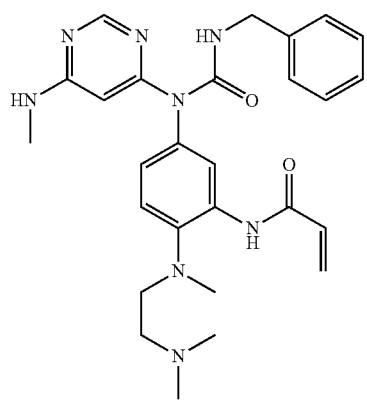 [SMILES: C=CC(=O)Nc1cc(N(C(=O)NCc2ccccc2)c2cc(NC)ncn2)ccc1N(C)CCN(C)C] |

| Compound # | Structure |
|---|---|
| 103A | 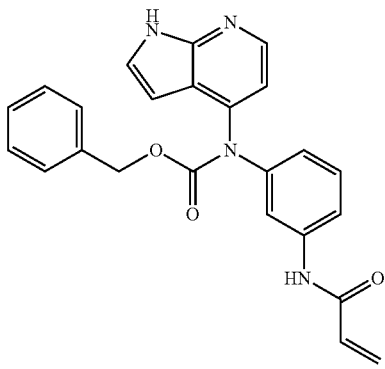 [SMILES: C=CC(=O)Nc1cccc(N(C(=O)OCc2ccccc2)c2ccnc3[nH]ccc23)c1] |
| 104A | 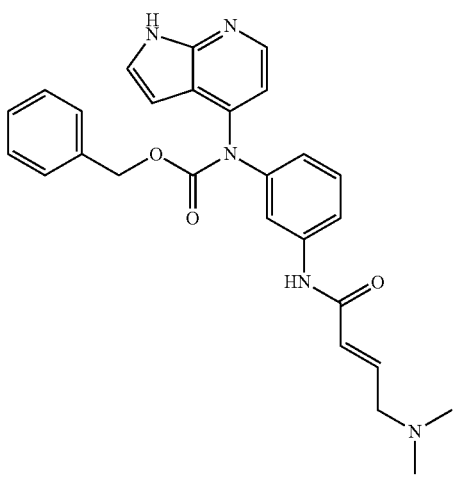 [SMILES: CN(C)C/C=C/C(=O)Nc1cccc(N(C(=O)OCc2ccccc2)c2ccnc3[nH]ccc23)c1] |
| 105A | 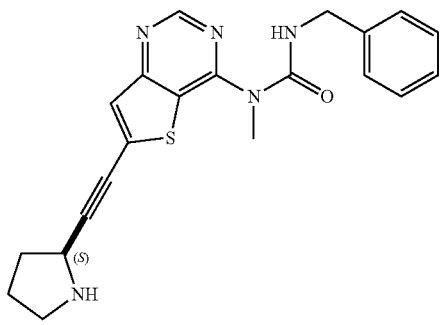 |

The invention includes a pharmaceutical composition comprising a compound of the invention or a pharmaceutically acceptable salt thereof and a pharmaceutical carrier, diluent, or excipient.

The present invention relates to a method of synthesizing a compound of the invention or a pharmaceutically acceptable salt thereof. A compound of the invention can be synthesized using a variety of methods known in the art.

Compounds of the present invention can be prepared in a variety of ways using commercially available starting materials and compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 5th edition, John Wiley & Sons: New York, 2001; and Greene, T. W., Wuts, P. G. M., Protective Groups in Organic Synthesis, 3rd edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.
General Synthesis Schemes
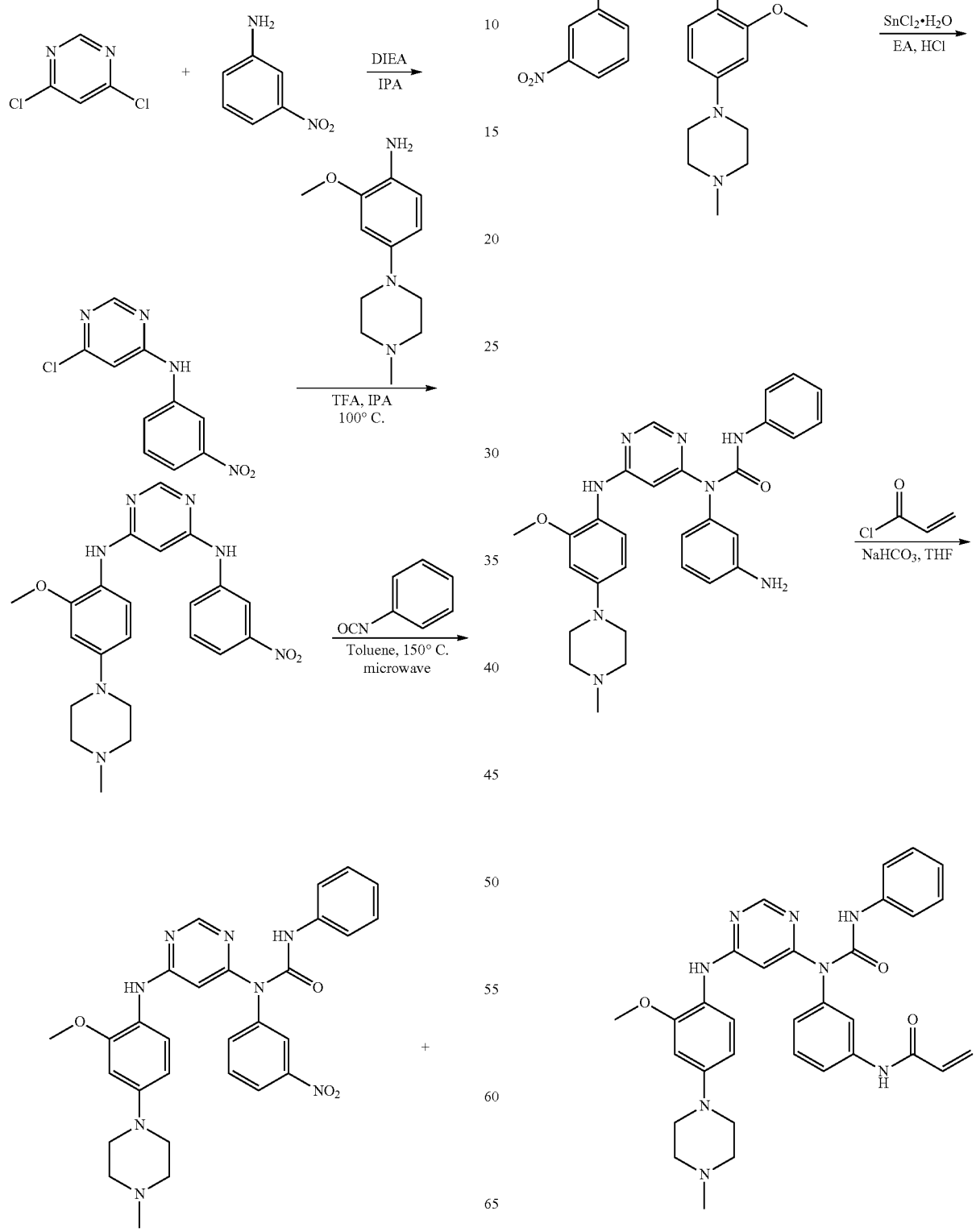

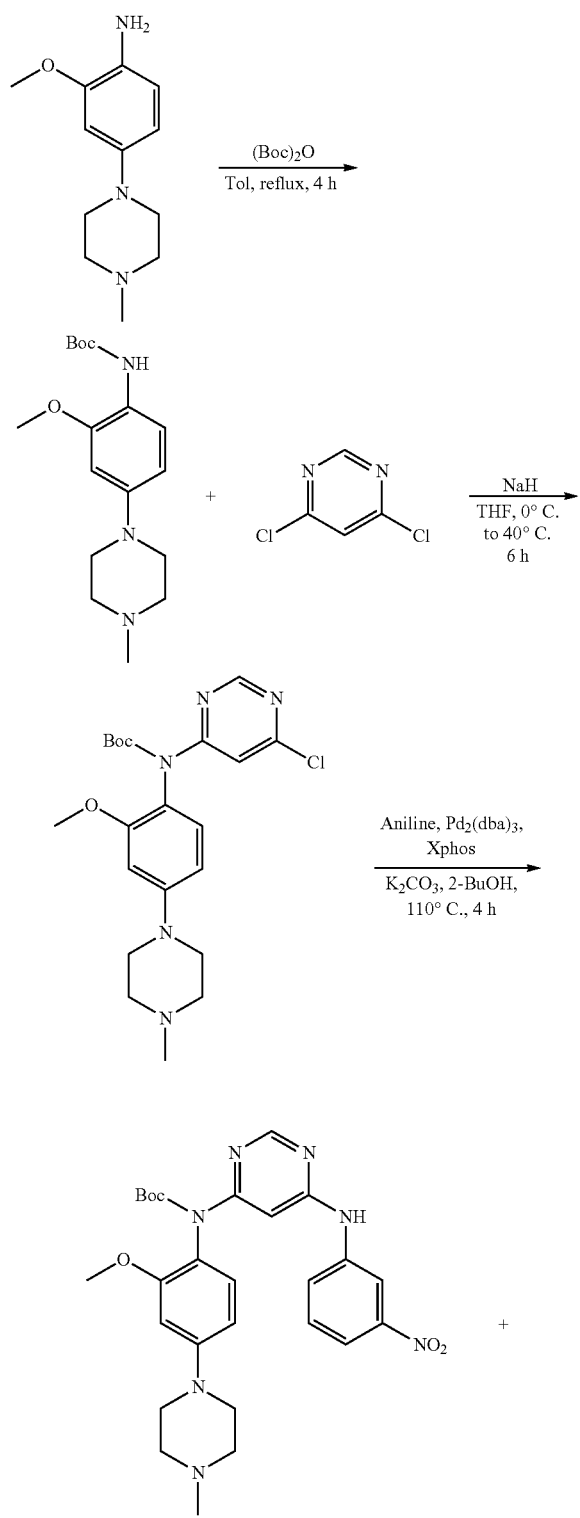
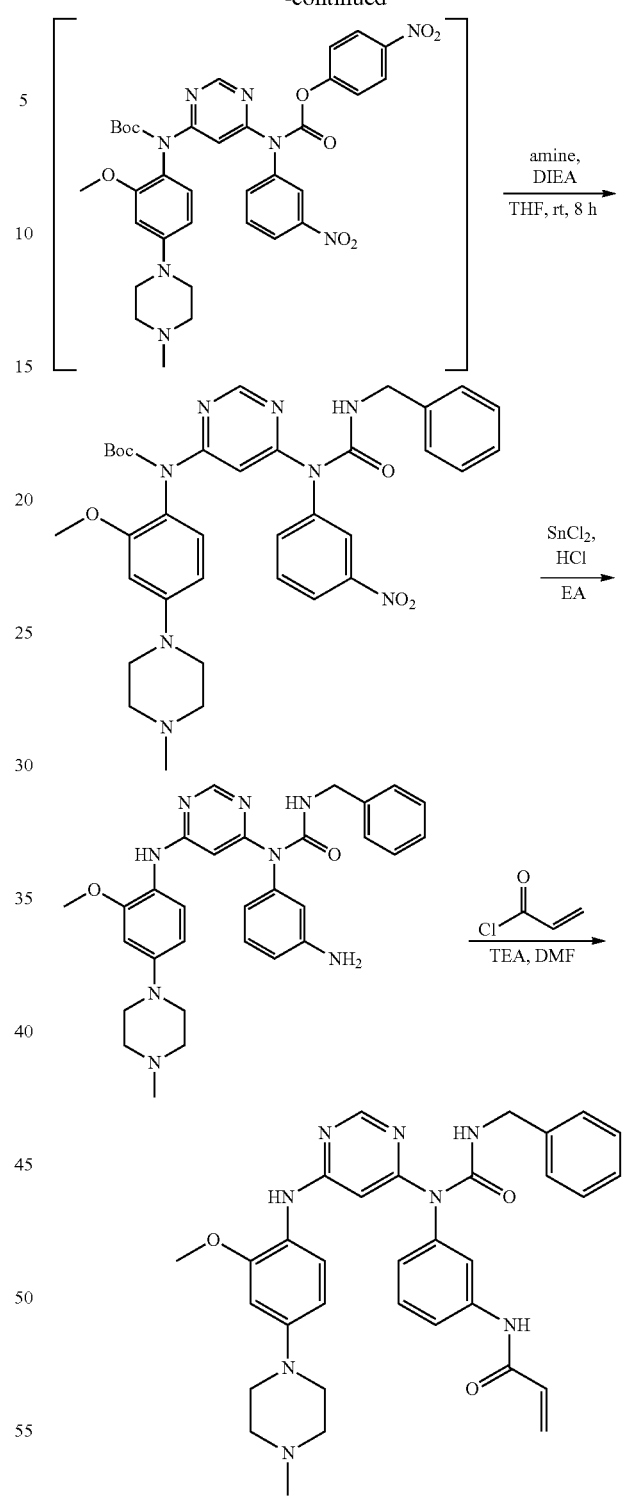

85
-continued
86
-continued
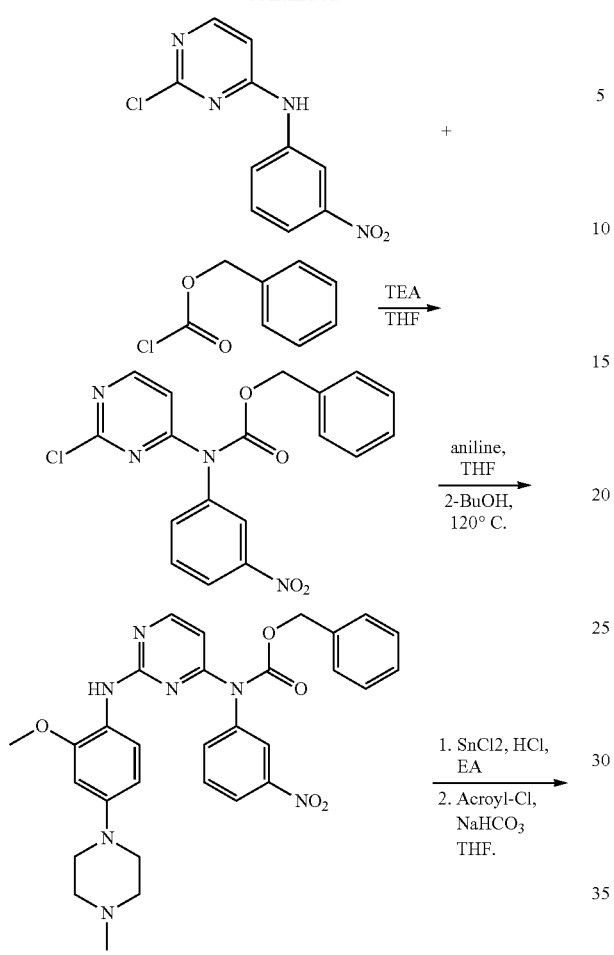
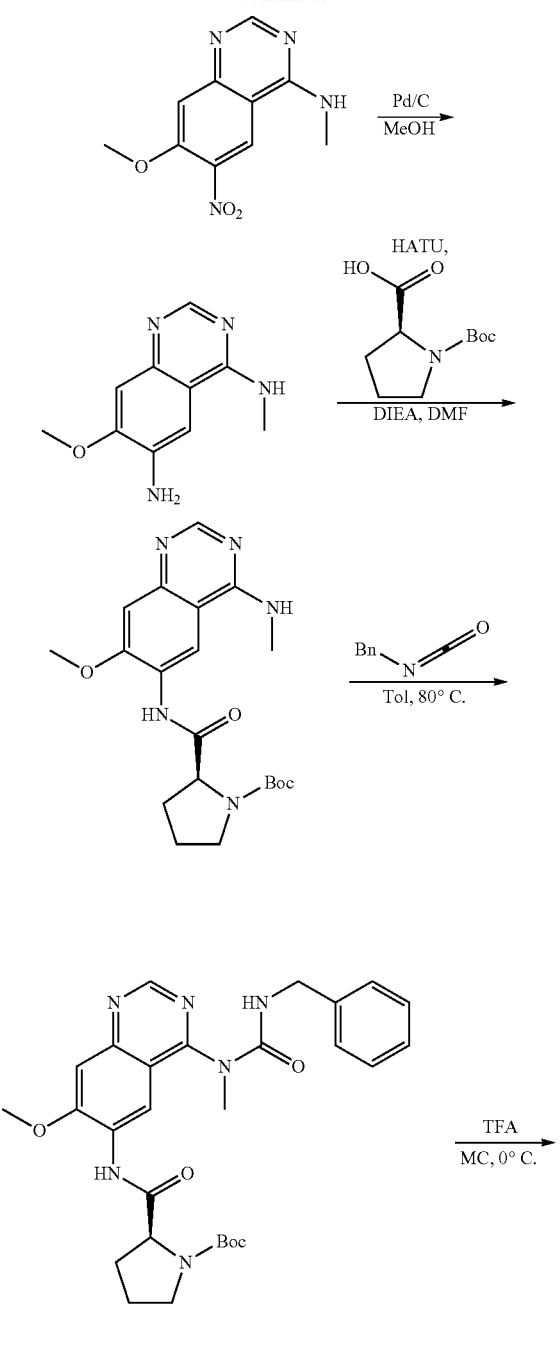
Scheme 4.
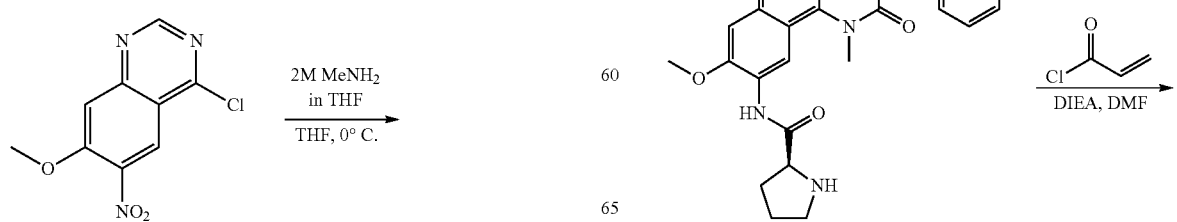

87
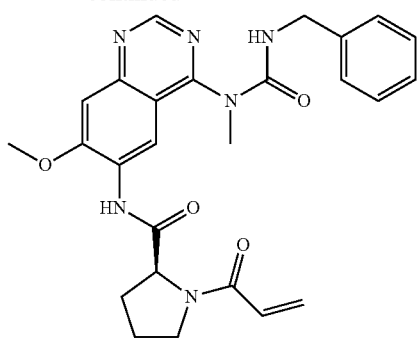
88
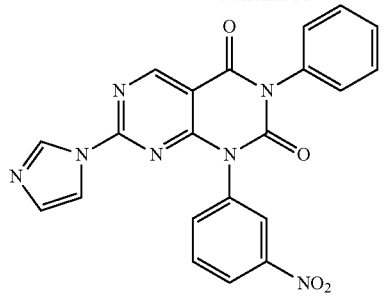
aniline,
TFA
2-BuOH
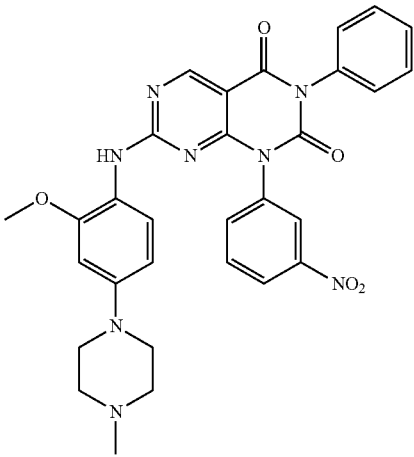
SnCl₂,
HCl
EA
Scheme 5.
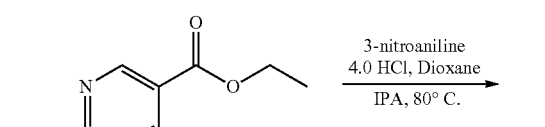
3-nitroaniline
4.0 HCl, Dioxane
IPA, 80° C.
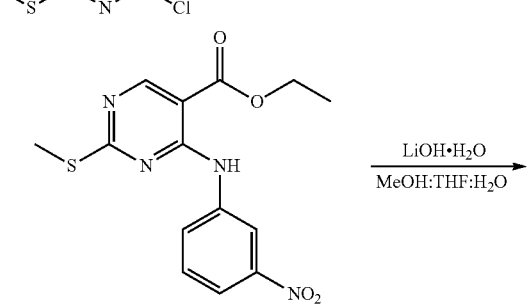
LiOH·H₂O
MeOH:THF:H₂O
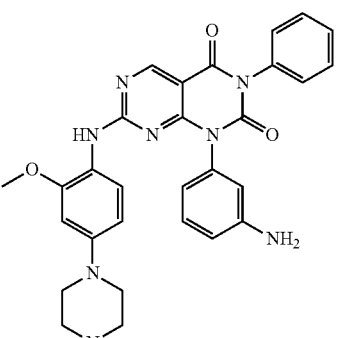
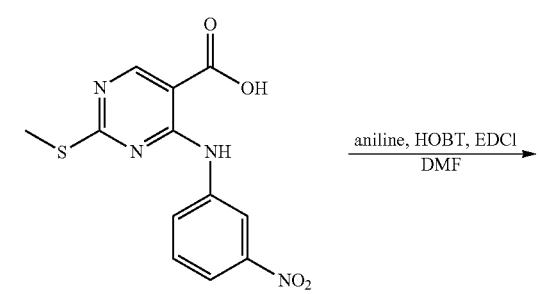
aniline, HOBT, EDCl
DMF
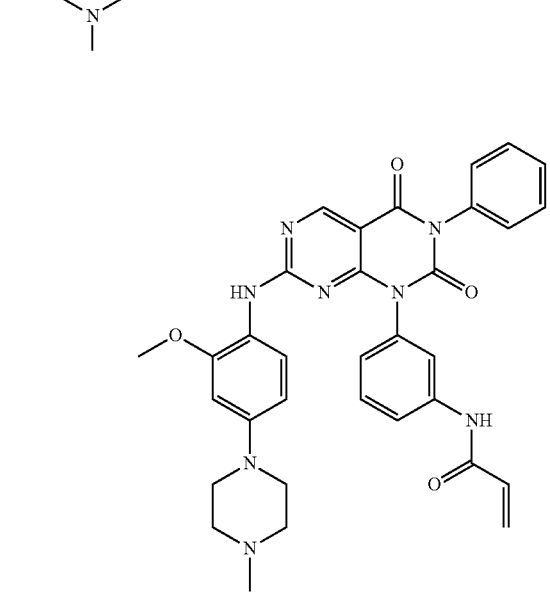
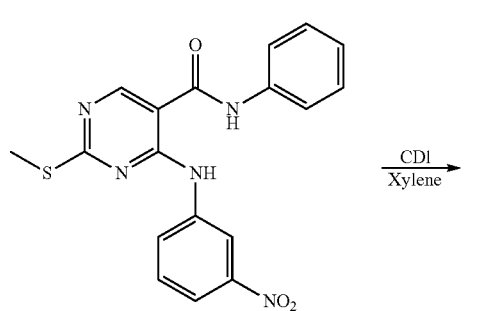
CDI
Xylene

Scheme 6.

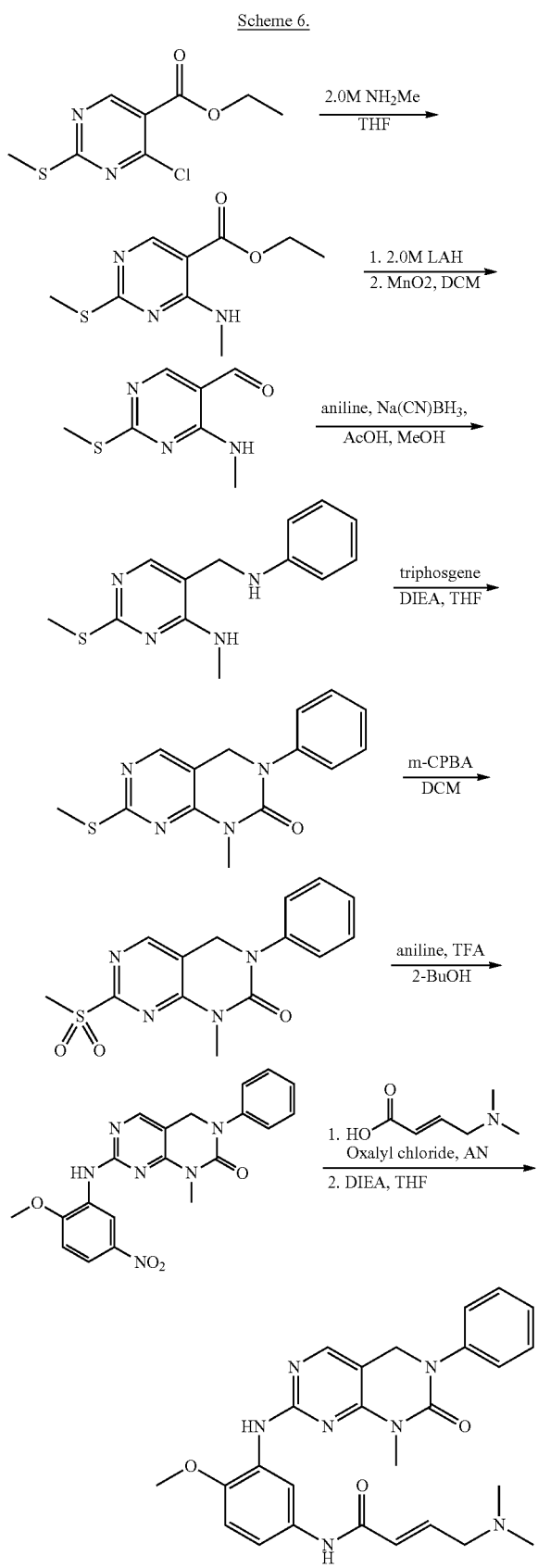

Methods of Use

The invention relates to methods for the use of compounds of the invention. The compounds of the invention have a useful pharmacological activity spectrum and are therefore particularly suitable for the prophylaxis and/or treatment of disease.

The invention provides the use of a compound of the invention for the preparation of a medicament for administration to a subject for use in the treatment and/or prevention of disease. In one aspect, the medicament is for use in treatment. In one aspect, the medicament is for use in prevention.

The invention provides a method of inhibiting a kinase in a subject, comprising administering to the subject in need thereof a compound of the invention or a pharmaceutically acceptable salt thereof. In one aspect, the invention provides a method of inhibiting epidermal growth factor receptor (EGFR) in a subject, comprising administering to the subject a compound of the invention or a pharmaceutically acceptable salt thereof. In one aspect, the EGFR is Her-Kinase. In another aspect, the invention provides a method of inhibiting fibroblast growth factor receptor (FGFR) in a subject, comprising administering to the subject a compound of the invention or a pharmaceutically acceptable salt thereof. In yet another aspect, the invention provides a method of inhibiting fibroblast growth factor receptor (FGFR) and epidermal growth factor receptor (EGFR) in a subject, comprising administering to the subject a compound of the invention or a pharmaceutically acceptable salt thereof.

The invention provides a method of treating and/or preventing a disease in a subject comprising administering to the subject in need thereof a compound of the invention or a pharmaceutically acceptable salt thereof. In one aspect, the disease is mediated by a kinase. Further illustrating this aspect, the disease is mediated by EGFR and/or FGFR.

In one subclass, the disease is cancer or a proliferation disease. Exemplifying this aspect, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In one aspect, the disease is lung cancer. In one aspect, the lung cancer is non-small cell lung cancer (NSCLC).

In another subclass, the disease is inflammation, arthritis, rheumatoid arthritis, spondyloarthropathies, gouty arthritis, osteoarthritis, juvenile arthritis, and other arthritic conditions, systemic lupus erythematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoidosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body, chronic myelogenous leukemia (CML), acute myeloid leukemia (AML) and acute promyelocyte leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy, or B-Cell Lymphoma.

In another aspect, the disease is inflammation, arthritis, rheumatoid arthritis, spondyloarthropathies, gouty arthritis, osteoarthritis, juvenile arthritis, and other arthritic conditions, systemic lupus erythematosus (SLE), skin-related conditions, psoriasis, eczema, dermatitis, pain, pulmonary disorders, lung inflammation, adult respiratory distress syndrome, pulmonary sarcoidosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia, or lymphoma.

The invention provides a method of treating a kinase mediated disorder in a subject comprising administering to the subject in need thereof a compound of the invention or a pharmaceutically acceptable salt thereof. In one aspect, the compound covalently modifies one or more of ALK, ROS1, EGFR, and FGFR tyrosine kinases.

The invention provides a method of treating a kinase mediated disorder in a subject comprising administering to the subject in need thereof a compound of the invention or a pharmaceutically acceptable salt thereof, and the subject is administered an additional therapeutic agent. The additional therapeutic agent can be any therapeutic agent. In another aspect, the compound and the additional therapeutic agent are administered simultaneously or sequentially.

The invention provides a method of treating a disease in a subject, wherein the disease is resistant to an EGFR targeted therapy, comprising administering to the subject in need thereof a compound of the invention or a pharmaceutically acceptable salt thereof. In one aspect, the EGFR targeted therapy comprises treatment with gefitinib, erlotinib, lapatinib, XL-647, HKI-272, BIBW2992, AV-412, CI-1033, PF00299804, BMS 690514, cetuximab, panitumumab, or matuzumab. In one aspect, the disease comprises an EGFR mutation. In one aspect, the EGFR mutation is an EGFR T790M, T854A, D761Y or L718Q resistance mutation. In another aspect, EGFR L718Q is a resistance mutation to the compound WZ4002 (a third generation EGFR inhibitor) and other compounds in the same class as WZ4002. In one aspect, the L718Q resistance mutation is present with the activating mutation alone or with an activating mutation and the T790M mutation. In one aspect, the L718Q resistance mutation is present with the activating mutation L858R alone. In one aspect, the L718Q resistance mutation is present with the activating mutation L858R and the TM790 mutation. In a further aspect, the disease is cancer. Further illustrating this aspect, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In one aspect, the disease is lung cancer. In one aspect, the lung cancer is non-small cell lung cancer (NSCLC). The invention includes a method of treating cancer in a subject, wherein the cancer comprises EGFR activated tumors, comprising administering to the subject in need thereof a compound of the invention or a pharmaceutically acceptable salt thereof. In one aspect, the EGFR activation is selected from mutation of EGFR, amplification of EGFR, expression of EGFR, and ligand mediated activation of EGFR. In one aspect, the mutation of EGFR is located at G719S, G719C, G719A, L858R, L861Q, an exon 19 deletion mutation or an exon 20 insertion mutation. In one aspect, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In one aspect, the cancer is lung cancer. In one aspect, the lung cancer is non-small cell lung cancer (NSCLC).

The invention includes a method of preventing resistance to gefitnib or erlotinib in a disease in a subject, comprising administering to a subject in need thereof a compound of the invention or a pharmaceutically acceptable salt thereof. In one aspect, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In one aspect, the disease is lung cancer. In one aspect, the lung cancer is non-small cell lung cancer (NSCLC).

The invention includes a method as described herein, wherein the subject is human.

Pharmaceutical Compositions

The invention provides a pharmaceutical composition comprising a compound of the invention or a pharmaceutically acceptable salt thereof, together with a pharmaceutically acceptable carrier.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances.

Suitable formulations for transdermal applications include an effective amount of a compound of the invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other anti-proliferative, anti-cancer, immunomodulatory or anti-inflammatory substances. Where the compounds of the invention are administered in conjunction with other therapies, dosages of the co-administered compounds will vary depending on the type of co-drug employed, on the specific drug employed, on the condition being treated and so forth.

Combination therapy includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, a compound of the invention may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g., HER2/neu, HER3, HER4, ErbB, ErbB2, ErbB3, ErbB4, Xmrk, DER, Let23); fibroblast growth factor (FGF) receptor (e.g., FGF-R1, GFF-R2/BEK/CEK3, FGF-R3/CEK2, FGF-R4ATKF, KGF-R); hepatocyte growth/scatter factor receptor (HGFR) (e.g, MET, RON, SEA, SEX); insulin receptor (e.g., IGFI-R); Eph (e.g., CEK5, CEK8, EBK, ECK, EEK, EHK-I, EHK-2, ELK, EPH, ERK, HEK, MDK2, MDK5, SEK); AxI (e.g., Mer/Nyk, Rse); RET; and platelet-derived growth factor receptor (PDGFR) (e.g., PDGF.alpha.-R, PDG.beta.-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g., p43.sup.abl, ARG); BTK (e.g., ITK/EMT, TEC); CSK, FAK, FPS, JAK, SRC, BMX, FER, CDK and SYK.

In another aspect of the invention, a compound of the invention may be administered in combination with one or more agents that modulate non-kinase biological targets or processes. Such targets include histone deacetylases (HDAC), DNA methyltransferase (DNMT), heat shock proteins (e.g., HSP90), and proteosomes. In one embodiment, a compound of the invention may be combined with antineoplastic agents (e.g., small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG 108, BMS387032, Affinitak, Avastin, Herceptin, Erbitux, AG24322, PD325901, ZD6474, PDl 84322, Obatodax, ABT737 and AEE788. Such combinations may enhance therapeutic efficacy over efficacy achieved by any of the agents alone and may prevent or delay the appearance of resistant mutational variants.

In one embodiment, a compound of the invention is administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cis-platin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplasties such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA). In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, a compound of the invention is administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that a compound of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121: 487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that a compound of the invention may advantageously be used in conjunction with one or more adjunctive therapeutic agents. Examples of suitable agents for adjunctive therapy include a 5HTi agonist, such as a triptan (e.g., sumatriptan or naratriptan); an adenosine A1 agonist; an EP ligand; an NMDA modulator, such as a glycine antagonist; a sodium channel blocker (e.g., lamotrigine); a substance P antagonist (e.g., an NKi antagonist); a cannabinoid; acetaminophen or phenacetin; a 5-lipoxygenase inhibitor; a leukotriene receptor antagonist; a DMARD (e.g., methotrexate); gabapentin and related compounds; a tricyclic antidepressant (e.g., amitryptilline); a neurone stabilising antiepileptic drug; a mono-aminergic uptake inhibitor (e.g., venlafaxine); a matrix metalloproteinase inhibitor; a nitric oxide synthase (NOS) inhibitor, such as an iNOS or an nNOS inhibitor; an inhibitor of the release, or action, of tumour necrosis factor a; an antibody therapy, such as a monoclonal antibody therapy; an antiviral agent, such as a nucleoside inhibitor (e.g., lamivudine) or an immune system modulator (e.g., interferon); an opioid analgesic; a local anaesthetic; a stimulant, including caffeine; an $H_2$-antagonist (e.g., ranitidine); a proton pump inhibitor (e.g., omeprazole); an antacid (e.g., aluminium or magnesium hydroxide; an antiflatulent (e.g., simethicone); a decongestant (e.g., phenylephrine, phenylpropanolamine, pseudoephedrine, oxymetazoline, epinephrine, naphazoline, xylometazoline, propylhexedrine, or levo-desoxyephedrine); an antitussive (e.g., codeine, hydrocodone, carmiphen, carbetapentane, or dextramethorphan); a diuretic; or a sedating or non-sedating antihistamine.

The pharmaceutical compositions of the invention comprise a therapeutically effective amount of a compound of the invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracistemally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, diseases are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention, as used herein, means a sufficient amount of the compound so as to decrease the symptoms of a disorder in a subject. As is well understood in the medical arts a therapeutically effective amount of a compound of this invention will be at a reasonable benefit/risk ratio applicable to any medical treatment. In general, a compound of the invention will be administered in a therapeutically effective amount via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In certain embodiments, a therapeutic amount or dose of a compound of the invention may range from about 0.1 mg/Kg to about 500 mg/Kg, alternatively from about 1 to about 50 mg/Kg. In general, treatment regimens according to the invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents. Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The invention also provides for a pharmaceutical combinations, e.g., a kit, comprising a) a first agent which is a compound of the invention as disclosed herein, in free form or in pharmaceutically acceptable salt form, and b) at least one co-agent. The kit can comprise instructions for its administration. The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the invention and a co-agent, are both administered to a patient simultaneously in the form of a single entity or dosage. The term "non-fixed combination" means that the active ingredients, e.g., a compound of the invention and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

In certain embodiments, these compositions optionally further comprise one or more additional therapeutic agents. For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents that a compound of this invention may also be combined with include, without limitation: treatments for Alzheimer's Disease such as Ariceptl 8 and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-I RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, antileukemic agents, and growth factors; and agents for treating immunodeficiency disorders such as gamma globulin. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present invention.

In another aspect, the invention provides a kit comprising a compound capable of inhibiting kinase activity selected from one or more compounds of the invention, and instructions for use in treating cancer. In certain embodiments, the kit further comprises components for performing a test to determine whether a subject has activating and/or drug resistance mutations in EGFR.

The following Examples are illustrative and should not be interpreted in any way so as to limit the scope of the invention.

EXAMPLES

Examples 1-92: Compound Synthesis

General

The urea formation was performed using a Biotage® Initiator+ Microwave Synthesizer. All reactions were monitored by thin layer chromatography (TLC) with 0.25 mm E. Merck pre-coated silica gel plates (60 $F_{254}$) and Waters LCMS system (Waters 2489 UV/Visible Detector, Waters 3100 Mass, Waters 515 HPLC pump, Waters 2545 Binary Gradient Module, Waters Reagent Manager and Waters 2767 Sample Manager) using SunFire™ C18 column (4.6×50 mm, 5 µm particle size): solvent gradient=100% A at 0 min, 1% A at 5 min; solvent A=0.035% TFA in Water; solvent B=0.035% TFA in MeOH; flow rate: 2.5 mL/min. Purification of reaction products was carried out by flash chromatography using CombiFlash®Rf with Teledyne Isco RediSep®Rf High Performance Gold or Silicycle SiliaSep™ High Performance columns (4 g, 12 g, 24 g, 40 g, or 80 g) and Waters LCMS system using SunFire™ Prep C18 column (19×50 mm, 5 µm particle size): solvent gradient=80% A at 0 min, 10% A at 8 min; solvent A=0.035% TFA in Water; solvent B=0.035% TFA in MeOH; flow rate: 25 mL/min. The purity of all compounds was over 95% and was analyzed with Waters LCMS system. $^1$H NMR and $^{13}$C NMR spectra were obtained using a Varian Inova-600 (600 MHz for $^1$H, and 125 MHz for $^{13}$C) spectrometer. Chemical shifts are reported relative to chloroform (6=7.24) for $^1$H NMR or dimethyl sulfoxide (6=2.50) for $^1$H NMR and dimethyl sulfoxide (6=39.51) for $^{13}$C NMR. Data are reported as (br=broad, s=singlet, d=doublet, t=triplet, q=quartet, m=multiplet).

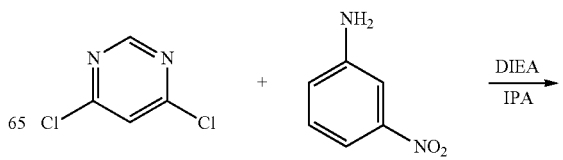

Scheme 1.

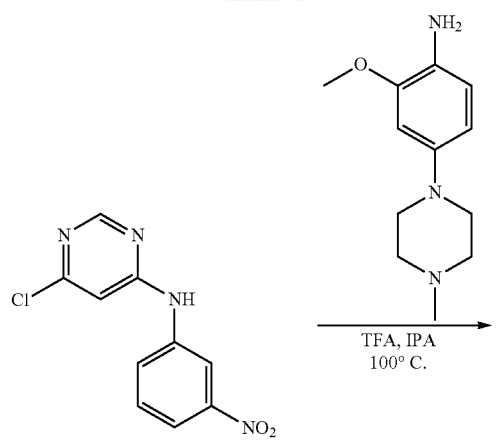
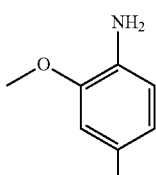
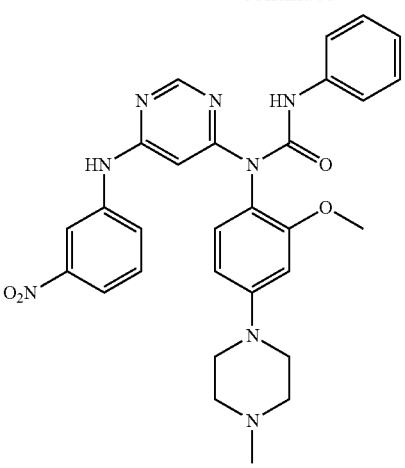
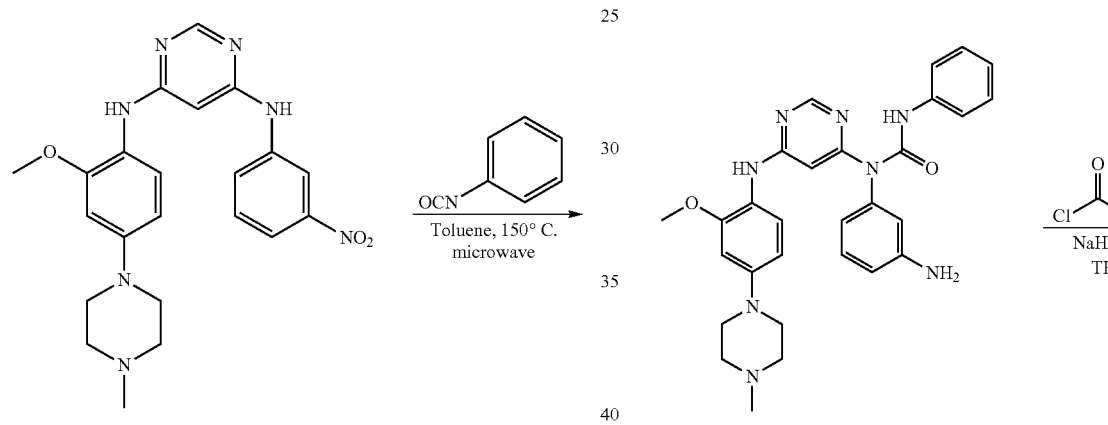

Example 1. N-(3-(1-(6-((2-methoxy-4-(4-methylpiperazin-1-yl)phenyl)amino)pyrimidin-4-yl)-3-phenylureido)phenyl)acrylamide (1A)

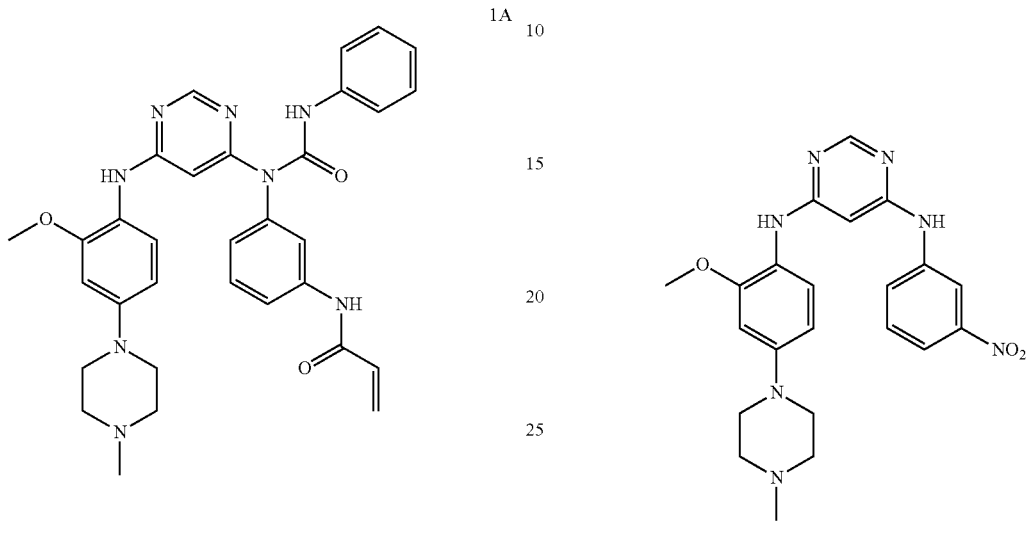

A. 6-chloro-N-(3-nitrophenyl)pyrimidin-4-amine

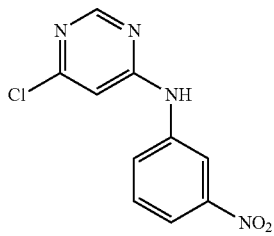 [SMILES: O=[N+]([O-])c1cccc(Nc2cc(Cl)ncn2)c1]

To a solution of 4,6-dichloropyrimidine (2.0 g, 13.52 mmol) in 2-propanol (34 mL) was added 3-nitroaniline (1.86 g, 13.52 mmol) and 4N HCl in dioxane (3.38 ml, 13.52 mmol). The reaction mixture was stirred at 80° C. for 24 hrs and concentrated to half of the original volume of solvent under reduced pressure. To the reaction mixture was added water (150 mL) and the resulting precipitate was collected by filtration. The solid was blown dry using nitrogen gas to give 6-chloro-N-(3-nitrophenyl)pyrimidin-4-amine (2.3 g, 68% yield) as bright yellow solid. Rt=4.15 min; $^1$H NMR 600 MHz (DMSO-$d_6$) δ 8.71 (t, J=2.4 Hz, 1H), 8.58 (s, 1H), 8.98 (dd, J=1.2 Hz, J=8.4 Hz, 1H), 7.88 (dd, J=1.8 Hz, J=7.8 Hz, 1H), 7.61 (t, J=7.8 Hz, 1H), 6.87 (s, 1H); MS m/z: 251.06 [M+1].

B. N4-(2-methoxy-4-(4-methylpiperazin-1-yl)phenyl)-N6-(3-nitrophenyl)pyrimidine-4,6-diamine To a solution 6-chloro-N-(3-nitrophenyl)pyrimidin-4-amine (1.0 g, 4.00 mmol) in 2-butanol (10 mL) and trifluoroacetic acid (0.3 mL) was added 2-methoxy-4-(4-methylpiperazin-1-yl)aniline (606 mg, 4.39 mmol). The reaction mixture was stirred at 120° C. for 10 hrs and the solvent concentrated under reduced pressure. The reaction mixture was diluted with dichloromethane and washed with saturated aqueous potassium carbonate solution and brine. The organic layer was dried over MgSO$_4$, filtered through a pad of celite and concentrated under reduced pressure. The residue was purified by column chromatography on silica gel (1:99 to 3:97, ammonia solution 7.0 N in methanol/dichloromethane) to afford N4-(2-methoxy-4-(4-methylpiperazin-1-yl)phenyl)-N6-(3-nitrophenyl)pyrimidine-4,6-diamine (1.3 g, 75% yield) as an solid. Rt=2.73 min; $^1$H NMR 600 MHz (DMSO-$d_6$) δ 9.50 (s, 1H), 8.72 (s, 1H), 8.24 (s, 1H), 8.22 (s, 1H), 7.91 (dd, J=1.2 Hz, J=8.4 Hz, 1H), 7.27 (d, J=8.4 Hz, 1H), 7.50 (t, J=8.4 Hz, 1H), 7.21 (d, J=8.4 Hz, 1H), 6.49 (d, J=2.4 Hz, 1H), 6.51 (dd, J=2.4 Hz, J=9.0 Hz, 1H), 5.76 (s, 1H), 3.77 (s, 3H), 3.16 (m, 4H), 2.46 (m, 4H), 2.32 (s, 3H); MS m/z: 436.45 [M+1].

C. 1-(6-((2-methoxy-4-(4-methylpiperazin-1-yl)phenyl)amino)pyrimidin-4-yl)-1-(3-nitrophenyl)-3-phenylurea and 1-(2-methoxy-4-(4-methylpiperazin-1-yl)phenyl)-1-(6-((3-nitrophenyl)amino)pyrimidin-4-yl)-3-phenylurea

D. 1-(3-aminophenyl)-1-(6-((2-methoxy-4-(4-methylpiperazin-1-yl)phenyl)amino)pyrimidin-4-yl)-3-phenylurea

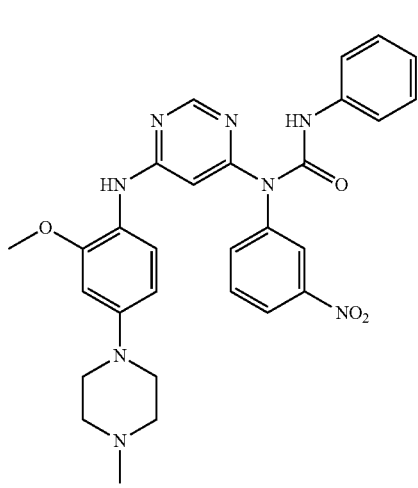

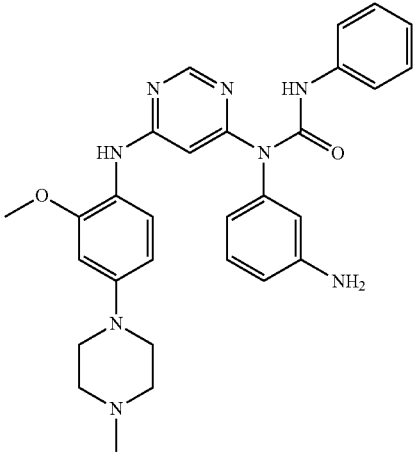 [SMILES: COc1cc(N2CCN(C)CC2)ccc1Nc1cc(N(C(=O)Nc2ccccc2)c2cccc(N)c2)ncn1]

To a solution 1-(6-((2-methoxy-4-(4-methylpiperazin-1-yl)phenyl)amino)pyrimidin-4-yl)-1-(3-nitrophenyl)-3-phenylurea (80 mg, 0.14 mmol) in ethyl acetate (1 mL) and conc. HCl (0.1 mL) was added Tin(II) chloride dihydrate (162 mg, 0.76 mmol). The reaction mixture was stirred at 60° C. for 6 hrs. The reaction mixture was diluted with ethyl acetate and neutralized with satd. NaHCO$_3$ solution. The organic layer was dried over MgSO$_4$, filtered through a pad of celite and concentrated under reduced pressure. The crude product was used in the next reaction without further purification. Rt=3.45 min; MS m/z: 525.55 [M+1]

E. N-(3-(1-(6-((2-methoxy-4-(4-methylpiperazin-1-yl)phenyl)amino)pyrimidin-4-yl)-3-phenylureido)phenyl)acrylamide

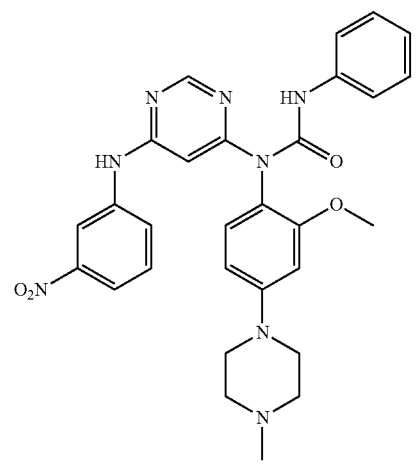

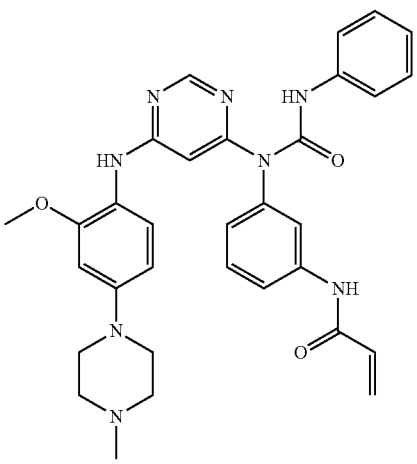 [SMILES: C=CC(=O)Nc1cccc(N(C(=O)Nc2ccccc2)c2cc(Nc3ccc(N4CCN(C)CC4)cc3OC)ncn2)c1]

A 5 mL microwave vial was charged with N4-(2-methoxy-4-(4-methylpiperazin-1-yl)phenyl)-N6-(3-nitrophenyl)pyrimidine-4,6-diamine (200 mg, 0.46 mmol), phenyl isocyanate (164 mg, 1.38 mmol) and toluene (2 mL). The reaction vial was sealed and heated at 130° C. for 1 h. To a reaction vial was additionally added phenyl isocyanate (109 mg, 2.35 mmol) and heated at 130° C. for 1 h. The reaction mixture was concentrated under reduced pressure. The residue was purified by column chromatography on silica gel (1:99 to 7:93, methanol/dichloromethane) and additionally purified using HPLC to afford 1-(6-((2-methoxy-4-(4-methylpiperazin-1-yl)phenyl)amino)pyrimidin-4-yl)-1-(3-nitrophenyl)-3-phenylurea (90 mg, 35% yield) as an off-white solid Rt=3.78 min; MS m/z: 555.41 [M+1] and 1-(2-methoxy-4-(4-methylpiperazin-1-yl)phenyl)-1-(6-((3-nitrophenyl)amino)pyrimidin-4-yl)-3-phenylurea (70 mg, 27% yield) as an off-white solid Rt=4.17 min; MS m/z: 555.41 [M+1].

To a solution 1-(3-aminophenyl)-1-(6-((2-methoxy-4-(4-methylpiperazin-1-yl)phenyl)amino)pyrimidin-4-yl)-3-phenylurea (60 mg, 0.11 mmol) in THF (1 mL) and satd. NaHCO$_3$ solution (1 mL) was added acryloyl chloride (10 µl, 0.13 mmol) at 0° C. The reaction mixture was stirred at 0° C. for 30 min. The reaction mixture was partitioned between ethyl acetate and water. The water layer was extracted with ethyl acetate and the combined organic layer was washed with brine. The organic layer was dried over MgSO$_4$, filtered through a pad of celite and concentrated under reduced pressure. The residue was purified by column chromatography on silica gel (1:99 to 10:90, methanol/dichloromethane) to afford N-(3-(1-(6-((2-methoxy-4-(4-methylpiperazin-1-yl)phenyl)amino)pyrimidin-4-yl)-3-phenylureido)phenyl)acrylamide (42 mg, 63% yield) as an off-white solid. Rt=3.73 min; $^1$H NMR 600 MHz (DMSO-d$_6$) δ 12.57 (s, 1H), 10.30 (s, 1H), 8.68 (s, 1H), 8.39 (s, 1H), 7.72 (d, J=7.2 Hz, 1H), 7.61 (s, 1H), 7.55 (d, J=8.4 Hz, 2H), 7.45 (t, J=8.4 Hz, 1H), 7.32 (t, J=8.4 Hz, 2H), 7.23 (m, 1H), 7.05 (t, J=7.8 Hz, 1H), 6.99 (d, J=7.8 Hz, 1H), 6.49 (s, 1H), 6.45 (dd, J=10.8 Hz, J=16.8 Hz, 1H), 6.38 (d, J=8.4 Hz, 1H), 6.28 (dd, J=1.8 Hz, J=16.8 Hz, 1H), 5.78 (dd, J=1.8 Hz, J=10.8 Hz, 1H), 5.24 (br, 1H), 3.66 (s, 3H), 3.08 (m, 4H), 2.44 (m, 4H), 2.22 (s, 3H); MS m/z: 579.48 [M+1].

Example 2. N-(3-((6-(1-(2-methoxy-4-(4-methylpiperazin-1-yl)phenyl)-3-phenylureido)pyrimidin-4-yl)amino)phenyl)acrylamide (2A)

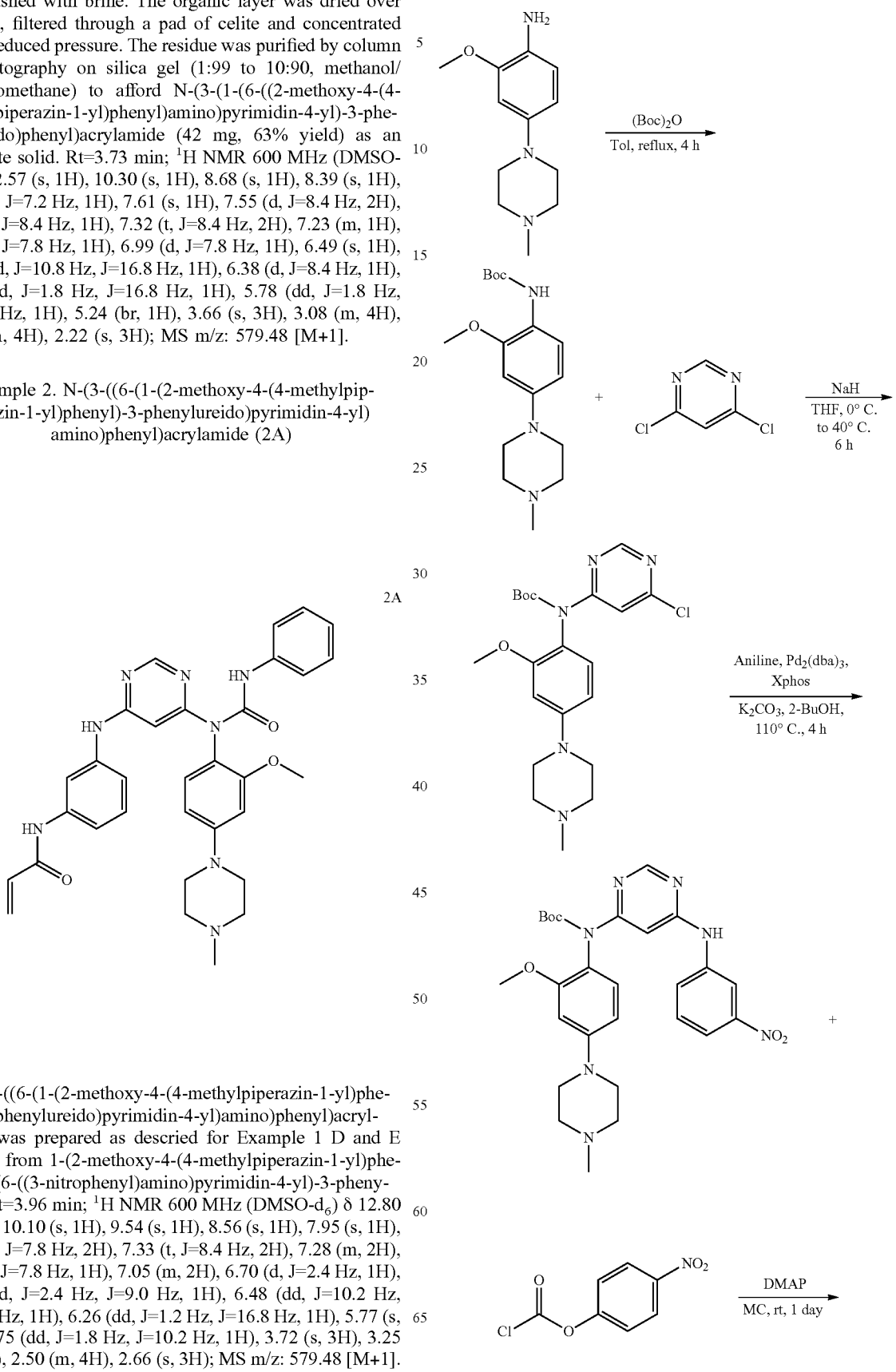

N-(3-((6-(1-(2-methoxy-4-(4-methylpiperazin-1-yl)phenyl)-3-phenylureido)pyrimidin-4-yl)amino)phenyl)acrylamide was prepared as descried for Example 1 D and E starting from 1-(2-methoxy-4-(4-methylpiperazin-1-yl)phenyl)-1-(6-((3-nitrophenyl)amino)pyrimidin-4-yl)-3-phenylurea Rt=3.96 min; $^1$H NMR 600 MHz (DMSO-d$_6$) δ 12.80 (s, 1H), 10.10 (s, 1H), 9.54 (s, 1H), 8.56 (s, 1H), 7.95 (s, 1H), 7.57 (d, J=7.8 Hz, 2H), 7.33 (t, J=8.4 Hz, 2H), 7.28 (m, 2H), 7.21 (t, J=7.8 Hz, 1H), 7.05 (m, 2H), 6.70 (d, J=2.4 Hz, 1H), 6.60 (dd, J=2.4 Hz, J=9.0 Hz, 1H), 6.48 (dd, J=10.2 Hz, J=17.4 Hz, 1H), 6.26 (dd, J=1.2 Hz, J=16.8 Hz, 1H), 5.77 (s, 1H), 5.75 (dd, J=1.8 Hz, J=10.2 Hz, 1H), 3.72 (s, 3H), 3.25 (m, 4H), 2.50 (m, 4H), 2.66 (s, 3H); MS m/z: 579.48 [M+1].

109

-continued

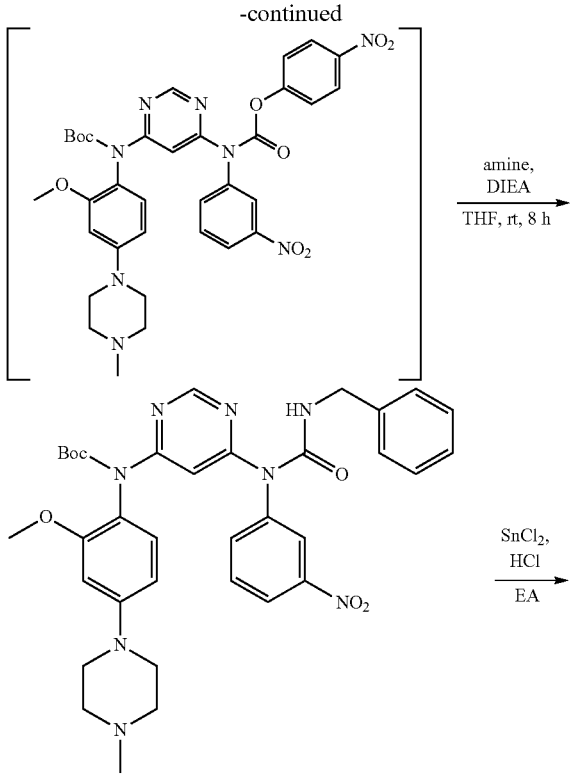

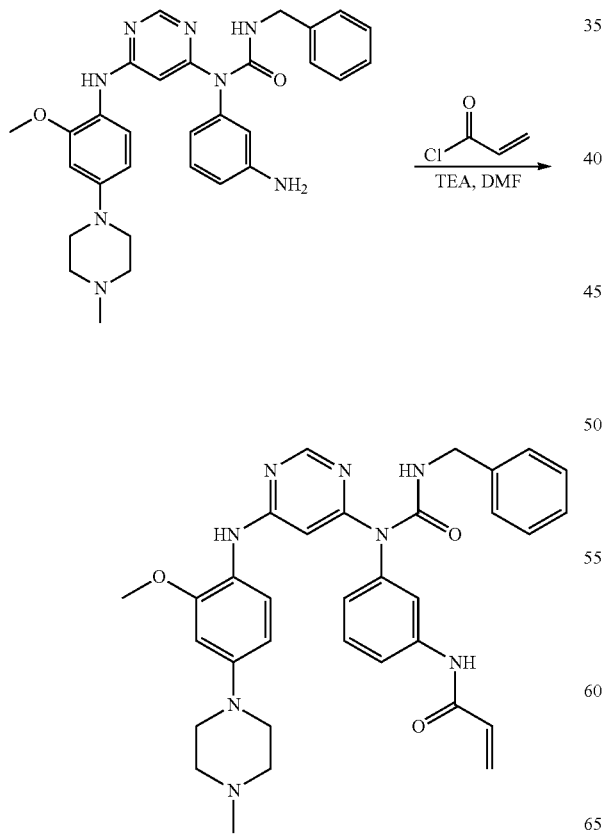

110

Example 3. N-(3-(3-benzyl-1-(6-((2-methoxy-4-(4-methylpiperazin-1-yl)phenyl)amino)pyrimidin-4-yl)ureido)phenyl)acrylamide (3A)

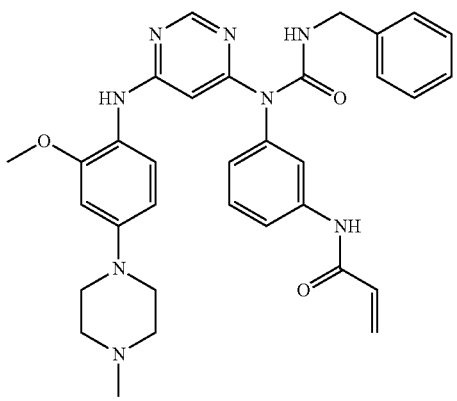

A. tert-butyl (2-methoxy-4-(4-methylpiperazin-1-yl)phenyl)carbamate

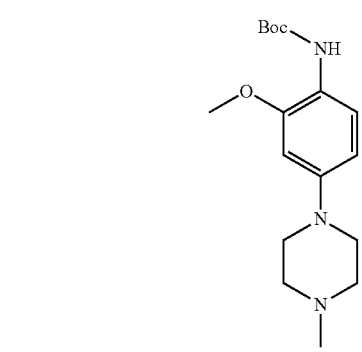

To a solution of 2-methoxy-4-(4-methylpiperazin-1-yl)aniline (10 g, 45.2 mmol) in toluene (230 mL) was added Di-tert-butyl dicarbonate (9.87 g, 45.2 mmol). The reaction mixture was stirred at 120° C. for 6 hrs and concentrated under reduced pressure. The residue was purified by column chromatography on silica gel (3:97 to 10:90, ammonia solution 7.0 N in methanol/dichloromethane) to afford title compound (12.5 g, 86% yield). Rt=3.23 min; $^1$H NMR 600 MHz (DMSO-d$_6$) δ 7.62 (s, 1H), 7.31 (br, 1H), 6.52 (d, J=2.4 Hz, 1H), 6.38 (dd, J=2.4 Hz, J=9.0 Hz, 1H), 3.72 (s, 3H), 3.04 (m, 4H), 2.39 (m, 4H), 2.17 (s, 3H), 1.38 (s, 9H); MS m/z: 321.99 [M+1].

B. tert-butyl (6-chloropyrimidin-4-yl)(2-methoxy-4-(4-methylpiperazin-1-yl)phenyl)carbamate

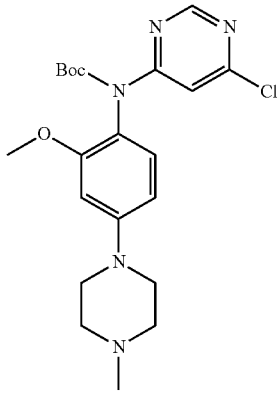 [SMILES: COc1cc(N2CCN(C)CC2)ccc1N(C(=O)OC(C)(C)C)c1cc(Cl)ncn1]

To a solution of tert-butyl (2-methoxy-4-(4-methylpiperazin-1-yl)phenyl)carbamate (10 g, 31.1 mmol) in anhydrous THF (160 mL) was added NaH (1.9 g, 46.7 mmol) at 0° C. After 30 min, 4,6-dichloropyrimidine (6.9 g, 46.7 mmol) was added to the reaction mixture at 0° C. The reaction mixture was heated to 60° C. for 6 hours after which it was cooled to room temperature and quenched with water. The remained THF was concentrated under reduced pressure and then water (200 mL) was added to the reaction mixture. The residue was triturated with EtOH (15 mL) for 2 hours. The produced solid was filtered and washed was water. The product was dried to give brown solid (10.2 g, 76% yield). Rt=3.65 min; $^1$H NMR 600 MHz (DMSO-$d_6$) δ 8.57 (s, 1H), 7.97 (s, 1H), 7.31 (br, 1H), 6.92 (d, J=9.0 Hz, 1H), 6.60 (d, J=2.4 Hz, 1H), 6.48 (dd, J=2.4 Hz, J=8.4 Hz, 1H), 3.70 (s, 3H), 3.20 (m, 4H), 2.45 (m, 4H), 2.22 (s, 3H), 1.34 (s, 9H); MS m/z: 448.49 [M+1].

C. tert-butyl (2-methoxy-4-(4-methylpiperazin-1-yl)phenyl)(6-((3-nitrophenyl)amino)pyrimidin-4-yl)carbamate

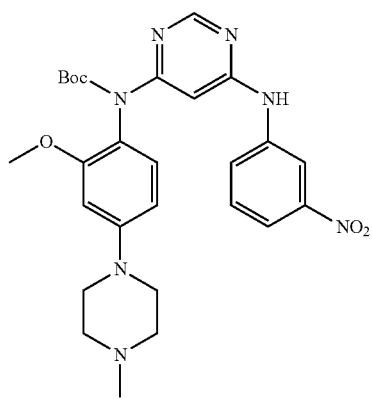 [SMILES: COc1cc(N2CCN(C)CC2)ccc1N(C(=O)OC(C)(C)C)c1cc(Nc2cccc([N+](=O)[O-])c2)ncn1]

A mixture of tert-butyl (6-chloropyrimidin-4-yl)(2-methoxy-4-(4-methylpiperazin-1-yl)phenyl)carbamate (10.0 g, 23.08 mmol), 3-nitroaniline (6.37 g, 46.17 mmol), $K_2CO_3$ (9.6 g, 69.25 mmol) in 2-butanlol (230 mL) was degassed for 10 min. To a reaction mixture were added Pd$_2$(dba)$_3$ (1.26 g, 1.39 mmol) and X-phos (990 mg, 2.08 mmol) and heated at 120° C. for 6 hours after which, it was filtered with a pad of celite and concentrated under reduced pressure. The residue was purified by column chromatography on silica gel (3:97 to 10:90, ammonia solution 7.0 N in methanol/dichloromethane) to afford title compound (10.3 g, 83% yield). Rt=3.70 min; $^1$H NMR 600 MHz (DMSO-$d_6$) δ 10.01 (s, 1H), 8.78 (s, 1H), 8.32 (s, 1H), 7.95 (dd, J=1.2 Hz, J=7.8 Hz, 1H), 7.77 (dd, J=2.4 Hz, J=8.4 Hz, 1H), 7.53 (t, J=8.4 Hz, 1H), 7.30 (s, 1H), 6.85 (d, J=7.8 Hz, 1H), 6.55 (d, J=2.4 Hz, 1H), 6.42 (dd, J=1.8 Hz, J=9.0 Hz, 1H), 3.67 (s, 3H), 3.15 (m, 4H), 2.43 (m, 4H), 2.20 (s, 3H), 1.31 (s, 9H); MS m/z: 536.13 [M+1].

D. tert-butyl (6-(3-benzyl-1-(3-nitrophenyl)ureido)pyrimidin-4-yl)(2-methoxy-4-(4-methylpiperazin-1-yl)phenyl)carbamate

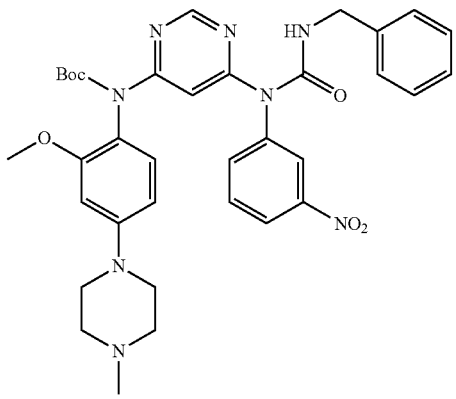 [SMILES: COc1cc(N2CCN(C)CC2)ccc1N(C(=O)OC(C)(C)C)c1cc(N(C(=O)NCc2ccccc2)c2cccc([N+](=O)[O-])c2)ncn1]

To a solution tert-butyl (2-methoxy-4-(4-methylpiperazin-1-yl)phenyl)(6-((3-nitrophenyl)amino)pyrimidin-4-yl)carbamate (1000 mg, 1.87 mmol) in dichloromethane (19 mL) were added DMAP (342 mg, 2.80 mmol) and 4-nitrophenyl chloroformate (375 mg, 1.87 mmol). After 1 hour, DMAP (342 mg, 2.80 mmol) and 4-nitrophenyl chloroformate (375 mg, 1.87 mmol) were added to the reaction mixture which was stirred for 8 hours. When the reaction was completed, the reaction mixture was diluted with dichloromethane (100 mL) and washed with brine twice. The organic layer was dried over MgSO$_4$, filtered and concentrated under reduced pressure.

To a solution of the crude product in THF (20 mL) was added DIEA (0.65 mL, 3.74 mmol) and benzyl amine (0.61 mL, 5.60 mmol). The reaction mixture was stirred for 4 hours after which it was partitioned between ethyl acetate and water. The organic layer was separated and the aqueous layer was extracted with ethyl acetate. The combined organic extracts were washed with brine, dried over MgSO$_4$, filtered and concentrated under reduced pressure. The crude product was purified by column chromatography on silica gel (3:97 to 10:90, methanol/dichloromethane) to afford title compound (760 mg, 61% yield). Rt=4.03 min; $^1$H NMR 600 MHz (DMSO-$d_6$) δ 8.97 (t, J=6.0 Hz, 1H), 8.37 (d, J=1.2 Hz, 1H), 8.28 (m, 1H), 8.18 (s, 1H), 7.80 (d, J=5.4 Hz, 2H), 7.40 (s, 1H), 7.33 (m, 4H), 7.25 (m, 1H), 6.83 (d, J=8.4 Hz, 1H), 6.56 (d, J=1.8 Hz, 1H), 6.43 (dd, J=1.8 Hz, J=7.8 Hz, 1H), 4.40 (d, J=6.0 Hz, 2H), 3.25 (s, 3H), 3.17 (m, 4H), 2.47 (m, 4H), 2.23 (s, 3H), 1.25 (s, 9H); MS m/z: 669.36 [M+1].

E. 1-(3-aminophenyl)-3-benzyl-1-(6-((2-methoxy-4-(4-methylpiperazin-1-yl)phenyl)amino)pyrimidin-4-yl)urea

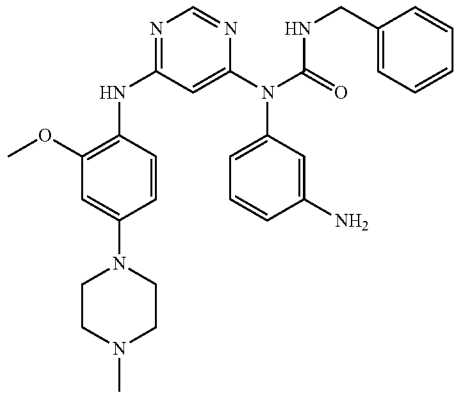 [SMILES: COc1cc(N2CCN(C)CC2)ccc1Nc1cc(N(C(=O)NCc2ccccc2)c2cccc(N)c2)ncn1]

To a solution of tert-butyl (6-(3-benzyl-1-(3-nitrophenyl)ureido)pyrimidin-4-yl)(2-methoxy-4-(4-methylpiperazin-1-yl)phenyl)carbamate (500 mg, 0.75 mmol) in Ethyl acetate (10 mL) were Tin (II) chloride dihydrate (844 mg, 3.74 mmol) and conc. HCl (1 mL). The reaction mixture was stirred for 6 hours at 60° C. after which, it was cooled down to room temperature. Ammonium hydroxide solution (28~30% NH$_3$) was added to the reaction mixture until the pH reached around 5 and Na$_2$CO$_3$ was added to the reaction mixture until pH comes to 7. The reaction mixture was filtered through a pad of celite and concentrated under reduced pressure. The crude product was used in the next reaction without further purification. Rt=3.05 min; $^1$H NMR 600 MHz (DMSO-d$_6$) δ 10.15 (t, J=6.0 Hz, 1H), 8.57 (s, 1H), 8.20 (s, 1H), 7.35 (m, 4H), 7.24 (m, 1H), 7.19 (m, 1H), 7.07 (t, J=7.8 Hz, 1H), 6.56 (d, J=8.4 Hz, 1H), 6.51 (d, J=1.8 Hz, 1H), 6.40 (dd, J=2.4 Hz, J=8.4 Hz, 1H), 6.35 (s, 1H), 6.30 (d, J=7.2 Hz, 1H), 5.61 (br, 1H), 5.21 (s, 2H). 4.42 (d, J=6.0 Hz, 2H), 3.69 (s, 3H), 3.10 (m, 4H), 2.44 (m, 4H), 2.23 (s, 3H); MS m/z: 539.16 [M+1].

F. N-(3-(3-benzyl-1-(6-((2-methoxy-4-(4-methylpiperazin-1-yl)phenyl)amino)pyrimidin-4-yl)ureido)phenyl)acrylamide

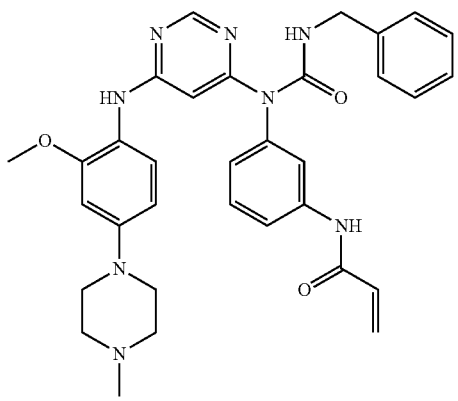

N-(3-(3-benzyl-1-(6-((2-methoxy-4-(4-methylpiperazin-1-yl)phenyl)amino)pyrimidin-4-yl)ureido)phenyl)acrylamide was prepared as described for Example 1E starting from 1-(3-aminophenyl)-3-benzyl-1-(6-((2-methoxy-4-(4-methylpiperazin-1-yl)phenyl)amino)pyrimidin-4-yl)urea.

Rt=3.13 min; $^1$H NMR 600 MHz (DMSO-d$_6$) δ 10.27 (s, 1H), 10.13 (m, 1H), 8.57 (s, 1H), 8.24 (s, 1H), 7.70 (d, J=8.4 Hz, 1H), 7.54 (s, 1H), 7.41 (t, J=8.4 Hz, 1H), 7.83 (m, 4H), 7.24 (m, 1H), 6.92 (d, J=7.8 Hz, 1H), 6.54 (s, 1H), 6.41 (m, 1H), 6.45 (dd, J=10.2 Hz, J=16.8 Hz, 1H), 6.39 (dd, J=1.8 Hz, J=8.4 Hz, 1H), 6.28 (dd, J=1.8 Hz, J=16.2 Hz, 1H), 5.78 (dd, J=1.8 Hz, J=10.8 Hz, 1H), 5.72 (br, 1H), 4.43 (d, J=6.0 Hz, 2H), 3.67 (s, 3H), 3.09 (m, 4H), 2.45 (m, 4H), 2.23 (s, 3H).; MS m/z: 593.38 [M+1].

Scheme 3.

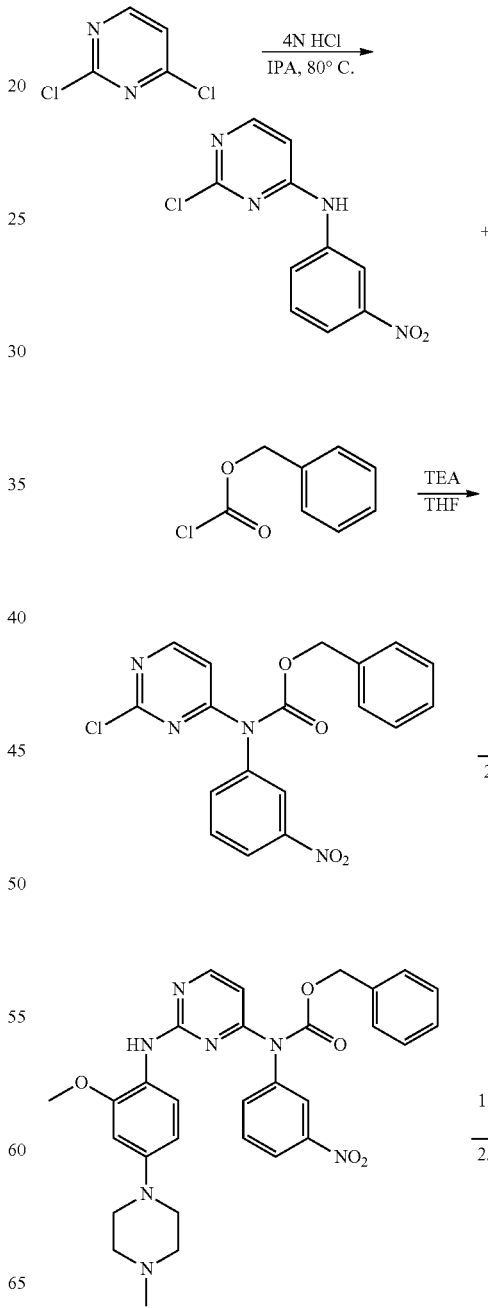

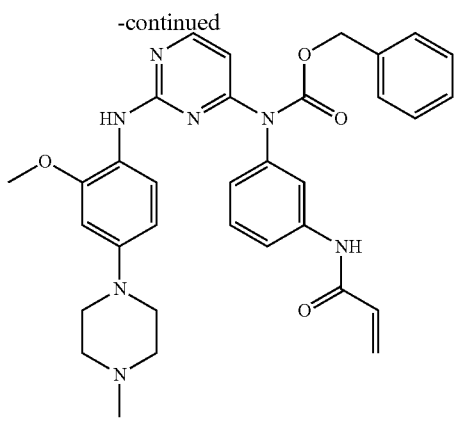

Example 4. Benzyl (3-acrylamidophenyl)(2-((2-methoxy-4-(4-methylpiperazin-1-yl)phenyl)amino)pyrimidin-4-yl)carbamate

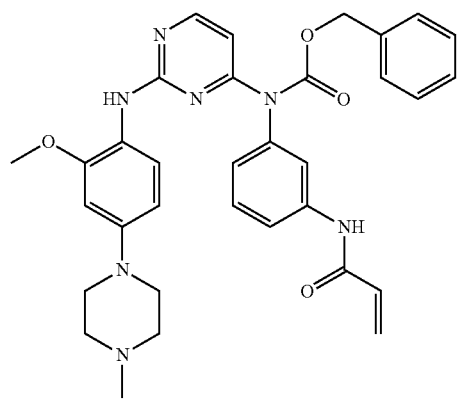

A. 2-chloro-N-(3-nitrophenyl)pyrimidin-4-amine

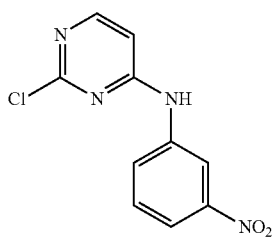 [SMILES: O=[N+]([O-])c1cccc(Nc2ccnc(Cl)n2)c1]

2-chloro-N-(3-nitrophenyl)pyrimidin-4-amine was prepared as descried for Example 1A starting from 2,4-dichloropyrimidine. Rt=2.83 min; MS m/z: 250.81 [M+1].

B. benzyl (2-chloropyrimidin-4-yl)(3-nitrophenyl)carbamate

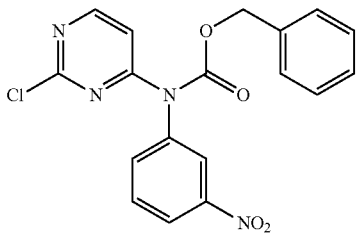 [SMILES: O=C(OCc1ccccc1)N(c1cccc([N+](=O)[O-])c1)c1ccnc(Cl)n1]

To a solution of 2-chloro-N-(3-nitrophenyl)pyrimidin-4-amine (160 mg, 0.64 mmol) in THF (3 mL) was added DIEA (0.22 mL, 1.28 mmol) and benzyl chloroformate (0.91 µL, 0.64 mmol). The reaction mixture was stirred for 24 hours after which, it was partitioned between ethyl acetate and water. The organic layer was separated and the aqueous layer was extracted with ethyl acetate. The combined organic extracts were washed with brine, dried over $MgSO_4$, filtered and concentrated under reduced pressure. The crude product was purified by column chromatography on silica gel (0:100 to 1:99, methanol/dichloromethane) to afford title compound (190 mg, 77% yield). Rt=3.65 min; MS m/z: 385.21 [M+1].

C. benzyl (2-((2-methoxy-4-(4-methylpiperazin-1-yl)phenyl)amino)pyrimidin-4-yl)(3-nitrophenyl)carbamate

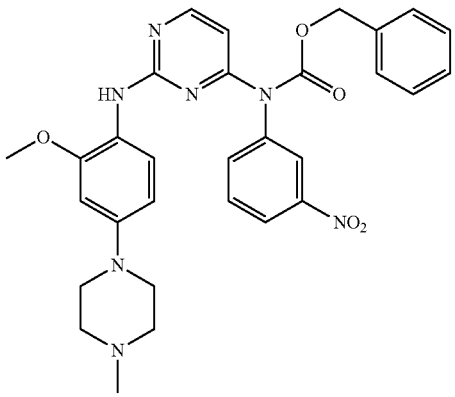 [SMILES: COc1cc(N2CCN(C)CC2)ccc1Nc1nccc(N(C(=O)OCc2ccccc2)c2cccc([N+](=O)[O-])c2)n1]

benzyl (2-((2-methoxy-4-(4-methylpiperazin-1-yl)phenyl)amino)pyrimidin-4-yl)(3-nitrophenyl)carbamate was prepared as descried for Example 1B starting from benzyl (2-chloropyrimidin-4-yl)(3-nitrophenyl)carbamate

D. benzyl (3-acrylamidophenyl)(2-((2-methoxy-4-(4-methylpiperazin-1-yl)phenyl)amino)pyrimidin-4-yl)carbamate

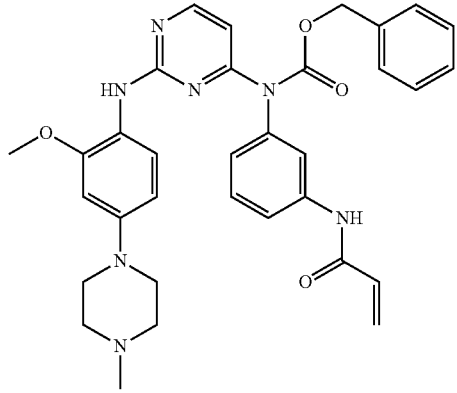

Benzyl (3-acrylamidophenyl)(2-((2-methoxy-4-(4-methylpiperazin-1-yl)phenyl)amino)pyrimidin-4-yl)carbamate was prepared as described for Example 3E and F starting from benzyl (2-((2-methoxy-4-(4-methylpiperazin-1-yl)phenyl)amino)pyrimidin-4-yl)(3-nitrophenyl)carbamate. Rt=3.30 min, MS m/z: 594.39 [M+1], $^1$H NMR 600 MHz (DMSO-d$_6$) δ 10.29 (s, 1H), 9.70 (br, 1H), 8.32 (d, J=6.0 Hz, 1H), 7.85 (d, J=6.6 Hz, 1H), 7.51 (s, 1H), 7.40 (m, 2H), 7.26 (m, 4H), 7.23 (m, 2H), 7.01 (dd, J=1.2 Hz, J=7.8 Hz, 1H), 6.55 (d, J=2.4 Hz, 1H), 6.40 (m, 1H), 6.24 (dd, J=1.8 Hz, J=17.4 Hz, 1H), 6.02 (br, 1H), 5.74 (dd, J=1.8 Hz, J=10.2 Hz, 1H), 5.18 (s, 2H), 3.74 (s, 3H), 3.68 (m, 2H), 3.48 (m, 2H), 3.10 (m, 2H), 2.83 (s, 3H), 2.79 (m, 2H).

Scheme 4.

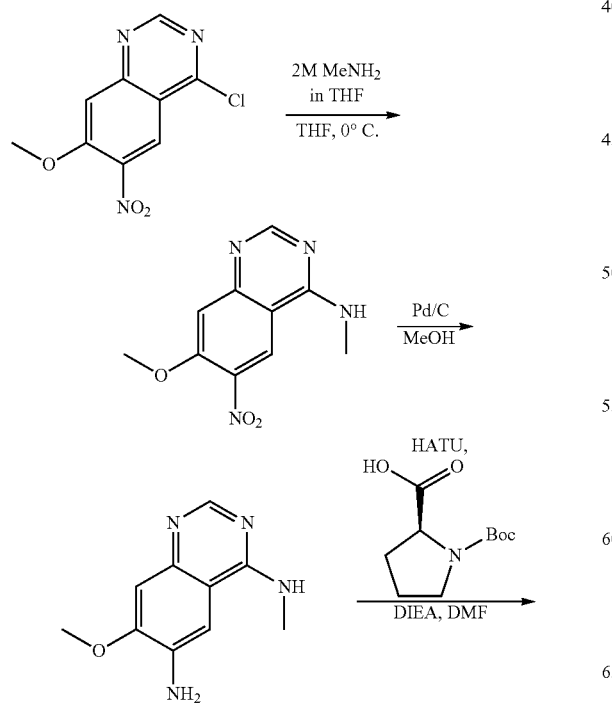

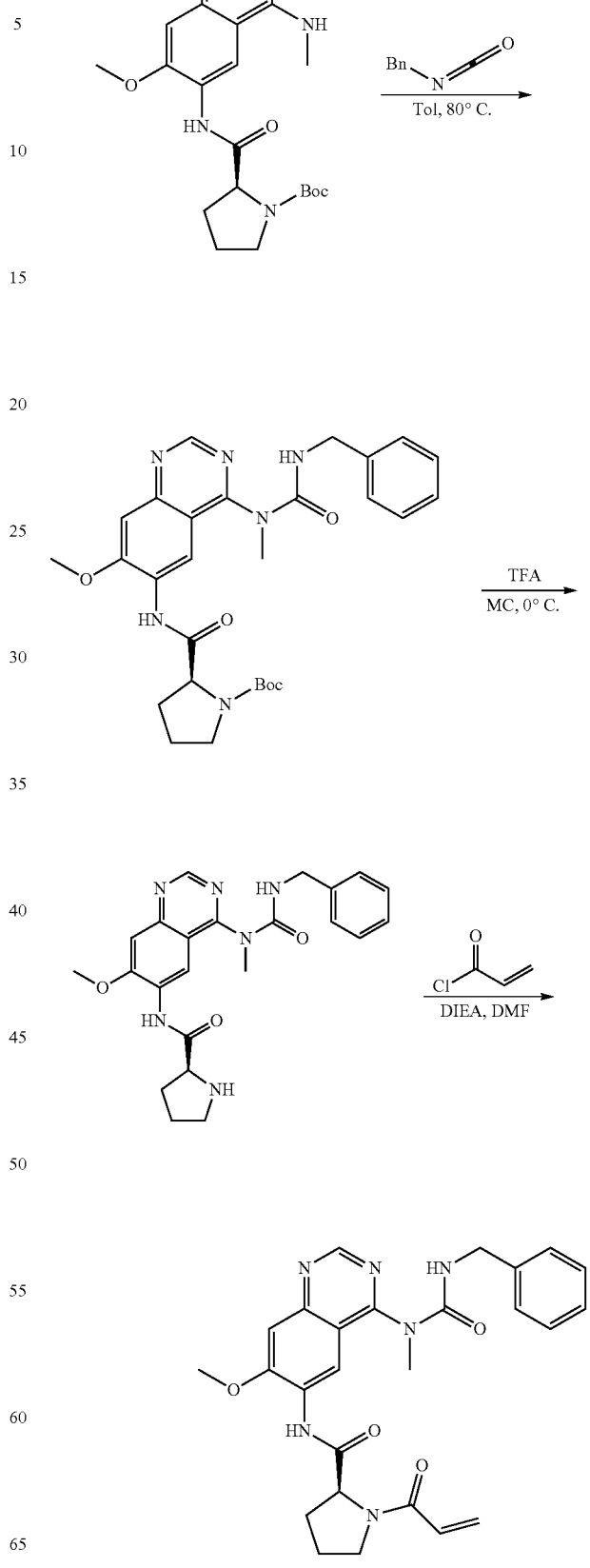

Example 5. (S)-1-acryloyl-N-(4-(3-benzyl-1-methylureido)-7-methoxyquinazolin-6-yl)pyrrolidine-2-carboxamide (5A)

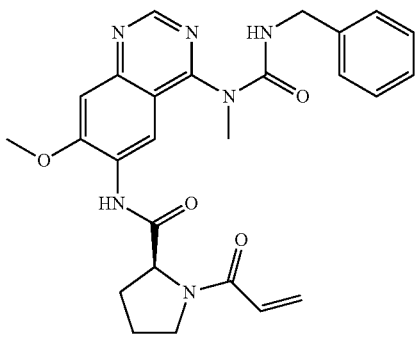

5A

A. 7-methoxy-N-methyl-6-nitroquinazolin-4-amine

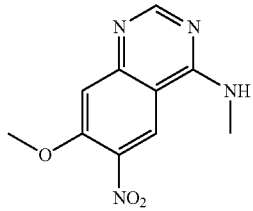

To a solution of 4-chloro-7-methoxy-6-nitroquinazoline (1.0 g, 4.18 mmol) in anhydrous THF (10 mL) was added 2.0 M methylamine solution in THF (4.4 mL) at 0° C. The reaction mixture was stirred for 4 hours at room temperature and concentrated to half of the original volume of solvent under reduced pressure. To the reaction mixture was added water (100 mL) and the resulting precipitate was collected by filtration. The solid was blown dry using nitrogen gas to give 7-methoxy-N-methyl-6-nitroquinazolin-4-amine (870 mg, 89% yield) as a bright yellow solid.

B. 7-methoxy-N4-methylquinazoline-4,6-diamine

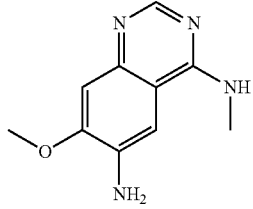

To a solution of 7-methoxy-N-methyl-6-nitroquinazolin-4-amine (800 mg. 3.42 mmol) in methanol (8 mL) was added Palladium, 10 wt. % (dry basis) on activated carbon, wet, Degussa type E101 NE/W under nitrogen atmosphere. The reaction mixture was hydrogenated under balloon pressure for 6 hrs. The resulting suspension was filtered through a pad of celite then the filtrate was concentrated to afford 7-methoxy-N4-methylquinazoline-4,6-diamine (670 mg, 96% yield) as a white solid.

C. (S)-tert-butyl 2-((7-methoxy-4-(methylamino)quinazolin-6-yl)carbamoyl)pyrrolidine-1-carboxylate

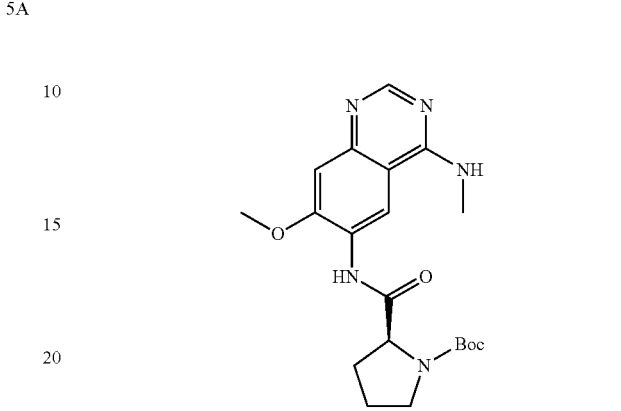

To a solution of 7-methoxy-N4-methylquinazoline-4,6-diamine (600 mg, 2.94 mmol) and (S)-1-(tert-butoxycarbonyl)pyrrolidine-2-carboxylic acid (632 mg, 2.94 mmol) in DMF (12 mL) were added HATU (3.3 g, 8.82 mmol) and DIEA (2.56 mL, 14.70 mmol). The reaction mixture stirred at room temperature for overnight after which, it was partitioned ethyl acetate and sat. NH$_4$Cl solution. The water layer was extracted with ethyl acetate. The combined organic layer was washed with brine, dried with MgSO$_4$, filtered with a pad of celite and concentrated under reduced pressure. The crude compound purified with flesh silica chromatography (0:100 to 3:97, methanol/dichloromethane) as a solvent to afford (S)-tert-butyl 2-((7-methoxy-4-(methylamino)quinazolin-6-yl)carbamoyl)pyrrolidine-1-carboxylate (910 mg, 77% yield) as a white solid.

D. (S)-tert-butyl 2-((4-(3-benzyl-1-methylureido)-7-methoxyquinazolin-6-yl)carbamoyl)pyrrolidine-1-carboxylate

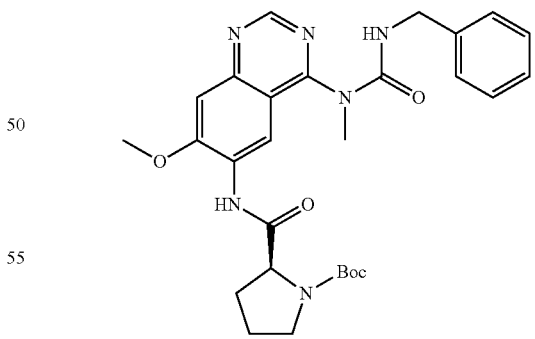

A 5 mL sealed vial was charged with (S)-tert-butyl 2-((7-methoxy-4-(methylamino)quinazolin-6-yl)carbamoyl) pyrrolidine-1-carboxylate (200 mg, 0.50 mmol), benzyl isocyanate (92 µL, 0.75 mmol) and toluene (2 mL). The reaction vial was sealed and heated at 100° C. for 4 hrs. The reaction mixture was concentrated under reduced pressure and the residue was purified by column chromatography on silica gel (1:99 to 5:95, methanol/dichloromethane) to afford (S)-tert-butyl 2-((4-(3-benzyl-1-methylureido)-7-methoxyquinazolin-6-yl)carbamoyl)pyrrolidine-1-carboxylate (190 mg, 71% yield) as an off-white solid.

E. (S)—N-(4-(3-benzyl-1-methylureido)-7-methoxyquinazolin-6-yl)pyrrolidine-2-carboxamide

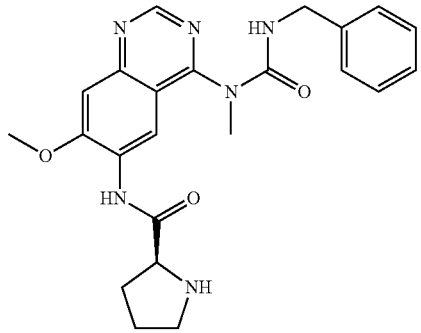 [SMILES: COc1cc2ncnc(N(C)C(=O)NCc3ccccc3)c2cc1NC(=O)[C@@H]1CCCN1]

To a solution of 2-((4-(3-benzyl-1-methylureido)-7-methoxyquinazolin-6-yl)carbamoyl)pyrrolidine-1-carboxylate (100 mg, 0.19 mmol) in dichloromethane (1 mL) was added TFA (1 mL). The reaction mixture was stirred for 4 hrs and concentrated under reduced pressure. The crude mixture was partitioned dichloromethane and sat. NaHCO$_3$ solution. The water layer was extracted with dichloromethane. The combined organic layer was washed with brine, dried with MgSO$_4$, filtered with a pad of celite and concentrated under reduced pressure. The crude product was used in the next reaction without further purification.

F. (S)-1-acryloyl-N-(4-(3-benzyl-1-methylureido)-7-methoxyquinazolin-6-yl)pyrrolidine-2-carboxamide

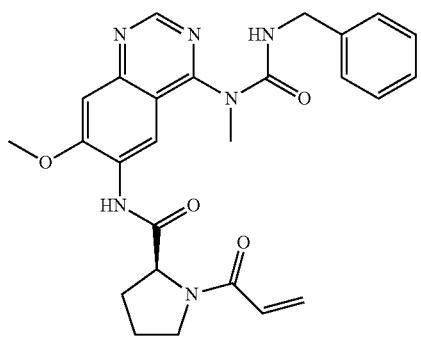 [SMILES: C=CC(=O)N1CCC[C@H]1C(=O)Nc1cc2c(N(C)C(=O)NCc3ccccc3)ncnc2cc1OC]

To a solution of (S)—N-(4-(3-benzyl-1-methylureido)-7-methoxyquinazolin-6-yl)pyrrolidine-2-carboxamide (50 mg, 0.12 mmol) in anhydrous DMF (1 mL) and DIEA (40 µL, 0.23 mmol) was added acryloyl chloride (10 µl, 0.12 mmol) at 0° C. The reaction mixture was stirred at 0° C. for 2 hrs. The reaction mixture was partitioned between ethyl acetate and water. The water layer was extracted with ethyl acetate and the combined organic layer was washed with brine. The organic layer was dried over MgSO$_4$, filtered through a pad of celite and concentrated under reduced pressure. The residue was purified by column chromatography on silica gel (1:99 to 10:90, methanol/dichloromethane) to afford (S)-1-acryloyl-N-(4-(3-benzyl-1-methylureido)-7-methoxyquinazolin-6-yl)pyrrolidine-2-carboxamide (38 mg, 68% yield) as an off-white solid. Rt=3.13 min, MS m/z: 489.36 [M+1], $^1$H NMR 600 MHz (DMSO-d$_6$) δ 9.78 (s, 1H), 8.89 (s, 1H), 8.79 (s, 1H), 7.63 (t, J=6.0 Hz, 1H), 7.36 (s, 1H), 7.22 (m, 4H), 7.16 (m, 1H), 6.68 (dd, J=10.2 Hz, 16.2 Hz, 1H), 6.17 (dd, J=2.4 Hz, J=16.2 Hz, 1H), 7.72 (dd, J=2.4 Hz, J=10.2 Hz, 1H), 4.83 (dd, J=2.4 Hz, J=8.4 Hz, 1H), 4.22 (d, J=6.0 Hz, 2H), 4.02 (s, 3H), 3.66 (m, 1H), 3.64 (m, 1H), 3.34 (s, 3H), 1.90-2.05 (m, 4H).

Scheme 5.

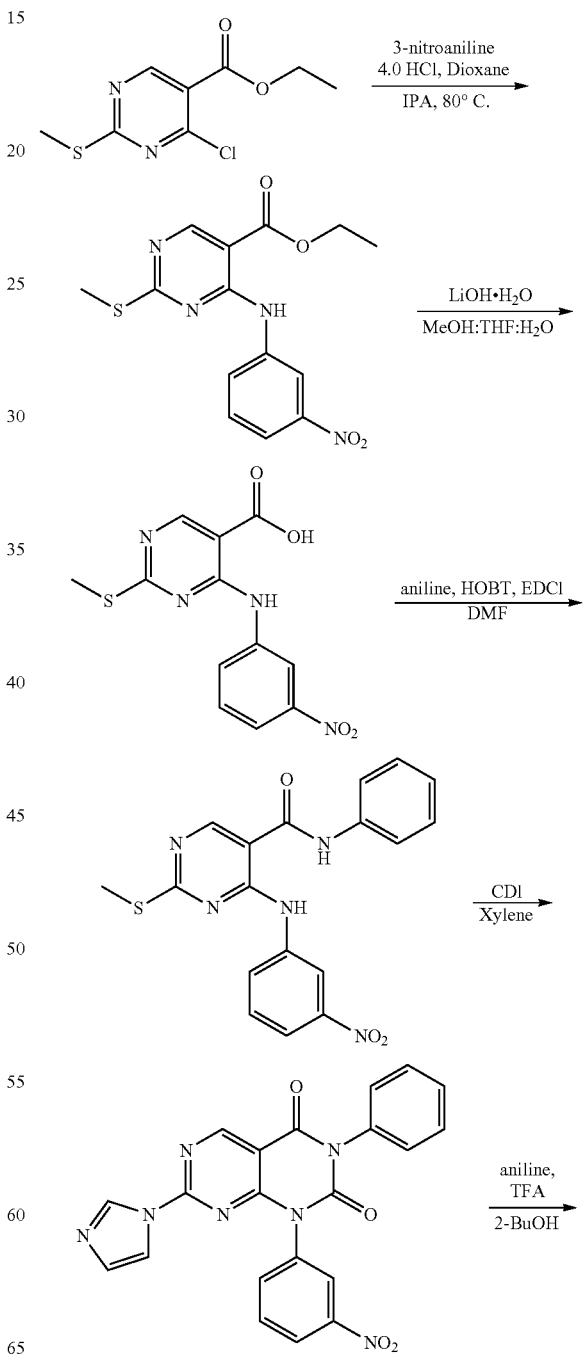

-continued

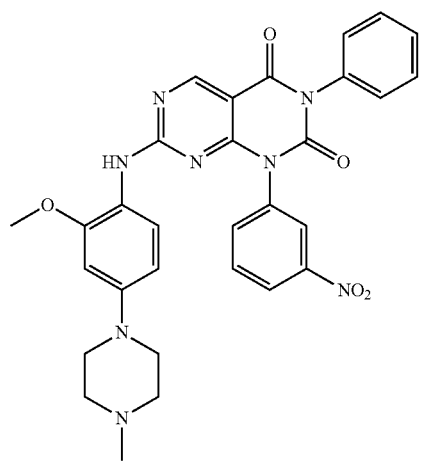

SnCl₂, HCl
EA
→

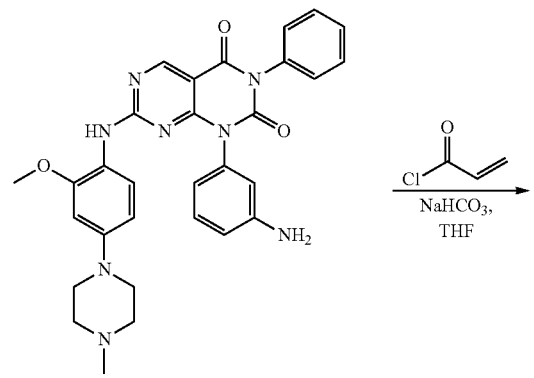

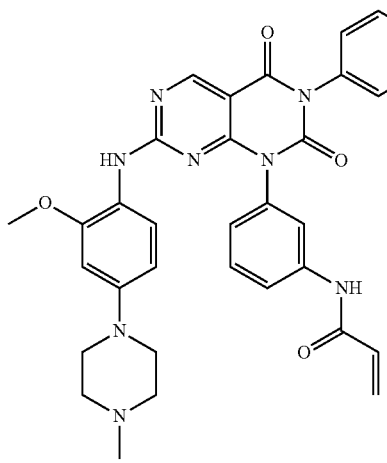

Example 6. N-(3-(7-((2-methoxy-4-(4-methylpiperazin-1-yl)phenyl)amino)-2,4-dioxo-3-phenyl-3,4-dihydropyrimido[4,5-d]pyrimidin-1(2H)-yl)phenyl)acrylamide (6A)

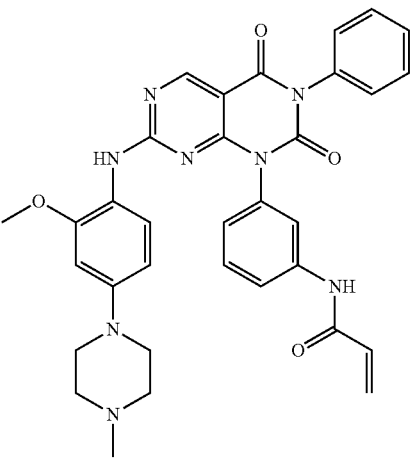

6A

A. ethyl 2-(methylthio)-4-((3-nitrophenyl)amino)pyrimidine-5-carboxylate

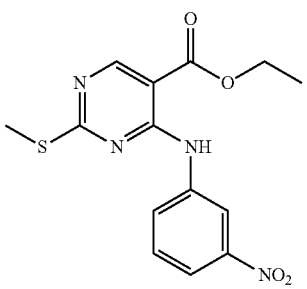 [SMILES: CCOC(=O)c1cnc(SC)nc1Nc1cccc([N+](=O)[O-])c1]

Ethyl 2-(methylthio)-4-((3-nitrophenyl)amino)pyrimidine-5-carboxylate was prepared as descried for Example 1A starting from ethyl 4-chloro-2-(methylthio)pyrimidine-5-carboxylate.

B. 2-(methylthio)-4-((3-nitrophenyl)amino)pyrimidine-5-carboxylic Acid

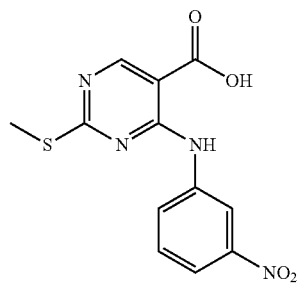 [SMILES: CSc1ncc(C(=O)O)c(Nc2cccc([N+](=O)[O-])c2)n1]

To a solution of ethyl 2-(methylthio)-4-((3-nitrophenyl)amino)pyrimidine-5-carboxylate (1.0 g, 2.99 mmol) in THF (5 mL) and MeOH (5 mL) was added LiOH.H₂O (628 mg, 14.97 mmol) in water (5 mL). The reaction mixture was stirred for overnight at room temperature. The organic solvent was removed under reduced pressure and water (4 mL) was added to the reaction mixture. To a reaction mixture was added 1N HCl solution to produce solid. The solid product was filtered and dried with nitrogen gas flow. The title product (720 mg, 79% yield) was used next reaction without further purification.

C. 2-(methylthio)-4-((3-nitrophenyl)amino)-N-phenylpyrimidine-5-carboxamide

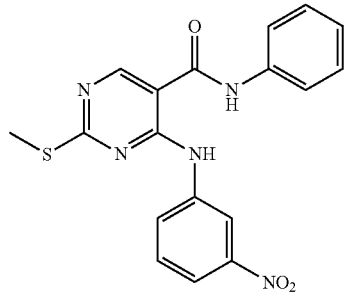 [SMILES: CSc1ncc(C(=O)Nc2ccccc2)c(Nc2cccc([N+](=O)[O-])c2)n1]

To a solution of 2-(methylthio)-4-((3-nitrophenyl)amino)pyrimidine-5-carboxylic acid (600 mg, 1.96 mmol) and aniline (268 μL, 2.94 mmol) in DMF (6 mL) were added EDCI (563 mg, 2.94 mmol), HOBt hydrate (450 mg, 3.33 mmol) and TEA (409 μL, 2.94 mmol). The reaction mixture stirred at room temperature for overnight after which, it was partitioned ethyl acetate and sat. NH₄Cl solution. The water layer was extracted with ethyl acetate. The combined organic layer was washed with brine, dried with MgSO₄, filtered with a pad of celite and concentrated under reduced pressure. The crude compound purified with flesh silica chromatography (0:100 to 3:97, methanol/dichloromethane) as a solvent to afford 2-(methylthio)-4-((3-nitrophenyl)amino)-N-phenylpyrimidine-5-carboxamide (620 mg, 83% yield).

D. 7-(1H-imidazol-1-yl)-1-(3-nitrophenyl)-3-phenylpyrimido[4,5-d]pyrimidine-2,4(1H,3H)-dione

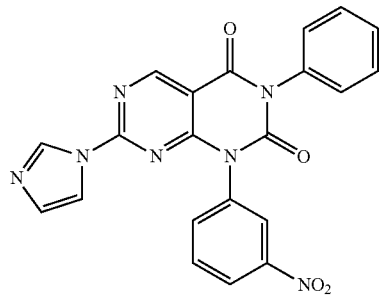 [SMILES: O=c1c2cnc(-n3ccnc3)nc2n(-c2cccc([N+](=O)[O-])c2)c(=O)n1-c1ccccc1]

A 25 mL sealed vial was charged with (of 2-(methylthio)-4-((3-nitrophenyl)amino)-N-phenylpyrimidine-5-carboxamide (620 mg, 1.63 mmol), CDI (2.6 g, 16.27 mmol) and xylene (6 mL). The reaction vial was sealed and heated at 160° C. for 24 hrs. The reaction mixture was concentrated under reduced pressure and the residue was purified by column chromatography on silica gel (1:99 to 7:95, methanol/dichloromethane) to afford 7-(1H-imidazol-1-yl)-1-(3-nitrophenyl)-3-phenylpyrimido[4,5-d]pyrimidine-2,4(1H,3H)-dione (240 mg, 35% yield).

E. 7-((2-methoxy-4-(4-methylpiperazin-1-yl)phenyl)amino)-1-(3-nitrophenyl)-3-phenylpyrimido[4,5-d]pyrimidine-2,4(1H,3H)-dione

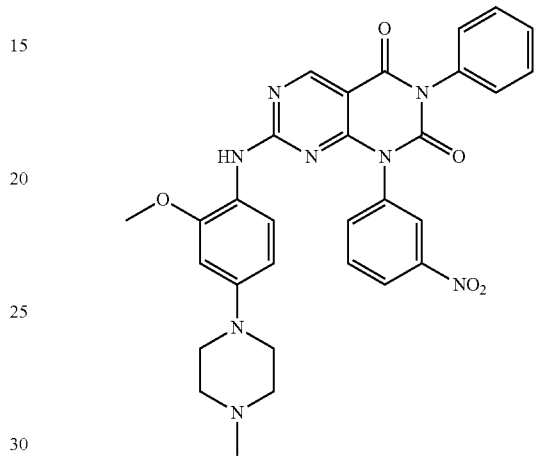

7-((2-methoxy-4-(4-methylpiperazin-1-yl)phenyl)amino)-1-(3-nitrophenyl)-3-phenylpyrimido[4,5-d]pyrimidine-2,4(1H,3H)-dione was prepared as descried for Example 1B starting from 7-(1H-imidazol-1-yl)-1-(3-nitrophenyl)-3-phenylpyrimido[4,5-d]pyrimidine-2,4(1H,3H)-dione.

F. N-(3-(7-((2-methoxy-4-(4-methylpiperazin-1-yl)phenyl)amino)-2,4-dioxo-3-phenyl-3,4-dihydropyrimido[4,5-d]pyrimidin-1(2H)-yl)phenyl)acrylamide

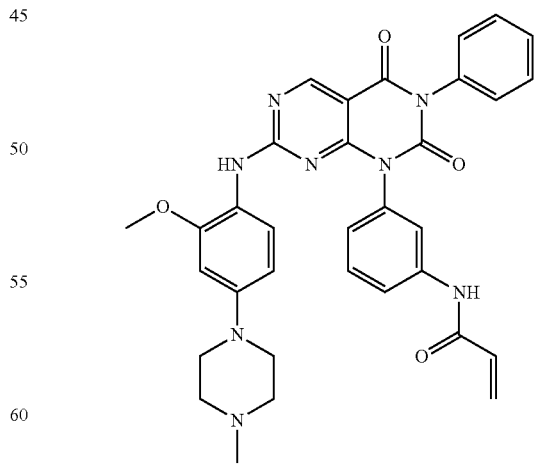

N-(3-(7-((2-methoxy-4-(4-methylpiperazin-1-yl)phenyl)amino)-2,4-dioxo-3-phenyl-3,4-dihydropyrimido[4,5-d]pyrimidin-1(2H)-yl)phenyl)acrylamide carbamate was prepared as descried for Example 3E and F starting from 7-((2-methoxy-4-(4-methylpiperazin-1-yl)phenyl)amino)-1-(3-nitrophenyl)-3-phenylpyrimido[4,5-d]pyrimidine-2,4(1H,3H)-dione. Rt=2.93 min, MS m/z: 605.47 [M+1], $^1$H NMR 600 MHz (DMSO-$d_6$) δ 10.27 (s, 1H), 8.74 (s, 1H), 8.54 (s, 1H), 7.71 (br, 1H), 7.68 (s, 1H), 7.36 (m, 3H), 7.31 (m, 2H), 7.27 (m, 2H), 7.09 (m, 1H), 7.03 (d, J=6.0 Hz, 1H), 6.39 (s, 1H), 6.34 (m, 1H), 6.16 (dd, J=1.8 Hz, J=16.8 Hz, 1H), 5.66 (dd, J=1.8 Hz, J=9.6 Hz, 1H), 3.65 (s, 3H), 2.92 (m, 4H), 2.31 (m, 4H), 2.11 (s, 3H).

Scheme 6.

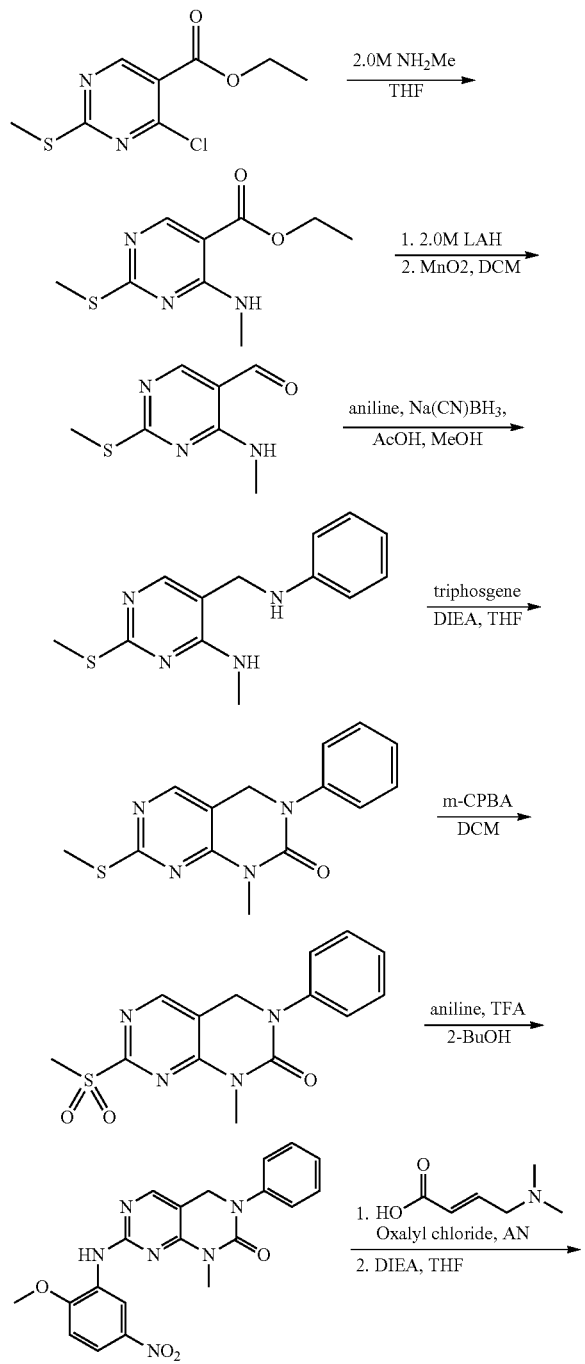

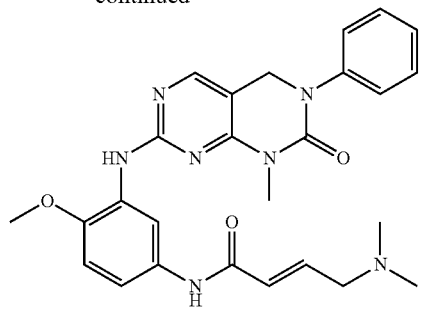

Example 7. (E)-4-(dimethylamino)-N-(4-methoxy-3-((8-methyl-7-oxo-6-phenyl-5,6,7,8-tetrahydropyrimido[4,5-d]pyrimidin-2-yl)amino)phenyl)but-2-enamide (7A)

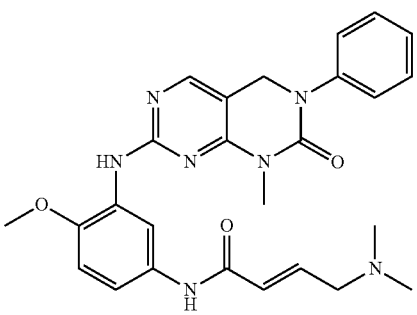

A. Ethyl 4-(methylamino)-2-(methylthio)pyrimidine-5-carboxylate

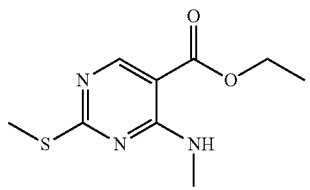

To a solution of ethyl 4-chloro-2-(methylthio)pyrimidine-5-carboxylate (2.0 g, 8.6 mmol) in THF (20 mL) was added 2.0 M methylamine solution in THF (11.34 mL, 21.4 mmol) at 0° C. The reaction mixture was stirred at room temperature for 1 h and concentrated to half of the original volume of solvent under reduced pressure. To the reaction mixture was added water (2000 mL) and the resulting precipitate was collected by filtration. The solid was blown dry using nitrogen gas to give ethyl 4-(methylamino)-2-(methylthio)pyrimidine-5-carboxylate (1.75 g, 89% yield) as a white solid. $^1$H NMR 600 MHz (CDCl$_3$) δ 8.60 (s, 1H), 8.16 (bs, 1H), 4.32 (q, J=7.2 Hz, J=13.8 Hz, 2H), 3.07 (d, J=5.4 Hz, 3H), 2.54 (s, 3H), 1.36 (t, J=7.2 Hz, 3H); $^1$H NMR 400 MHz (DMSO-$d_6$) δ 8.49 (s, 1H), 8.23 (bs, 1H), 4.26 (q, J=7.1 Hz, J=14.1 Hz, 2H), 2.96 (d, J=4.8 Hz, 3H), 2.48 (s, 3H), 1.28 (t, J=7.1 Hz, 3H).

B. 4-(methylamino)-2-(methylthio)pyrimidine-5-carbaldehyde

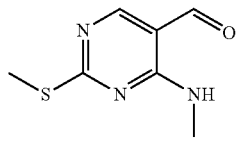

To a solution of 4-(methylamino)-2-(methylthio)pyrimidine-5-carboxylate (300 mg, 1.32 mmol) in THF (6.6 mL) was added 2.0 M lithium aluminum hydride solution in THF (0.79 mL, 1.58 mmol) at 0° C. The reaction mixture was stirred at room temperature for 2 hrs and treated with saturated NH$_4$Cl solution (2 mL). After stirring at room temperature for 30 min, the reaction mixture was filtered through a pad of celite. The filtrate was partitioned between ethyl acetate (30 mL) and water (20 mL). The organic layer was washed with brine, dried over MgSO$_4$, filtered through a pad of celite and concentrated under reduced pressure. The resulting white solid (210 mg, 86% yield) was used for the next step without further purification.

To a solution of (4-(methylamino)-2-(methylthio)pyrimidin-5-yl)methanol (210 mg, 1.14 mmol) in dichloromethane (3.8 mL) was added activated Manganese(IV) oxide (980 mg, 11.4 mmol) at room temperature and stirred for overnight. The reaction mixture was filtered through a pad of celite and concentrated under reduced pressure. The resulting crude product was purified by flash silica gel chromatography with ethyl acetate/hexane (1/9 to 1/4) to give (190 mg, 89% yield) of the title product as a white solid. $^1$H NMR 600 MHz (CDCl$_3$) δ 9.67 (s, 1H), 8.52 (bs, 1H), 8.27 (s, 1H), 3.10 (d, J=5.4 Hz, 3H), 2.54 (s, 3H).

C. N-methyl-2-(methylthio)-5-((phenylamino)methyl)pyrimidin-4-amine

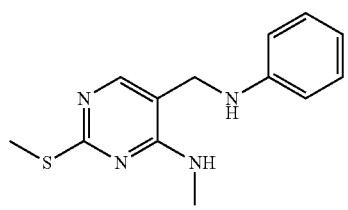 [SMILES: CNc1nc(SC)ncc1CNc1ccccc1]

To a solution of 4-(methylamino)-2-(methylthio)pyrimidine-5-carbaldehyde (190 mg, 1.04 mmol) in methanol (5 mL) were added acetic acid (0.12 mL, 2.06 mmol), aniline 9 (106 mg, 1.14 mmol) and Na(CN)BH$_3$ (325 mg, 5.18 mmol) at the resulting solution was stirred at room temperature overnight. The reaction mixture was partitioned between ethyl acetate (30 mL) and saturated NaHCO$_3$ (20 mL) and then the water layer was extracted with ethyl acetate (10 mL×3). The combined organic layer was washed with brine, dried over MgSO$_4$, filtered through a pad of celite and concentrated under reduced pressure. The resulting crude product was purified by silica gel chromatography with ethyl acetate/hexane (1/4 to 2/3) to give N-methyl-2-(methylthio)-5-((phenylamino)methyl)pyrimidin-4-amine (180 mg, 67% yield) of the title product as a white solid.

D. 1-methyl-7-(methylthio)-3-phenyl-3,4-dihydropyrimido[4,5-d]pyrimidin-2(1H)-one

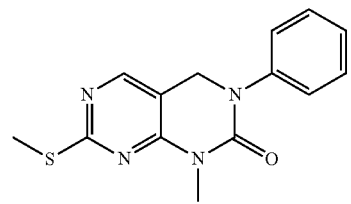 [SMILES: CSc1ncc2c(n1)N(C)C(=O)N(c1ccccc1)C2]

To a solution of N-methyl-2-(methylthio)-5-((phenylamino)methyl)pyrimidin-4-amine (180 mg, 0.69 mmol) in 1,4-dioxane (3.60 mL) were added DIEA (0.36 mL, 2.08 mmol) and triphosgene (82 mg, 0.28 mmol) at 0° C. and stirred at room temperature for 1 h. The precipitate was filtered off and the filtrate was stirred at 110° C. for 3 hrs. The reaction mixture was cooled to room temperature and was partitioned between ethyl acetate (20 mL) and saturated NaHCO$_3$ (20 mL) solution. The organic layer was washed with brine, dried over MgSO$_4$, filtered through a pad of celite and concentrated under reduced pressure. The resulting crude product was purified by column chromatography on silica gel (0:100 to 3:97, methanol/dichloromethane) to give 1-methyl-7-(methylsulfonyl)-3-phenyl-3,4-dihydropyrimido[4,5-d]pyrimidin-2(1H)-one (140 mg, 71% yield) of the title product as a white solid.

E. 1-methyl-7-(methylsulfonyl)-3-phenyl-3,4-dihydropyrimido[4,5-d]pyrimidin-2(1H)-one

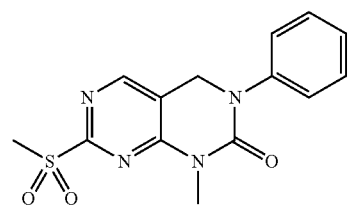 [SMILES: CN1C(=O)N(c2ccccc2)Cc2cnc(S(C)(=O)=O)nc21]

To a solution of 1-methyl-7-(methylsulfonyl)-3-phenyl-3,4-dihydropyrimido[4,5-d]pyrimidin-2(1H)-one (140 mg, 0.49 mmol) in dichloromethane (2 mL) was added m-chloroperbenzoic acid (361 mg, 1.47 mmol) at 0° C. The reaction F. 7-((2-methoxy-5-nitrophenyl)amino)-1-methyl-3-phenyl-3,4-dihydropyrimido[4,5-d]pyrimidin-2(1H)-one

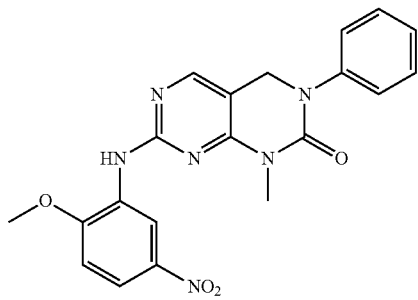 [SMILES: COc1ccc([N+](=O)[O-])cc1Nc1ncc2c(n1)N(C)C(=O)N(c1ccccc1)C2]

To a solution of 1-methyl-7-(methylsulfonyl)-3-phenyl-3,4-dihydropyrimido[4,5-d]pyrimidin-2(1H)-one (130 mg, 0.41 mmol) in 2-butanol (1.0 mL) were added 2-methoxy-5-nitroaniline (137 mg, 0.82 mmol) and TFA (0.1 mL). The reaction mixture was stirred for 24 hrs at 120° C. in sealed reaction vessel. The reaction mixture was cooled to room temperature and concentrated under reduced pressure. The crude reaction mixture was partitioned between ethyl acetate (10 mL) and sat. NaHCO₃ solution. The water layer was extracted with ethyl acetate. The combined organic layer was washed with brine, dried with MgSO₄, filtered through a pad of celite and concentrated under reduced pressure. The resulting crude product was purified by column chromatography on silica gel (0:100 to 5:95, methanol/dichloromethane) to give 7-((2-methoxy-5-nitrophenyl)amino)-1-methyl-3-phenyl-3,4-dihydropyrimido[4,5-d]pyrimidin-2(1H)-one (120 mg, 72% yield).

G. (E)-4-(dimethylamino)-N-(4-methoxy-3-((8-methyl-7-oxo-6-phenyl-5,6,7,8-tetrahydropyrimido[4,5-d]pyrimidin-2-yl)amino)phenyl)but-2-enamide

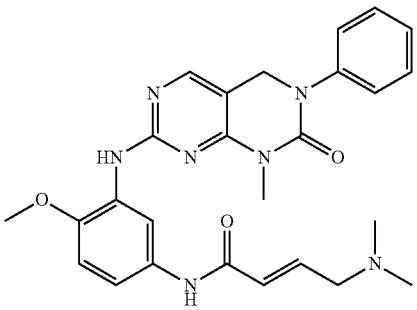

To a solution of 7-((2-methoxy-5-nitrophenyl)amino)-1-methyl-3-phenyl-3,4-dihydropyrimido[4,5-d]pyrimidin-2(1H)-one (120 mg, 0.30 mmol) in methanol (2 mL) was added Palladium, 10 wt. % (dry basis) on activated carbon, wet, Degussa type E101 NE/W under nitrogen atmosphere. The reaction mixture was hydrogenated under balloon pressure for 6 hrs. The resulting suspension was filtered through a pad of celite and the filtrate was concentrated to afford 7-((5-amino-2-methoxyphenyl)amino)-1-methyl-3-phenyl-3,4-dihydropyrimido[4,5-d]pyrimidin-2(1H)-one (105 mg, 94% yield).

To a stirred solution of (E)-4-(dimethylamino)but-2-enoic acid hydrochloride (60 mg, 0.36 mmol) in CH₃CN (1.0 mL) was added oxalyl chloride (37 µL, 0.44 mmol) at 0° C. The reaction mixture was allowed to stir at 0° C. for 30 min and then at RT for 2 h. Finally it was heated at 45° C. for 5 min, cooled and the reaction mixture, (E)-4-(dimethylamino)but-2-enoyl chloride, was concentrated under reduced pressure.

To a solution of 7-((5-amino-2-methoxyphenyl)amino)-1-methyl-3-phenyl-3,4-dihydropyrimido[4,5-d]pyrimidin-2(1H)-one (105 mg, 0.28 mmol) in anhydrous THF (1 mL) were added DIEA (0.24 mL, 1.40 mmol) and (E)-4-(dimethylamino)but-2-enoyl chloride in anhydrous THF (1 mL) at 0° C. The reaction mixture was stirred at 0° C. for 1 h, quenched with cold water (5 mL) and extracted with CH₂Cl₂ (3×10 mL). The organic layer was washed with brine, dried over MgSO₄, filtered through a pad of celite and concentrated under reduced pressure. The resulting crude product was purified by Prep HPLC to give (E)-4-(dimethylamino)-N-(4-methoxy-3-((8-methyl-7-oxo-6-phenyl-5,6,7,8-tetrahydropyrimido[4,5-d]pyrimidin-2-yl)amino)phenyl)but-2-enamide (89 mg, 55% yield) as a TFA salt. Rt=2.95 min, MS m/z: 488.41 [M+1].

The following compounds were produced by using the corresponding starting compounds according to method similar to that described in Example 1, 3 and 4.

TABLE 2

| Compound # Synthetic method | Structure | NMR and/or Mass |
|---|---|---|
| Example 8 Scheme 1 | 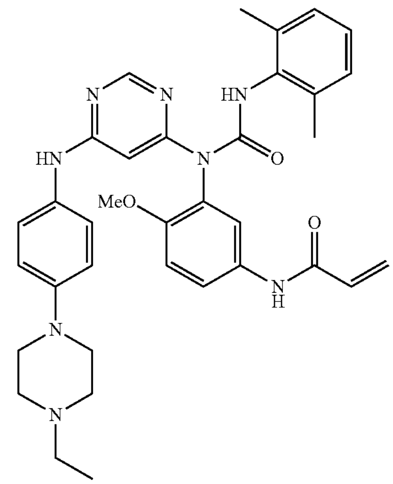 | Rt = 4.35 min, , MS m/z: 595.41 [M + 1] |
| Example 9 Scheme 1 | 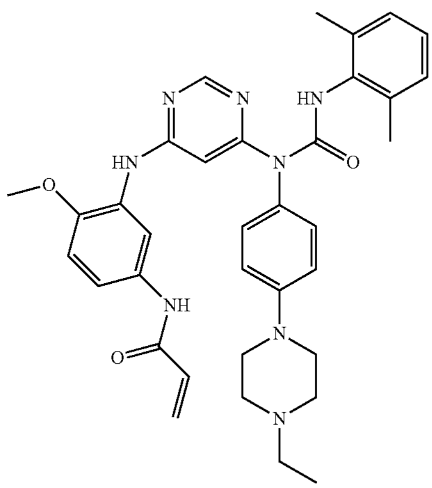 [SMILES: C=CC(=O)Nc1ccc(OC)c(Nc2cc(N(C(=O)Nc3c(C)cccc3C)c3ccc(N4CCN(CC)CC4)cc3)ncn2)c1] | Rt = 4.60 min, MS m/z: 621.35 [M + 1] |
| Example 10- Scheme 4 | 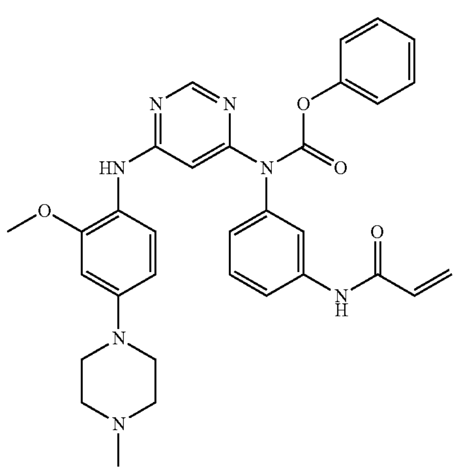 [SMILES: C=CC(=O)Nc1cccc(N(C(=O)Oc2ccccc2)c2cc(Nc3ccc(N4CCN(C)CC4)cc3OC)ncn2)c1] | Rt = 3.68 min, MS m/z: 580.53 [M + 1], $^1$H NMR 600 MHz (DMSO-d$_6$) δ 10.34 (s, 1H), 8.33 (d, J = 6.0 Hz, 1H), 7.84 (d, J = 7.8 Hz, 1H), 7.68 (m, 1H), 7.64 (s, 1H), 7.45 (t, J = 7.8 Hz, 1H), 7.37 (m, 2H), 7.31 (m, 1H), 7.24 (t, J = 7.8 Hz, 1H), 7.15 (m, 3H), 6.47 (d, J = 2.4 Hz, 1H), 6.40 (m, 1H), 6.23 (dd, J = 1.8 Hz, J = 16.8 Hz, 1H), 6.0 (br, 1H), 5.73 (dd, J = 1.8 Hz, J = 10.2 Hz, 1H), 3.72 (s, 3H), 2.97 (m, 4H), 2.39 (m, 4H), 2.17 (s, 3H). |

TABLE 2-continued

| Compound # Synthetic method | Structure | NMR and/or Mass |
|---|---|---|
| Example 11 Scheme 1 | 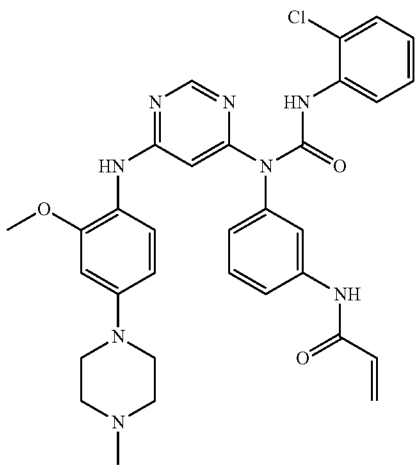 [SMILES: C=CC(=O)Nc1cccc(N(C(=O)Nc2ccccc2Cl)c2cc(Nc3ccc(N4CCN(C)CC4)cc3OC)ncn2)c1] | Rt = 4.20 min, MS m/z: 613.35 [M + 1], $^1$H NMR 600 MHz (DMSO-d$_6$) δ 10.03 (s, 1H), 8.96 (s, 1H), 8.08 (s, 1H), 7.99 (s, 1H), 7.83 (s, 1H), 7.22 (m, 2H), 7.14 (t, J = 5.4 Hz, 1H), 6.96 (t, J = 7.2 Hz, 1H), 6.74 (dd, J = 1.2 Hz, J = 8.4 Hz, 1H), 6.58 (d, J = 2.4 Hz, 1H), 6.48 (m, 1H), 6.43 (m, 2H), 6.22 (dd, J = 1.8 Hz, J = 16.8 Hz, 1H), 5.74 (s, 1H), 5.70 (dd, J = 1.8 Hz, J = 10.8 Hz, 1H), 5.25 (m, 2H), 3.72 (s, 3H), 3.10 (m, 4H), 2.43 (m, 4H), 2.20 (s, 3H). |
| Example 12 Scheme 1 | 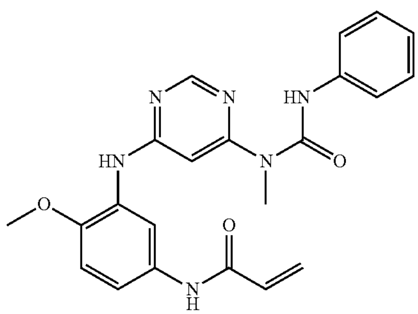 [SMILES: C=CC(=O)Nc1ccc(OC)c(Nc2cc(N(C)C(=O)Nc3ccccc3)ncn2)c1] | MS m/z: 419.11 [M + 1], $^1$H NMR 600 MHz (DMSO-d$_6$) δ 12.56 (s, 1H), 10.02 (s, 1H), 8.92 (s, 1H), 8.46 (s, 1H), 8.14 (d, J = 2.4 Hz, 1H), 7.53 (d, J = 7.2 Hz, 1H), 7.47 (dd, J = 2.4 Hz, J = 9.0 Hz, 1H), 7.28 (m, 3H), 7.00 (m, 2H), 6.61 (s, 1H), 6.42 (m, 1H), 6.20 (dd, J = 1.8 Hz, J = 16.8 Hz, 1H), 5.68 (dd, J = 1.8 Hz, J = 10.2 Hz, 1H), 3.78 (s, 3H), 3.25 (s, 3H). |
| Example 13 Scheme 1 | 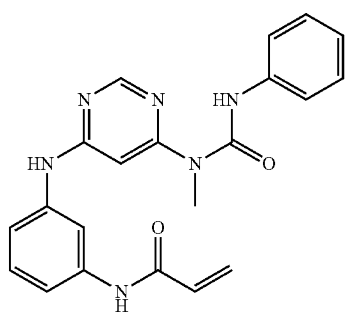 [SMILES: C=CC(=O)Nc1cccc(Nc2cc(N(C)C(=O)Nc3ccccc3)ncn2)c1] | MS m/z: 389.00 [M + 1], $^1$H NMR 600 MHz (DMSO-d$_6$) δ 12.40 (s, 1H), 10.15 (s, 1H), 9.71 (s, 1H), 8.53 (s, 1H), 8.01 (s, 1H), 7.56 (d, J = 7.2 Hz, 1H), 7.38 (d, J = 7.2 Hz, 1H), 7.32 (m, 4H), 7.26 (t, J = 7.8 Hz, 1H), 7.05 (t, J = 7.2 Hz, 1H), 6.52 (s, 1H), 6.47 (m, 1H), 6.26 (dd, J = 1.8 Hz, J = 16.8 Hz, 1H), 5.74 (dd, J = 1.8 Hz, J = 10.2 Hz, 1H), 3.31 (s, 3H). |
| Example 14 Scheme 1 | 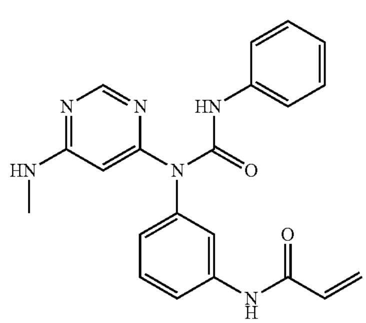 [SMILES: C=CC(=O)Nc1cccc(N(C(=O)Nc2ccccc2)c2cc(NC)ncn2)c1] | MS m/z: 389.25 [M + 1], $^1$H NMR 600 MHz (DMSO-d$_6$) δ 10.20 (s, 1H), 9.90 (br, 1H), 7.98 (br, 1H), 8.27 (s, 1H), 7.85 (s, 1H), 7.30 (m, 2H), 7.24 (m, 1H), 7.15 (m, 3H), 6.80 (d, J = 7.2 Hz, 2H), 6.43 (m, 1H), 6.24 (dd, J = 1.8 Hz, J = 17.4 Hz, 1H), 5.82 (s, 1H), 5.74 (dd, J = 1.8 Hz, J = 10.2 Hz, 1H), 2.78 (s, 3H). |

TABLE 2-continued

| Compound #<br>Synthetic method | Structure | NMR and/or Mass |
|---|---|---|
| Example 15<br>Scheme 1 | | MS m/z: 403.11 [M + 1], ¹H NMR 600 MHz (DMSO-d₆) δ 10.28 (s, 1H), 8.26 (s, 1H), 7.68 (d, J = 8.4 Hz, 1H), 7.58 (s, 1H), 7.42 (t, J = 8.4 Hz, 2H), 7.28 (m, 3H), 7.21 (m, 3H), 6.95 (d, J = 7.2 Hz, 1H), 6.41 (m, 1H), 6.24 (dd, J = 1.8 Hz, J = 15.6 Hz, 1H), 5.74 (dd, J = 1.8 Hz, J = 10.2 Hz, 1H), 5.40 (s, 1H), 4.36 (d, J = 6.0 Hz, 2H), 3.50 (s, 3H). |
| Example 16<br>Scheme 1 | | MS m/z: 433.03 [M + 1]. |
| Example 17<br>Scheme 1 | | MS m/z: 403.30 [M + 1]. |
| Example 18<br>Scheme 1 | | Rt = 4.28 min, MS m/z: 471.28 [M + 1], ¹H NMR 600 MHz (DMSO-d₆) δ 12.86 (s, 1H), 10.02 (s, 1H), 8.92 (s, 1H), 8.48 (s, 1H), 8.17 (d, J = 2.4 Hz, 1H), 7.88 (dd, J = 3.0 Hz, J = 7.2 Hz, 1H), 7.52 (m, 1H), 7.49 (dd, J = 2.4 Hz, J = 8.4 Hz, 1H), 7.37 (t, J = 9.0 Hz, 1H), 7.00 (d, J = 8.4 Hz, 1H), 6.64 (s, 1H), 6.44 (m, 1H), 6.22 (dd, J = 1.8 Hz, J = 16.2 Hz, 1H), 5.71 (dd, J = 1.8 Hz, J = 10.2 HZ, 1H), 3.80 (s, 3H), 3.27 (s, 3H). |
| Example 19<br>Scheme 1 | | Rt = 4.07 min, MS m/z: 441.23 [M + 1], ¹H NMR 600 MHz (DMSO-d₆) δ 12.47 (s, 1H), 10.13 (s, 1H), 9.70 (s, 1H), 8.51 (s, 1H), 7.99 (m, 1H), 7.86 (dd, J = 2.4 Hz, J = 7.2 Hz, 1H), 7.50 (m, 1H), 7.34 (m, 2H), 7.28 (d, J = 8.4 Hz, 1H), 7.24 (t, J = 8.4 Hz, 1H), 6.52 (s, 1H), 6.44 (m, 1H), 6.24 (dd, J = 1.8 Hz, J = 17.4 Hz, 1H), 5.72 (dd, J = 1.8 Hz, J = 10.2 HZ, 1H), 3.29 (s, 3H). |

TABLE 2-continued

| Compound # Synthetic method | Structure | NMR and/or Mass |
|---|---|---|
| Example 20 Scheme 1 | 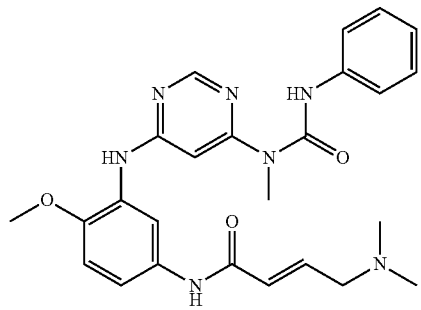 | Rt = 3.13 min, MS m/z: 476.38 [M + 1], $^1$H NMR 600 MHz (DMSO-d$_6$) δ 12.59 (s, 1H), 10.25 (s, 1H), 8.96 (s, 1H), 8.50 (s, 1H), 8.21 (d, J = 1.8 Hz, 1H), 7.57 (d, J = 7.8 Hz, 2H), 7.49 (dd, J = 2.4 Hz, J = 8.4 Hz, 1H), 7.34 (t, J = 7.8 Hz, 2H), 7.06 (m, 2H), 6.73 (m, 1H), 6.69 (m, 1H), 6.47 (d, J = 15.6 Hz, 1H), 3.93 (m, 2H), 3.82 (s, 3H), 3.30 (s, 3H), 2.80 (d, J = 3.0 Hz, 6H). |
| Example 21 Scheme 1 | 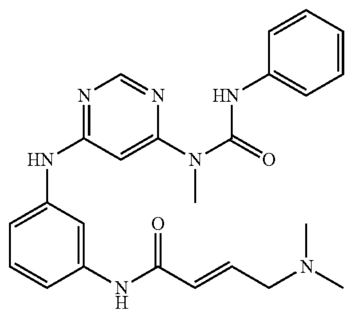 [SMILES: CN(C)C/C=C/C(=O)Nc1cccc(Nc2cc(N(C)C(=O)Nc3ccccc3)ncn2)c1] | Rt = 3.37 min, MS m/z: 446.27 [M + 1], $^1$H NMR 600 MHz (DMSO-d$_6$) δ 12.41 (s, 1H), 10.35 (s, 1H), 9.74 (s, 1H), 8.54 (s, 1H), 8.05 (d, J = 1.8 Hz, 1H), 7.58 (d, J = 7.2 Hz, 2H), 7.39 (d, J = 9.0 Hz, 1H), 7.34 (m, 3H), 7.29 (t, J = 8.4 Hz, 1H), 7.03 (t, J = 7.8 Hz, 1H), 6.76 (m, 1H), 6.55 (s, 1H), 6.50 (d, J = 15.0 Hz, 1H), 3.94 (m, 2H), 3.30 (s, 3H), 2.81 (d, J = 3.6 Hz, 6H). |
| Example 22 Scheme 2 | 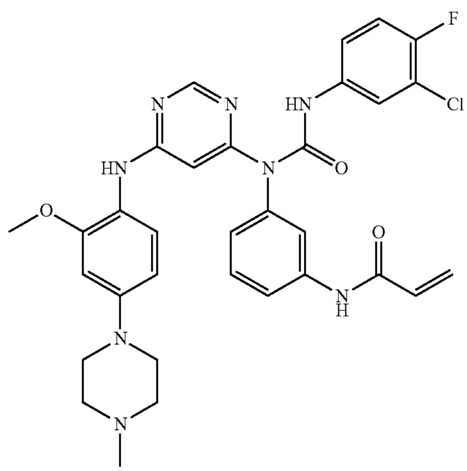 [SMILES: C=CC(=O)Nc1cccc(N(C(=O)Nc2ccc(F)c(Cl)c2)c2cc(Nc3ccc(N4CCN(C)CC4)cc3OC)ncn2)c1] | Rt = 4.33 min, MS m/z: 631.40 [M + 1]. |
| Example 23 Scheme 1 | 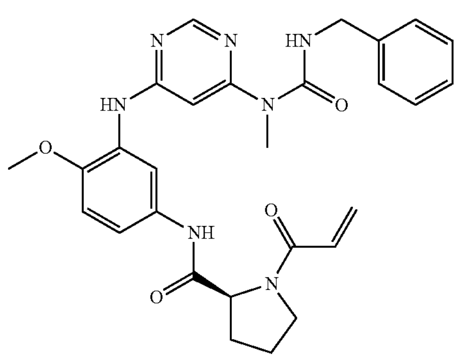 [SMILES: C=CC(=O)N1CCC[C@@H]1C(=O)Nc1ccc(OC)c(Nc2cc(N(C)C(=O)NCc3ccccc3)ncn2)c1] | Rt = 2.92 min, MS m/z: 530.37 [M + 1]. |

TABLE 2-continued

| Compound #<br>Synthetic method | Structure | NMR and/or Mass |
|---|---|---|
| Example 24<br>Scheme 1 | | Rt = 2.93 min, MS m/z: 530.37 [M + 1]. |
| Example 25<br>Scheme 1 | | MS m/z: 549.39 [M + 1]. |
| Example 26<br>Scheme 1 | | MS m/z: 549.39 [M + 1]. |

TABLE 2-continued
| Compound # Synthetic method | Structure | NMR and/or Mass |
|---|---|---|
| Example 27 Scheme 1 | 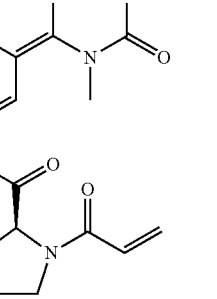 | MS m/z: 475.31 [M + 1]. |
| Example 28 Scheme 1 | 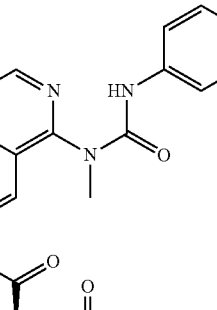 | Rt = 3.00 min, MS m/z: 497.30 [M + 1]. |
| Example 29 Scheme 1 | 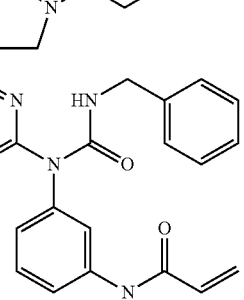 | Rt = 2.95 min, MS m/z: 563.45 [M + 1]. |
| Example 30 Scheme 1 | 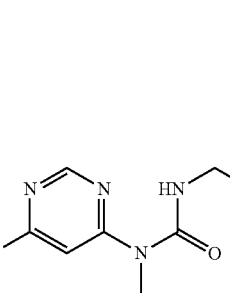 | Rt = 3.13 min, MS m/z: 563.45 [M + 1]. |

TABLE 2-continued

| Compound #<br>Synthetic method | Structure | NMR and/or Mass |
|---|---|---|
| Example 31<br>Scheme 4 | | Rt = 3.38 min, MS m/z: 533.34 [M + 1]. |
| Example 32<br>Scheme 1 | | Rt = 3.12 min, MS m/z: 571.39 [M + 1], $^1$H NMR 600 MHz (DMSO-d$_6$) δ 12.81 (br, 1H), 8.90 (s, 1H), 8.35 (s, 1H), 7.49 (m, 3H), 7.26 (m, 2H), 7.06 (dd, J = 2.4 Hz, J = 8.4 Hz, 1H), 7.00 (t, J = 7.8 Hz, 1H), 6.74 (s, 1H), 6.63 (dd, J = 2.4 Hz, J = 7.8 Hz, 1H), 6.49 (m, 1H), 6.07 (dd, J = 1.8 Hz, J = 16.8 Hz, 1H), 5.61 (m, 1H), 5.33 (br, 1H). |
| Example 33<br>Scheme 1 | | Rt = 3.13 min, MS m/z: 571.45 [M + 1], |

TABLE 2-continued

| Compound #<br>Synthetic method | Structure | NMR and/or Mass |
|---|---|---|
| Example 34<br>Scheme 2 | | Rt = 3.13 min, MS m/z: 607.43 [M + 1], ¹H NMR 600 MHz (DMSO-d₆) δ 10.30 (br, 1H), 10.25 (s, 1H), 9.70 (br, 1H), 8.71 (s, 1H), 8.28 (s, 1H), 7.67 (d, J = 7.8 Hz, 1H), 7.47 (s, 1H), 7.37 (t, J = 7.8 Hz, 1H), 7.32 (m, 4H), 7.20 (m, 1H), 6.88 (d, J = 8.4 Hz, 1H), 6.55 (d, J = 1.8 Hz, 1H), 6.43 (dd, J = 2.4 Hz, J = 9.0 Hz, 1H), 6.38 (m, 1H), 6.23 (dd, J = 1.8 Hz, J = 17.4 Hz, 1H), 5.74 (dd, J = 1.8 Hz, J = 10.2 Hz, 1H), 5.45 (br, 1H), 4.88 (m, 1H), 3.76 (m, 2H), 3.65 (s, 3H), 3.51 (m, 2H), 3.11 (m, 2H), 2.88 (m, 2H), 2.82 (s, 3H), 1.43 (d, J = 6.6 Hz, 3H). |
| Example 35<br>Scheme 2 | | Rt = 3.13 min, MS m/z: 607.43 [M + 1], ¹H NMR 600 MHz (DMSO-d₆) δ 10.36 (br, 1H), 10.25? (s, 1H), 9.72 (br, 1H), 8.67 (s, 1H), 8.27 (s, 1H), 7.67 (d, J = 7.8 Hz, 1H), 7.44 (s, 1H), 7.38 (t, J = 8.4 Hz, 1H), 7.29 (m, 4H), 7.20 (m, 1H), 6.87 (d, J = 7.8 Hz, 1H), 6.55 (d, J = 2.4 Hz, 1H), 6.43 (dd, J = 2.4 Hz, J = 9.0 Hz, 1H), 6.38 (m, 1H), 6.23 (dd, J = 1.8 Hz, J = 16.8 Hz, 1H), 5.74 (dd, J = 1.8 Hz, J = 10.2 Hz, 1H), 5.48 (br, 1H), 4.88 (m, 1H), 3.76 (m, 2H), 3.65 (s, 3H), 3.48 (m, 2H), 3.09 (m, 2H), 2.88 (m, 2H), 2.82 (s, 3H), 1.43 (d, J = 6.6 Hz, 3H). |
| Example 36<br>Scheme 2 | | Rt = 3.07 min, MS m/z: 607.36 [M + 1], ¹H NMR 600 MHz (DMSO-d₆) δ 10.26 (s, 1H), 9.71 (br, 1H), 9.56 (br, 1H), 8.69 (s, 1H), 8.11 (s, 1H), 7.67 (d, J = 7.8 Hz, 1H), 7.49 (s, 1H), 7.38 (t, J = 7.8 Hz, 1H), 7.28 (m, 2H), 7.22 (m, 2H), 7.19 (t, J = 7.2 Hz, 1H), 6.86 (d, J = 8.4 Hz, 1H), 6.56 (d, J = 2.4 Hz, 1H), 6.43 (m, 1H), 6.40 (m, 1H), 6.24 (dd, J = 1.8 Hz, J = 17.4 Hz, 1H), 5.75 (dd, J = 1.8 Hz, J = 10.8 Hz, 1H), 5.45 (s, 1H), 3.77 (m, 2H), 3.61 (s, 3H), 3.48 (m, 2H), 3.38 (m, 2H), 3.12 (m, 2H), 2.90 (m, 2H), 2.82 (s, 3H), 2.77 (m, 2H). |

TABLE 2-continued

| Compound #<br>Synthetic method | Structure | NMR and/or Mass |
|---|---|---|
| Example 37<br>Scheme 2 | | Rt = 2.95 min, MS m/z: 595.46 [M + 1], $^1$H NMR 600 MHz (DMSO-d$_6$) δ 10.01 (s, 1H), 9.92 (br, 1H), 9.72 (br, 1H), 8.73 (s, 1H), 8.24 (m, 2H), 7.62 (d, J = 7.8 Hz, 1H), 7.48 (s, 1H), 7.38 (t, J = 7.8 Hz, 1H), 7.28 (m, 3H), 7.20 (m, 2H), 6.89 (d, J = 7.8 Hz, 1H), 6.59 (d, J = 2.4 Hz, 1H), 6.47 (dd, J = 2.4 Hz, J = 9.0 Hz, 1H), 4.40 (d, J = 6.0 Hz, 2H), 3.80 (m, 4H), 3.69 (s, 3H), 3.14 (m, 2H), 2.93 (m, 2H), 2.85 (s, 3H), 2.31 (q, 2H), 1.07 (t, 3H). |
| Example 38<br>Scheme 2 | | Rt = 2.95 min, MS m/z: 615.49 [M + 1], $^1$H NMR 600 MHz (DMSO-d$_6$) δ 10.02 (br, 1H), 8.83 (br, 1H), 8.23 (s, 1H), 7.75 (d, J = 8.4 Hz, 1H), 7.63 (s, 1H), 7.61 (d, J = 8.4 Hz, 1H), 7.48 (s, 1H), 7.41 (t, J = 8.4 Hz, 1H), 7.28 (m, 3H), 7.20 (m, 2H), 6.95 (d, J = 7.8 Hz, 1H), 6.90 (m, 1H), 6.56 (s, 1H), 6.44 (dd, J = 3.0 Hz, J = 8.4 Hz, 1H), 4.37 (d, J = 5.4 Hz, 2H), 3.78 (m, 2H), 3.66 (s, 3H), 3.47 (m, 4H), 3.11 (m, 2H), 2.92 (m, 2H), 2.81 (s, 3H). |
| Example 39<br>Scheme 2 | | Rt = 2.83 min, MS m/z: 599.36 [M + 1], $^1$H NMR 600 MHz (DMSO-d$_6$) δ 10.30 (s, 1H), 9.84? (br, 1H), 9.70 (br, 1H), 8.81 (s, 1H), 8.25 (s, 1H), 7.72 (d, J = 8.4 Hz, 1H), 7.53 (s, 1H), 7.44 (t, J = 7.8 Hz, 1H), 7.38 (d, J = 1.2 Hz, J = 5.4 Hz, 1H), 7.30 (br, 1H), 6.98 (m, 1H), 6.94 (m, 1H), 6.92 (d, J = 7.8 Hz, 1H), 6.58 (d, J = 2.4 Hz, 1H), 6.46 (dd, J = 2.4 Hz, J = 9.0 Hz, 1H), 6.42 (m, 1H), 6.26 (dd, J = 1.8 Hz, J = 16.8 Hz, 1H), 5.77 (dd, J = 1.8 Hz, J = 10.8 Hz, 1H), 4.54 (d, J = 5.4 Hz, 2H), 3.80 (m, 4H), 3.68 (s, 3H), 3.11 (m, 2H), 2.92 (m, 2H), 2.84 (s, 3H). |
| Example 40<br>Scheme 2 | | Rt = 2.13 min, MS m/z: 594.39 [M + 1], $^1$H NMR 600 MHz (DMSO-d$_6$) δ 10.29 (s, 1H), 9.84 (br, 1H), 9.75 (br, 1H), 8.77 (s, 1H), 8.71 (s, 1H), 8.64 (d, J = 4.8 Hz, 1H), 8.25 (s, 1H), 8.17 (d, J = 7.2 Hz, 1H), 7.74 (m, 1H), 7.64 (d, J = 8.4 Hz, 1H), 7.56 (s, 1H), 7.41 (t, J = 7.8 Hz, 1H), 7.29 (m, 1H), 6.93 (d, J = 7.8 Hz, 1H), 6.57 (d, J = 2.4 Hz, 1H), 6.44 (dd, J = 3.0 Hz, J = 8.4 Hz, 1H), 6.40 (m, 1H), 6.24 (dd, J = 1.8 Hz, J = 17.4 Hz, 1H), 5.75 (dd, J = 1.8 Hz, J = 10.2 Hz, 1H), 4.49 (d, J = 5.4 Hz, 2H), 3.77 (m, 4H), 3.66 (s, 3H), 2.88 (m, 4H), 2.82 (s, 3H). |

TABLE 2-continued
| Compound #<br>Synthetic method | Structure | NMR and/or Mass |
|---|---|---|
| Example 41<br>Scheme 2 | 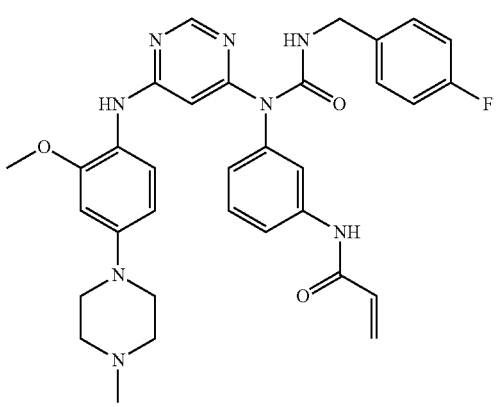 [SMILES: C=CC(=O)Nc1cccc(N(C(=O)NCc2ccc(F)cc2)c2cc(Nc3ccc(N4CCN(C)CC4)cc3OC)ncn2)c1] | Rt = 3.42 min, MS m/z: 611.48 [M + 1]. |
| Example 42<br>Scheme 2 | 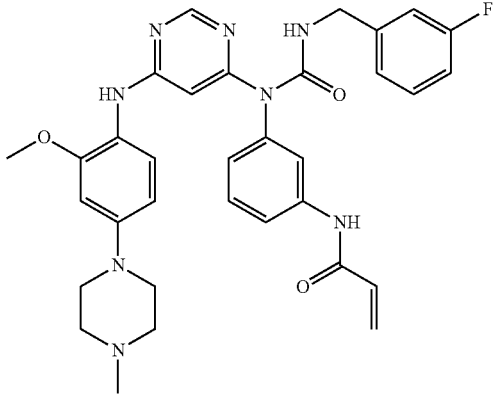 [SMILES: C=CC(=O)Nc1cccc(N(C(=O)NCc2cccc(F)c2)c2cc(Nc3ccc(N4CCN(C)CC4)cc3OC)ncn2)c1] | Rt = 3.45 min, MS m/z : 611.48 [M + 1]. |
| Example 43<br>Scheme 2 | 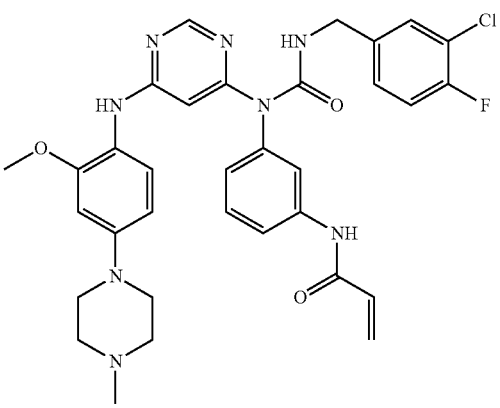 [SMILES: C=CC(=O)Nc1cccc(N(C(=O)NCc2ccc(F)c(Cl)c2)c2cc(Nc3ccc(N4CCN(C)CC4)cc3OC)ncn2)c1] | Rt = 3.15 min, MS m/z: 645.29 [M + 1], $^1$H NMR 600 MHz (DMSO-$d_6$) δ 10.27 (s, 1H), 10.01 (m, 1H), 8.58 (s, 1H), 8.24 (s, 1H), 7.69 (d, J = 8.4 Hz, 1H), 7.53 (s, 1H), 7.52 (d, J = 1.8 Hz, 1H), 7.40 (t, J = 8.4 Hz, 1H), 7.34 (m, 2H), 7.26 (m, 1H), 6.91 (d, J = 7.8 Hz, 1H), 6.49 (d, J = 1.8 Hz, 1H), 6.46 (m, 2H), 6.39 (dd, J = 1.8 Hz, J = 8.4 Hz, 1H), 6.27 (dd, J = 1.8 Hz, J = 16.2 Hz, 1H), 5.78 (dd, J = 1.8 Hz, J = 10.8 Hz, 1H), 4.39 (d, J = 5.4 Hz, 2H), 3.67 (s, 3H), 3.08 (m, 4H), 2.44 (m, 4H), 2.22 (s, 3H). |

TABLE 2-continued

| Compound #<br>Synthetic method | Structure | NMR and/or Mass |
|---|---|---|
| Example 44<br>Scheme 5 | 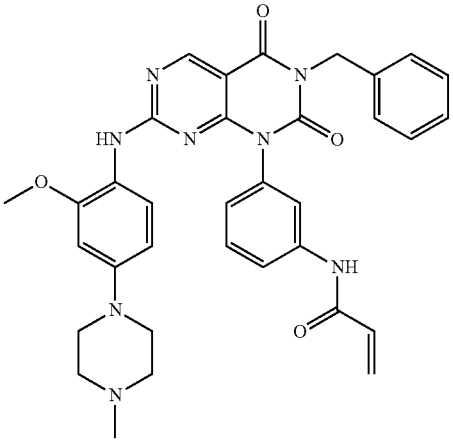 [SMILES: C=CC(=O)Nc1cccc(-n2c(=O)n(Cc3ccccc3)c(=O)c3cnc(Nc4ccc(N5CCN(C)CC5)cc4OC)nc32)c1] | Rt = 3.30 min, MS m/z: 619.40 [M + 1], $^1$H NMR 600 MHz (DMSO-d$_6$) δ 10.34 (s, 1H), 8.84 (s, 1H), 8.61 (s, 1H), 7.83 (br, 1H), 7.67 (s, 1H), 7.47 (t, J = 8.4 Hz, 1H), 7.37 (m, 2H), 7.30 (t, J = 7.2 Hz, 2H), 7.25 (m, 1H), 7.17 (m, 1H), 7.09 (m, 1H), 6.47 (s, 1H), 6.43 (m, 1H), 6.25 (dd, J = 1.8 Hz, J = 16.8 Hz, 1H), 5.95 (m, 1H), 5.76 (dd, J = 1.8 Hz, J = 9.6 Hz, 1H), 5.07 (s, 2H), 3.74 (s, 3H), 3.06 (m, 4H), 2.40 (m, 4H), 2.20 (s, 3H). |
| Example 45<br>Scheme 2 | 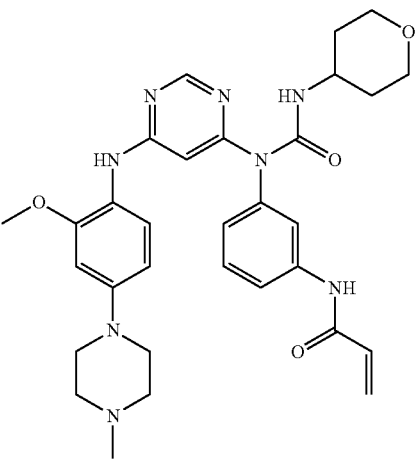 [SMILES: C=CC(=O)Nc1cccc(N(C(=O)NC2CCOCC2)c2cc(Nc3ccc(N4CCN(C)CC4)cc3OC)ncn2)c1] | Rt = 2.60 min, MS m/z: 587.39 [M + 1], $^1$H NMR 600 MHz (DMSO-d$_6$) δ 10.16 (s, 1H), 9.96 (m, 1H), 8.44 (s, 1H), 8.15 (s, 1H), 7.56 (d, J = 8.4 Hz, 1H), 7.41 (s, 1H), 7.30 (t, J = 7.8 Hz, 1H), 7.08 (m, 1H), 6.78 (d, J = 7.8 Hz, 1H), 6.37 (d, J = 1.8 Hz, 1H), 6.32 (m, 1H), 6.27 (d, J = 7.8 Hz, 1H), 6.16 (dd, J = 2.4 Hz, J = 15.6 Hz, 1H), 5.66 (m, 2H), 3.72 (m, 2H), 3.67 (m, 1H), 3.65 (s, 3H), 3.32 (m, 2H), 2.97 (m, 4H), 2.32 (m, 4H), 2.21 (s, 3H), 1.74 (m, 2H), 1.42 (m, 2H). |
| Example 46<br>Scheme 2 | 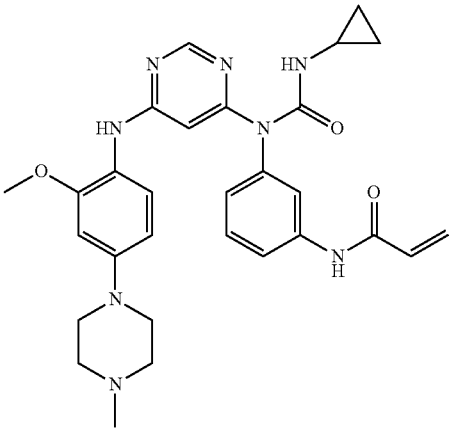 [SMILES: C=CC(=O)Nc1cccc(N(C(=O)NC2CC2)c2cc(Nc3ccc(N4CCN(C)CC4)cc3OC)ncn2)c1] | Rt = 2.60 min, MS m/z: 543.42 [M + 1], $^1$H NMR 600 MHz (DMSO-d$_6$) δ 10.25 (s, 1H), 9.86 (s, 1H), 8.54 (s, 1H), 8.22 (s, 1H), 7.67 (d, J = 7.8 Hz, 1H), 7.50 (m, 1H), 7.39 (t, J = 7.8 Hz, 1H), 7.21 (s, 1H), 6.87 (d, J = 7.8 Hz, 1H), 6.48 (d, J = 1.2 Hz, 1H), 6.46 (m, 1H), 6.37 (dd, J = 2.4 Hz, J = 9.0 Hz, 1H), 6.27 (dd, J = 2.4 Hz, J = 16.8 Hz, 1H), 5.77 (dd, J = 1.8 Hz, J = 10.8 Hz, 1H), 5.45 (s, 1H), 3.65 (s, 3H), 3.07 (m, 4H), 2.64 (m, 1H), 2.42 (m, 4H), 2.20 (s, 3H), 0.65 (m, 2H), 0.49 (m, 2H). |

TABLE 2-continued

| Compound #<br>Synthetic method | Structure | NMR and/or Mass |
|---|---|---|
| Example 47<br>Scheme 2 | 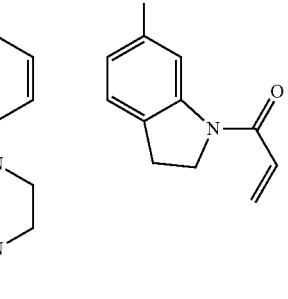 | Rt = 2.93 min, MS m/z : 619.33 [M + 1], $^1$H NMR 600 MHz (DMSO-d$_6$) δ 10.07 (m, 1H), 8.50 (s, 1H), 8.18 (s, 1H), 7.88 (s, 1H), 7.30 (m, 5H), 7.21 (m, 2H), 6.83 (dd, J = 1.8 Hz, J = 7.8 Hz, 1H), 6.72 (m, 1H), 6.46 (d, J = 2.4 Hz, 1H), 6.34 (dd, J = 2.4 Hz, J = 8.4 Hz, 1H), 6.26 (dd, J = 1.8 Hz, J = 16.2 Hz, 1H), 5.80 (dd, J = 1.8 Hz, J = 9.6 Hz, 1H), 5.27 (br, 1H), 4.39 (d, J = 5.4 Hz, 2H), 4.24 (m, 2H), 3.62 (s, 3H), 3.16 (m, 2H), 3.05 (m, 4H), 2.40 (m, 4H), 2.18 (s, 3H). |
| Example 48<br>Scheme 1 | 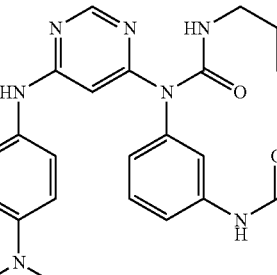 | Rt = 3.13 min, MS m/z: 621.29 [M + 1], $^1$H NMR 600 MHz (DMSO-d$_6$) δ 10.27 (s, 1H), 9.69 (s, 1H), 8.64 (s, 1H), 8.22 (s, 1H), 7.67 (d, J = 7.8 Hz, 1H), 7.55 (s, 1H), 7.40 (t, J = 8.4 Hz, 1H), 7.28 (m, 4H), 7.27 (m, 2H), 6.92 (d, J = 7.2 Hz, 1H), 6.57 (d, J = 1.8 Hz, 1H), 6.42 (m, 2H), 6.24 (dd, J = 1.8 Hz, J = 17.4 Hz, 1H), 5.75 (m, 2H), 4.49 (m, 1H), 4.36 (d, J = 6.0 Hz, 2H), 3.76 (m, 2H), 3.47 (m, 2H), 3.09 (m, 2H), 2.87 (m, 2H), 2.82 (s, 3H), 1.15 (d, J = 6.6 Hz, 6H). |
| Example 49<br>Scheme 2 | 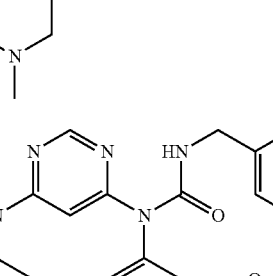 | Rt = 2.95 min, MS m/z: 607.43 [M + 1], $^1$H NMR 600 MHz (DMSO-d$_6$) δ 9.72 (br, 1H), 9.49 (s, 1H), 8.87 (br, 1H), 8.23 (s, 1H), 7.51 (s, 1H), 7.28 (m, 6H), 7.20 (m, 1H), 6.96 (d, J = 8.4 Hz, 1H), 6.58 (d, J = 3.0 Hz, 1H), 6.55 (m, 1H), 6.45 (dd, J = 2.4 Hz, J = 8.4 Hz, 1H), 6.22 (dd, J = 2.4 Hz, J = 16.8 Hz, 1H), 5.73 (d, J = 11.4 Hz, 1H), 5.70 (br, 1H), 4.36 (d, J = 6.0 Hz, 2H), 3.97 (m, 2H), 3.67 (s, 3H), 3.48 (m, 2H), 3.10 (m, 2H), 2.88 (m, 2H), 2.82 (s, 3H), 2.25 (s, 3H). |
| Example 50<br>Scheme 2 | 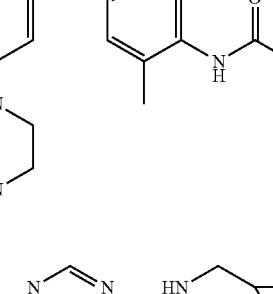 | Rt = 2.78 min, MS m/z: 557.47 [M + 1], $^1$H NMR 600 MHz (DMSO-d$_6$) δ 10.25 (s, 1H), 9.85 (m, 1H), 8.54 (s, 1H), 8.24 (s, 1H), 7.67 (d, J = 1.2 Hz, 1H), 7.51 (m, 1H), 7.39 (t, J = 8.4 Hz, 1H), 7.20 (br, 1H), 6.88 (d, J = 7.8 Hz, 1H), 6.48 (d, J = 1.8 Hz, 1H), 6.42 (m, 1H), 6.37 (dd, J = 2.4 Hz, J = 9.0 Hz, 1H), 6.26 (dd, J = 1.8 Hz, J = 16.8 Hz, 1H), 5.77 (dd, J = 1.8 Hz, J = 10.2 Hz, 1H), 5.48 (br, 1H), 3.66 (s, 3H), 3.08 (m, 6H), 2.43 (m, 4H), 2.20 (s. 3H), 1.01 (m, 1H), 0.43 (m, 2H), 0.20 (m, 2H). |

TABLE 2-continued

| Compound # Synthetic method | Structure | NMR and/or Mass |
|---|---|---|
| Example 51 Scheme 2 | 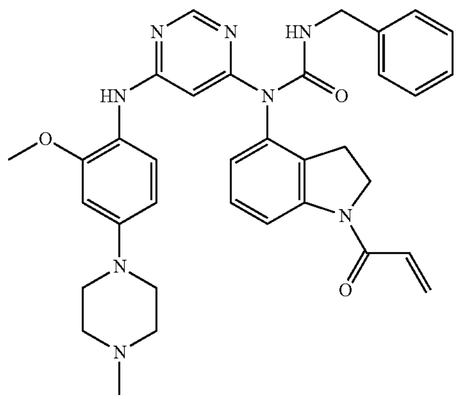 [SMILES: C=CC(=O)N1CCc2c1cccc2N(C(=O)NCc1ccccc1)c1cc(Nc2ccc(N3CCN(C)CC3)cc2OC)ncn1] | Rt = 3.10 min, MS m/z: 619.40 [M + 1], $^1$H NMR 600 MHz (DMSO-d$_6$) δ 9.74 (br, 1H), 8.79 (s, 1H), 8.24 (s, 1H), 8.16 (d, J = 7.2 Hz, 1H), 7.29 (m, 6H), 7.21 (m, 1H), 6.87 (d, J = 8.4 Hz, 1H), 6.71 (m, 1H), 6.57 (d, J = 2.4 Hz, 1H), 6.43 (dd, J = 2.4 Hz, J = 8.4 Hz, 1H), 6.30 (dd, J = 1.8 Hz, J = 16.2 Hz, 1H), 6.82 (dd, J = 1.8 Hz, J = 10.8 Hz, 1H), 5.69 (br, 1H), 4.38 (d, J = 6.0 Hz, 2H), 4.18 (m, 4H), 3.77 (m, 2H), 3.67 (s, 3H), 3.48 (m, 2H), 3.12 (m, 2H), 2.96 (m, 2H), 2.91 (s, 3H). |
| Example 52 Scheme 2 | 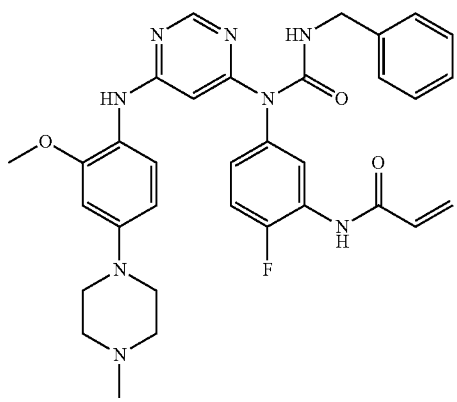 [SMILES: C=CC(=O)Nc1cc(N(C(=O)NCc2ccccc2)c2cc(Nc3ccc(N4CCN(C)CC4)cc3OC)ncn2)ccc1F] | Rt = 2.97 min, MS m/z: 611.40 [M + 1]. |
| Example 53 Scheme 1 | 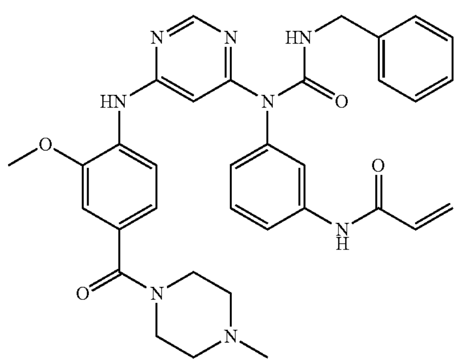 [SMILES: C=CC(=O)Nc1cccc(N(C(=O)NCc2ccccc2)c2cc(Nc3ccc(C(=O)N4CCN(C)CC4)cc3OC)ncn2)c1] | Rt = 3.00 min, MS m/z: 621.41 [M + 1], $^1$H NMR 600 MHz (DMSO-d$_6$) δ 10.29 (s, 1H), 9.85 (m, 1H), 8.99 (s, 1H), 8.35 (s, 1H), 7.98 (d, J = 8.4 Hz, 1H), 7.70 (d, J = 9.0 Hz, 1H), 7.56 (s, 1H), 7.42 (t, J = 7.2 Hz, 1H), 7.30 (m, 4H), 7.21 (m, 1H), 7.00 (d, J = 1.8 Hz, 1H), 6.96 (dd, J = 1.8 Hz, J = 9.0 Hz, 1H), 6.93 (dd, J = 1.8 Hz, J = 8.4 Hz, 1H), 6.40 (m, 1H), 6.24 (dd, J = 1.8 Hz, J = 17.4 Hz, 1H), 6.07 (s, 1H), 5.75 (dd, J = 1.8 Hz, J = 10.2 Hz, 1H), 4.40 (d, J = 6.0 Hz, 2H), 3.75 (s, 3H), 3.40 (m, 4H), 3.03 (m, 4H), 2.78 (s, 3H). |
| Example 54 Scheme 1 | 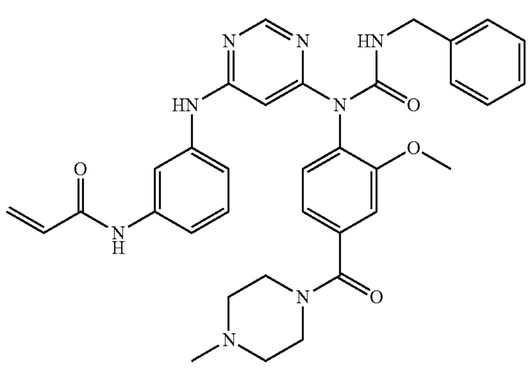 [SMILES: C=CC(=O)Nc1cccc(Nc2cc(N(C(=O)NCc3ccccc3)c3ccc(C(=O)N4CCN(C)CC4)cc3OC)ncn2)c1] | Rt = 3.28 min, MS m/z: 621.41 [M + 1], $^1$H NMR 600 MHz (DMSO-d$_6$) δ 10.07 (s, 1H), 9.81 (m, 1H), 9.47 (s, 1H), 8.36 (s, 1H), 7.88 (s, 1H), 7.31 (m, 5H), 7.21 (m, 4H), 7.15 (t, J = 7.8 Hz, 1H), 7.09 (dd, J = 1.8 Hz, J = 8.4 Hz, 1H), 6.41 (m, 1H), 6.21 (dd, J = 2.4 Hz, J = 16.8 Hz, 1H), 5.92 (s, 1H), 5.70 (dd, J = 2.4 Hz, J = 10.8 Hz, 1H), 4.40 (d, J = 6.0 Hz, 2H), 3.73 (s, 3H), 3.43 (m, 4H), 3.09 (m, 4H), 2.78 (s, 3H). |

TABLE 2-continued

| Compound # Synthetic method | Structure | NMR and/or Mass |
|---|---|---|
| Example 55 Scheme 2 | 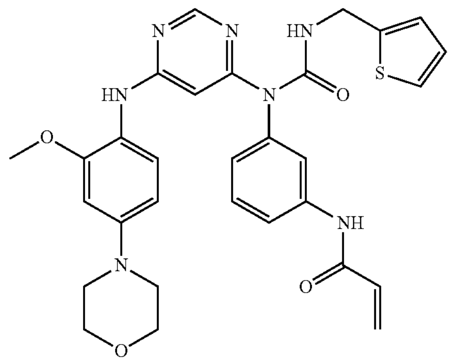 [SMILES: C=CC(=O)Nc1cccc(N(C(=O)NCc2cccs2)c2cc(Nc3ccc(N4CCOCC4)cc3OC)ncn2)c1] | Rt = 3.57 min, MS m/z: 586.32 [M + 1], $^1$H NMR 600 MHz (DMSO-d$_6$) δ 10.27 (s, 1H), 10.17 (m, 1H), 8.61 (s, 1H), 8.24 (s, 1H), 7.71 (d, J = 7.8 Hz, 1H), 7.52 (s, 1H), 7.43 (t, J = 7.8 Hz, 1H), 7.39 (dd, J = 1.2 Hz, J = 4.2 Hz, 1H), 7.25 (br, 1H) 7.01 (m, 1H), 6.97 (m, 1H), 6.91 (d, J= 7.8 Hz, 1H), 6.51 (d, J = 1.8 Hz, 1H), 6.45 (m, 1H), 6.39 (m, 1H), 6.28 (dd, J = 1.8 Hz, J = 16.8 Hz, 1H), 5.78 (dd, J = 1.8 Hz, J = 10.2 Hz, 1H), 5.72 (bs, 1H), 4.58 (d, J = 6.0 Hz, 2H), 3.73 (m, 4H), 3.67 (s, 3H), 3.06 (m, 4H). |
| Example 56 Scheme 2 | 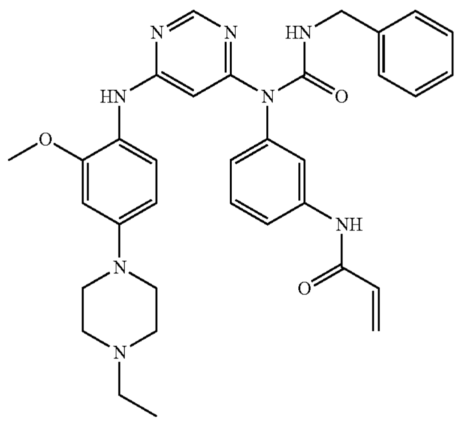 [SMILES: C=CC(=O)Nc1cccc(N(C(=O)NCc2ccccc2)c2cc(Nc3ccc(N4CCN(CC)CC4)cc3OC)ncn2)c1] | Rt = 2.95 min, MS m/z: 607.43 [M + 1], $^1$H NMR 600 MHz (DMSO-d$_6$) δ 10.26 (5, 1H), 10.12 (m, 1H), 8.57 (s, 1H), 8.22 (s, 1H), 7.69 (d, J = 8.4 Hz, 1H), 7.53 (m, 1H), 7.41 (t, J = 8.4 Hz, 1H), 7.34 (m, 4H), 7.24 (m, 2H), 6.91 (d, J = 9.0 Hz, 1H), 6.48 (m, 1H), 6.43 (m, 1H), 6.38 (dd, J = 1.8 Hz, J = 9.0 Hz, 1H), 6.27 (dd, J = 1.8 Hz, J = 16.8 Hz, 1H), 5.77 (dd, J = 1.8 Hz, J = 10.2 Hz, 1H), 5.56 (bs, 1H), 4.42 (d, J = 6.0 Hz, 2H), 3.66 (s, 3H), 3.08 (m, 4H), 2.48 (m, 4H), 2.37 (m, 2H), 1.08 (t, J = 7.2 Hz, 3H). |
| Example 57 Scheme 2 | 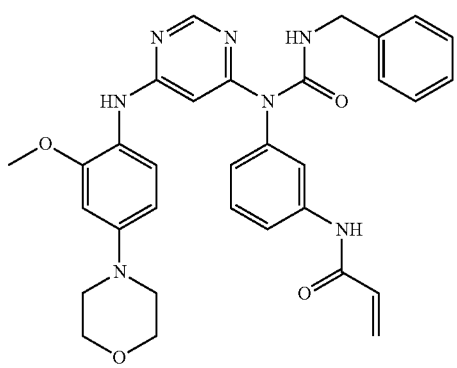 [SMILES: C=CC(=O)Nc1cccc(N(C(=O)NCc2ccccc2)c2cc(Nc3ccc(N4CCOCC4)cc3OC)ncn2)c1] | Rt = 3.63 min, MS m/z: 580.21 [M + 1], $^1$H NMR 600 MHz (DMSO-d$_6$) δ 10.25 (s, 1H), 10.13 (t, J = 6.0 Hz, 1H), 8.57 (s, 1H), 8.22 (s, 1H), 7.68 (d, J = 8.4 Hz, 1H), 7.52 (m, 1H), 7.41 (t, J = 8.4 Hz, 1H), 7.34 (m, 4H), 7.24 (m, 2H), 6.91 (d, J = 7.8 Hz, 1H), 6.49 (d, J = 1.8 Hz, 1H), 6.41 (m, 2H), 6.26 (dd, J = 1.8 Hz, J = 16.8 Hz, 1H), 5.76 (dd, J = 1.8 Hz, J = 9.6 Hz, 1H), 5.58 (bs, 1H), 4.41 (d, J = 6.0 Hz, 2H), 3.71 (m, 4H), 3.65 (s, 3H), 3.04 (m, 4H). |
| Example 58 Scheme 2 | 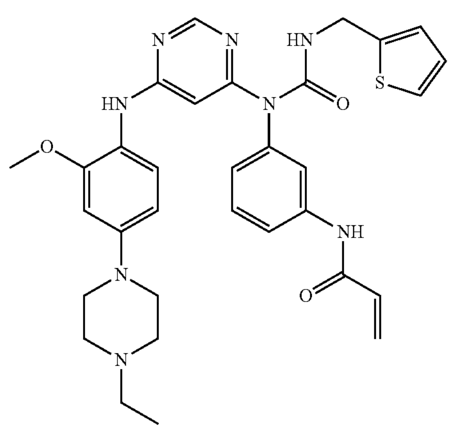 [SMILES: C=CC(=O)Nc1cccc(N(C(=O)NCc2cccs2)c2cc(Nc3ccc(N4CCN(CC)CC4)cc3OC)ncn2)c1] | Rt = 2.92 min, MS m/z: 613.35 [M + 1], $^1$H NMR 600 MHz (DMSO-d$_6$) δ 10.28 (s, 1H), 9.87 (s, 1H), 9.46 (s, 1H), 8.76 (s, 1H), 8.22 (s, 1H), 7.70 (d, J = 8.4 Hz, 1H), 7.51 (s, 1H), 7.40 (t, J = 8.4 Hz, 1H), 7.35 (dd, J = 1.2 Hz, J = 4.8 Hz, 1H), 7.29 (m, 1H), 6.96 (m, 1H), 6.92 (m, 1H), 6.90 (d, J = 9.6 Hz, 1H), 6.57 (d, J = 1.8 Hz, 1H), 6.45 (dd, J = 2.4 Hz, J = 8.4 Hz, 1H), 6.40 (m, 1H), 6.24 (dd, J = 1.8 Hz, J = 17.4 Hz, 1H), 5.75 (dd, J = 1.8 Hz, 10.2 Hz, 1H), 5.65 (bs, 1H), 4.52 (d, J = 4.8 Hz, 2H), 3.79 (m, 2H), 3.66 (s, 3H), 3.53 (m, 2H), 3.17 (m, 2H), 3.07 (m, 2H), 2.89 (m, 2H), 1.23 (t, J = 7.2 Hz, 3H). |

TABLE 2-continued

| Compound # Synthetic method | Structure | NMR and/or Mass |
|---|---|---|
| Example 59 Scheme 2 | 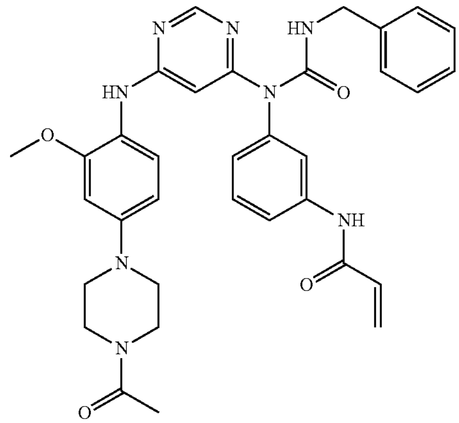 [SMILES: C=CC(=O)Nc1cccc(N(C(=O)NCc2ccccc2)c2cc(Nc3ccc(N4CCN(C(C)=O)CC4)cc3OC)ncn2)c1] | Rt = 3.55 min, MS m/z: 621.41 [M + 1], $^1$H NMR 600 MHz (DMSO-d$_6$) δ 10.26 (s, 1H), 10.15 (t, J = 6.0 Hz, 1H), 8.61 (s, 1H), 8.24 (s, 1H), 7.70 (d, J = 9.0 Hz, 1H), 7.53 (m, 1H), 7.42 (t, J = 7.8 Hz, 1H), 7.34 (m, 4H), 7.24 (m, 2H), 6.92 (d, J = 7.2 Hz, 1H), 6.54 (d, J = 1.8 Hz, 1H), 6.43 (m, 2H), 6.28 (dd, J = 2.4 Hz, J = 16.8 Hz, 1H), 5.78 (dd, J = 1.8 Hz, J = 10.2 Hz, 1H), 5.58 (bs, 1H), 4.43 (d, J = 5.4 Hz, 2H), 3.68 (s, 3H), 3.56 (m, 4H), 3.11 (m, 2H), 3.05 (m, 2H), 2.05 (s, 3H). |
| Example 60 Scheme 2 | 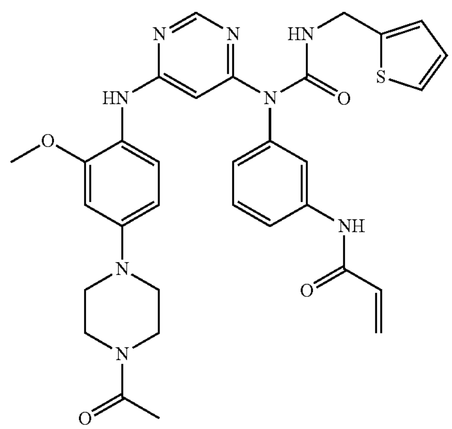 [SMILES: C=CC(=O)Nc1cccc(N(C(=O)NCc2cccs2)c2cc(Nc3ccc(N4CCN(C(C)=O)CC4)cc3OC)ncn2)c1] | Rt = 3.43 min, MS m/z: 627.43 [M + 1], $^1$H NMR 600 MHz (DMSO-d$_6$) δ 10.27 (s, 1H), 10.17 (m, 1H), 8.61 (s, 1H), 8.23 (s, 1H), 8.05 (d, J = 1.8 Hz, 1H), 7.71 (d, J = 7.8 Hz, 1H), 7.51 (s, 1H), 7.41 (t, J = 8.4 Hz. 1H), 7.39 (dd, J = 1.2 Hz, J = 4.8 Hz, 1H), 7.25 (m, 1H), 7.01 (m, 1H), 6.96 (m, 1H), 6.90 (d, J = 7.2 Hz, 1H), 6.53 (d, J = 2.4 Hz, 1H), 6. 44 (m, 2H), 6.27 (dd, J = 2.4 Hz, J = 16.8 Hz, 1H), 5.78 (dd, J = 1.8 Hz, J = 10.2 Hz, 1H), 4.57 (d, J = 5.4 Hz, 2H), 3.67 (s, 3H), 3.57 (m, 4H), 3.10 (m, 2H), 3.04 (m, 2H), 2.03 (s, 3H). |
| Example 61 Scheme 1 | 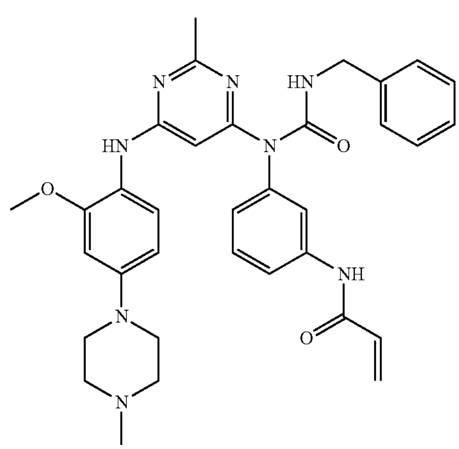 [SMILES: C=CC(=O)Nc1cccc(N(C(=O)NCc2ccccc2)c2cc(Nc3ccc(N4CCN(C)CC4)cc3OC)nc(C)n2)c1] | MS m/z: 607.44 [M + 1]. |

TABLE 2-continued

| Compound #<br>Synthetic method | Structure | NMR and/or Mass |
|---|---|---|
| Example 62<br>Scheme 1 | | MS m/z: 641.39 [M + 1]. |
| Example 63<br>Scheme 1 | | MS m/z: 691 [M + 1], $^1$H NMR 400 MHz (DMSO-d$_6$) δ 12.32 (s, 1H), 10.14 (s, 1H), 9.34 (s, 1H), 8.37 (s, 1H), 7.62 (d, J = 8.8 Hz, 2H), 7.17 (d, J = 8.0 Hz, 2H), 7.14 (m, 2H), 6.90 (s, 1H), 6.82 (d, J = 9.2 Hz, 2H), 6.41 (dd, J = 16.8, 10.0 Hz, 2H), 6.23 (dd, J = 16.8, 2.0 Hz, 1H), 6.18 (s, 1H), 5.75 (dd, J = 10.0, 2.0 Hz, 1H), 5.03 (s, 2H), 3.93 (s, 6H), 3.15 (m, 2H), 3.07 (m, 4H), 2.50 (m, 2H), 2.24 (m, 3H). |
| Example 64<br>Scheme 6 | | MS m/z: 656 [M + 1], $^1$H NMR 600 MHz (DMSO-d$_6$) δ 10.10 (s, 1H), 9.10 (s, 1H), 7.96 (s, 2H), 7.56 (d, J = 8.4 Hz, 1H), 7.25 (m, 2H), 7.20 (m, 1H), 6.98 (s, 1H), 6.40 (dd, J = 16.8, 9.6 Hz, 1H), 6.21 (d, J = 16.8 Hz, 1H), 5.74 (s, 1H), 5.71 (d, J = 10.8 Hz, 1H), 5.08 (s, 2H), 4.48 (s, 2H), 3.94 (s, 6H), 3.18 (m, 2H), 2.58 (m, 6H), 1.41 (m, 4H), 0.98 (m, 6H). |

TABLE 2-continued

| Compound # Synthetic method | Structure | NMR and/or Mass |
|---|---|---|
| Example 65 Scheme 6 | 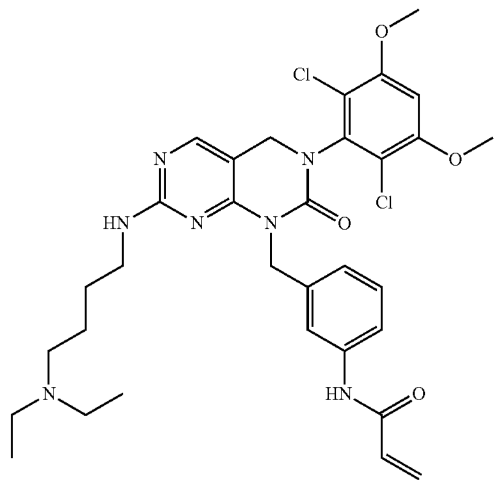 [SMILES: C=CC(=O)Nc1cccc(CN2C(=O)N(c3c(Cl)c(OC)cc(OC)c3Cl)Cc3cnc(NCCCCN(CC)CC)nc32)c1] | MS m/z: 657 [M + 1], $^1$H NMR 600 MHz (TFA salt, DMSO-d$_6$) δ 10.12 (s, 1H), 9.10 (s, 1H), 8.03 (s, 1H), 7.70 (s, 1H), 7.50 (d, J = 8.4 Hz, 1H), 7.25 (d, J = 7.8 Hz, 1H), 7.02 (d, J = 9.6 Hz, 1H), 6.46 (dd, J = 10.2, 6.6 Hz, 1H), 6.25 (dd, J = 15.0, 1.8 Hz, 1H), 5.75 (dd, J = 7.8, 1.8 Hz, 1H), 5.15 (s, 2H), 4.55 (s, 2H), 3.94 (s, 6H), 3.11 (m, 8H), 1.55 (m, 4H), 1.15 (t, J = 7.2 Hz, 6H). |
| Example 66 Scheme 6 | 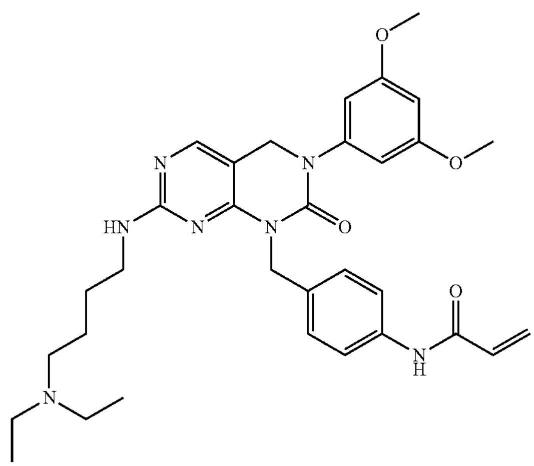 [SMILES: C=CC(=O)Nc1ccc(CN2C(=O)N(c3cc(OC)cc(OC)c3)Cc3cnc(NCCCCN(CC)CC)nc32)cc1] | MS m/z: 588 [M + 1], $^1$H NMR 400 MHz (TFA salt, DMSO-d$_6$) δ 10.12 (s, 1H), 9.10 (s, 1H), 8.00 (s, 1H), 7.58 (d, J = 8.4 Hz, 2H), 7.28 (d, J = 8.8 Hz, 2H), 6.54 (d, J = 2.0 Hz, 2H), 6.44 (m, 1H), 6.40 (dd, J = 16.8, 10.0 Hz, 1H), 6.21 (dd, J = 16.8, 2.0 Hz, 1H), 5.72 (dd, J = 10.0, 2.0 Hz, 1H), 5.12 (s, 2H), 4.67 (s, 2H), 3.72 (s, 6H), 3.24 (m, 4H), 3.06 (m, 4H), 1.65-1.32 (m, 4H), 1.14 (t, J = 7.2 Hz, 6H). |
| Example 67 Scheme 6 | 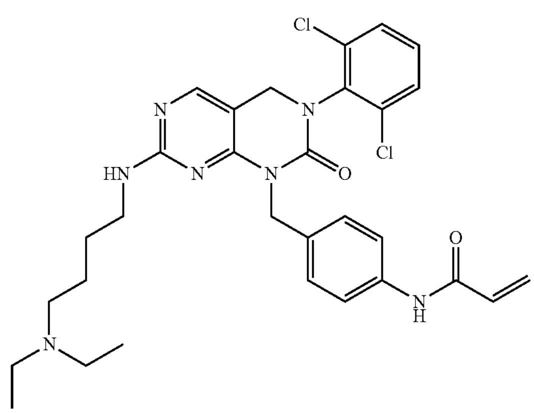 [SMILES: C=CC(=O)Nc1ccc(CN2C(=O)N(c3c(Cl)cccc3Cl)Cc3cnc(NCCCCN(CC)CC)nc32)cc1] | MS m/z: 596 [M + 1], $^1$H NMR 400 MHz (TFA salt, DMSO-d$_6$) δ 10.13 (s, 1H), 9.08 (s, 1H), 8.02 (s, 1H), 7.63 (d, J = 8.4 Hz, 1H), 7.57 (d, J = 8.8 Hz, 1H), 7.47 (d, J = 8.0 Hz, 1H), 7.26 (d, J = 8.4 Hz, 2H), 6.40 (dd, J = 16.8, 9.6 Hz, 1H), 6.21 (dd, J = 16.8, 2.0 Hz, 1H), 5.72 (dd, J = 10.0, 2.0 Hz, 1H), 5.11 (s, 2H), 4.55 (s, 2H), 3.23 (m, 2H), 3.06 (m, 4H), 2.93 (m, 2H), 1.66-1.34 (m, 4H), 1.14 (t, J = 7.2 Hz, 6H). |

TABLE 2-continued

| Compound #<br>Synthetic method | Structure | NMR and/or Mass |
|---|---|---|
| Example 68<br>Scheme 6 | | MS m/z: 606 [M + 1], $^1$H NMR 600 MHz (TFA salt, DMSO-d$_6$) δ 9.92 (s, 1H), 9.13 (s, 1H), 8.01 (s, 1H), 7.84 (m, 1H), 7.21 (d, J = 8.4 Hz, 2H), 7.15 (d, J = 8.4 Hz, 2H), 6.57 (m, 1H), 6.55 (s, 2H), 6.43 (s, 1H), 6.23 (dd, J = 16.8, 2.0 Hz, 1H), 5.75 (dd, J = 10.2, 2.0 Hz, 1H), 5.12 (s, 2H), 4.68 (s, 2H), 3.73 (s, 6H), 3.24 (m, 4H), 3.06 (m, 4H), 1.65-1.32 (m, 4H), 1.14 (t, J = 7.2 Hz, 6H). |
| Example 69<br>Scheme 6 | | MS m/z: 635 [M + 1], $^1$H NMR 600 MHz (DMSO-d$_6$) δ 10.04 (s, 1H), 9.18 (s, 1H), 8.05 (s, 1H), 7.53 (d, J = 8.4 Hz, 2H), 7.32 (d, J = 7.8 Hz, 2H), 7.21 (d, J = 7.8 Hz, 2H), 6.74 (d, J = 8.4 Hz, 2H), 6.52 (s, 2H), 6.37 (s, 1H), 6.34 (dd, J = 16.8, 9.6 Hz, 1H), 6.16 (d, J = 16.8 Hz, 1H), 5.65 (d, J = 10.2, 1H), 5.09 (s, 2H), 4.67 (s, 1H), 3.68 (s, 6H), 3.02 (m, 4H), 2.54 (m, 4H), 2.27 (m, 3H). |
| Example 70<br>Scheme 6 | | MS m/z: 674 [M + 1], $^1$H NMR 600 MHz (TFA salt, DMSO-d$_6$) δ 9.89 (s, 1H), 7.98 (s, 1H), 7.87 (m, 1H), 7.23 (m, 1H), 7.11 (m, 2H), 6.99 (s, 1H), 6.57 (dd, J = 16.8, 10.2 Hz, 1H), 6.25 (dd, J = 16.8, 2.4 Hz, 1H), 5.74 (dd, J = 10.2, 1.8 Hz, 1H), 5.09 (s, 2H), 4.49 (s, 2H), 3.95 (s, 6H), 3.16 (m, 4H), 2.80-2.40 (m, 6H), 1.58-1.30 (m, 4H), 0.98 (m, 6H). |

TABLE 2-continued

| Compound #<br>Synthetic method | Structure | NMR and/or Mass |
|---|---|---|
| Example 71<br>Scheme 1 | | MS m/z: 644 [M + 1], $^1$H NMR 600 MHz (TFA salt, DMSO-d$_6$) δ 12.40 (s, 1H), 10.09 (s, 1H), 8.92 (br, 1H), 8.23 (br, 1H), 7.56 (d, J = 8.4 Hz, 2H), 7.50 (m, 1H), 7.17 (m, 2H), 6.85 (s, 1H), 6.36 (dd, J = 16.8, 9.6 Hz, 1H), 6.17 (dd, J = 16.8, 1.8 Hz, 1H), 5.92 (m, 1H), 5.68 (dd, J = 10.2, 1.8 Hz, 1H), 4.97 (br, 2H), 3.88 (s, 6H), 3.26 (m, 2H), 3.01 (m, 4H), 2.94 (m, 2H), 1.51 (m, 2H), 1.43 (m, 2H), 1.09 (t, J = 7.2 Hz, 6H). |
| Example 72<br>Scheme 1 | | MS m/z: 644 [M + 1], $^1$H NMR 600 MHz (TFA salt, DMSO-d$_6$) δ 11.96 (br, 1H), 10.13 (s, 1H), 9.00 (br, 1H), 8.28 (br, 1H), 7.60 (d, J = 8.4 Hz, 2H), 7.27 (d, J = 8.4 Hz, 2H), 6.87 (s, 1H), 6.41 (dd, J = 16.8, 10.2 Hz, 1H), 6.22 (dd, J = 16.8, 1.8 Hz, 1H), 5.73 (dd, J = 10.2, 1.8 Hz, 1H), 4.49 (br, 2H), 3.91 (s, 6H), 3.86 (m, 2H), 3.05 (m, 6H), 1.61 (m, 4H), 1.14 (t, J = 7.2 Hz, 6H). |
| Example 73 | | MS m/z: 458 [M + 1]. |

TABLE 2-continued

| Compound # Synthetic method | Structure | NMR and/or Mass |
|---|---|---|
| Example 74 | 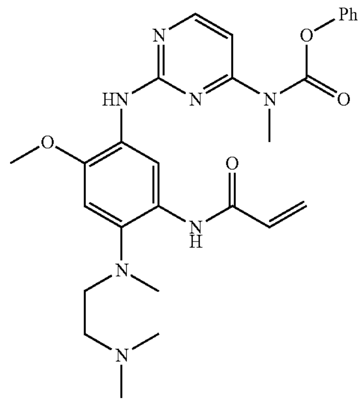 [SMILES: C=CC(=O)Nc1cc(Nc2nccc(N(C)C(=O)Oc3ccccc3)n2)c(OC)cc1N(C)CCN(C)C] | MS m/z: 520 [M + 1]. |
| Example 75 | 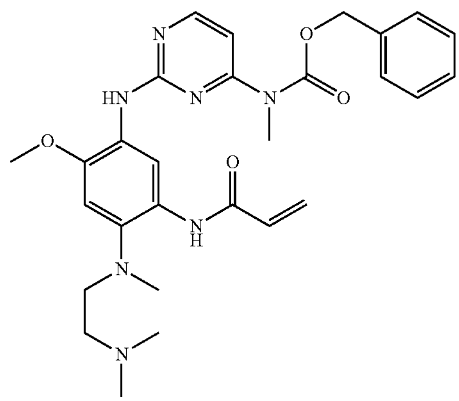 [SMILES: C=CC(=O)Nc1cc(Nc2nccc(N(C)C(=O)OCc3ccccc3)n2)c(OC)cc1N(C)CCN(C)C] | MS m/z: 534 [M + 1]. |
| Example 76 | 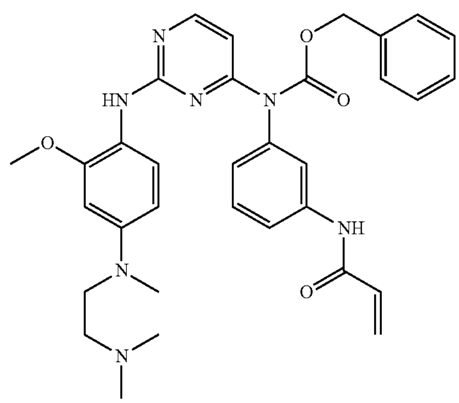 [SMILES: C=CC(=O)Nc1cccc(N(C(=O)OCc2ccccc2)c2ccnc(Nc3ccc(N(C)CCN(C)C)cc3OC)n2)c1] | MS m/z: 596 [M + 1], $^1$H NMR 600 MHz (TFA salt, DMSO-d$_6$) δ 10.35 (s, 1H), 9.78 (br, 1H), 8.33 (s, 1H), 7.83 (br, 1H), 7.58 (s, 1H), 7.43 (t, J = 7.8 Hz, 2H), 7.32 (m, 3H), 7.24 (m, 2H), 7.04 (dd, J = 1.8 Hz, J = 7.8 Hz, 1H), 6.90 (br, 1H), 6.45 (dd, J = 10.2 Hz, J = 16.8 Hz, 1H), 6.36 (d, J = 3.0 Hz, 1H), 6.27 (dd, J = 1.8 Hz, J = 15 Hz, 1H), 5.94 (br, 1H), 5.77 (dd, J = 1.8 Hz, J = 8.4 Hz, 1H), 5.22 (s, 2H), 3.79 (s, 3H), 3.58 (m, 2H), 3.17 (m, 2H), 2.83 (m, 9H). |
| Example 77 | 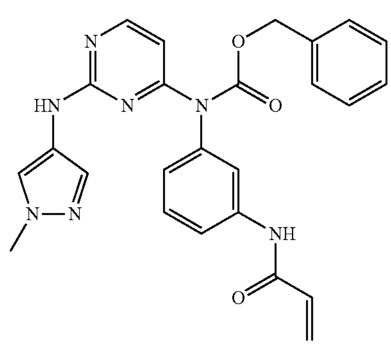 [SMILES: C=CC(=O)Nc1cccc(N(C(=O)OCc2ccccc2)c2ccnc(Nc3cnn(C)c3)n2)c1] | MS m/z: 470 [M + 1], $^1$H NMR 600 MHz (TFA salt, DMSO-d$_6$) δ 10.34 (s, 1H), 9.49 (s, 1H), 8.33 (d, J = 5.4 Hz, 1H), 7.78 (s, 1H), 7.70 (s, 1H), 7.52 (s, 1H), 7.42 (m, 2H), 7.30 (m, 3H), 7.22 (m, 2H), 7.10 (m, 1H), 7.02 (s, 1H), 6.47 (s, 1H), 6.43 (dd, J = 10.2 Hz, J = 16.8 Hz, 1H), 6.26 (dd, J = 1.8 Hz, J = 15 Hz, 1H), 5.77 (dd, J = 1.2 Hz, J = 9 Hz, 1H), 5.21 (s, 2H), 3.50 (s, 3H). |

TABLE 2-continued

| Compound # Synthetic method | Structure | NMR and/or Mass |
|---|---|---|
| Example 78 | 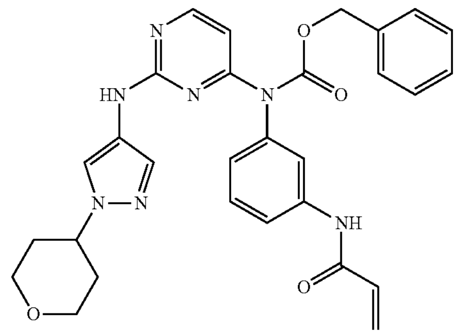 [SMILES: C=CC(=O)Nc1cccc(N(C(=O)OCc2ccccc2)c2ccnc(Nc3cnn(C4CCOCC4)c3)n2)c1] | MS m/z: 540 [M + 1], $^1$H NMR 600 MHz (TFA salt, DMSO-d$_6$) δ 10.37 (s, 1H), 9.54 (s, 1H), 8.34 (d, J = 6.0 Hz, 1H), 7.83 (s, 1H), 7.67 (s, 1H), 7.51 (s, 1H), 7.40 (m, 2H), 7.30 (m, 3H), 7.22 (m, 2H), 7.12 (m, 1H), 7.08 (s, 1H), 6.60 (s, 1H), 6.44 (dd, J = 9.6 Hz, J = 17.4 Hz, 1H), 6.27 (dd, J = 1.2 Hz, J = 16.8 Hz, 1H), 5.78 (dd, J = 1.8 Hz, J = 10.2 Hz, 1H), 5.21 (s, 2H), 3.92 (m, 2H), 3.83 (m, 1H), 3.45 (m, 2H), 1.79 (m, 2H), 1.59 (m, 2H). |
| Example 79 | 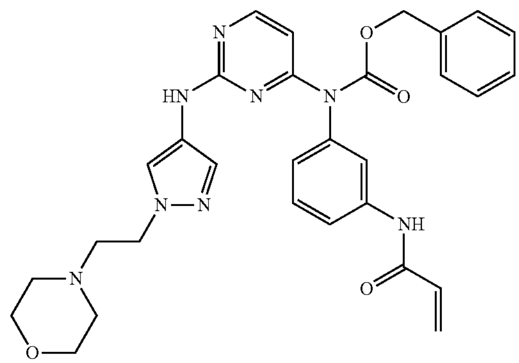 [SMILES: C=CC(=O)Nc1cccc(N(C(=O)OCc2ccccc2)c2ccnc(Nc3cnn(CCN4CCOCC4)c3)n2)c1] | MS m/z: 569 [M + 1]. |
| Example 80 | 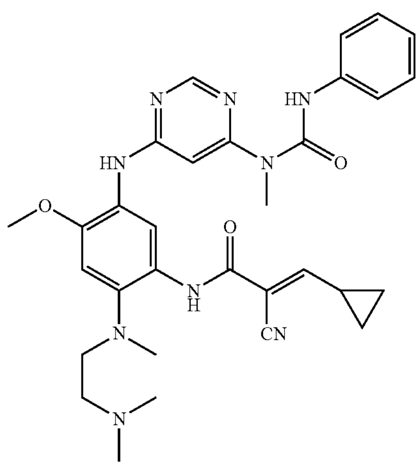 [SMILES: COc1cc(N(C)CCN(C)C)c(NC(=O)/C(C#N)=C/C2CC2)cc1Nc1cc(N(C)C(=O)Nc2ccccc2)ncn1] | MS m/z: 584 [M + 1]. |
| Example 81 | 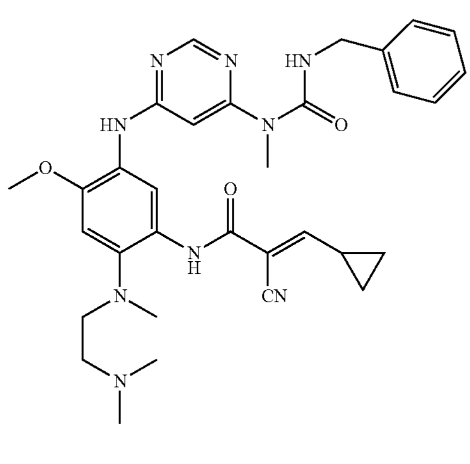 [SMILES: COc1cc(N(C)CCN(C)C)c(NC(=O)/C(C#N)=C/C2CC2)cc1Nc1cc(N(C)C(=O)NCc2ccccc2)ncn1] | MS m/z: 598 [M + 1]. |

TABLE 2-continued

| Compound #<br>Synthetic method | Structure | NMR and/or Mass |
|---|---|---|
| Example 82 | 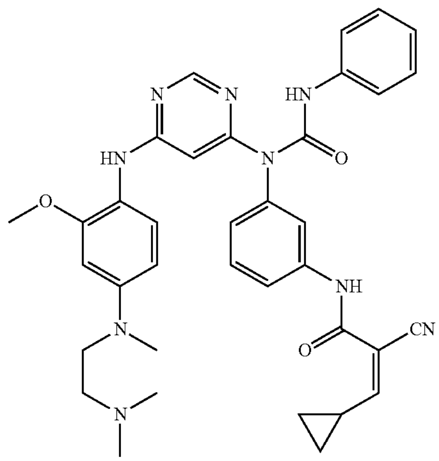 [SMILES: COc1cc(N(C)CCN(C)C)ccc1Nc1cc(N(C(=O)Nc2ccccc2)c2cccc(NC(=O)/C(C#N)=C\C3CC3)c2)ncn1] | MS m/z: 646 [M + 1]. |
| Example 83 | 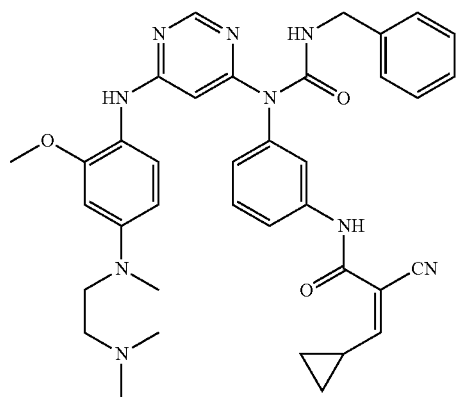 [SMILES: COc1cc(N(C)CCN(C)C)ccc1Nc1cc(N(C(=O)NCc2ccccc2)c2cccc(NC(=O)/C(C#N)=C\C3CC3)c2)ncn1] | MS m/z: 660 [M + 1]. |
| Example 84 | 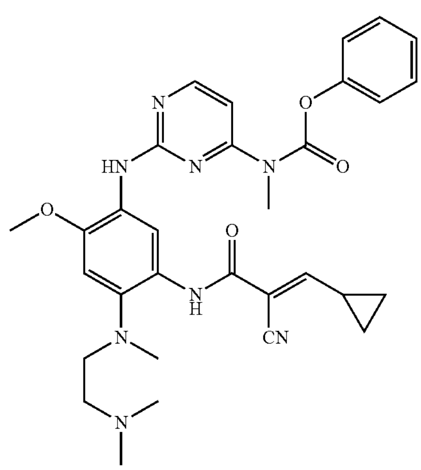 [SMILES: COc1cc(N(C)CCN(C)C)c(NC(=O)/C(C#N)=C/C2CC2)cc1Nc1nccc(N(C)C(=O)Oc2ccccc2)n1] | MS m/z: 585 [M + 1]. |

TABLE 2-continued

| Compound #<br>Synthetic method | Structure | NMR and/or Mass |
|---|---|---|
| Example 85 | (structure) | MS m/z: 599 [M + 1]. |
| Example 86 | (structure) | MS m/z: 647 [M + 1]. |
| Example 87 | (structure) | MS m/z: 661 [M + 1]. |

TABLE 2-continued

| Compound #<br>Synthetic method | Structure | NMR and/or Mass |
|---|---|---|
| Example 88 | 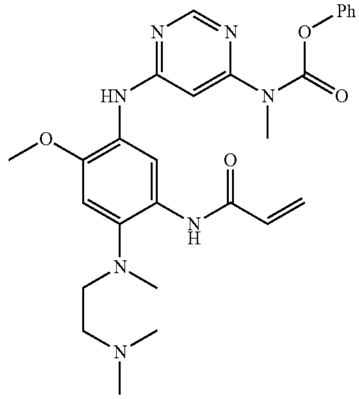 [SMILES: C=CC(=O)Nc1cc(Nc2cc(N(C)C(=O)Oc3ccccc3)ncn2)c(OC)cc1N(C)CCN(C)C] | MS m/z: 519 [M + 1]. |
| Example 89 | 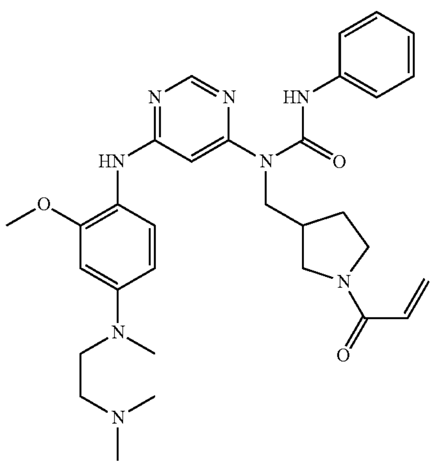 [SMILES: C=CC(=O)N1CCC(CN(C(=O)Nc2ccccc2)c2cc(Nc3ccc(N(C)CCN(C)C)cc3OC)ncn2)C1] | MS m/z: 573 [M + 1]. |
| Example 90 | 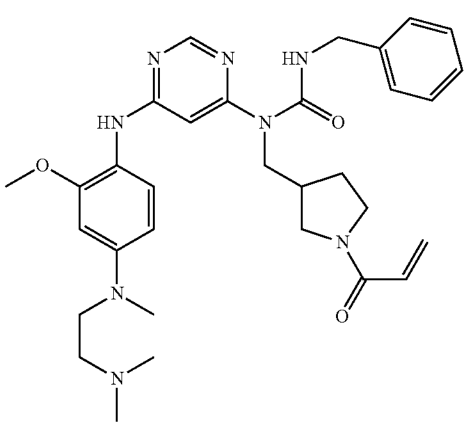 [SMILES: C=CC(=O)N1CCC(CN(C(=O)NCc2ccccc2)c2cc(Nc3ccc(N(C)CCN(C)C)cc3OC)ncn2)C1] | MS m/z: 587 [M + 1]. |

TABLE 2-continued

| Compound # Synthetic method | Structure | NMR and/or Mass |
|---|---|---|
| Example 91 | 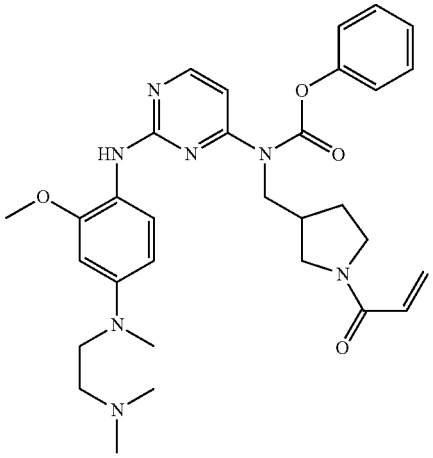 [SMILES: C=CC(=O)N1CCC(CN(C(=O)Oc2ccccc2)c2ccnc(Nc3ccc(N(C)CCN(C)C)cc3OC)n2)C1] | MS m/z: 574 [M + 1]. |
| Example 92 | 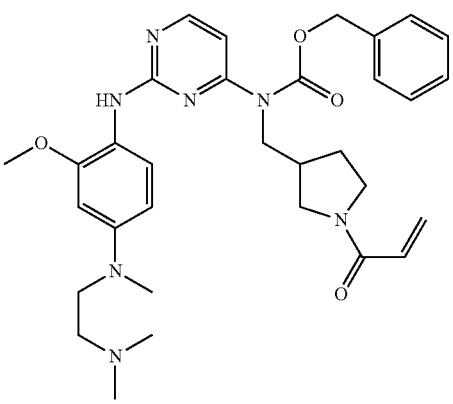 [SMILES: C=CC(=O)N1CCC(CN(C(=O)OCc2ccccc2)c2ccnc(Nc3ccc(N(C)CCN(C)C)cc3OC)n2)C1] | MS m/z: 588 [M + 1]. |

Example 93: Biological Activity

Generation of Ba/F3 Cells

The specific cDNAs encoding the oncogenic alterations (EGFR: Del 19, L858R, L718Q, L844V, Del/T790M, L858R/T790M, Del 19/L718Q, Del 19/L844V, Del 19/T790M/L718Q and L858R/T790M/L718Q; FGFR: TEL-FGFR1, TEL-FGFR2, TEL-FGFR1 V561M, TEL-FGFR2 V561M; ALK: EML4-ALK; ROS1: CD74-ROS1) were cloned into the pDNA-Dual (BD Biosciences) vector using standard molecular biology techniques. Mutations were introduced using site-directed mutagenesis (Agilent) with mutant specific primers according to the manufacturer's instructions. All constructs were confirmed by DNA sequencing. The constructs were introduced into Ba/F3 cells using retroviral infection. Polyclonal cell lines were established by puromycin selection and subsequently cultured in the absence of interleukin-3 (IL-3). Uninfected Ba/F3 cells or cell lines expressing green fluorescent protein (GFP) were used as controls.

Evaluation of Drug Efficacy

Growth and inhibition of growth was assessed by MTS assay. This assay, a colorimetric method for determining the number of viable cells, is based on the bioreduction of 3-(4,5-dimethylthiazol-2-yl)-5-(3-carboxymethoxyphenyl)-2-(4-sulfophenyl)-2H-tetrazolium (MTS) by cells to a formazan product that is soluble in cell culture medium, can be detected spectrophotometrically and was performed according to the manufacturer's recommended conditions. Ba/F3 cells were exposed to treatment for 72 hours and the number of cells used per experiment determined empirically to assure linear growth kinetics over that time period. All experimental points were set up in six to twelve wells and all experiments were repeated at least three times. The data was graphically displayed using GraphPad Prism version 5.0 for Windows, (GraphPad Software; http://www.graphpad.com). The curves were fitted using a non-linear regression model with a sigmoidal dose response. The results are shown in the Tables below.

BTK Kinase Assay

BTK kinase assay was conducted using LanthaScreen® Kinase assay.

1. Optimization of kinase concentration required to determine ATP Km,app. The assay was first performed at a high concentration of ATP (1 mM) against a dilution series of kinase in order to determine the amount of kinase required to elicit an approximately 80% change between the minimum and maximum TR-FRET emission ratios (the EC80 value).

2. Determination of ATP Km,app. Using the concentration of enzyme determined in step 1, the assay was then performed against a dilution series of ATP in order to determine the amount of ATP required to elicit a 50% change between the minimum and maximum TR-FRET emission ratios (the EC50 value). This concentration of ATP was referred to as the "apparent" Km value for ATP, or the ATP Km,app.

3. Optimization of kinase concentration required for assay at ATP Km,app. Using the ATP Km,app concentration of ATP determined in step 2, the kinase titration was repeated in order to determine the concentration of kinase required to elicit an approximately 80% change between the minimum and maximum TR-FRET emission ratios at the ATP Km,app concentration of ATP (the EC80 value). This was the concentration of kinase that will be used in an assay to determine an IC50 value for a compound of the invention.

Using the ATP and kinase concentrations determined above, the reaction was then performed in the presence of a dilution series of various compounds of the invention, and the amount of compounds required to elicit a 50% change in TR-FRET ratio (the IC50) was determined. The experiments can be performed over two days, with steps one and two being performed on the first day, and step three and the inhibitor IC50 determination(s) being performed on the second day.

TABLE C $IC_{50}$ (nM) of representative compounds of the invention in inhibiting BTK

| CMPD # | BTK $IC_{50}$ (nM) |
|---|---|
| 25A | 31.2 |
| 29A | 19.4 |
| 103A | 2240 |
| 104A | >10000.0 |
| 83A | 5.13 |
| 84A | 3.12 |
| 85A | 5.74 |

TABLE D

Kinase inhibition (% control, 1000 nM compound)

| CMPD # | BLK | ITK | TEC | TXK |
|---|---|---|---|---|
| 3A | 19 | 100 | 55 | 7.4 |
| 4A | 20 | 100 | 83 | 27 |
| 80A | 14 | 94 | 90 | 12 |
| 83A | 0.4 | 66 | 5.7 | 3.8 |

TABLE A

| CMPD # | Microsome Stability Mouse min | Screen | Assay 1 Wild type vIII | Assay 1 Del | Assay 1 Del/T790M | EGFR Ba/F3 cells IC 50 (nM) Assay 1 Del/T/L718Q | Assay 1 L858R | Assay 1 L858R/ T790M | Assay 1 L718Q/ L858R | Assay 2 L718Q/ L858R | NT = Not tested IC 50 (nM) Assay 1 T/L/L718Q |
|---|---|---|---|---|---|---|---|---|---|---|---|
| 1A | 14 | 1 | 16.4 | 6.33 | 19.04 | 47% inhibition 1.0 uM | 1.56 | 3.1 | 49.83 | 149.21 | 178 |
| 10A | 18.5 | | 28.1 | 4.64 | 22.86 | inhibition > 1.0 uM | 1.52 | 14.78 | 146 | 204 | 270 |
| 74A | | 2 | | 5.16 | 277.7 | NT | 0.572 | 215 | 243 | | 780 |
| 15A | | 2 | | 91.9 | 841.7 | NT | 17.72 | 376 | 2150 | | 3260 |
| 17A | | 2 | | 63.94 | 681.5 | NT | 7.62 | 275 | 1960 | | 2503 |
| 20A | | 2 | | 2.58 | 211.2 | NT | 0.994 | 99.14 | 256 | | 917 |
| 34A | 9.4 | 4 | 10.1 | 19.69 | 60.4 | | 0.51 | 20 | | | 312 |
| 55A | 1.8 | 7 | 2.3 | 2 | 15.85 | NT | 0.5 | 2.4 | NT | | 657 |
| 78A | | 8 | 19.86 | 23.94 | 68.24 | NT | 2.66 | 41.82 | NT | NT | 2242 |

TABLE B

| CMPD # | Microsome Stability Mouse min | Screen | Assay 1 Wild type vIII | Assay 1 Del | Assay 1 Del/T790M | EGFR Ba/F3 cells IC 50 (nM) Assay 1 Del/T/L718Q | Assay 1 L858R | Assay 1 L858R/ T790M | Assay 1 L718Q/ L858R | Assay 2 L718Q/ L858R | NT = Not tested IC 50 (nM) Assay 1 T/L/L718Q |
|---|---|---|---|---|---|---|---|---|---|---|---|
| 10A | 18.5 | | 28.1 | 4.64 | 22.86 | 1.0 uM | 1.52 | 14.78 | 146 | 204 | 270 |
| 4A | 29 | 7 | 2.92 | 14.21 | 17.3 | NT | 0.5 | 7.6 | | | 293 |

TABLE E

EGFR activity (% control)
EGFR activity (% Control, 1.0 μM drug)

| | Assay 1 | | | | | Assay 2 | | | |
|---|---|---|---|---|---|---|---|---|---|
| | Del | Del/T790M | Del/T790M/L718Q | L858R | KIF5B/Ret_V804M | Del | Del/T790M | Del/T790M/L718Q | L858R |
| 8A | 3 | 1 | 113 | 2 | 108 | 72 | 100 | 93 | 10 |
| 9A | 3 | 2 | 90 | 2 | 93 | 4 | 39 | 86 | 2 |
| 3A | 2 | 1 | 53 | 2 | 102 | 1 | 2 | 86 | 4 |
| 10A | 4 | 2 | 76 | 4 | 91 | 1 | 2 | 84 | 3 |
| 11A | 3 | 1 | 84 | 2 | 103 | 4 | 5 | 82 | 3 |
| 1A | 4 | 3 | 63 | 2 | 65 | 0 | 1 | 83 | 5 |
| WZ4002 | 3 | 1 | 91 | 2 | 93 | 6 | 3 | 85 | 2 |
| Ponatinib | 17 | 79 | 48 | 98 | 2 | | | | |

TABLE F

EGFR activity (% control)
EGFR activity (% Control, 100 nM drug)

| | Del | DEL/T790M | L858R | L858R/L718Q | L858R/T790M | L858R/T790M/L718Q |
|---|---|---|---|---|---|---|
| 12A | 0 | 117 | 1 | 47 | 48 | 84 |
| 13A | 13 | 90 | 3 | 90 | 71 | 89 |
| 14A | 24 | 98 | 1 | 76 | 75 | 87 |
| 15A | 47 | 107 | 3 | 81 | 48 | 86 |
| 16A | 78 | 86 | 117 | 75 | 71 | 92 |
| 17A | 28 | 85 | 2 | 81 | 52 | 85 |
| 18A | 30 | 84 | 1 | 88 | 85 | 92 |
| 19A | 79 | 71 | 100 | 74 | 101 | 99 |
| 20A | 2 | 126 | 2 | 48 | 26 | 93 |
| 21A | 10 | 107 | 4 | 94 | 100 | 102 |
| 22A | 3 | 84 | 3 | 84 | 4 | 106 |
| 7A | 35 | 94 | 5 | 96 | 102 | 106 |
| WZ4002 | 2 | 2 | 2 | 94 | 3 | 104 |

TABLE G

EGFR activity (% control)
EGFR activity (% Control, 100 nM drug)

| | Del | Del/T790M | L858R | L858R/T790M |
|---|---|---|---|---|
| 23A | 106 | 102 | 99 | 111 |
| 24A | 95 | 101 | 84 | 108 |
| 25A | 14 | 53 | 1 | 24 |
| 26A | 87 | 91 | 11 | 100 |
| 27A | 95 | 76 | 87 | 102 |
| 28A | 102 | 83 | 94 | 97 |
| 29A | 2 | 6 | 0 | 13 |
| 30A | 94 | 104 | 10 | 103 |
| 31A | 111 | 110 | 108 | 112 |
| 32A | 104 | 106 | 99 | 110 |
| 33A | 102 | 109 | 101 | 106 |
| 5A | 100 | 110 | 107 | 96 |
| WZ4002 | 36 | 6 | 0 | 30 |
| ZD1839 | 2 | 105 | 2 | 103 |

TABLE H $IC_{50}$ (μM) of representative compounds of the
invention in inhibiting various Ba/F3 cell lines

| | Ba/F3 TEL-ABL | Ba/F3 TYK2_E957D | Ba/F3 TEL-JAK1 | Ba/F3 TEL-JAK2 | Ba/F3 TEL-JAK3 |
|---|---|---|---|---|---|
| TL6-144 | 3.125 | 3.445 | 3.473 | 3.884 | 0.08403 |
| Compound 83A | 16.65 | 2.949 | 8.997 | 17.47 | 0.1074 |
| Compound 84A | 11.30 | 4.168 | 7.412 | 18.11 | 0.1393 |
| Compound 85A | 16.12 | 4.371 | 8.859 | 18.32 | 0.1894 |

The invention claimed is:
1. A compound of formula I:

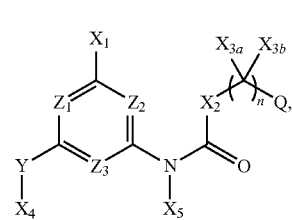

(I)

or a pharmaceutically acceptable salt thereof, wherein:

$Z_1$ is N or $CR_1$;

$Z_2$ is N or $CR_2$;

$Z_3$ is N or $CR_3$, provided that when Y is $NR_4$, then two of $Z_1$, $Z_2$ or $Z_3$ are N;

R1 is H, $C_1$-$C_8$ alkyl, halogen, or halo($C_1$-$C_8$ alkyl);

R2 is H, $C_1$-$C_8$ alkyl, halogen, or halo($C_1$-$C_8$ alkyl);

$X_2$ is O or $NR_{10}$;

$R_{10}$ is hydrogen or $C_1$-$C_8$ alkyl;

$R_3$ is H, $C_1$-$C_8$ alkyl, halogen, or halo($C_1$-$C_8$ alkyl);

Y is $NR_4$;

or taken together Y—$X_4$ and $R_3$ form unsubstituted or substituted $C_6$ aryl or unsubstituted or substituted 5- or 6-membered heteroaryl, wherein said substituted aryl or heteroaryl is substituted with one or more $R_5$;

$R_4$ is H or $C_1$-$C_8$ alkyl;

each $R_5$ is independently halogen, $OR_6$, $NR_7R_8$, $NR_7C(O)R_8$, $SR_9$, $C_1$-$C_8$ alkyl, $C_2$-$C_8$ alkynyl optionally substituted with 5- or 6-membered heterocyclic, or halo($C_1$-$C_8$ alkyl);

each $R_6$ is independently hydrogen or $C_1$-$C_8$ alkyl;

each $R_7$ and $R_8$ are independently hydrogen, $C_1$-$C_8$ alkyl, or unsubstituted or substituted 5- or 6-membered heterocyclic, wherein said substituted heterocyclic is substituted with one or more $R_{16}$;

each $R_9$ is independently hydrogen or $C_1$-$C_8$ alkyl;

$X_1$ is H, $C_1$-$C_8$ alkyl, or halogen;

each $X_{3a}$ and $X_{3b}$ are independently hydrogen, $C_1$-$C_8$ alkyl, or absent (when n is 0);

Q is substituted $C_6$-$C_{10}$ aryl, substituted 5- or 6-membered heteroaryl, substituted 3- to 8-membered cycloalkyl, or substituted 3- to 8-membered heterocyclic, wherein said substituted aryl, heteroaryl, cycloalkyl, or heterocyclic is substituted with four $R_{11}$;

each $R_{11}$ is independently methyl, methoxy, or chloro;

n is 0, 1, 2, 3, or 4;

$X_4$ is unsubstituted or substituted $C_6$-$C_{10}$ aryl, unsubstituted or substituted 5- or 6-membered heteroaryl, unsubstituted or substituted $C_1$-$C_8$ alkyl, or unsubstituted or substituted $(CH_2)_{1-3}$—$C_6$-$C_{10}$ aryl, wherein said substituted aryl, heteroaryl, or alkyl is substituted with one or more $R_{16}$;

each $R_{16}$ is independently halogen, $OR_{17}$, $NR_{18}R_{19}$, $SR_{20}$, unsubstituted or substituted $C_1$-$C_8$ alkyl, halo($C_1$-$C_8$ alkyl), $C(O)(C_1$-$C_8$ alkyl), $C(O)($halo$(C_1$-$C_8$ alkyl)), $C(O)(C_2$-$C_8$ alkenyl), unsubstituted or substituted heterocyclic, or $C(O)$-unsubstituted or substituted heterocyclic, wherein said substituted alkyl or heterocyclic is substituted with one or more $R_{21}$;

each $R_{17}$ is independently hydrogen or $C_1$-$C_8$ alkyl;

each $R_{18}$ and $R_{19}$ are independently hydrogen, $C_1$-$C_8$ alkyl, $C(O)(C_1$-$C_8$ alkyl), $C(O)(C_2$-$C_8$ alkenyl), or $C(O)$-unsubstituted or substituted heterocyclic, wherein said alkyl or alkenyl is optionally substituted with one or more OH, CN, halogen, $C_3$-$C_8$ cycloalkyl, $O(C_1$-$C_8$ alkyl), $NH_2$, $NH(C_1$-$C_8$ alkyl), or $N(C_1$-$C_8$ alkyl)$_2$, and wherein said substituted heterocyclic is substituted with one or more $R_{21}$;

each $R_{20}$ is independently hydrogen or $C_1$-$C_8$ alkyl;

each $R_{21}$ is independently $C_1$-$C_8$ alkyl, $C(O)(C_1$-$C_8$ alkyl), $C(O)(C_2$-$C_8$ alkenyl), or heterocyclic;

$X_5$ is unsubstituted or substituted $C_6$-$C_{10}$ aryl, unsubstituted or substituted 5- to 8-membered heteroaryl, or unsubstituted or substituted $C_1$-$C_8$ alkyl, wherein said substituted aryl, heteroaryl, or alkyl is substituted with one or more $R_{22}$;

each $R_{22}$ is independently halogen, $OR_{23}$, $NR_{24}R_{25}$, $SR_{26}$, $C_1$-$C_8$ alkyl, halo($C_1$-$C_8$ alkyl), $C(O)(C_1$-$C_8$ alkyl), $C(O)(C_2$-$C_8$ alkenyl), unsubstituted or substituted heterocyclic, unsubstituted or substituted $C_6$-$C_{10}$ aryl, or $C(O)$-unsubstituted or substituted heterocyclic, wherein said substituted heterocyclic or aryl is substituted with one or more $R_{27}$;

or two or more $R_{22}$, together with the atoms to which they attach, form an unsubstituted or substituted 3- to 8-membered cycloalkyl, or unsubstituted or substituted 5- to 6-membered heterocyclic, wherein said substituted cycloalkyl or heterocyclic is substituted with one or more $R_{27}$;

each $R_{23}$ is independently hydrogen or $C_1$-$C_8$ alkyl;

each $R_{24}$ and $R_{25}$ are independently hydrogen, $C_1$-$C_8$ alkyl, $C(O)(C_1$-$C_8$ alkyl), or $C(O)(C_2$-$C_8$ alkenyl), wherein said alkyl or alkenyl is optionally substituted with one or more OH, CN, halogen, $C_3$-$C_8$ cycloalkyl, $O(C_1$-$C_8$ alkyl), $NH_2$, $NH(C_1$-$C_8$ alkyl), or $N(C_1$-$C_8$ alkyl)$_2$;

each $R_{26}$ is independently hydrogen or $C_1$-$C_8$ alkyl;

each $R_{27}$ is independently halogen, $C_1$-$C_8$ alkyl, $C(O)(C_1$-$C_8$ alkyl), $C(O)(C_2$-$C_8$ alkenyl), $NR_{29}C(O)(C_1$-$C_8$ alkyl), or $NR_{29}C(O)(C_2$-$C_8$ alkenyl); and each $R_{29}$ is hydrogen or $C_1$-$C_8$ alkyl.

2. The compound of claim 1, selected from formulae IIa, IIb, and III:

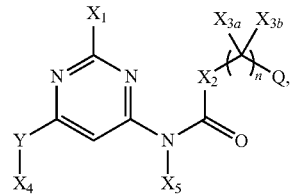

(IIa)

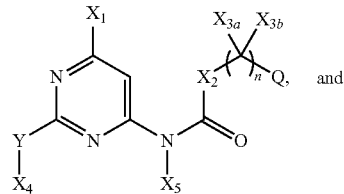

(IIb)

and

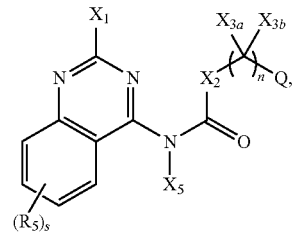

(III)

or a pharmaceutically acceptable salt thereof, wherein s is 1, 2, 3, or 4.

3. The compound of claim 1, selected from formulae Va and Vb:

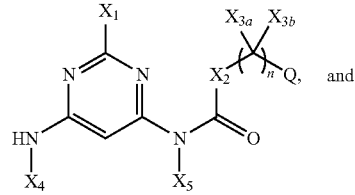

(Va)

and

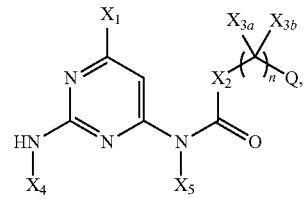

(Vb)

or a pharmaceutically acceptable salt thereof.

4. The compound of claim 1, selected from formulae VIa and VIb:

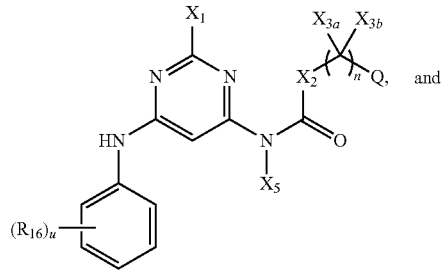

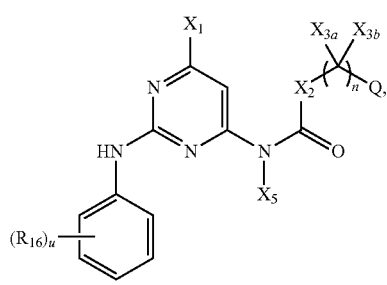

or a pharmaceutically acceptable salt thereof, wherein u is 0, 1, 2, 3, 4, or 5.

5. The compound of claim 1, wherein $X_1$ is hydrogen or halogen.

6. The compound of claim 1, wherein $X_1$ is hydrogen.

7. The compound of claim 1, wherein n is 0 or 1.

8. The compound of claim 1, wherein n is 0.

9. The compound of claim 1, wherein Q is phenyl or 5- or 6-membered heteroaryl.

10. The compound of claim 1, wherein Q is phenyl.

11. The compound of claim 1, wherein $X_2$ is $NR_{10}$.

12. The compound of claim 1, wherein each $R_{11}$ is independently methoxy or chloro.

13. The compound of claim 1, wherein $X_4$ is substituted phenyl or methyl.

14. The compound of claim 13, wherein $X_4$ is phenyl substituted with methylpiperazinyl.

15. The compound of claim 1, wherein $X_5$ is substituted phenyl or substituted methyl.

16. A compound selected from:

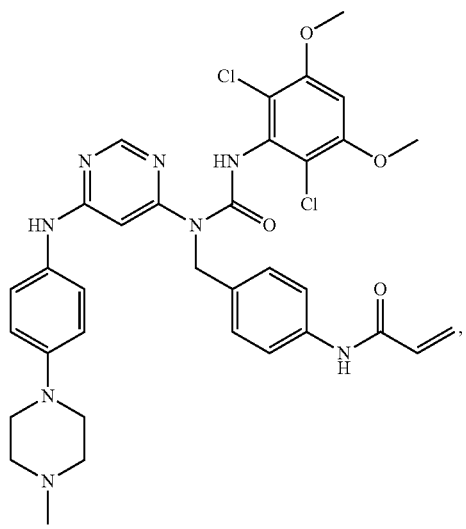

-continued

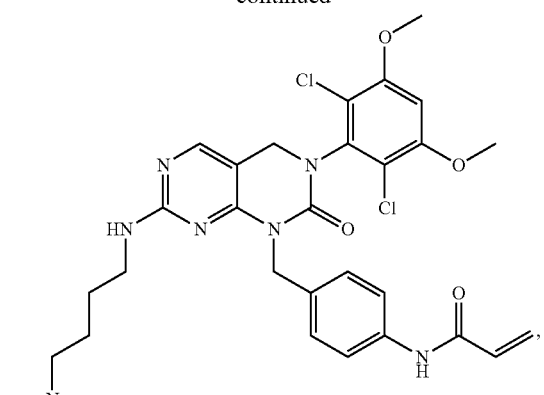

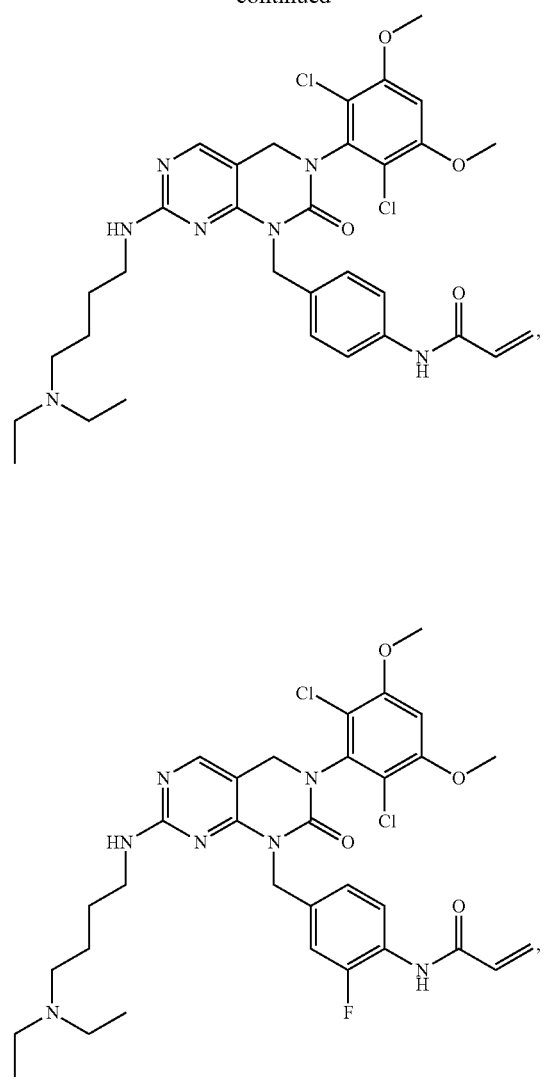

-continued
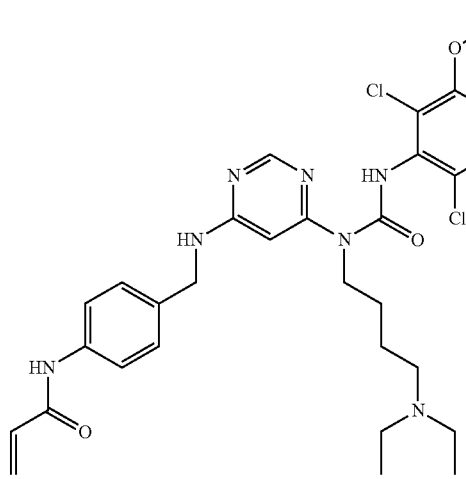
,
-continued
and
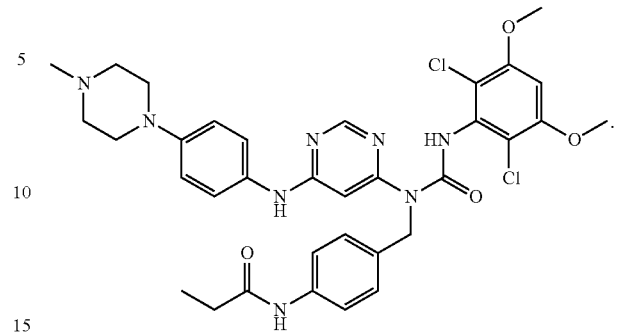
17. A pharmaceutical composition comprising a compound of claim 1 or a pharmaceutically acceptable salt thereof and a pharmaceutical carrier, diluent, or excipient.
18. A pharmaceutical composition comprising a compound of claim 16 or a pharmaceutically acceptable salt thereof and pharmaceutical carrier, diluent, or excipient.
* * * * *

UNITED STATES PATENT AND TRADEMARK OFFICE
CERTIFICATE OF CORRECTION

PATENT NO.         : 10,316,002 B2
APPLICATION NO.    : 15/696309
DATED              : June 11, 2019
INVENTOR(S)        : Nathanael S. Gray et al.

Page 1 of 1

It is certified that error appears in the above-identified patent and that said Letters Patent is hereby corrected as shown below:

In the Claims

At Column 186, Claim number 1, Line number 37:
"R1 is H, $C_1$-$C_8$ alkyl, halogen, or halo($C_1$-$C_8$ alkyl);"
Should read:
-- $R_1$ is H, $C_1$-$C_8$ alkyl, halogen, or halo($C_1$-$C_8$ alkyl); --

At Column 186, Claim number 1, Line number 38:
"R2 is H, $C_1$-$C_8$ alkyl, halogen, or halo($C_1$-$C_8$ alkyl);"
Should read:
-- $R_2$ is H, $C_1$-$C_8$ alkyl, halogen, or halo($C_1$-$C_8$ alkyl); --

Signed and Sealed this
Thirteenth Day of August, 2019

Andrei Iancu
*Director of the United States Patent and Trademark Office*

UNITED STATES PATENT AND TRADEMARK OFFICE
CERTIFICATE OF CORRECTION

PATENT NO. : 10,316,002 B2
APPLICATION NO. : 15/696309
DATED : June 11, 2019
INVENTOR(S) : Nathanael S. Gray et al.

Page 1 of 1

It is certified that error appears in the above-identified patent and that said Letters Patent is hereby corrected as shown below:

In the Specification

At Column 1, after Line number 15, please insert:
--This invention was made with government support under grant numbers CA135257, CA148164, and CA130876 awarded by The National Institutes of Health. The government has certain rights in the invention.--

Signed and Sealed this
Tenth Day of September, 2019

Andrei Iancu
*Director of the United States Patent and Trademark Office*